US011200963B2

(12) United States Patent
Mazloom et al.

(10) Patent No.: US 11,200,963 B2
(45) Date of Patent: Dec. 14, 2021

(54) GENETIC COPY NUMBER ALTERATION CLASSIFICATIONS

(71) Applicant: Sequenom, Inc., San Diego, CA (US)

(72) Inventors: Amin Mazloom, San Diego, CA (US); Cosmin Deciu, San Diego, CA (US); Chen Zhao, San Diego, CA (US); Tong Liu, San Diego, CA (US); Yijin Wu, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 1078 days.

(21) Appl. No.: 15/661,804

(22) Filed: Jul. 27, 2017

(65) Prior Publication Data

US 2018/0032671 A1 Feb. 1, 2018

Related U.S. Application Data

(60) Provisional application No. 62/367,557, filed on Jul. 27, 2016.

(51) Int. Cl.
*G16B 20/10* (2019.01)
*G16B 40/00* (2019.01)
*G16B 20/00* (2019.01)
*G16B 20/20* (2019.01)
*G06N 7/00* (2006.01)

(52) U.S. Cl.
CPC .............. *G16B 20/10* (2019.02); *G06N 7/005* (2013.01); *G16B 20/00* (2019.02); *G16B 20/20* (2019.02); *G16B 40/00* (2019.02)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,075,212 A | 12/1991 | Rotbart |
| 5,091,652 A | 2/1992 | Mathies et al. |
| 5,432,054 A | 7/1995 | Saunders et al. |
| 5,445,934 A | 8/1995 | Fodor et al. |
| 5,670,325 A | 9/1997 | Lapidus et al. |
| 5,720,928 A | 2/1998 | Schwartz |
| 5,786,146 A | 7/1998 | Herman et al. |
| 5,928,870 A | 7/1999 | Lapidus et al. |
| 5,939,598 A | 8/1999 | Kucherlapati et al. |
| 6,015,714 A | 1/2000 | Baldarelli et al. |
| 6,090,550 A | 7/2000 | Collinge et al. |
| 6,100,029 A | 8/2000 | Lapidus et al. |
| 6,214,558 B1 | 4/2001 | Shuber et al. |
| 6,214,560 B1 | 4/2001 | Yguerabide et al. |
| 6,235,475 B1 | 5/2001 | Brenner et al. |
| 6,258,540 B1 | 7/2001 | Lo et al. |
| 6,263,286 B1 | 7/2001 | Gilmanshin et al. |
| 6,403,311 B1 | 6/2002 | Chan |
| 6,566,101 B1 | 5/2003 | Shuber et al. |
| 6,617,133 B1 | 9/2003 | Noda et al. |
| 6,772,070 B2 | 8/2004 | Gilmanshin et al. |
| 6,818,395 B1 | 11/2004 | Quake et al. |
| 6,927,028 B2 | 8/2005 | Dennis et al. |
| 6,936,422 B2 | 8/2005 | El Solh et al. |
| 7,005,264 B2 | 2/2006 | Su et al. |
| 7,169,560 B2 | 1/2007 | Lapidus et al. |
| 7,279,337 B2 | 10/2007 | Zhu |
| 7,282,337 B1 | 10/2007 | Harris |
| 7,947,454 B2 | 5/2011 | Akeson et al. |
| 7,960,105 B2 | 6/2011 | Schwartz et al. |
| 7,972,858 B2 | 7/2011 | Meller et al. |
| 8,688,388 B2 | 4/2014 | Dzakula et al. |
| 9,260,745 B2 | 2/2016 | Rava et al. |
| 2001/0014850 A1 | 8/2001 | Gilmanshin et al. |
| 2001/0049102 A1 | 12/2001 | Huang et al. |
| 2002/0006621 A1 | 1/2002 | Bianchi |
| 2002/0045176 A1 | 4/2002 | Lo et al. |
| 2002/0110818 A1 | 8/2002 | Chan |
| 2002/0119469 A1 | 8/2002 | Shuber et al. |
| 2002/0164629 A1 | 11/2002 | Quake et al. |
| 2003/0013101 A1 | 1/2003 | Balasubramanian |
| 2003/0082600 A1 | 5/2003 | Olek et al. |
| 2003/0180779 A1 | 9/2003 | Lofton-Day et al. |

(Continued)

FOREIGN PATENT DOCUMENTS

| | | |
|---|---|---|
| WO | 00006770 | 2/2000 |
| WO | 0132887 | 5/2001 |

(Continued)

OTHER PUBLICATIONS

Shendure et al. Next-generation DNA sequencing Nature Biotechnology vol. 26, pp. 1135-1145 (Year: 2008).*
Li et al. A survey of sequence alignment algorithms for next-generation sequencing Briefings in Bioinformatics vol. 11 pp. 473-483 (Year: 2010).*
Klambauer et al., "cn.MOPS: Mixture of Poissons for Discovering Copy Number Variations in Next-Generation Sequencing Data with a Low False Discovery Rate", Nucleic Acids Research, vol. 40, No. 9, Feb. 1, 2012, pp. 1-14.
Patent Cooperation Treaty Application No. PCT/US2017/044185, International Search Report and Written Opinion dated Nov. 13, 2017, 13 pages.
A Map of Human Genome Sequence Variation Containing 1.42 Million Single Nucleotide Polymorphisms, The International SNP Map Working Group, vol. 409, Feb. 15, 2001, pp. 928-933.

(Continued)

*Primary Examiner* — John S Brusca
(74) *Attorney, Agent, or Firm* — Kilpatrick Townsend & Stockton LLP

(57) ABSTRACT

Technology provided herein relates in part to non-invasive classification of one or more genetic copy number alterations (CNAs) for a test sample. Certain methods include sampling a quantification of sequence reads from parts of a genome, generating a confidence determination, and using the confidence determination to enhance classification. Technology provided herein is useful for classifying a genetic CNA for a sample as part of non-invasive pre-natal (NIPT) testing and oncology testing, for example.

19 Claims, 15 Drawing Sheets

(56) References Cited

U.S. PATENT DOCUMENTS

| | | |
|---|---|---|
| 2003/0207326 A1 | 11/2003 | Su et al. |
| 2003/0232346 A1 | 12/2003 | Su |
| 2004/0081993 A1 | 4/2004 | Cantor et al. |
| 2004/0110208 A1 | 6/2004 | Chan et al. |
| 2004/0137470 A1 | 7/2004 | Dhallan |
| 2005/0019784 A1 | 1/2005 | Su et al. |
| 2005/0095599 A1 | 5/2005 | Pittaro et al. |
| 2005/0112590 A1 | 5/2005 | Boom et al. |
| 2005/0147980 A1 | 7/2005 | Berlin et al. |
| 2005/0164241 A1 | 7/2005 | Hahn et al. |
| 2005/0227278 A1 | 10/2005 | Wall |
| 2005/0287592 A1 | 12/2005 | Kless |
| 2006/0046258 A1 | 3/2006 | Lapidus et al. |
| 2006/0063171 A1 | 3/2006 | Akeson et al. |
| 2006/0068440 A1 | 3/2006 | Chan et al. |
| 2006/0252071 A1 | 11/2006 | Lo et al. |
| 2007/0026406 A1 | 2/2007 | El Ghaoui et al. |
| 2007/0065823 A1 | 3/2007 | Dressman et al. |
| 2007/0202525 A1 | 8/2007 | Quake et al. |
| 2008/0020390 A1 | 1/2008 | Mitchell et al. |
| 2008/0070792 A1 | 3/2008 | Stoughton et al. |
| 2008/0081330 A1 | 4/2008 | Kahvejian |
| 2008/0138809 A1 | 6/2008 | Kapur et al. |
| 2008/0187915 A1 | 8/2008 | Polonsky et al. |
| 2008/0233575 A1 | 9/2008 | Harris et al. |
| 2009/0026082 A1 | 1/2009 | Rothberg et al. |
| 2009/0029377 A1 | 1/2009 | Lo et al. |
| 2009/0075252 A1 | 3/2009 | Harris et al. |
| 2009/0129647 A1 | 5/2009 | Dimitrova et al. |
| 2009/0191565 A1 | 7/2009 | Lapidus et al. |
| 2009/0197257 A1 | 8/2009 | Harris |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0109197 A1 | 5/2010 | Hansen et al. |
| 2010/0112575 A1 | 5/2010 | Fan et al. |
| 2010/0112590 A1 | 5/2010 | Lo et al. |
| 2010/0138165 A1 | 6/2010 | Fan et al. |
| 2010/0151471 A1 | 6/2010 | Faham et al. |
| 2010/0216151 A1 | 8/2010 | Lapidus et al. |
| 2010/0216153 A1 | 8/2010 | Lapidus et al. |
| 2010/0261285 A1 | 10/2010 | Goldstein et al. |
| 2010/0310421 A1 | 12/2010 | Oliver et al. |
| 2010/0330557 A1 | 12/2010 | Yakhini et al. |
| 2011/0086769 A1 | 4/2011 | Oliphant et al. |
| 2011/0105353 A1 | 5/2011 | Lo et al. |
| 2011/0159601 A1 | 6/2011 | Golovchenko et al. |
| 2011/0171634 A1 | 7/2011 | Xiao et al. |
| 2011/0174625 A1 | 7/2011 | Akeson et al. |
| 2011/0177498 A1 | 7/2011 | Clarke et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0288780 A1 | 11/2011 | Rabinowitz et al. |
| 2011/0294699 A1 | 12/2011 | Lee et al. |
| 2011/0312503 A1 | 12/2011 | Chuu et al. |
| 2011/0319272 A1 | 12/2011 | Fan et al. |
| 2012/0046877 A1 | 2/2012 | Hyland et al. |
| 2012/0122701 A1 | 5/2012 | Ryan et al. |
| 2012/0165203 A1 | 6/2012 | Quake et al. |
| 2012/0184449 A1 | 7/2012 | Hixson et al. |
| 2012/0214678 A1 | 8/2012 | Rava et al. |
| 2012/0264115 A1 | 10/2012 | Rava |
| 2012/0270212 A1 | 10/2012 | Rabinowitz et al. |
| 2012/0270739 A1 | 10/2012 | Rava et al. |
| 2013/0012399 A1 | 1/2013 | Myers et al. |
| 2013/0022977 A1 | 1/2013 | Lapidus et al. |
| 2013/0029852 A1 | 1/2013 | Rava et al. |
| 2013/0034546 A1 | 2/2013 | Rava et al. |
| 2013/0085681 A1 | 4/2013 | Deciu et al. |
| 2013/0096011 A1 | 4/2013 | Rava et al. |
| 2013/0130921 A1 | 5/2013 | Gao et al. |
| 2013/0130923 A1 | 5/2013 | Ehrich et al. |
| 2013/0150253 A1 | 6/2013 | Deciu et al. |
| 2013/0196317 A1 | 8/2013 | Lapidus et al. |
| 2013/0237431 A1 | 9/2013 | Lo et al. |
| 2013/0245961 A1 | 9/2013 | Lo et al. |
| 2013/0261983 A1 | 10/2013 | Dzakula et al. |
| 2013/0288244 A1 | 10/2013 | Deciu et al. |
| 2013/0304392 A1 | 11/2013 | Deciu et al. |
| 2013/0309666 A1 | 11/2013 | Deciu et al. |
| 2013/0310260 A1 | 11/2013 | Kim et al. |
| 2013/0325360 A1 | 12/2013 | Deciu et al. |
| 2013/0338933 A1 | 12/2013 | Deciu et al. |
| 2014/0038830 A1 | 2/2014 | Srinivasan et al. |
| 2014/0100792 A1 | 4/2014 | Deciu et al. |
| 2014/0180594 A1 | 6/2014 | Kim et al. |
| 2014/0235474 A1 | 8/2014 | Tang et al. |
| 2014/0242588 A1 | 8/2014 | Van Den Boom et al. |
| 2014/0322709 A1 | 10/2014 | Lapidus et al. |
| 2015/0005176 A1 | 1/2015 | Kim et al. |
| 2015/0064695 A1 | 3/2015 | Katz et al. |
| 2015/0100244 A1 | 4/2015 | Hannum |
| 2015/0347676 A1 | 12/2015 | Zhao et al. |
| 2016/0034640 A1 | 2/2016 | Zhao et al. |
| 2016/0110497 A1 | 4/2016 | Dzakula et al. |
| 2018/0032671 A1 | 2/2018 | Mazloom et al. |

FOREIGN PATENT DOCUMENTS

| | | |
|---|---|---|
| WO | 02042496 | 5/2002 |
| WO | 03000920 | 1/2003 |
| WO | 03070894 | 8/2003 |
| WO | 03106620 | 12/2003 |
| WO | 2005023091 | 3/2005 |
| WO | 2006056480 | 6/2006 |
| WO | 2007121276 | 10/2007 |
| WO | 2007140417 | 12/2007 |
| WO | 2007147063 | 12/2007 |
| WO | 2008032779 | 3/2008 |
| WO | 2008045505 | 4/2008 |
| WO | 2008121828 | 10/2008 |
| WO | 2009007743 | 1/2009 |
| WO | 2009032781 | 3/2009 |
| WO | 2009046445 | 4/2009 |
| WO | 2010004265 | 1/2010 |
| WO | 2010033578 | 3/2010 |
| WO | 2010033639 | 3/2010 |
| WO | 2010056728 | 5/2010 |
| WO | 2010059731 | 5/2010 |
| WO | 2010065470 | 6/2010 |
| WO | 2010115016 | 10/2010 |
| WO | 2011034631 | 3/2011 |
| WO | 2011038327 | 3/2011 |
| WO | 2011050147 | 4/2011 |
| WO | 2011057094 | 5/2011 |
| WO | 2011087760 | 7/2011 |
| WO | 2011090556 | 7/2011 |
| WO | 2011090558 | 7/2011 |
| WO | 2011090559 | 7/2011 |
| WO | 2011091063 | 7/2011 |
| WO | 2011102998 | 8/2011 |
| WO | 2011143659 | 11/2011 |
| WO | 2011146632 | 11/2011 |
| WO | 2012012703 | 1/2012 |
| WO | 2012071621 | 6/2012 |
| WO | 2012088348 | 6/2012 |
| WO | 2012088456 | 6/2012 |
| WO | 2012103031 | 8/2012 |
| WO | 2012108920 | 8/2012 |
| WO | 2012118745 | 9/2012 |
| WO | 2012177792 | 12/2012 |
| WO | 2013000100 | 1/2013 |
| WO | 2013052907 | 4/2013 |
| WO | 2013052913 | 4/2013 |
| WO | 2013055817 | 4/2013 |
| WO | 2013109981 | 7/2013 |
| WO | 2013177086 | 11/2013 |
| WO | 2013192562 | 12/2013 |
| WO | 2014014497 | 1/2014 |
| WO | 2014039556 | 3/2014 |
| WO | 2014055774 | 4/2014 |
| WO | 2014055790 | 4/2014 |

(56) References Cited

FOREIGN PATENT DOCUMENTS

| WO | 2014116598 | 7/2014 |
|---|---|---|
| WO | 2014165596 | 10/2014 |
| WO | 2014190286 | 11/2014 |
| WO | 2014205401 | 12/2014 |
| WO | 2015028576 | 3/2015 |
| WO | 2015040591 | 3/2015 |
| WO | 2015051163 | 4/2015 |
| WO | 2015054080 | 4/2015 |
| WO | 2015067796 | 5/2015 |
| WO | 2015183872 | 12/2015 |
| WO | 2016019042 | 2/2016 |
| WO | 2018/022890 A1 | 2/2018 |

OTHER PUBLICATIONS

Adinolfi et al., Rapid Detection of Aneuploidies by Microsatellite and the Quantitative Fluorescent Polymerase Chain Reaction, Prenatal Diagnosis, vol. 17, No. 13, Dec. 1997, pp. 1299-1311.
Agarwal et al., Commercial Landscape of Noninvasive Prenatal Testing in the United States, Prenatal Diagnosis, vol. 33, No. 6, Jun. 2013, pp. 521-531.
Akeson et al., Microsecond Time-Scale Discrimination Among Polycytidylic Acid, Polyadenylic Acid, and Polyuridylic Acid as Homopolymers or as Segments Within Single RNA Molecules, Biophysical Journal, vol. 77, No. 6, Dec. 1999, pp. 3227-3233.
Alkan et al., Personalized Copy Number and Segmental Duplication Maps Using Next-Generation Sequencing, Nature Genetics, vol. 41, No. 10, Oct. 2009, pp. 1061-1067.
Amicucci et al., Prenatal Diagnosis of Myotonic Dystrophy Using Fetal DNA Obtained from Maternal Plasma, Clinical Chemistry, vol. 46, No. 2, Feb. 1, 2000, pp. 301-302.
Anantha, et al., Porphyrin Binding to Quadruplexed T4G4, Biochemistry, vol. 37, No. 9, Available Online at: http://pubs.acs.org/doi/pdf/10.1021/bi973009v, Mar. 3, 1998, pp. 2709-2714.
Armour et al., Measurement of Locus Copy Number by Hybridization with Amplifiable Probes, Nucleic Acids Research, vol. 28, No. 2, Jan. 15, 2000, pp. 605-609.
Armour et al., The Detection of Large Deletions or Duplications in Genomic DNA, Human Mutation, vol. 20, No. 5, Nov. 2002, pp. 325-337.
Ashkenasy et al., Recognizing a Single Base in an Individual DNA Strand: A Step Toward Nanopore DNA Sequencing, Angewandte Chemie International Edition, vol. 44, No. 9, Feb. 18, 2005, pp. 1401-1404.
Ashoor et al., Chromosome-Selective Sequencing of Maternal Plasma Cell-Free DNA for First-Trimester Detection of Trisomy 21 and Trisomy 18, American Journal Obstetrics & Gynecology, vol. 206, No. 322, Apr. 2012, pp. e1-e5.
Aston et al., Optical Mapping and its Potential for Large-scale Sequencing Projects, Trends in Biotechnology, vol. 17, No. 7, Jul. 1999, pp. 297-302.
Aston et al., Optical Mapping: An Approach for Fine Mapping, Methods in Enzymology, vol. 303, 1999, pp. 55-73.
Avent et al., Non-Invasive Diagnosis of Fetal Sex; Utilization of Free Fetal DNA in Maternal Plasma and Ultrasound, Prenatal Diagnosis, vol. 26, No. 7, Jul. 2006, pp. 598-603.
Avent, Refining Noninvasive Prenatal Diagnosis with Single-Molecule Next-Generation Sequencing, Clinical Chemistry., vol. 58, No. 4, Apr. 1, 2012, pp. 657-658.
Beaucage et al., Deoxynucleoside Phosphoramidites—A New Class of Key Intermediates for Deoxypolynucleotide Synthesis, Tetrahedron Letters, vol. 22, No. 20, Dec. 1981, pp. 1859-1862.
Beaudet, Progress Toward Noninvasive Prenatal Diagnosis, Clinical Chemistry, vol. 57, No. 6, Jun. 2011, pp. 802-804.
Benjamini et al., Summarizing and Correcting the GC Content Bias in High-Throughput Sequencing, Nucleic Acids Research, vol. 40, No. 10, May 2012, 14 pages.
Berger et al., Universal Bases for Hybridization, Replication and Chain Termination, Nucleic Acids Research, vol. 28, No. 15, Aug. 1, 2000, pp. 2911-2914.
Berghe et al., A New Characteristic Karyotypic Anomaly in Lymphoproliferative Disorders, Cancer, vol. 44, No. 1, Jul. 1979, 1 page.
Bergstrom et al., Synthesis, Structure, and Deoxyribonucleic Acid Sequencing with a Universal Nucleoside: 1 -(2'-Deoxy-β-D-ribofuranosyl)-3-Nitropyrrole, Journal of the American Chemical Society, vol. 117, No. 4, Feb. 1995, pp. 1201-1209.
Bianchi et al., Isolation of Fetal DNA from Nucleated Erythrocytes in Maternal Blood, Proceedings of the National Academy of Sciences U.S.A., vol. 87, No. 9, May 1990, pp. 3279-3283.
Boeva et al., Control-Free Calling of Copy Number Alterations in Deep-Sequencing Data Using GC-Content Normalization, Bioinformatics, vol. 27, No. 2, Jan. 15, 2011, pp. 268-269.
Bollen, Bioconductor: Microarray Versus Next-Generation Sequencing Toolsets, Utrecht University, Available Online at: http://dspace.library.uu.nl/bitstream/handle/1874/290489/Sander_Bollen_writing_assignment.pdf, Feb. 11, 2014, pp. 1-14.
Borsenberger et al., Chemically Labeled Nucleotides and Oligonucleotides Encode DNA for Sensing with Nanopores, Journal of the American Chemical Society, vol. 131, No. 22, May 14, 2009, pp. 7530-7531.
Branton et al., The Potential and Challenges of Nanopore Sequencing, Nature Biotechnology, vol. 26, No. 10, Oct. 9, 2008, pp. 1146-1153.
Braslavsky et al., Sequence Information can be Obtained from Single DNA Molecules, Pro National Academy Science USA, vol. 100, No. 7, Apr. 1, 2003, pp. 3960-3964.
Brizot et al., Maternal Serum HCG and Fetal Nuchal Translucency Thickness for the Prediction of Fetal Trisomies in the First Trimester of Pregnancy, British Journal of Obstetrics Gynaecology, vol. 102, No. 2, Feb. 1995, pp. 127-132.
Brizot et al., Maternal Serum Pregnancy-Associated Plasma Protein A and Fetal Nuchal Translucency Thickness for the Prediction of Fetal Trisomies in Early Pregnancy, Obstetrics & Gynecology, vol. 84, No. 6, Dec. 1994, pp. 918-922.
Brown et al., Synthesis and Duplex Stability of Oligonucleotides Containing Adenineguanine Analogues, Carbohydrate Research, vol. 216, Sep. 2, 1992, pp. 129-139.
Brown et al., Validation of QF-PCR for Prenatal Aneuploidy Screening in the United States, Prenatal Diagnosis, vol. 26, No. 11, Nov. 2006, pp. 1068-1074.
Brown, A Step-By-Step Guide to Non-Linear Regression Analysis of Experimental Data Using a Microsoft Excel Spreadsheet, Computer Methods and Programs in Biomedicine, vol. 65, No. 3, Jun. 2001, pp. 191-200.
Bruch et al., Trophoblast-Like Cells Sorted from Peripheral Maternal Blood Using Flow Cytometry: A Multiparametric Study Involving Transmission Electron Microscopy and Fetal DNA Amplification, Prenatal Diagnosis, vol. 11, No. 10, Oct. 11, 1991, pp. 787-798.
Brunger, Free R Value: A Novel Statistical Quantity for Assessing the Accuracy of Crystal Structures, Nature, vol. 355, Jan. 30, 1992, pp. 472-475.
Buckheit et al., Wavelab and Reproducible Research, Wavelets and Statistics, Jan. 1995, pp. 1-27.
Budinska et al., MSMAD: A Computationally Efficient Method for the Analysis of Noisy Array CGH Data, Bioinformatics, vol. 25, No. 6, Mar. 15, 2009, pp. 703-713.
Burlingame et al., Mass Spectrometry, Analytical Chemistry, vol. 70, No. 16, Available Online at: http://pubs.acs.org/doi/pdf/10.1021/a1980023%2B, Jul. 9, 1998, pp. 647-716.
Campbell et al., Identification of Somatically Acquired Rearrangements in Cancer Using Genome-Wide Massively Parallel Paired-End Sequencing, Nature Genetics, vol. 40, No. 6, Jun. 2008, pp. 722-729.
Canick et al., DNA Sequencing of Maternal Plasma to Identify Down Syndrome and Other Trisomies in Multiple Gestations, Prenatal Diagnosis, vol. 32, No. 8, Aug. 2012, pp. 730-734.
Canick et al., The Impact of Maternal Plasma DNA Fetal Fraction on Next Generation Sequencing Tests for Common Fetal Aneuploidies, Prenatal Diagnosis, vol. 33, No. 7, Jul. 2013, pp. 667-674.

(56) References Cited

OTHER PUBLICATIONS

Canick, A New Prenatal Blood Test for Down Syndrome (RNA), Jul. 2012, 3 pages.
Cann et al., A Heterodimeric DNA Polymerase Evidence that Members of Euryarchaeota Possess a Distinct DNA Polymerase, Proceedings of the National Academy of Sciences USA, vol. 95, No. 24, Nov. 24, 1998, pp. 14250-14255.
Cariello et al., Fidelity of Thermococcus Litoralis DNA Polymerase (Vent) in PCR Determined by Denaturing Gradient Gel Electrophoresis, Nucleic Acids Research, vol. 19, No. 15, Aug. 11, 1991, pp. 4193-4198.
Carlson et al., Molecular Definition of 22q11 Deletions in 151 Velo-Cardia-Facial Syndrome Patients, The American Journal of Human Genetics, vol. 61, No. 3, Sep. 1, 1997, pp. 620-629.
Chan et al., Size Distributions of Maternal and Fetal DNA in Maternal Plasma, Clinical Chemistry, vol. 50, No. 1, Jan. 2004, pp. 88-92.
Chandrananda et al., Investigating and Correcting Plasma DNA Sequencing Coverage Bias to Enhance Aneuploidy Discovery, PloS One, vol. 9, No. 1, Jan. 29, 2014, 14 pages.
Chen et al., A Method for Noninvasive Detection of Fetal Large Deletions/Duplications by Low Coverage Massively Parallel Sequencing, Prenatal Diagnosis, vol. 33, No. 6, Jun. 17, 2013, pp. 584-590.
Chen et al., Identification of Avian W-linked Contigs by Short-read Sequencing, BMC Genomics, vol. 13, No. 183, 2012, 9 pages.
Chen et al., Noninvasive Prenatal Diagnosis of Fetal Trisomy 18 and Trisomy 13 by Maternal Plasma DNA Sequencing, PLOS One, vol. 6, No. 7, e21791, Jul. 6, 2011, pp. 1-7.
Chiang et al., High-Resolution Mapping of Copy-Number Alterations with Massively Parallel Sequencing, Nature Methods, vol. 6, No. 1, Jan. 2009, pp. 99-103.
Chien et al., Deoxyribonucleic Acid Polymerase from the Extreme Thermophile Thermus Aquaticus, Journal of Bacteriology, vol. 127, No. 3, Sep. 1976, pp. 1550-1557.
Chim et al., Systematic Search for Placental DNA-Methylation Markers on Chromosome 21: Toward a Maternal Plasma-Based Epigenetic Test for Fetal Trisomy 21, Clinical Chemistry, vol. 54, No. 3, Mar. 2008, pp. 500-511.
Chiu et al., Maternal Plasma DNA Analysis with Massively Parallel Sequencing by Ligation for Noninvasive Prenatal Diagnosis of Trisomy 21, Clinical Chemistry, vol. 56, No. 3, Mar. 2010, pp. 459-463.
Chiu et al., Non-Invasive Prenatal Assessment of Trisomy 21 by Multiplexed Maternal Plasma DNA Sequencing Large Scale Validity Study, British Medical Journal, vol. 342, Jan. 11, 2011, pp. 1-9.
Chiu et al., Noninvasive Prenatal Diagnosis of Fetal Chromosomal Aneuploidy by Massively Parallel Genomic Sequencing of DNA in Maternal Plasma, Proceedings of the National Academy of Sciences, vol. 105, No. 51, Dec. 23, 2008, pp. 20458-20463.
Chiu et al., Prenatal Exclusion of β Thalassaemia Major by Examination of Maternal Plasma, Lancet, vol. 360, No. 9338, Sep. 28, 2002, pp. 998-1000.
Chromosomes Fact Sheet, National Human Genome Research Institute, Available Online at http://www.genome.gov/26524120, 2015, 2 pages.
Chu et al., Statistical Model for Whole Genome Sequencing and its Application to Minimally Invasive Diagnosis of Fetal Genetic Disease, Bioinformatics, vol. 25, No. 10, May 2009, pp. 1244-1250.
Chung et al., Discovering Transcription Factor Binding Sites in Highly Repetitive Regions of Genomes with Multi-Read Analysis of ChiP-Seq Data, PLoS Computational Biology, vol. 7, No. 7, Jul. 2011, 17 pages.
Cohen et al., GC Composition of the Human Genome: In Search of Isochores, Molecular Biology and Evolution, vol. 22, No. 5, May 2005, pp. 1260-1272.
Cooper et al., Human Genome Mutations, BIOS Publishers, 1993, 12 pages.
Costa et al., Fetal RHD Genotyping in Maternal Serum During the First Trimester of Pregnancy, British Journal of Haematology, vol. 119, vol. 1, Oct. 1, 2002, pp. 255-260.
Costa et al., New Strategy for Prenatal Diagnosis of X-linked Disorders, The New England Journal of Medicine, vol. 346, No. 19, May 9, 2002, p. 1502.
Cunningham et al., In Williams Obstetrics, McGraw-Hill, New York, 2002, 1 page.
Current Protocols in Molecular Biology, John Wiley & Sons, N.Y., 1989, pp. 6.3.1-6.3.6.
D'Alton, Prenatal Diagnostic Procedures, Semin Perinatol, vol. 18, No. 3, Jun. 1994, pp. 140-162.
Dan et al., Clinical Application of Massively Parallel Sequencing-based Prenatal Noninvasive Fetal Trisomy Test for Trisomies 21 and 18 in 11,105 Pregnancies with Mixed Risk Factors, Prenatal Diagnosis, vol. 32, No. 13, Dec. 2012, pp. 1225-1232.
Dan et al., Prenatal Detection of Aneuploidy and Imbalanced Chromosomal Arrangements by Massively Parallel Sequencing, PLoS ONE, vol. 7, No. 2, 2012, 7 pages.
Davanos et al., Relative Quantitation of Cell-Free Fetal DNA in Maternal Plasma using Autosomal DNA Markers, Clinica Chi Mica Acta, vol. 412, Nos. 17-18, Aug. 17, 2011, pp. 1539-1543.
Deamer et al., Nanopores and Nucleic Acids: Prospects for ultrarapid Sequencing, Focus Tibtech, vol. 18, No. 4, Apr. 2000, pp. 147-151.
Deligezer et al., Sequence-Specific Histone Methylation is Detectable on Circulating Nucleosomes in Plasma, Clinical Chemistry, vol. 54, No. 7, Jul. 2008, pp. 1125-1131.
Derrien et al., Fast Computation and Applications of Genome Mappability, Plos One, vol. 7, No. 1, e30377, Jan. 2012, pp. 1-16.
Dhallan et al., Methods to Increase the Percentage of Free Fetal DNA Recovered from the Maternal Circulation, Journal of the American Medical Association, vol. 291, No. 9, Mar. 3, 2004, pp. 1114-1119.
Diaz et al., Accuracy of Replication in the Polymerase Chain Reaction. Comparison Between Thermotoga Maritima DNA Polymerase and Thermus Aquaticus DNA Polymerase, Brazilian Journal of Medical and Biological Research, vol. 31, No. 10, Oct. 1, 1998, pp. 1239-1242.
Ding et al., A High-Throughput Gene Expression Analysis Technique Using Competitive PCR And Matrix-Assisted Laser Desorption Ionization Time-of-Flight MS, Proceedings of National Academy of Science, USA, vol. 100, No. 6, Mar. 18, 2003, pp. 3059-3064.
Dohm et al., Substantial Biases in Ultra-Short Read Data Sets from High-Throughput DNA Sequencing, Nucleic Acids Research, vol. 36, No. 16, Jul. 26, 2008, pp. 1-10.
Drmanac et al., Sequencing by Hybridization: Towards an Automated Sequencing of One Million M13 Clones Arrayed on Membranes, Electrophoresis, vol. 13, No. 1, Available Online at: https://doi.org/10.1002/elps.11501301115, Aug. 1992, pp. 566-573.
Edelmann et al., A Common Molecular Basis for Rearrangement Disorders on Chromosome 22q11, Human Molecular Genetics, vol. 8, No. 7, Jul. 1999, pp. 1157-1167.
Egger et al., Reverse Transcription Multiplex PCR for Differentiation Between Polio-and Enteroviruses from Clinical and Environmental Samples, Journal of Clinical Microbiology, vol. 33, No. 6, Jun. 1995, pp. 1442-1447.
Ehrich et al., Noninvasive Detection of Fetal Trisomy 21 by Sequencing of DNA in Maternal Blood: A Study in a Clinical Setting, Reports of Major Impact, American Journal of Obstetrics and Gyenocology, vol. 204, No. 3, Mar. 2011, p. 205e1-205e11.
Eiben et al., First-Trimester Screening: An Overview, Journal of Histochemistry and Cytochemistry, vol. 53, No. 3, Mar. 2005, pp. 281-283.
Ensenauer et al., Microduplication 22q11.2, An Emerging Syndrome: Clinical, Cytogenetic, and Molecular Analysis of Thirteen Patients, American Journal of Human Genetics, vol. 73, No. 5, Nov. 2003, pp. 1027-1040.
European Application No. EP11745050.2, Partial Supplementary European Search Report dated Aug. 10, 2015, 9 pages.
European Application No. EP13709696.2, Office Action dated Apr. 5, 2017, 5 pages.
European Application No. EP13709696.2, Office Action dated Feb. 16, 2016, 4 pages.
European Application No. EP13709696.2, Office Action dated Sep. 25, 2015, 3 pages.

(56) References Cited

OTHER PUBLICATIONS

European Application No. EP15753247.4, Notice of Decision to Grant dated Jul. 2, 2020, 2 pages.
European Application No. EP15753247.4, Office Action dated Aug. 19, 2019, 5 pages.
European Application No. EP15753247.4, Office Action dated Oct. 14, 2019, 4 pages.
European Application No. EP15753247.4, Office Action dated Oct. 17, 2018, 6 pages.
European Application No. EP18174047.3, Extended European Search Report dated Aug. 13, 2018, 8 pages.
European Application No. EP18174047.3, Notice of Decision to Grant dated Mar. 26, 2020, 2 pages.
European Application No. EP18174047.3, Office Action dated Jul. 5, 2019, 4 pages.
European Application No. EP19169503.0, Extended European Search Report dated Oct. 11, 2019, 13 pages.
Fan et al., Analysis of the Size Distributions of Fetal and Maternal Cell-Free DNA by Paired-End Sequencing, Clinical Chemistry, vol. 56, No. 8, Aug. 2010, pp. 1279-1286.
Fan et al., Noninvasive Diagnosis of Fetal Aneuploidy by Shotgun Sequencing DNA from Maternal Blood, Proceedings of the National Academy of Sciences of the United States (PNAS), vol. 105, No. 42, Oct. 21, 2008, pp. 16266-16271.
Fan et al., Sensitivity of Noninvasive Prenatal Detection of Fetal Aneuploidy from Maternal Plasma Using Shotgun Sequencing is Limited only by Counting Statistics, PLOS One, vol. 5, No. 5, Mar. 2010, pp. 1-7.
Forabosco et al., Incidence of Non-Age-Dependent Chromosomal Abnormalities: A Population-Based Study on 88965 Amniocenteses, European Journal of Human Genetics, vol. 17, No. 7, Jul. 2009, pp. 897-903.
Fromer, Discovery and Statistical Genotyping of Copy-number Variation from Whole-exome Sequencing Depth, American Journal of Human Genetics, vol. 91, No. 4, Oct. 5, 2012, 11 pages.
Gebhard et al.. Genome-wide Profiling of CpG Methylation Identifies Novel Targets of Aberrant Hypermthylation in Myeloid Leukemia, Cancer Research, vol. 66, No. 12, Jun. 15, 2006, pp. 6118-6128.
Go et al., Non-lnvasive Aneuploidy Detection Using Free Fetal DNA and RNA in Maternal Plasma: Recent Progress and Future Possibilities, Human Reproduction Update, vol. 17, No. 3, May 2011, pp. 372-382.
Goya et al., SNVMix: Predicting Single Nucleotide Variants from Next-Generation Sequencing of Tumors, Bioinformatics, vol. 26, No. 6, Mar. 15, 2010, pp. 730-736.
Grati et al., Fetoplacental Mosaicism: Potential Implications for False-Positive and False-Negative Noninvasive Prenatal Screening Results, Genetics in Medicine, vol. 16, No. 8, Aug. 2014, pp. 628-624.
Grati, Chromosomal Mosaicism in Human Feto-Piacental Development: Implications for Prenatal Diagnosis, Journal of Clinical Medicine, vol. 3, No. 3, Jul. 24, 2014, pp. 809-837.
Haar, On the Theory of Orthogonal Function Systems, Mathematische Annalen, vol. 69, No. 3, Jan. 2009, pp. 1-37.
Hahn et al., Cell-Free Nucleic Acids as Potential Markers for Preeclampsia, Placenta, vol. 32, Feb. 2011, pp. SI7-S20.
Harris et al., Single-Molecule DNA Sequencing of a Viral Genome, Science, vol. 320, No. 5872, Apr. 4, 2008, pp. 106-109.
Herzenberg et al., Fetal Cells in the Blood of Pregnant Women: Detection and Enrichment by Fluorescence-Activated Cell Sorting, Proceedings of the National Academy of Sciences U.S.A., vol. 76, No. 3, Mar. 1979, pp. 1453-1455.
Hill et al., Uses of Cell Free Fetal DNA In Maternal Circulation, Best Practice & Research: Clinical Obstetrics & Gynaecology, vol. 26, No. 5, Oct. 2012, pp. 639-654.
Hill, Gen-Probe Transcription-Mediated Amplification: System Principles, Gen-Probe Incorporated, Available Online at: httl://www.qen-probe.com/pdfs/tma_whiteppr.pdf, Jan. 1996, 4 pages.
Hinds et al., Whole-Genome Patterns of Common DNA Variation in Three Human Populations, Science, vol. 307, Feb. 18, 2005, pp. 1072-1079.
Hinnisdaels et al., Direct Cloning of PCR Products Amplified with Pwo DNA Polymerase, Biotechniques, vol. 20, No. 2, Feb. 1996, pp. 186-188.
Holdenrieder et al., Circulating Nucleosomes Predict the Response to Chemotherapy in Patients with Advanced Non-Small Cell Lung Cancer, Clinical Cancer Research, vol. 10, No. 18, Sep. 15, 2004, pp. 5981-5987.
Hsu et al., A Model-Based Circular Binary Segmentation Algorithm for the Analysis of Array CGH Data, BMC Research Notes, vol. 4, No. 394, Oct. 10, 2011, 12 pages.
Hsu et al., Denoising Array-Based Comparative Genomic Hybridization Data Using Wavelets, Biostatistics (Oxford, England), vol. 6, No. 2, Apr. 2005, pp. 211-226.
Huber et al., High-Resolution Liquid Chromatography of DNA Fragments on Non-Porous Poly(Styrene-Divinylbenzene) Particles, Nucleic Acids Research, vol. 21, No. 5, Mar. 11, 1993, pp. 1061-1066.
Hudecova et al., Maternal Plasma Fetal DNA Fractions in Pregnancies with Low and High Risks for Fetal Chromosomal Aneuploidies, PLoS One, vol. 9, No. 2, e88484, Feb. 28, 2014, 7 pages.
Hudson et al., An STS-Based Map of the Human Genome, Science, vol. 270, Dec. 22, 1995, pp. 1945-1954.
Hulten et al., Rapid and Simple Prenatal Diagnosis of Common Chromosome Disorders: Advantages and Disadvantages of the Molecular Methods Fish and QF-PCR, Reproduction, vol. 126, No. 3, Sep. 2003, pp. 279-297.
Hupe et al., Analysis of Array CGH Data: from Signal Ratio to Gain and Loss of DNA Regions, Bioinformatics, vol. 20, No. 18, Dec. 12, 2004, pp. 3413-3422.
Huse et al., Accuracy and Quality of Massively Parallel DNA Pyrosequencing, Genome Biology, R143, vol. 8, No. 7, Jul. 20, 2007, 9 pages.
Initial Sequencing and Analysis of the Human Genome, International Human Genome Sequencing Consortium, Macmillan Magazines Ltd., vol. 409, Available Online at: www.nature.com, Feb. 15, 2001, pp. 860-921.
Innis et al., PCR Protocols: A Guide to Methods and Applications, Academic Press, Inc., 1990, 8 pages.
International Application No. PCT/US2011/024132, International Search Report and Written Opinion dated Aug. 8, 2011, 14 pages.
International Application No. PCT/US2011/066639, International Search Report and Written Opinion dated Sep. 26, 2012, 9 pages.
International Application No. PCT/US2012/043388, International Preliminary Report on Patentability dated Jan. 9, 2014, 8 pages.
International Application No. PCT/US2012/043388, Written Opinion dated Apr. 5, 2013, 6 pages.
International Application No. PCT/US2012/059114, International Preliminary Report on Patentability dated Jun. 9, 2014, 5 pages.
International Application No. PCT/US2012/059114, International Search Report and Written Opinion dated Sep. 9, 2013, 14 pages.
International Application No. PCT/US2012/059123, International Preliminary Report on Patentability dated Feb. 27, 2014, 3 pages.
International Application No. PCT/US2012/059123, International Search Report and Written Opinion dated Sep. 9, 2013, 15 pages.
International Application No. PCT/US2012/059123, Invitation to Pay Additional Fees and Where Applicable Protest Fee dated Jul. 3, 2013.
International Application No. PCT/US2012/059592, International Preliminary Report on Patentability and Written Opinion dated Apr. 24, 2014, 9 pages.
International Application No. PCT/US2012/059592, Invitation to Pay Additional Fees and, Where Applicable, Protest Fee dated Jan. 18, 2013, 10 pages.
International Application No. PCT/US2012/059592, Search Report and Written Opinion dated Mar. 6, 2013, 12 pages.
International Application No. PCT/US2013/022290, International Preliminary Report on Patentability dated Jul. 31, 2014, 9 pages.
International Application No. PCT/US2013/022290, International Search Report and Written Opinion dated Jul. 4, 2013, 11 pages.

(56) References Cited

OTHER PUBLICATIONS

International Application No. PCT/US2013/047131, International Preliminary Reporton Patentability dated Dec. 31, 2014, 9 pages.
International Application No. PCT/US2013/047131, International Search Report and Written Opinion dated Sep. 18, 2013, 11 pages.
International Application No. PCT/US2013/063287, International Preliminary Report on Patentability dated Apr. 16, 2015, 9 pages.
International Application No. PCT/US2013/063287, International Search Report and Written Opinion dated Dec. 13, 2013,11 pages.
International Application No. PCT/US2013/063314, International Preliminary Report on Patentability dated Apr. 16, 2015, 8 pages.
International Application No. PCT/US2013/063314, International Search Report and Written Opinion dated Apr. 2, 2014, 6 pages.
International Application No. PCT/US2014/012369, International Preliminary Report on Patentability dated Aug. 6, 2015, 8 pages.
International Application No. PCT/US2014/012369, International Search Report and Written Opinion dated May 9, 2014, 9 pages.
International Application No. PCT/US2014/032687, International Preliminary Report on Patentability dated Oct. 15, 2015, 10 pages.
International Application No. PCT/US2014/032687, International Search Report and Written Opinion dated Jul. 14, 2014, 13 pages.
International Application No. PCT/US2014/039389, International Preliminary Report on Patentability dated Dec. 3, 2015, 12 pages.
International Application No. PCT/US2014/039389, International Search Report and Written Opinion dated Dec. 17, 2014, 18 pages.
International Application No. PCT/US2014/043497, International Search Report and Written Opinion dated Sep. 24, 2014, 9 pages.
International Application No. PCT/US2014/058885, International Preliminary Report on Patentability dated Apr. 14, 2016, 11 pages.
International Application No. PCT/US2014/058885, International Search Report and Written Opinion dated Feb. 18, 2015, 13 pages.
International Application No. PCT/US2014/059156, International Preliminary Report on Patentability dated Apr. 21, 2016, 8 pages.
International Application No. PCT/US2015/032550, International Search Report and Written Opinion dated Oct. 2, 2015, 10 pages.
International Application No. PCT/US2015/042701, International Preliminary Report on Patentability dated Feb. 9, 2017, 14 pages.
International Application No. PCT/US2015/042701, International Search Report and Written Opinion dated May 1, 2016, 20 pages.
International Application No. PCT/US2015/042701, Invitation to Pay Additional Fees and Where Applicable Protest Fee dated Oct. 14, 2015, 8 pages.
International Application No. PCT/US2018/015081, International Search Report and Written Opinion dated May 7, 2018, 12 pages.
International Application No. PCT/US2018/023151, International Search Report and Written Opinion dated May 23, 2018, 14 pages.
James, Mathematics Dictionary, Fifth Edition, Chapman & Hall, International Thomson Publishing, 1992, pp. 266-267.
Jensen et al., Detection of Microdeletion 22q11.2 in a Fetus by Next-Generation Sequencing of Maternal Plasma, Clinical Chemistry, vol. 58, No. 7, Jul. 2012, pp. 1148-1151.
Jensen et al., High-Throughput Massively Parallel Sequencing for Fetal Aneuploidy Detection from Maternal Plasma, PLOS One, vol. 8, No. 3, Mar. 6, 2013, pp. 1-8.
Jiang et al., FetalQuant: Deducing Fractional Fetal DNA Concentration from Massively Parallel Sequencing of DNA in Maternal Plasma, Bioinformatics, vol. 28, No. 22, Nov. 15, 2012, pp. 2883-2890.
Jiang et al., Noninvasive Fetal Trisomy (NIFTY) Test: An Advanced Noninvasive Prenatal Diagnosis Methodology for Fetal Autosomal and Sex Chromosomal Aneuploidies, BMC Medical Genomics, vol. 5, No. 57, Dec. 1, 2012, pp. 1-11.
Jing et al., Automated High Resolution Optical Mapping Using Arrayed, Fluid-Fixed DNA Molecules, Proceedings of the National Academy of Sciences, vol. 95, No. 14, Jul. 1998, pp. 8046-8051.
Johnston et al., Autoradiography Using Storage Phosphor Technology, Electrophoresis, vol. 11, No. 5, May 1990, pp. 355-360.
Joos et al., Covalent Attachment of Hybridizable Oligonucleotides to Glass Supports, Analytical Biochemistry, vol. 247, No. 1, Apr. 5, 1997, pp. 96-101.

Jorgez et al., Improving Enrichment of Circulating Fetal DNA for Genetic Testing: Size Fractionation Followed by Whole Gene Amplification, Fetal Diagnosis and Therapy, vol. 25, No. 3, 2009, pp. 314-319.
Juncosa-Ginesta et al., Improved Efficiency in Site-Directed Mutagenesis by PCR Using a *Pyrococcus* Sp. GB-D Polymerase, Biotechniques, vol. 16, No. 5, May 1, 1994, pp. 820-823.
Jurinke et al., Maldi-TOF Mass Spectrometry: A Versatile Tool for High-Performance DNA Analysis, Molecular Biotechnology, vol. 26, Feb. 2004, pp. 147-164.
Kalinina et al., Nanoliter Scale PCR with TaqMan Detection, Nucleic Acids Research, vol. 25, No. 10, May 15, 1997, pp. 1999-2004.
Kato et al., A New Packing for Separation of DNA Restriction Fragments by High Performance Liquid Chromatography, The Journal of Biochemistry, vol. 95, No. 1, Jan. 1984, pp. 83-86.
Khandjian, UV Crosslinking of RNA to Nylon Membrane Enhances Hybridization Signals, Molecular Biology Reports, vol. 11, No. 2, Jun. 1986, pp. 107-115.
Kim et al., Determination of Fetal DNA Fraction from the Plasma of Pregnant Women Using Sequence Read Counts, Prenatal Diagnosis, vol. 35, No. 8, Aug. 3, 2015, pp. 810-815.
Kim et al., Identification of Significant Regional Genetic Variations Using Continuous CNV Values in aCGH data, Genomics, vol. 94, No. 5, Nov. 2009, pp. 317-323.
Kitzman et al., Noninvasive Whole-Genome Sequencing of a Human Fetus, Science Translation Medicine, vol. 4, Nos. 137-140, Jun. 2012, 11 pages.
Kornberg et al., DNA Replication, Second Edition, Trends in Biochemical Sciences, 1991, 8 pages.
Krumm et al., Copy Number Variation Detection and Genotyping from Exome Sequence Data, Genome Research, vol. 22, No. 8, Aug. 2012, pp. 1525-1532.
Kulkarni et al., Global DNA Methylation Patterns in Placenta and its Association with Maternal Hypertension in Pre-Eclampsia, DNA Cell Biology, vol. 30, No. 2, Feb. 2011, pp. 79-84.
Lai et al., A Shotgun Optical Map of the Entire Plasmodium Falciparum Genome, Nature Genetics, vol. 23, No. 3, Nov. 1999, pp. 309-313.
Lai et al., Comparative Analysis of Algorithms for Identifying Amplifications and Deletions in Array CGH Data, Bioinformatics, vol. 21, No. 19, Oct. 1, 2005, pp. 3763-3770.
Langmead et al., Ultrafast and Memory-Efficient Alignment of Short DNA Sequences to the Human Genome, Genome Biology, vol. 10, No. 3, Mar. 4, 2009, 10 pages.
Lecomte et al., Selective Inactivation of the 3' To 5' Exonuclease Activity of *Escherichia coli* DNA Polymerase I by Heat, Nucleic Acids Research, vol. 11, No. 21, Nov. 11, 1983, pp. 7505-7515.
Leek et al., Tackling the Widespread and Critical Impact of Batch Effects in Highthroughput Data, Nature Reviews Genetics, vol. 11, No. 10, Oct. 2010, pp. 733-739.
Lefkowitz et al.. Clinical Validation of a Noninvasive Prenatal Test for Genomewide Detection of Fetal Copy Number Variants, American Journal of Obstetrics & Gynecology, vol. 215, No. 2, Aug. 1, 2016, pp. 227.e1-227.e16.
Levin, It's Prime Time for Reverse Transcriptase, Cell, vol. 88, No. 1, Jan. 10, 1997, pp. 5-8.
Li et al., Detection of Paternally Inherited Fetal Point Mutations for Beta-Thalassemia Using Size-Fractionated Cell-Free DNA in Maternal Plasma, Journal of the American Medical Association, vol. 293, No. 7, Feb. 16, 2005, pp. 843-849.
Li et al., Mapping Short DNA Sequencing Reads and Calling Variants Using Mapping Quality Scores, Genome Research, vol. 18, No. 11, Nov. 2008, pp. 1851-1858.
Liao et al., Noninvasive Prenatal Diagnosis of Fetal Trisomy 21 by Allelic Ratio Analysis Using Targeted Massively Parallel Sequencing of Maternal Plasma DNA, PLoS One, vol. 7, No. 5, May 29, 2012, 7 pages.
Liao et al., Targeted Massively Parallel Sequencing of Maternal Plasma DNA Permits Efficient and Unbiased Detection of Fetal Alleles, Clinical Chemistry, vol. 57, No. 1, Jan. 2011, pp. 92-101.

(56) References Cited

OTHER PUBLICATIONS

Lin et al., Synthesis and Duplex Stability of Oligonucleotides Containing Cytosine-Thymine Analogues, Nucleic Acids Research, vol. 17, No. 24, 1989, pp. 10373-10383.
Lin et al., Synthesis of Oligodeoxyribonucleotides Containing Degenerate Bases and Their Use as Primers in the Polymerase Chain Reaction, Nucleic Acids Research, vol. 20, No. 19, 1992, pp. 5149-5152.
Liu et al., Computational Methods for Detecting Copy Number Variations in Cancer Genome Using Next Generation Sequencing: Principles and Challenges, Oncotarget, vol. 4, No. 11, Nov. 19, 2013, pp. 1868-1881.
Liu et al., Cushaw: A Cuda Compatible Short Read Aligner to Large Genomes Based on the Burrows-Wheeler Transform, vol. 28, No. 14, May 2012, pp. 1830-1837.
Lo et al., Digital PCR for the Molecular Detection of Fetal Chromosomal Aneuploidy, Proceedings of the National Academy of Sciences, vol. 104, No. 32, Aug. 7, 2007, p. 13116-13121.
Lo et al., Genomic Analysis of Fetal Nucleic Acids in Maternal Blood, Annual Review of Genomics and Human Genetics, vol. 13, No. 1, Sep. 22, 2012, pp. 285-306.
Lo et al., Increased Fetal DNA Concent aliens in the Plasma of Pregnant Women Carrying Fetuses with Trisomy 21, Clinical Chemistry, vol. 45, No. 10, Oct. 1999, pp. 1747-1751.
Lo et al., Maternal Plasma DNA Sequencing Reveals the Genome-Wide Genetic and Mutational Profile of the Fetus, Science Translation Medicine, vol. 2, No. 61, Dec. 8, 2010, pp. 1-13.
Lo et al., Plasma Placental RNA Allelic Ratio Permits Noninvasive Prenatal Chromosomal Aneuploidy Detection, Nature Medicine, vol. 13, No. 2, Feb. 2007, pp. 218-223.
Lo et al., Prenatal Diagnosis of Fetal RhD Status by Molecular Analysis of Maternal Plasma, The New England Journal of Medicine, vol. 339, No. 24, Dec. 10, 1998, pp. 1734-1738.
Lo et al., Presence of Fetal DNA in Maternal Plasma and Serum, The Lancet, vol. 350, No. 9076, Aug. 16, 1997, pp. 485-487.
Lo et al., Quantitative Abnormalities of Fetal DNA in Maternal Serum in Preeclampsia, Clinical Chemistry, vol. 45, No. 2, Feb. 1, 1999, pp. 184-188.
Lo et al., Quantitative Analysis of Fetal DNA in Maternal Plasma and Serum: Implications for Noninvasive Prenatal Diagnosis, American Journal of Human Genetics, vol. 62, No. 4, Apr. 1998, pp. 768-775.
Lo, Fetal DNA in Maternal Plasma: Application to Non-Invasive Blood Group Genotyping of the Fetus, Transfusion Clinique et Biologique, vol. 8, No. 3, Jul. 2001, pp. 306-310.
Lo, Recent Advances in Fetal Nucleic Acids in Maternal Plasma, Journal of Histochemistry & Cytochemistry, vol. 53, No. 3, Mar. 2005, pp. 293-296.
Loakes, Survey and Summary: The Applications of Universal DNA Base Analogues, Nucleic Acids Research, vol. 29, No. 12, 2001, pp. 2437-2447.
Lun et al., Microfluidics Digital PCR Reveals a Higher than Expected Fraction of Fetal DNA in Maternal Plasma, Clinical Chemistry, vol. 54, No. 10, Oct. 2008, pp. 1664-1672.
Lundberg et al., High-Fidelity Amplification Using a Thermostable DNA Polymerase Isolated from Pyrococcus Furiosus, Gene, vol. 108, No. 1, Dec. 1, 1991, pp. 1-6.
Magi et al., Read Count Approach for DNA Copy Number Variants Detection, Bioinformatics, vol. 28, No. 4, Feb. 15, 2012, pp. 470-478.
Mann et al.. Development and Implementation of a New Rapid Aneuploidy Diagnostic Service Within the UK National Health Service and Implications for the Future of Prenatal Diagnosis, The Lancet, vol. 358, No. 9287, Sep. 29, 2001, pp. 1057-1061.
Margulies et al., Genome Sequencing in Microfabricated High-Density Picolitre Reactors, Nature, vol. 437, No. 7057, Sep. 15, 2005, pp. 376-380.
Mazloom, Gender Prediction with Bowtie Alignments using Male Specific Regions, May 10, 2012, 13 pages.

Metzker, Sequencing Technologies—the Next Generation, Nature Revie, vol. 11, No. 1, Jan. 2010, pp. 31-46.
Miller et al., Consensus Statement: Chromosomal Microarray is a First-Tier Clinical Diagnostic Test for Individuals with Developmental Disabilities or Congenital Anomalies, American Journal of Human Genetics, vol. 86, No. 5, May 14, 2010, pp. 749-764.
Mitchell et al., Chemical Tags Facilitate the Sensing of Individual DNA Strands with Nanopores, Angewandte Chemie International Edition, vol. 47, No. 30, Jul. 14, 2008, pp. 5565-5568.
Morton, Parameters of the Human Genome, Proceedings of the National Academy of Sciences, USA, vol. 88, No. 17, Sep. 1991, pp. 7474-7476.
Moudrianakis et al., Base Sequence Determination in Nucleic Acids with the Electron Microscope, III. Chemistry and Microscopy of Guanine-Labeled DNA, Proceedings of the National Academy of Sciences of the USA, vol. 53, No. 3, Mar. 1965, pp. 564-571.
Murtaza et al., Non-lnvasive Analysis of Acquired Resistance to Cancer Therapy by Sequencing of Plasma DNA, Nature, vol. 497, No. 7447, May 2, 2013, pp. 108-112.
Myers et al., Reverse Transcription and DNA Amplification by a Thermus Thermophilus DNA Polymerase, Biochemistry, vol. 30, No. 31, Aug. 6, 1991, pp. 7661-7666.
Nakano et al., Single-Molecule PCR Using Water-in-Oil Emulsion, Journal of Biotechnology, vol. 102, No. 2, Apr. 24, 2003, pp. 117-124.
Nason, Wavelet Methods in Statistics with R, Springer, New York ISBN: 978-0-387-75960-9, Jan. 2008, 1 page.
Nason, Wavethresh: Wavelets Statistics and Transforms and a Detailed Description of Wave Thresh, Available Online at: http://cran.rproject.org/web/packages/wavethresh/index.html, Aug. 29, 2013, 396 pages.
Needham-Vandevanter et al., Characterization of an Adduct Between CC-1065 and a Defined Oligodeoxynucleotide Duplex, Nucleic Acids Research, vol. 12, No. 15, Aug. 10, 1984, pp. 6159-6168.
Nevin, Future Direction of Medical Genetics, The Ulster Medical Journal, vol. 70, No. 1, May 2001, pp. 1-2.
Nextera™ DNA Sample Prep Kit (lllumina®-Compatible), Epicentre, an Illumina Company Cat. Nos. GA09115, GA091120, GA0911-50, GA0911-96, and GABC0950, Literature# 307, Jun. 2011, 12 pages.
Ng et al., MRNA of Placental Origin is Readily Detectable in Maternal Plasma, Proceedings of the National Academy of Sciences, vol. 100, No. 8, Apr. 15, 2003, pp. 4748-4753.
Ng et al., The Concentration of Circulating Corticotropin-Releasing Hormone mRNA in Maternal Plasma Is Increased in Preeclampsia, Clinical Chemistry, vol. 49, No. 5, May 2003, pp. 727-731.
Nguyen et al., Denoising of Array-Based DNA Copy Number Data Using the Dual-Tree Complex Wavelet Transform, Institute of Electrical and Electronics Engineers 7th International Symposium on BioInformatics and BioEngineering, Oct. 14-17, 2007, pp. 137-144.
Nichols et al., A Universal Nucleoside for Use at Ambiguous Sites in DNA Primers, Nature, vol. 369, No. 6480, Jun. 9, 1994, pp. 492-493.
Nicolaides et al., One-Stop Clinic for Assessment of Risk of Chromosomal Defects at 12 Weeks of Gestation, The Journal of Maternal-Fetal & Neonatal Medicine, vol. 12, No. 1, Jul. 2002, pp. 9-18.
Nolte, Branched DNA Signal Amplification for Direct Quantitation of Nucleic Acid Sequences in Clinical Specimens, Advances in Clinical Chemistry, vol. 33, 1998, pp. 201-235.
Nordstrom et al., Characterization of Bacteriophage T7 DNA Polymerase Purified to Homogeneity by Antithioredoxin Immunoadsorbent Chromatography, Journal of Biological Chemistry vol. 256, No. 6, Mar. 25, 1981, pp. 3112-3117.
Nygren et al., Quantification of Fetal DNA by Use of Methylation-Based DNA Discrimination, Clinical Chemistry, vol. 56, No. 10, Available Online at: http://www.clinchem.org/content/suppl/2010/07/28/clinchem.2010.146290.DC1/clinchem.2010.146290-1.pdf, Aug. 20, 2010, pp. 1627-1635.
Oh et al., CAM: A Web Tool for Combining Array CGH and Microarray Gene Expression Data from Multiple Samples, Computers in Biology and Medicine, vol. 40, No. 9, Sep. 2010, pp. 781-785.

(56) References Cited

OTHER PUBLICATIONS

Ohno, Sex Chromosomes and Sex-Linked Genes, Monographs on Endocrinology, vol. 1, 1967, 1 page.
Old et al., Candidate Epigenetic Biomarkers for Non-lnvasive Prenatal Diagnosis of Down Syndrome, Reproductive Biomedicine Online, Reproductive Healthcare Ltd., vol. 15, No. 2, Jan. 1, 2007, pp. 227-235.
Oldridge et al., Optimizing Copy Number Variation Analysis Using Genome-wide Short Sequence Oligonucleotide Arrays, Nucleic Acids Research, vol. 38, No. 10, Jun. 2010, pp. 3275-3286.
Olshen et al., Circular Binary Segmentation for the Analysis of Array-Based DNA Copy Number Data, Biostatistics vol. 5, No. 4, Oct. 1, 2004, pp. 557-572.
Omont et al., Gene-Based Bin Analysis of Genome-Wide Association Studies, BMC Proceedings, vol. 2, No. 4, S6, Dec. 17, 2008, pp. 1-9.
Oroskar et al., Detection of Immobilized Amplicons by ELISA-Like Techniques, Clinical Chemistry, vol. 42, No. 9, Sep. 1996, pp. 1547-1555.
Oudejans et al., Detection of Chromosome 21-Encoded mRNA of Placental Origin in Maternal Plasma, Clinical Chemistry, vol. 49, No. 9, Sep. 2003, pp. 1445-1449.
Palomaki et al., DNA Sequencing of Maternal Plasma Reliably Identifies Trisomy 18 and Trisomy 13 as well as Down Syndrome: An International Collaborative Study, Genetics in Medicine, vol. 14, No. 3, Mar. 2012, pp. 296-305.
Palomaki et al., DNA Sequencing of Maternal Plasma to Detect Down Syndrome: An International Clinical Validation Study, Genetics in Medicine, vol. 13, No. 11, Nov. 2011, pp. 913-920.
Pandya et al., Screening for Fetal Trisomies by Maternal Age and Fetal Nuchal Translucency Thickness at 10 To 14 Weeks of Gestation, British Journal of Obstetrics and Gynaecology, vol. 102, No. 12, Dec. 1995, pp. 957-962.
Pearson et al., High-Performance Anion-Exchange Chromatogrtaphy of Oligonucleotides, Journal of Chromatography A, vol. 255, Jan. 21, 1983, pp. 137-149.
Pekalska et al., Classifiers for Dissimilarity-Based Pattern Recognition, 15th International Conference on Pattern Recognition (ICPR'00), vol. 2, Sep. 3-8, 2000, pp. 12-16.
Pertile et al., Rare Autosomal Trisomies, Revealed by Maternal Plasma DNA Sequencing, Suggest Increased Risk of Feto-Placental Disease, Science Translational Medicine, vol. 9, No. 405, Aug. 30, 2017, pp. 1-11.
Pertl et al., Rapid Molecular Method for Prenatal Detection of Down's Syndrome, Lancet, vol. 343, No. 8907, May 14, 1994, pp. 1197-1198.
Peters et al., Noninvasive Prenatal Diagnosis of a Fetal Microdeletion Syndrome, New England Journal of Medicine, vol. 365, No. 19, Nov. 10, 2011, pp. 1847-1848.
Poon et al., Differential DNA Methylation Between Fetus and Mother as a Strategy for Detecting Fetal DNA in Maternal Plasma, Clinical Chemistry, vol. 48, No. 1, Jan. 2002, pp. 35-41.
Purnell et al., Discrimination of Single Base Substitutions in a DNA Strand Immobilized in a Biological Nanopore, ACS Nano, vol. 3, No. 9, Sep. 22, 2009, pp. 2533-2538.
Pushkarev et al., Single-Molecule Sequencing of an Individual Human Genome, Nature Biotechnology, vol. 27, No. 9, Sep. 2009, pp. 847-852.
Qu et al., Analysis of Drug-DNA Binding Data, Methods in Enzymology, vol. 321, 2000, pp. 353-369.
Robin et al., Defining the Clinical Spectrum of Deletion 22q11.2, vol. 147, No. 1, Jul. 2005, pp. 90-96.
Romero et al., Diagnostic Molecular Biology: Principles and Applications, Mayo Foundation, Rochester, Minn., 1993, pp. 401-406.
Romiguier et al., Contrasting GC-Content Dynamics Across 33 Mammalian Genomes: Relationship with Life-History Traits and Chromosome Sizes, Genome Research, vol. 20, No. 8, Aug. 2010, pp. 1001-1009.
Ross et al., The DNA Sequence of the Human X Chromosome, Nature, vol. 434, No. 7031, Mar. 17, 2005, pp. 325-337.
Roth et al., JointSNVMix: A Probabilistic Model for Accurate Detection of Somatic Mutations in Normal/Tumour Paired Next-Generation Sequencing Data, Bioinformatics, vol. 28, No. 7, Apr. 1, 2012, pp. 907-913.
Saito et al., Prenatal DNA Diagnosis of a Single-Gene Disorder from Maternal Plasma, The Lancet, vol. 356, No. 9236, Sep. 30, 2000, 1 page.
Sambrook et al., Molecular Cloning: A Laboratory Manual, Cold Spring Harbor Laboratory Press, 3rd Edition, vols. 1, 2 and 3, 2001.
Schouten et al., Relative Quantification of 40 Nucleic Acid Sequences by Multiplex Ligationdependent Probe Amplification, Nucleic Acids Research, vol. 30, No. 12, Jun. 15, 2002, 13 pages.
Schwinger et al., Clinical Utility Gene Card for: DiGeorge Syndrome, Velocardiofacial Syndrome, Shprintzen Syndrome, Chromosome 22q11.2 Deletion Syndrome (22q11.2, TBX1), European Journal of Human Genetics, vol. 18, No. 9, Sep. 2010, 3 pages.
Sehnert et al., Optimal Detection of Fetal Chromosomal Abnormalities by Massively Parallel DNA Sequencing of Cell-Free Fetal DNA From Maternal Blood, Clinical Chemistry, vol. 57, No. 7, Apr. 25, 2011, pp. 1042-1049.
Sekizawa et al., Cell-free Fetal DNA is Increased in Plasma of Women with Hyperemesis Gravidarum, Clinical Chemistry, vol. 47, No. 12, 2001, pp. 2164-2165.
Seshan et al., DNACopy: A Package for Analyzing DNA Copy Data, Available Online at: http://bioconductor.org/packages/2.12/bioc/html/DNAcopy.html, Apr. 3, 2013, 7 pages.
Shah et al., Mutational Evolution in a Lobular Breast Tumour Profiled at Single Nucleotide Resolution, Nature, vol. 461, Oct. 8, 2009, pp. 809-813.
Shen et al., A Hidden Markov Model for Copy Number Variant Prediction from Whole Genome Resequencing Data, BMC Bioinformatics, Jul. 28, 2011, pp. 1-7.
Shendure et al., Next-Generation DNA Sequencing, Nature Biotechnology, vol. 26, No. 10, Oct. 1, 2008, pp. 1135-1145.
Sherman et al., Epidemiology of Down Syndrome, Mental Retardation and Developmental Disabilities Research Reviews, vol. 13, No. 3, 2007, pp. 221-227.
Shin et al., Prevalence of Down Syndrome Among Children and Adolescents in 10 Regions of the United States, Pediatrics, vol. 124, No. 6, Dec. 2009, pp. 1565-1571.
Skaletsky et al., The Male-Specific Region of the Human Y Chromosome is a Mosaic of Discrete Sequence Classes, Nature, vol. 423, Jun. 19, 2003, pp. 825-237.
Slater et al., Rapid, High Throughput Prenatal Detection of Aneuploidy Using a Novel Quantitative Method (MLPA), Journal Medical Genetics, vol. 40, No. 12, Dec. 2003, pp. 907-912.
Smid et al., Evaluation of Different Approaches for Fetal DNA Analysis from Maternal Plasma and Nucleated Blood Cells, Clinical Chemistry, vol. 45, No. 9, Sep. 1999, pp. 1570-1572.
Smith et al., Direct Mechanical Measurements of the Elasticity of Single DNA Molecules by Using Magnetic Beads, Science, vol. 258, No. 5058, Nov. 13, 1992, pp. 1122-1126.
Snijders et al., Assembly of Microarrays for Genome-Wide Measurement of DNA Copy Number Nature Genetics, vol. 29, No. 3, Nov. 2001, pp. 263-264.
Snijders et al., First-Trimester Ultrasound Screening for Chromosomal Defects, Ultrasound in Obstetrics & Gynecology, vol. 7, No. 3, Mar. 1996, pp. 216-226.
Snijders et al., UK Multicentre Project on Assessment of Risk of Trisomy 21 by Maternal Age and Fetal Nuchal-translucency Thickness at 10-14 Weeks of Gestation. Fetal Medicine Foundation First Trimester Screening Group, Lancet, vol. 352, No. 9125, Aug. 1, 1998, pp. 343-346.
Soni et al., Progress Toward Ultrafast DNA Sequencing Using Solid-State Nanopores, Clinical Chemistry, vol. 53, No. 11, 2007, pp. 1996-2001.
Sparks et al., Non-invasive Prenatal Detection and Selective Analysis of Cell-Free DNA Obtained from Maternal Blood: Evaluation for Trisomy 21 and Trisomy 18, American Journal of Obstetrics & Gynecology, vol. 206, No. 4, Apr. 2012, pp. 319.e1-319.e9.
Sparks et al., Selective Analysis of Cell-Free DNA in Maternal Blood for Evaluation of Fetal Trisomy, Prenatal Diagnosis, vol. 32, No. 1, Jan. 2012, pp. 3-9.

(56) References Cited

OTHER PUBLICATIONS

Srinivasan et al., Noninvasive Detection of Fetal Subchromosome Abnormalities Via Deep Sequencing of Maternal Plasma, The American Journal of Human Genetics, vol. 92, No. 2, Feb. 7, 2013, pp. 167-176.

Stagi et al., Bone Density and Metabolism in Subjects with Microdeletion of Chromosome 22q11 (Del22q11), European Journal of Endocrinology, vol. 163, No. 2, Aug. 2010, pp. 329-337.

Stanghellini et al.. Quantitation of Fetal DNA in Maternal Serum During the First Trimester of Pregnancy by the Use of a DAZ Repetitive Prob, Molecular Human Reproduction, vol. 12, No. 9, Sep. 2006, pp. 587-591.

Stenesh et al., DNA Polymerase from Mesophilic and Thermophilic Bacteria III. Lack of Fidelity in the Replication of Synthetic Polydeoxyribonucleotides by DNA Polymerase from Bacillus Licheniformis snd Bacillus Stearothermophilus, Biochimica et Biophysica Acta, vol. 475, No. 1, Mar. 2, 1977, pp. 32-41.

Stoddart et al., Single-Nucleotide Discrimination in Immobilized DNA Oligonucleotides with a Biological Nanopore, Proceedings of the National Academy of Sciences USA, vol. 106, No. 19, May 12, 2009, pp. 7702-7707.

Strachan, The Human Genome, BIOS Scientific Publishers, 1992, 2 pages.

Tabor et al., Randomised Controlled Trial of Genetic Amniocentesis in 4606 Low-Risk Women, Lancet, 1986, pp. 1287-1293.

Takagi et al., Characterization of DNA Polymerase from *Pyrococcus* Sp. Strain KOD1 and its Application to PCR, Applied and Environmental Microbiology, vol. 63, No. 11, Nov. 1997, pp. 4504-4510.

Taylor et al., Characterization of Chemisorbed Monolayers by Surface Potential Measurements, Journal of Physics D Applied Physics, vol. 24, No. 8, Apr. 1991, pp. 1443-1450.

Timp et al., Nanopore Sequencing: Electrical Measurements of the Code of Life, Institute of Electrical and Electronics Engineers Transactions on Nanotechnology, vol. 9, No. 3, May 1, 2010, pp. 281-294.

Trapnell et al., How to Map Billions of Short Reads onto Genomes, Nature Biotechnology, vol. 27, No. 5, May 2009, pp. 455-457.

TruSeq™ RNA and DNA Library Preparation Kits V2, Data Sheet: Illumina® Sequencing, Apr. 27, 2011, 4 pages.

Veltman et al., High-Throughput Analysis of Subtelomeric Chromosome Rearrangements by Use of Array-Based Comparative Genomic Hybridization, American Journal of Human Genetics, vol. 70, No. 5, May 2002, pp. 1269-1276.

Venkatraman et al., A Faster Circular Binary Segmentation Algorithm for the Analysis of Array CGH Data, Bioinformatics, vol. 23, No. 6, Mar. 15, 2007, pp. 657-663.

Verbeck et al., A Fundamental Introduction to Ion Mobility Mass Spectrometry Applied to the Analysis of Biomolecules, Journal of Biomolecular Techniques, vol. 13, No. 2, Jun. 2002, pp. 56-61.

Verma et al., Rapid and Simple Prenatal DNA Diagnosis of Down's Syndrome, Lancet, vol. 352, No. 9121, Jul. 4, 1998, pp. 9-12.

Verma, The Reverse Transcriptase, Biochim Biophys Acta, vol. 473, No. 1, Mar. 21, 1977, pp. 1-38.

Vincenet et al., Helicase-Dependent isothermal DNA Amplification, European Molecular Biology Organization Reports, vol. 5, No. 8, Aug. 2004, pp. 795-800.

Voelkerding et al., Next-Generation Sequencing: From Basic Research to Diagnostics, Clinical Chemistry, vol. 55, No. 4, Apr. 2009, pp. 641-658.

Vogelstein et al., Digital PCR, Proceedings of the National Academy of Sciences, vol. 96, No. 16, Aug. 1999, pp. 9236-9241.

Wang et al., A Method for Calling Gains and Losses in Array CGH Data, Biostatistics, vol. 6, No. 1, Jan. 1, 2005, pp. 45-58.

Wang et al., A Novel Stationary Wavelet Denoising Algorithm for Array-Based DNA Copy Number Data, International Journal of Bioinformatics Research and Applications, vol. 3, No. 2, 2007, pp. 206-222.

Wapner et al., First-Trimester Screening for Trisomies 21 and 18, The New England Journal of Medicine, vol. 349, No. 15, Oct. 9, 2003, pp. 1405-1413.

Wei et al., Detection and Quantification by Homogenous PCR of Cell-Free Fetal DNA in Maternal Plasma, Clinical Chemistry, vol. 47, No. 2, Feb. 2001, pp. 336-338.

Willenbrock et al., A Comparison Study: Applying Segmentation to Array CGH Data for Downstream Analyses, Bioinformatics, vol. 21, No. 22, Nov. 15, 2005, pp. 4084-4091.

Wright et al., The Use of Cell-free Fetal Nucleic Acids in Maternal Blood for non-invasive Prenatal Diagnosis, Human Reproduction Update, vol. 15, No. 1, Jan. 2009, pp. 139-151.

Wu et al., Genetic and Environmental Influences on Blood Pressure and Body Mass Index in Han Chinese: A Twin Study, Hypertension Research, vol. 34, No. 2, Feb. 2011, pp. 173-179.

Wu et al., Reverse Transcriptase, CRC Critical Reviews in Biochemistry, vol. 3, No. 3, Dec. 1975, pp. 289-347.

Yang et al., A Novel k-mer Mixture Logistic Regression for Methylation Susceptibility Modeling of CpG Dinucleotides in Human Gene Promoters, BMC Bioinformatics, vol. 13, No. 3, Mar. 12, 2012, 9 pages.

Yershov et al., DNA Analysis and Diagnostics on Oligonucleotide Microchips, Proceedings of the National Academy of Sciences USA, vol. 93, No. 10, May 14, 1996, pp. 4913-4918.

Yoon et al., Sensitive and Accurate Detection of Copy Number Variants using Read Depth of Coverage, Genome Research, vol. 19, No. 9, Available Online at: http://www.genome.org, Sep. 2009, pp. 1586-1592.

Yu et al., Combined Count- and Size-Based Analysis of Maternal Plasma DNA for Noninvasive Prenatal Detection of Fetal Subchromosomal Aberrations Facilitates Elucidation of the Fetal and/or Maternal Origin of the Aberrations, Molecular Diagnostics and Genetics, vol. 63, No. 2, Feb. 2017, pp. 495-502.

Yu et al., Noninvasive Prenatal Molecular Karyotyping from Maternal Plasma, PLoS One, vol. 8, No. 4, Apr. 2013, 8 pages.

Yu et al., Size-Based Molecular Diagnostics Using Plasma DNA for Noninvasive Prenatal Testing, Proceedings of the National Academy of Sciences, vol. 111, No. 23, Jun. 10, 2014, pp. 8583-8588.

Zhang et al., A Single Cell Level Based Method for Copy Number Variation Analysis by Low Coverage Massively Parallel Sequencing, PLoS ONE, vol. 8, No. 1, 2013, 9 pages.

Zhao et al., Detection of Fetal Subchromosomal Abnormalities by Sequencing Circulating Cell-Free DNA from Maternal Plasma, Clinical Chemistry, vol. 61, No. 4, Apr. 2015, pp. 608-616.

Zhao et al., Quantification and Application of the Placental Epigenetic Signature of the RASSF1A Gene in Maternal Plasma, Pretat Diagnosis, vol. 30, No. 8, Aug. 2010, pp. 778-782.

Zhong et al., Cell-Free Fetal DNA in the Maternal Circulation Does Not Stem from the Transplacental Passage of Fetal Erythroblasts, Molecular Human Reproduction, vol. 8, No. 9, 2002, pp. 864-870.

Zhong et al., Elevation of Both Maternal and Fetal Extracellular Circulating Deoxyribonucleic Acid Concentrations in the Plasma of Pregnant Women with Preeclampsia, American Journal of Obstetrics & Gynecology, vol. 184, No. 3, Feb. 2001, pp. 414-419.

Zhou et al., Detection of DNA Copy Number Abnormality by Microarray Expression Analysis, Human Genetics, vol. 114, 2004, pp. 464-467.

Zhou et al., Recent Patents of Nanopore DNA Sequencing Technology: Progress and Challenges, Recent Patents on DNA & Gene Sequences, Nov. 2010, pp. 192-201.

Zimmermann et al., Real-Time Quantitative Polymerase Chain Reaction Measurement of Male Fetal DNA in Maternal Plasma, Methods in Molecular Medicine, vol. 132, 2007, pp. 43-49.

U.S. Appl. No. 12/727,824, Final Office Action dated Mar. 22, 2016, 46 pages.

U.S. Appl. No. 12/727,824, Non-Final Office Action dated Sep. 18, 2015, 44 pages.

U.S. Appl. No. 13/333,842, Final Office Action dated Jan. 17, 2014, 19 pages.

U.S. Appl. No. 13/333,842, Final Office Action dated Oct. 27, 2015, 27 pages.

U.S. Appl. No. 13/333,842, Non-Final Office Action dated May 3, 2013, 19 pages.

(56) References Cited

OTHER PUBLICATIONS

U.S. Appl. No. 13/333,842, Non-Final Office Action dated May 13, 2015, 20 pages.
U.S. Appl. No. 13/656,328, Final Office Action dated Sep. 12, 2013, 11 pages.
U.S. Appl. No. 13/656,328, Non-Final Office Action dated Feb. 20, 2013, 13 pages.
U.S. Appl. No. 13/656,328, Notice of Allowance dated Oct. 18, 2013, 10 pages.
U.S. Appl. No. 13/669,136, Applicant Initiated Interview Summary dated May 12, 2015, 13 pages.
U.S. Appl. No. 13/669,136, Final Office Action dated Sep. 12, 2013, 10 pages.
U.S. Appl. No. 13/669,136, Final Office Action dated Apr. 16, 2015, 8 pages.
U.S. Appl. No. 13/669,136, Non-Final Office Action dated Feb. 15, 2013, 13 pages.
U.S. Appl. No. 13/669,136, Non-Final Office Action dated Aug. 13, 2014, 7 pages.
U.S. Appl. No. 13/669,136, Non-Final Office Action dated Sep. 8, 2015, 9 pages.
U.S. Appl. No. 13/669,136, Notice of Allowance dated Oct. 17, 2013, 9 pages.
U.S. Appl. No. 13/754,817, Final Office Action dated Apr. 7, 2014, 13 pages.
U.S. Appl. No. 13/754,817, Final Office Action dated Apr. 21, 2015, 7 pages.
U.S. Appl. No. 13/754,817, Non-Final Office Action dated Oct. 2, 2015, 11 pages.
U.S. Appl. No. 13/754,817, Non-Final Office Action dated Oct. 6, 2014, 12 pages.
U.S. Appl. No. 13/754,817, Non-Final Office Action dated May 7, 2013, 15 pages.
U.S. Appl. No. 13/779,638, Non-Final Office Action dated Sep. 22, 2015, 11 pages.
U.S. Appl. No. 13/781,530, Non-Final Office Action dated Oct. 22, 2015, 14 pages.
U.S. Appl. No. 13/782,857, Final Office Action dated Jul. 27, 2015, 14 pages.
U.S. Appl. No. 13/782,857, Non-Final Office Action dated Mar. 11, 2016, 15 pages.
U.S. Appl. No. 13/782,883, Non-Final Office Action dated Oct. 2, 2015, 14 pages.
U.S. Appl. No. 13/797,508, Final Office Action dated Mar. 19, 2015, 11 pages.
U.S. Appl. No. 13/797,508, Final Office Action dated Apr. 26, 2016, 12 pages.
U.S. Appl. No. 13/797,508, Non-Final Office Action dated Aug. 22, 2013, 17 pages.
U.S. Appl. No. 13/797,508, Non-Final Office Action dated Jul. 28, 2014, 7 pages.
U.S. Appl. No. 13/797,508, Non-Final Office Action dated Sep. 8, 2015, 9 pages.
U.S. Appl. No. 13/797,508, Notice of Allowance dated Dec. 26, 2013, 9 pages.
U.S. Appl. No. 13/829,164, Final Office Action dated Apr. 17, 2015, 9 pages.
U.S. Appl. No. 13/829,164, Final Office Action dated Apr. 27, 2016, 9 pages.
U.S. Appl. No. 13/829,164, Non-Final Office Action dated Sep. 1, 2015, 10 pages.
U.S. Appl. No. 13/829,164, Non-Final Office Action dated Sep. 11, 2013, 15 pages.
U.S. Appl. No. 13/829,164, Non-Final Office Action dated Aug. 13, 2014, 6 pages.
U.S. Appl. No. 13/829,164, Notice of Allowance dated Jan. 27, 2014, 9 pages.
U.S. Appl. No. 13/933,935, Final Office Action dated Apr. 16, 2015, 9 pages.
U.S. Appl. No. 13/933,935, Final Office Action dated Apr. 27, 2016, 9 pages.
U.S. Appl. No. 13/933,935, Non-Final Office Action dated Aug. 27, 2015, 11 pages.
U.S. Appl. No. 13/933,935, Non-Final Office Action dated Oct. 16, 2013, 11 pages.
U.S. Appl. No. 13/933,935, Non-Final Office Action dated Aug. 14, 2014, 6 pages.
U.S. Appl. No. 13/933,935, Notice of Allowance dated Jan. 30, 2014, 6 pages.
U.S. Appl. No. 14/187,876, Final Office Action dated Sep. 28, 2015, 55 pages.
U.S. Appl. No. 14/812,432, Final Office Action dated Sep. 6, 2016, 14 pages.

\* cited by examiner

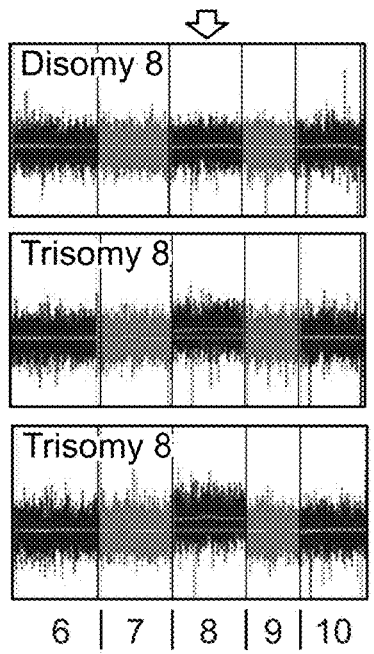
FIG. 4A
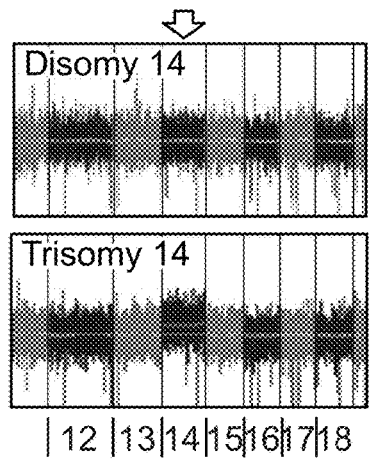
FIG. 4B
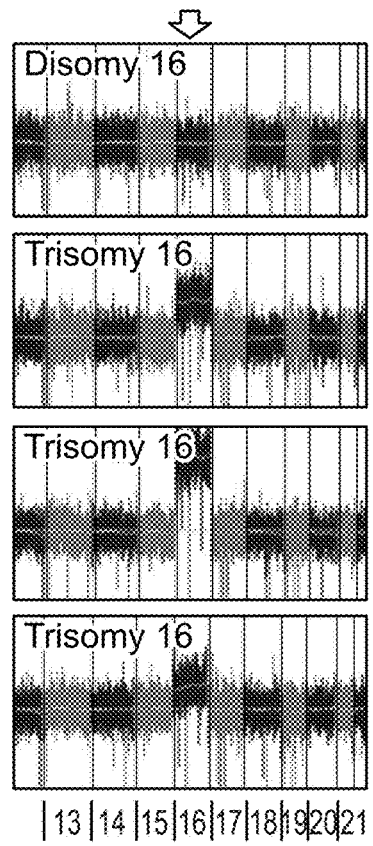
FIG. 4C
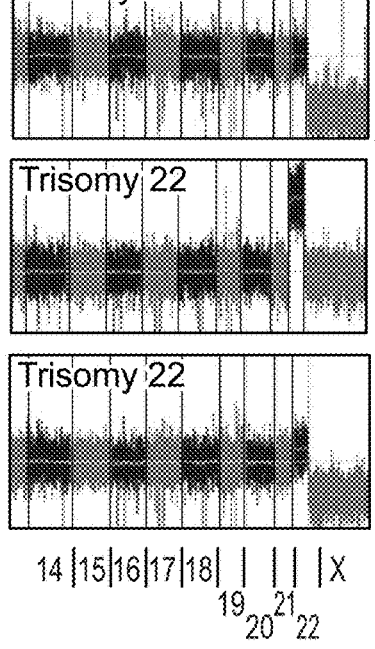
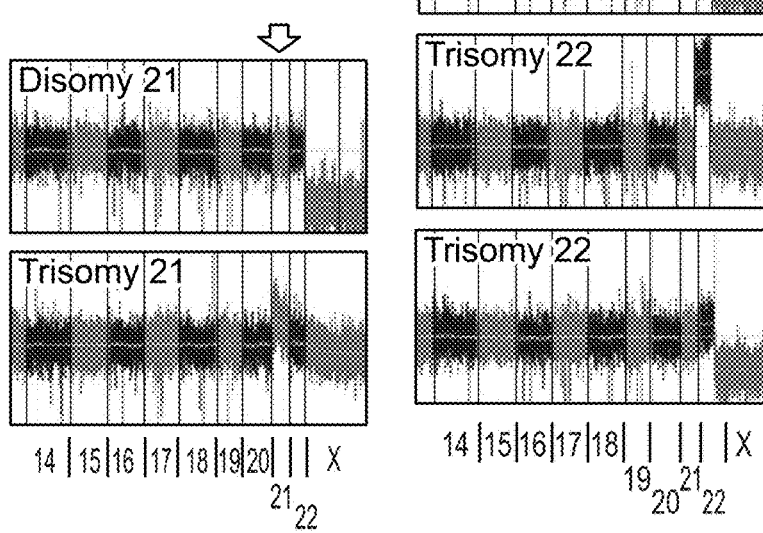
FIG. 4D   FIG. 4E

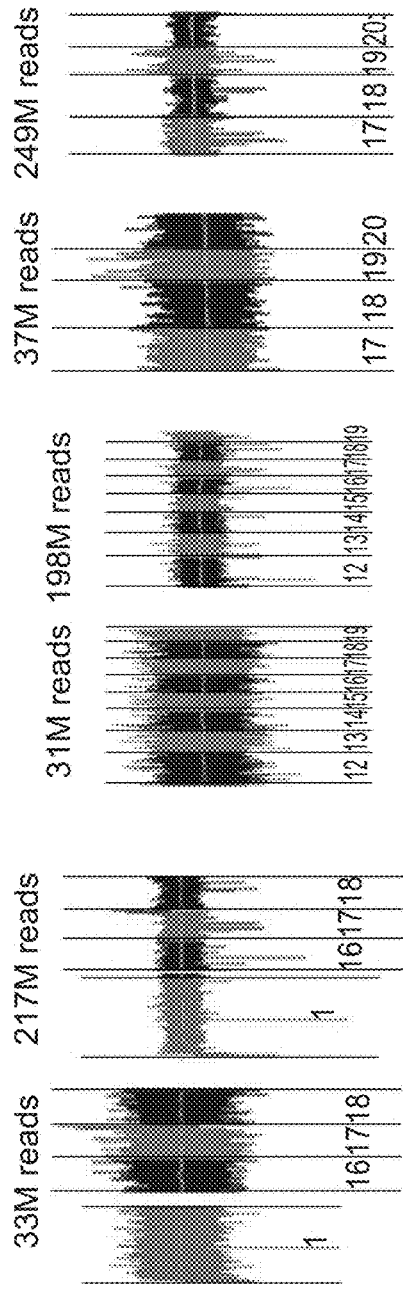
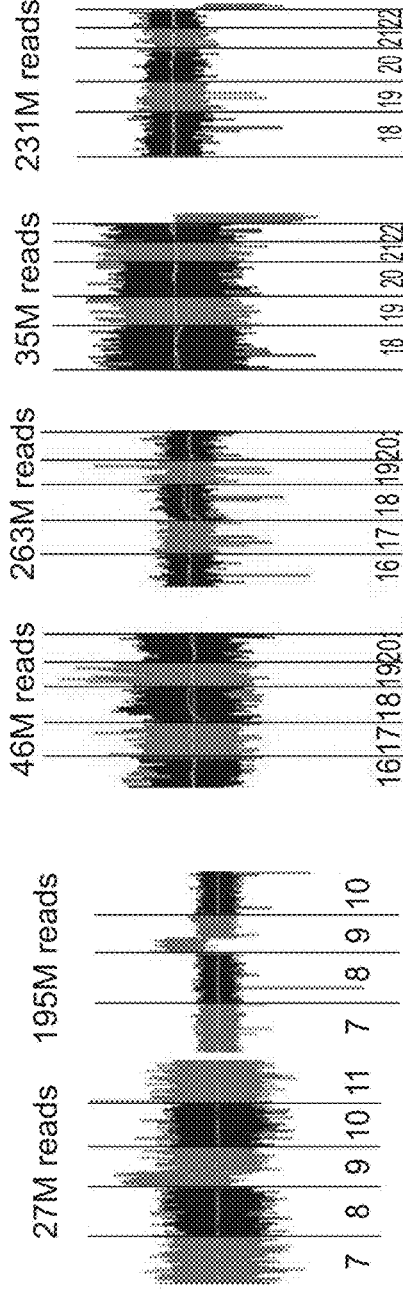
FIG. 5A  FIG. 5B  FIG. 5C
FIG. 5D  FIG. 5E  FIG. 5F

GENETIC COPY NUMBER ALTERATION CLASSIFICATIONS

RELATED APPLICATIONS

This application claims priority to U.S. Provisional Patent Application 62/367,557 filed Jul. 27, 2016. The entire contents of U.S. Provisional Patent Application 62/367,557 is incorporated by reference in its entirety herein.

FIELD

Technology provided herein relates in part to methods, systems, machines and computer program products for non-invasive classification of a genetic copy number alteration (CNA) for a test sample. Technology provided herein is useful for classifying a genetic CNA for a sample as part of non-invasive pre-natal (NIPT) testing and oncology testing, for example.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on 24 chromosomes (i.e., 22 autosomes, an X chromosome and a Y chromosome; see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations. Certain genetic variations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Monosomy X (Turner's Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and cancer (e.g., colorectal, breast, ovarian, lung).

Identifying one or more genetic variations (e.g., copy number alterations, single nucleotide variations, chromosome alterations, translocations, deletions, insertions, and the like) or variances can lead to diagnosis of, or determining predisposition to, a particular medical condition. Identifying a genetic variance can result in facilitating a medical decision and/or employing a helpful medical procedure. In certain embodiments, identification of one or more genetic variations or variances involves the analysis of circulating cell-free nucleic acid. Circulating cell-free nucleic acid (CCF-NA), such as cell-free DNA (CCF-DNA) for example, is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

SUMMARY

Provided in part herein are methods, systems, machines and computer program products useful for classifying presence or absence of a chromosome copy number alteration (CNA) or sub-chromosome CNA for a test sample with enhanced confidence. Certain methods include sampling a quantification of sequence reads from parts of a genome, generating a confidence determination, and using the confidence determination to enhance classification. Methods described herein can be used to enhance confidence of a presence or absence of a CNA classification for non-invasive prenatal testing or oncology testing, for example. Certain embodiments are described in the following description, examples, claims and drawings.

In various embodiments, a method is provided for classifying presence or absence of a chromosome copy number variation or sub-chromosome copy number variation for a test sample. The method may include shifting, by a computing device, a quantification of sequence reads mapped to genomic portions of a reference genome for a candidate region at or near a quantification of sequence reads mapped to genomic portions outside the candidate region and within a selected region. The genomic portions may be each coupled to a sequence read quantification for a test sample, and the genomic portions may comprise portions of a reference genome to which sequence reads obtained for a sample nucleic acid from the test subject have been mapped. The genomic portions may comprise (A) genomic portions within a candidate region identified as a candidate copy number variation region, and/or (B) genomic portions outside the candidate region and within a selected region larger than the candidate region that includes the candidate region. The candidate region may be a chromosome or sub-chromosome region.

The method may further include sampling, by the computing device, genomic portions from the selected region. The number of sampled genomic portions may be about equal to the number of genomic portions in the candidate region, thereby generating a sampled region, and repeating the sampling to generate a plurality of sampled regions. The method may further include normalizing, by the computing device, a sequence read quantification for each of the sampled regions, thereby generating a normalized quantification for each of the sampled regions.

The method may further include generating, by the computing device, a confidence determination for the candidate region by a process comprising comparing each normalized quantification to a measure of variability of sequence read quantifications for the candidate region for reference samples not having a significant copy number variation in the candidate region. The method may further include providing, by the computing device, a classification for presence or absence of the copy number variation for the candidate region for the test sample according to the confidence determination.

In some embodiments, the shifting further comprises determining a median read count of genomic portions in the candidate region, thereby providing a candidate region median count; determining a median read count of genomic portions outside the candidate region and in the selected region, thereby providing an outside median count; and subtracting the outside median count from the candidate region median count, thereby determining a shift.

In some embodiments, the method further includes obtaining, by the computing device, sequence reads mapped to the genomic portions and quantifying the sequence reads mapped to each of the genomic portions, thereby generating a quantification of the sequence reads mapped to the genomic portions.

In some embodiments, the method further includes normalizing, by the computing device, the quantification of sequence reads mapped to the genomic portions, thereby generating a normalized quantification of sequence reads mapped to the genomic portions. Optionally, certain genomic portions are filtered prior to, or after, the normalizing or the adjusting.

In other embodiments, a system is provided for that comprises one or more processors, a non-transitory machine readable storage medium, and program instructions for selecting a set of genomic portions each coupled to a sequence read quantification for a test sample. The genomic portions may comprise portions of a reference genome to which sequence reads obtained for sample nucleic acid from the test subject have been mapped. The genomic portions may comprise (i) genomic portions within a candidate region identified as a candidate copy number variation region, and/or (ii) genomic portions outside the candidate region and within a selected region larger than the candidate region that includes the candidate region. The candidate region may be a chromosome or sub-chromosome region.

The system further includes program instructions for shifting the quantification of the sequence reads mapped to the genomic portions for the candidate region at or near a quantification of sequence reads mapped to genomic portions outside the candidate region and within the selected region; and program instructions for sampling genomic portions from the selected region. The number of sampled genomic portions may be about equal to the number of genomic portions in the candidate region, thereby generating a sampled region, and repeating the sampling to generate a plurality of sampled regions The system may further include program instructions for normalizing a sequence read quantification for each of the sampled regions, thereby generating a normalized quantification for each of the sampled regions; program instructions for generating a confidence determination for the candidate region by a process comprising comparing each normalized quantification to a measure of variability of sequence read quantifications for the candidate region for reference samples not having a significant copy number variation in the candidate region; and program instructions for providing a classification for presence or absence of the copy number variation for the candidate region for the test sample according to the confidence determination. The program instructions may be stored on the non-transitory machine readable storage medium for execution by the one or more processors.

In other embodiments, a non-transitory machine readable storage medium is provided for that comprises program instructions that when executed by one or more processors cause the one or more processors to perform a method comprising selecting a set of genomic portions each coupled to a sequence read quantification for a test sample. The genomic portions may comprise portions of a reference genome to which sequence reads obtained for sample nucleic acid from the test subject have been mapped. The genomic portions may comprise (i) genomic portions within a candidate region identified as a candidate copy number variation region, and/or (ii) genomic portions outside the candidate region and within a selected region larger than the candidate region that includes the candidate region. The candidate region may be a chromosome or sub-chromosome region.

The method performed by the one or more processors may further comprise shifting the quantification of the sequence reads mapped to the genomic portions for the candidate region at or near a quantification of sequence reads mapped to genomic portions outside the candidate region and within the selected region; and sampling genomic portions from the selected region. The number of sampled genomic portions may be about equal to the number of genomic portions in the candidate region, thereby generating a sampled region, and repeating the sampling to generate a plurality of sampled regions.

The method performed by the one or more processors may further comprise normalizing a sequence read quantification for each of the sampled regions, thereby generating a normalized quantification for each of the sampled regions; generating a confidence determination for the candidate region by a process comprising comparing each normalized quantification to a measure of variability of sequence read quantifications for the candidate region for reference samples not having a significant copy number variation in the candidate region; and providing a classification for presence or absence of the copy number variation for the candidate region for the test sample according to the confidence determination.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIGS. 4A-4E show an analysis of disomy and trisomy in accordance with some embodiments.

FIGS. 5A-5F show an analysis of sequencing and karyotypes in accordance with some embodiments.

DETAILED DESCRIPTION

Figure 1:
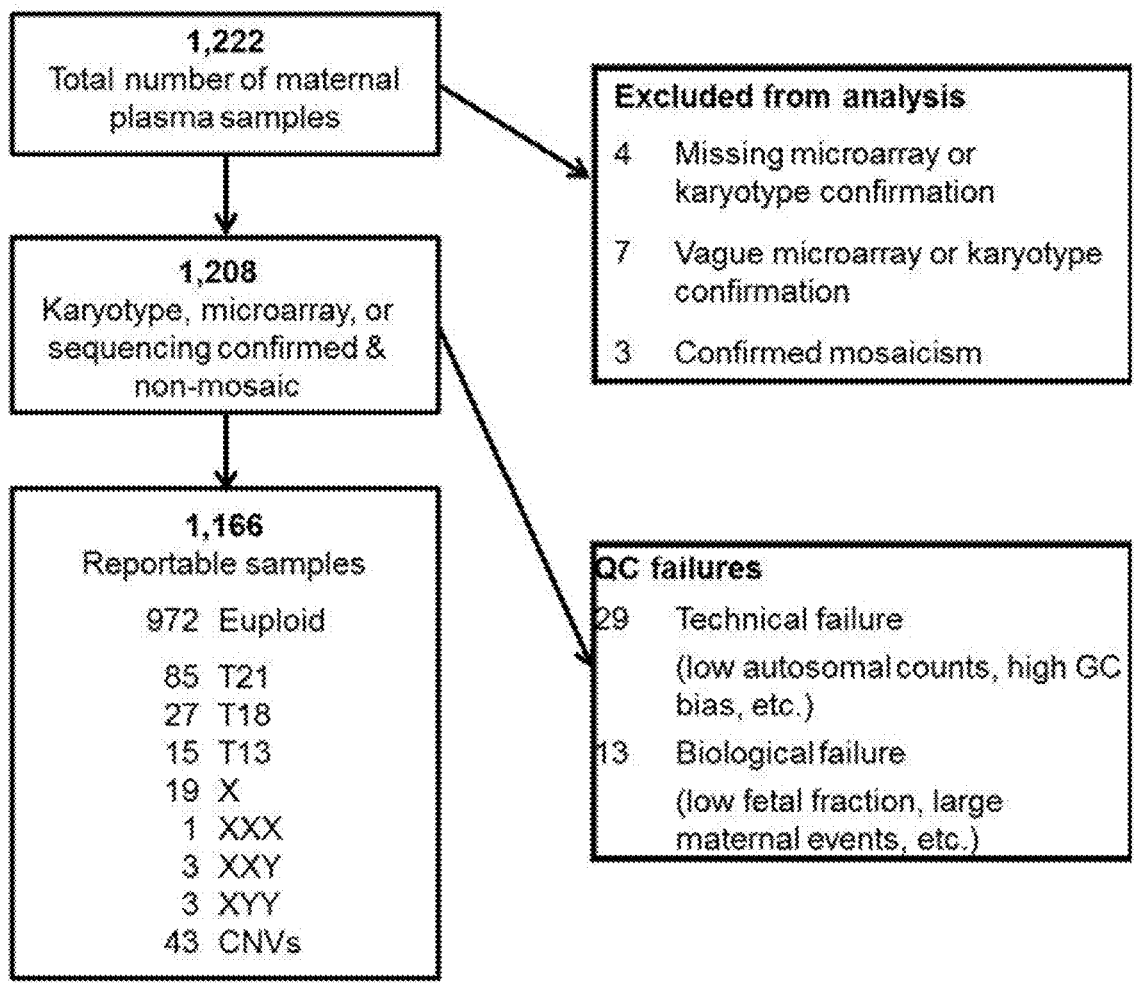
FIG. 1 is a flow chart showing sample exclusions and reasons for nonreportable samples in accordance with some embodiments.

Sequence read quantifications (e.g., sequence read counts) for genomic portions in a candidate region identified as a possible CNA region often are higher (in the case of a copy number duplication) or lower (in the case of a copy number deletion) than in surrounding genomic portions not identified as associated with a CNA. Methods described herein can provide a measure of confidence that a candidate CNA region has been correctly identified, rather than incorrectly identified due to increased noise in the candidate region. Methods herein can identify whether there is increased noise in a candidate region and provide a confidence determination based on noise or lack of noise in a candidate region. In certain embodiments, methods herein include a sampling process that ascertains whether noise in a candidate region and surrounding region for a test sample is significantly greater than or about the same as noise in the candidate region for a set of reference samples. In some embodiments, methods herein assemble sampled segments of a size about equal to the candidate region from parts of a selected region that includes the candidate region and is larger than the candidate region. In certain embodiments, methods herein provide a confidence determination based on the number of sampled segments having a signal that is not significantly different than signal from the candidate region in reference samples not having a CNA in the candidate region.

Thus, provided in certain embodiments is a method for classifying presence or absence of a chromosome CNA or sub-chromosome CNA for a test sample, that includes: (a) providing a set of genomic portions each coupled to a sequence read quantification for a test sample, where: the genomic portions comprise portions of a reference genome to which sequence reads obtained for sample nucleic acid from the test subject have been mapped, the genomic portions comprise (i) genomic portions within a candidate region identified as a candidate CNA region, and/or (ii) genomic portions outside the candidate region and within a selected region larger than the candidate region that includes the candidate region, and the candidate region is a chromosome or sub-chromosome region; (b) shifting the quantification of the sequence reads mapped to the genomic portions for the candidate region at or near a quantification of sequence reads mapped to genomic portions outside the candidate region and within the selected region; (c) sampling genomic portions from the selected region, wherein the number of sampled genomic portions is about equal to the number of genomic portions in the candidate region, thereby generating a sampled region, and repeating the sampling to generate a plurality of sampled regions; (d) normalizing a sequence read quantification for each of the sampled regions, thereby generating a normalized quantification for each of the sampled regions; (e) generating a confidence determination for the candidate region by a process comprising comparing each normalized quantification to a deviation of sequence read count quantifications for the candidate region for reference samples not having a significant CNA in the candidate region; and (f) providing a classification for presence or absence of the CNA for the candidate region for the test sample according to the confidence determination.

Provided in other embodiments is a method for classifying presence or absence of a chromosome copy number variation or sub-chromosome copy number variation for a test sample. The method may include shifting, by a computing device, a quantification of sequence reads mapped to genomic portions of a reference genome for a candidate region at or near a quantification of sequence reads mapped to genomic portions outside the candidate region and within a selected region. The genomic portions may be each coupled to a sequence read quantification for a test sample, and the genomic portions may comprise portions of a reference genome to which sequence reads obtained for a sample nucleic acid from the test subject have been mapped. The genomic portions may comprise (A) genomic portions within a candidate region identified as a candidate copy number variation region, and/or (B) genomic portions outside the candidate region and within a selected region larger than the candidate region that includes the candidate region. The candidate region may be a chromosome or sub-chromosome region. The method may further include sampling, by the computing device, genomic portions from the selected region. The number of sampled genomic portions may be about equal to the number of genomic portions in the candidate region, thereby generating a sampled region, and repeating the sampling to generate a plurality of sampled regions. The method may further include: normalizing, by the computing device, a sequence read quantification for each of the sampled regions, thereby generating a normalized quantification for each of the sampled regions; generating, by the computing device, a confidence determination for the candidate region by a process comprising comparing each normalized quantification to a measure of variability of sequence read quantifications for the candidate region for reference samples not having a significant copy number variation in the candidate region; and providing, by the computing device, a classification for presence or absence of the copy number variation for the candidate region for the test sample according to the confidence determination.

Provided in yet other embodiments is a method for classifying presence or absence of a chromosome copy number variation or sub-chromosome copy number variation for a test sample, that includes: shifting a quantification of sequence reads mapped to genomic portions of a reference genome for a candidate region at or near a quantification of sequence reads mapped to genomic portions outside the candidate region and within a selected region, where: the genomic portions each are coupled to a sequence read quantification for a test sample, the genomic portions comprise portions of a reference genome to which sequence reads obtained for sample nucleic acid from the test subject have been mapped, the genomic portions comprise (i) genomic portions within a candidate region identified as a candidate copy number variation region, and/or (ii) genomic portions outside the candidate region and within a selected region larger than the candidate region that includes the candidate region, and the candidate region is a chromosome or sub-chromosome region; sampling genomic portions from the selected region, wherein the number of sampled genomic portions is about equal to the number of genomic portions in the candidate region, thereby generating a sampled region, and repeating the sampling to generate a plurality of sampled regions; normalizing a sequence read quantification for each of the sampled regions, thereby generating a normalized quantification for each of the sampled regions; generating a confidence determination for the candidate region by a process comprising comparing each normalized quantification to a measure of variability of sequence read quantifications for the candidate region for reference samples not having a significant copy number variation in the candidate region; and providing a classification for presence or absence of the copy number variation for the candidate region for the test sample according to the confidence determination.

Quantification of Sequence Reads

Sequence reads mapped to a particular region in a genome can be quantified by any suitable process, and such quantifications often are utilized as input for processes described herein. A region sometimes is a sub-chromosome region (e.g., one or more segments), a chromosome, two or more chromosomes, autosomes, sex chromosome or all chromosomes. A region sometimes is a CNA candidate region, which sometimes is a chromosome or sub-chromosome region. A sub-chromosome candidate region sometimes is identified by a process that includes a segmentation process. A region sometimes is a selected region larger than a candidate region and includes the candidate region, or is a region outside a candidate region and within the selected region. A candidate sub-chromosome CNA (i.e., a candidate region) sometimes is greater than or equal to a region of contiguous nucleotides in a reference genome of about 1 kilobase or greater in length (e.g., about 2, 3, 4, 5, 6, 7, 8, 9, 10, 20, 30, 40, 50, 60, 70, 80, 90, 100, 200, 300, 400, 500, 600, 700, 800, 900 kilobases, or greater, in length, or about 1, 2, 3, 4, 5, 6, 7, 8, 9, 10, 15, 20, 30, 40 or 50 megabases, or greater, in length). A candidate region sometimes is about 7 megabases or greater in length (e.g., greater than or equal to about 8, 9, 10, 11, 12, 13, 14, 15, 16, 17, 18, 19, 20 megabases), and sometimes is less than about 7 megabases in length (e.g., less than about 1, 2, 3, 4, 5, 6 megabases).

A genome and/or a particular region often is divided into genomic portions, and sequence reads mapped to each genomic portion often are quantified. Each reference genome portion is referred to herein as a genomic portion to which one or more sequence reads have been mapped in a mapping process performed after sequence reads for a sample have been obtained. A genomic portion sometimes is referred to as a "bin" or "window." Genomic portions sometimes are of fixed length, sometimes are of equal length, sometimes are about 1 kilobase to about 1,000 kilobases in length (e.g., about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900 kilobases in length), sometimes are of unequal length (e.g., at least two of the genomic portions are of unequal length), sometimes do not overlap (e.g., the 3' ends of the genomic portions sometimes abut the 5' ends of adjacent genomic portions), and/or sometimes overlap (e.g., at least two of the genomic portions overlap). In some embodiments, genomic portions are of fixed length, are of a substantially equal length of about 50 kilobases, and do not overlap. A quantification sometimes is of sequence reads mapped to one or more genomic portions (i.e., a quantification of sequence reads coupled to a genomic portion), and sometimes a quantification of sequence reads mapped to each genomic portion in a region is provided. A region sometimes includes a part of a genomic portion on the 5' end and/or the 3' end of the region, and a sequence read quantification from each partial genomic portion sometimes is factored, or sometimes is not factored, into a process described herein.

A quantification of sequence reads mapped to a particular region often is a read count and sometimes is a read density. A read count or read density sometimes is provided for each genomic portion in a region, and sometimes is provided for a group of genomic portions in a region (e.g., a sum of read counts in a group of genomic portions in a particular region). In some embodiments, a quantification of sequence reads mapped to a particular region is a fraction. A fraction sometimes is a count of reads mapped to one region divided by a count of reads mapped to a selected region. A fraction can be determined for a test sample, for a reference sample and/or for a sampled region, for example. A fraction sometimes is a count of reads mapped to a candidate CNA region divided by a count of reads mapped to a selected region that is larger than the candidate region and includes the candidate region. A fraction sometimes is a count of reads mapped to a sampled region (described herein) divided by a count of reads mapped to a selected region that is larger than the candidate region and includes the candidate region.

Sequence reads can be generated by any suitable sequencing process applied to nucleic acid extracted form a sample. Nucleic acid can be extracted from a biological sample obtained from a subject (e.g., test sample, reference sample), as described herein. A subject sometimes is female or male (e.g., human female or human male), and a female can be a pregnant female at any suitable stage of pregnancy (e.g., first, second or third trimester). Extracted nucleic acid from the test subject sometimes is circulating cell free nucleic acid, and circulating cell free nucleic acid sometimes is from a blood plasma, blood serum or urine sample from a test subject. Extracted circulating cell free nucleic acid sometimes is not manipulated prior to performing a sequencing process (e.g., the cell free nucleic acid often is not cleaved by an exonuclease or endonuclease). A sequencing process utilized often is a whole-genome sequencing process, and in some embodiments is a targeted sequencing process (e.g., a processes that sequences a subset of all nucleic acid in a sample). A sequencing process utilized sometimes includes sequencing by synthesis. Depth of sequencing or sequencing coverage sometimes is about 0.01-fold to about 1,000-fold (e.g., 0.02-fold, 0.03-fold, 0.04-fold, 0.05-fold, 0.06-fold, 0.07-fold, 0.08-fold, 0.09-fold, 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold).

In certain embodiments, read quantifications for the genomic portions are normalized by a process that reduces or removes the effect(s) of one or more biases. In some embodiments, normalizing read quantifications for genomic portions includes normalizing according to guanine-cytosine (GC) content (e.g., GC percentage). Any suitable GC normalization process can be utilized, non-limiting examples of which include LOESS, LOESS with repeat masking (GCRM) and GC bias coefficient-based correction according to multiple samples (see, e.g., Alkan et al., Nat. Genet. 41:1061-1067 (2009); Palomaki et al., Genet. Med. 14: 296-305 (2012); International patent application no. PCT/US2012/059123 filed on Oct. 5, 2012 and published as WO 2013/052913 on Apr. 11, 2013). In some embodiments, bias effects are reduced by a process that includes transforming genomic portion read quantifications (e.g., GC normalized genomic portion read quantifications) into principal components. Any suitable principal component transformation process can be utilized, non-limiting examples of which are described herein (e.g., singular value decomposition (SVD) principal component transformation, Eigen decomposition principal component transformation). In certain embodiments, bias associated with genomic portion sequence read quantifications is normalized by first normalizing GC bias by LOESS and then normalizing residual bias by principal component analysis (PCA), which is referred to herein as SPCA (see, e.g., International patent application no. PCT/US2014/058885 filed on Oct. 2, 2014 and published as WO 2015/051163 on Apr. 9, 2015). In some embodiments, a quantification of sequence reads for genomic portions in a candidate region, outside region and/or selected region is a normalized quantification generated by a normalization process that normalizes GC bias or other bias. In certain embodiments, a normalization process includes LOESS normalization (e.g., LOESS normalization according to GC content) and/or principal component analysis normalization. A quantification of sequence reads sometimes is normalized for GC bias and/or other bias prior to determining a fraction for a region (e.g., where a process includes determining a fraction for the region).

In certain PCA embodiments, principal components are utilized to generate a set of weights, one for each genomic portion, that are multiplied against genomic portion read quantifications to yield normalized read quantifications. In some PCA embodiments, principal components are utilized to generate predicted genomic portion read quantifications. Predicted read quantifications sometimes are obtained by a process that includes: (a) performing PCA using genomic portion read quantifications from a training set of samples, thereby generating principal components; (b) optionally selecting a subset of the principal components generated in (a); (c) estimating regression coefficients from all of the principal components generated in (a) or from the subset of principal components provided in (b); and (d) running a regression on genomic portion read quantifications for a test sample using the regression coefficients estimated in (c); whereby a PCA-predicted genomic portion read quantifications can be obtained from the regression. In some embodiments, the regression is a multivariate linear regression. The PCA-predicted genomic portion read quantifications can be subtracted from the experimentally derived read quantification for the same genomic portion for a test sample, thereby providing PCA-adjusted genomic portion read quantifications for the test sample.

In some embodiments certain genomic portions are filtered prior to, or after, normalization. Filtering, when implemented, sometimes is based on mappability, repeat masking, or a combination thereof. In certain embodiments, filtering is based on variability of genomic portion read quantifications (i.e., inconsistently mapped reads), and/or consistently no reads mapped to certain genomic portions, for a reference set of samples. A quantification of sequence reads for a genomic portion filtered away by a filtering process often is not considered in a process described herein after filtering is conducted. One or more genomic portions sometimes are filtered prior to determining a fraction for a region (e.g., where a process includes determining a fraction for the region).

A candidate CNA region can be identified by any suitable CNA detection or quantification process. A CNA region for a test sample sometimes is determined by a process comprising segmentation. A segment sometimes includes multiple genomic portions. A segmentation process sometimes provides a start and end position for each segment, and sometimes a CNA quantification or normalized CNA quantification for each segment. Any suitable segmentation process may be utilized, including without limitation a circular binary segmentation (CBS) process. Other processes can be utilized instead of, or in addition to, CBS, non-limiting examples of which include wavelet segmentation (e.g., Haar wavelet segmentation), Fourier transformation, sliding window z-scores, and Markov chain models. A segmentation process sometimes includes a merging process that assesses identified segments that are adjacent to one another and merges two or more adjacent segments into one segment. Merging sometimes is based in part on a probability that the adjacent segments are part of the same CNA event or not part of the same CNA event. Any suitable merging process can be utilized, a non-limiting example of which includes Wllenbrock-Fridlyand segment merging.

In some embodiments, a normalized CNA quantification is a z-score. A z-score sometimes is for a segment, and sometimes is assigned to each genomic portion included in a segment. In some embodiments, a z-score is determined according to $$z\text{-score}=(S_{scr}-S_{mcr})/MAD$$

where $S_{scr}$ is a test sample count representation of a segment (e.g., $S_{scr}$ is the total normalized counts in the segment divided by the total normalized autosome counts for the test sample), $S_{mcr}$ is a median count representation for the segment generated for a reference set of samples, and MAD is a median absolute deviation determined for the count representation of the segment for the reference set of samples. Non-limiting examples of methodology useful for generating z-score copy number quantifications based on CBS segmentation are described in Zhao et al., Clin. Chem. 61:4: 608-616 (2015); Lefkowitz et al., American Journal of Obstetrics & Gynecology 1.e1 (2016); and International patent application no. PCT/US2014/039389 filed on May 23, 2014 and published as WO 2014/190286 on Nov. 27, 2014. Instead of z-scores, other normalized CNA quantifications may be utilized, non-limiting examples of which include normal scores, z-values, standardized variables and t-statistics.

One or more or all steps for generating quantifications of sequence reads for genomic portions can be performed by an apparatus that includes memory and a processor (e.g., a computer). Quantifications for sequence reads mapped to genomic portions for a test sample and/or set of reference samples, sometimes are stored in memory. Quantifications of sequence reads mapped to one or more candidate CNA regions, one or more selected regions, one or more outside regions and/or one or more sampled regions sometimes are stored in memory. In some embodiments, instructions for normalizing genomic portion read quantifications, and/or resulting normalized genomic portion read quantifications for a test sample, are stored in memory and are accessible to a processor. In certain embodiments, instructions for segmenting normalized genomic portion read quantifications are stored in memory and are accessible to a processor. In some embodiments, resulting start and end positions for each segment, a confidence value for each segment, and/or a CNA quantification value for each segment, for a test sample, are stored in memory and are accessible to a processor. Programming instructions (e.g., module programming instructions) sometimes are in R programming language, and sometimes features of programming instructions for performing methods described herein are selected from the "stats" R package (e.g., "loess" for local polynomial regression fitting, function "prcomp" for principal components analysis, function "lm" for fitting linear models, and function "predict" for model predictions), "plyr" R package and/or "DNAcopy" R package.

Sampled Regions

Methods described herein often generate a plurality of sampled regions. A process used to generate sampled regions often includes shifting the level of a quantification of sequence reads mapped to a candidate region to or near a baseline quantification of sequence reads mapped to a region outside the candidate region. As a non-limiting example, for a candidate copy number duplication region, a quantification of sequence reads mapped to the candidate region often are reduced to or near a level of a quantification of sequence reads mapped to a region outside the candidate copy number duplication region.

A region outside the candidate region often is included in a selected region, where the selected region is larger than the candidate region and includes the candidate region. A selected region sometimes includes a flanking region of contiguous nucleotides in a reference genome that is 1 kilobase or greater in length (e.g., about 2, 3, 4, 5, 6, 7, 8, 9, 10, 20, 30, 40, 50, 60, 70, 80, 90, 100, 200, 300, 400, 500, 600, 700, 800, 900 kilobases, or greater, in length, or about 1, 2, 3, 4, 5, 6, 7, 8, 9, 10, 15, 20, 30, 40 or 50 megabases, or greater, in length). A flanking region sometimes flanks a candidate region 5' of the candidate region and/or 3' of the candidate region. A selected region sometimes is 5 megabases or greater in length (e.g., about 6, 7, 8, 9, 10, 11, 12, 13, 14, 15, 16, 17, 18, 19, 20, 25, 30, 35, 40, 50, 60, 70, 80, 90, 100 megabases or greater in length). A selected region sometimes is a chromosome or is a region that includes a chromosome and a region outside the chromosome (e.g., a region that includes 2 or more chromosomes (e.g., 2, 3, 4, 5, 6, 7, 8, 9, 10, 11, 12, 13, 14, 15, 16, 17, 18, 19, 20, 21, 22, 23, 24 chromosomes, autosomes, all autosomes, sex chromosome, all sex chromosomes)). Where sequence read counts have been mapped to genomic portions in a reference genome and counted, genomic portions included in a candidate region, selected region and/or region outside a candidate region and in a selected region (i.e., an outside region) can be ascertained.

In some embodiments, shifting a quantification of sequence reads mapped to a candidate region includes shifting a sequence read count coupled to each genomic portion in the candidate region. As described herein, the sequence read count sometimes has been normalized to reduce bias (e.g., GC bias and/or other bias), and sometimes has been filtered according to filtering criteria described herein, and the quantification of sequence reads shifted, sampled, and/or included as part of a fraction determination sometimes is a count of normalized and/or filtered sequence reads. Thus, a sequence read count quantification for sequence reads mapped to a genomic portion or other region (e.g., candidate region, selected region, outside region) sometimes is or is based on raw counts, normalized counts, filtered counts or combination thereof.

In embodiments for which a quantification of sequence reads is a sequence read count, a shifting process sometimes includes one or both of the following: (i) determining a median read count of genomic portions in a candidate region, thereby providing a candidate region median count, and (ii) determining a median read count of genomic portions outside the candidate region and in the selected region, thereby providing an outside median count. In certain embodiments, a shifting process includes subtracting or adding the outside median count from the candidate region median count, thereby determining a shift. A shift can be generated in other manners, and other measures of an average count can be used in lieu of a median count (e.g., mean count) to generate a shift. Shifting embodiments that include subtracting or adding a shift from sequence read counts in a genomic portion often result in different sequence read counts in different genomic portions in a candidate region. Shifting embodiments that include subtracting or adding a shift from sequence read counts in a genomic portion can shift sequence read counts in genomic portions in a candidate region towards the baseline level (e.g., near a baseline level), of sequence read counts outside the candidate region in the selected region (e.g., towards the median of counts in genomic portions outside the candidate region in the selected region). In certain embodiments, a shift is determined by subtracting an outside median count from the candidate region median count, which can result in a shift having a positive number of counts for a candidate copy number duplication region and can result in a shift having a negative number of counts for a candidate copy number deletion region.

A shift sometimes is stored and often is used in one or more aspects of a process described herein. For example, a shift can be applied to a quantification of sequence reads mapped to genomic portions in a candidate region. A shift can be applied in a manner that (i) shifts a quantification of sequence reads in each genomic portion towards a baseline quantification level for genomic portions in an outside region, and/or (ii) retains noise (e.g., sequence read count variability) in genomic portions within the candidate region. Where a quantification of sequence reads is for genomic portions in a candidate copy number duplication region, an absolute value of a shift often is effectively subtracted from the quantification of sequence reads in each genomic portion in the candidate region, thereby altering the quantification of sequence reads in each genomic portion in the candidate region towards a baseline quantification in an outside region. Where a quantification of sequence reads is for genomic portions in a candidate copy number deletion region, an absolute value of a shift often is effectively added to the quantification of sequence reads in each genomic portion in the candidate region, thereby altering the quantification or sequence reads in each genomic portion in the candidate region towards a baseline quantification in an outside region. In certain embodiments, a shift for a candidate copy number deletion region is a negative number of counts, and the shift is added to the quantification of sequence reads in each genomic portion in the candidate region, thereby effectively adjusting the quantification of sequence reads in each genomic portion in the candidate region towards baseline counts. The quantification of sequence reads to which a shift is applied often is a read count, sometimes is a read density, and sometimes is a fraction described herein.

A process used to generate a sampled region generally includes selecting genomic portions from a selected region. Genomic portions often are selected or sampled from a selected region after a shift has applied (e.g., after shifting the quantification of sequence reads mapped to a candidate region towards a baseline quantification of sequence reads mapped to a region outside the candidate region). Genomic portions often are sampled or selected from a selected region, and genomic portions can be sampled from a candidate region and from the outside region in the selected region. In certain embodiments, a contiguous run of genomic portions is selected from a selected region. A sampled region often includes the same number of genomic portions as the number of genomic portions in a candidate region, and sometimes the number of genomic portions selected for a sampled region is less than or greater than the number of genomic portions in a candidate region. A sampled region sometimes includes about one to about 20 genomic portions greater than, or less than, the number of genomic portions in a candidate region (e.g., a sampled region includes about 1, 2, 3, 4, 5, 6, 7, 8, 9, 10, 11, 12, 13, 14, 15, 16, 17, 18, 19 or 20 more or fewer genomic portions than in a candidate region). In a plurality of sampled regions, each sampled region sometimes includes for a test sample often includes the same number of genomic portions, and sometimes sampled regions include a variable number of genomic portions (e.g., vary by about 1 to about 20 genomic portions).

Genomic portions from a selected region often are randomly sampled, and sometimes are sampled by bootstrap sampling. Random sampling often is conducted according to individual genomic portions (e.g., each individual genomic portion can be selected from the selected region with an equal probability of being sampled as each other individual genomic portion remaining in the selected region), and sometimes is conducted according to a window of contiguous genomic portions (e.g., a window that includes a contiguous stretch of a predetermined number of genomic portions is sampled from the selected region). A window can be of any suitable length and can include fewer genomic portions than genomic portions in a candidate region (e.g., a window can be 2 or more, 5 or more, 10 or more, 15 or more, 20 or more, 25 or more, 30 or more, 40 or more, 50 or more, 60 or more, 70 or more, 80 or more, 90 or more, 100 or more genomic portions), or can include about the same number of genomic portions as in a candidate region. Sampling often is sampling with replacement, where genomic portions sampled from the selected region often are included in a sampled region along with a quantification of sequence reads coupled to the genomic portion selected (e.g., a quantification of sequence reads coupled to each genomic portion selected in a sampled region often is the same quantification for the genomic portion existing in the selected region prior to sampling). A plurality of sampled regions often is generated for a test sample by repeating a sampling process multiple times, and a plurality of sampled regions sometimes includes about 100 to about 1,000,000 sampled regions (e.g., about 100 or more sampled regions, about 1,000 or more sampled regions, about 10,000 or more sampled regions, about 50,000 or more sampled regions, about 100,000 or more sampled regions).

After sampled regions are generated, a quantification of sequence reads associated with each sampled region sometimes is manipulated. In certain embodiments, a shift is applied to a quantification of sequence reads in each genomic portion in each sampled region. Where a candidate region being assessed is a candidate copy number duplication region, an absolute value of a shift sometimes is added to the quantification of sequence reads in each genomic portion in each sampled region, which results in a shift away from a baseline quantification in an outside region. Where a candidate region being assessed is a candidate copy number deletion region, an absolute value of a shift sometimes is subtracted from the quantification of sequence reads in each genomic portion in each sampled region, which results in a shift away from a baseline quantification in an outside region. In certain embodiments, a shift for a candidate copy number deletion region is a negative number of counts, and the shift is added to the quantification of sequence reads in each genomic portion in each sampled region, thereby effectively adjusting the quantification of sequence reads in each genomic portion in each sampled region away from a baseline quantification in an outside region. A baseline quantification in an outside region often is a quantification of sequence reads in an outside region, and sometimes is an average count of sequence reads in an outside region (e.g., a median count). In some embodiments, a shift is not applied to the sequence read count of each genomic portion in each sampled region.

In certain embodiments, a read count fraction for each of the sampled regions is determined. If a shift is applied to sampled regions, a fraction often is determined after the shift is applied. Each read count fraction often is the sum of read counts of genomic portions in each of the sampled regions, optionally after the shift is added to or subtracted from each of the read counts of the genomic portions, divided by the sum of read counts in the selected region.

Processes provided herein often include normalizing a quantification of sequence reads for each of the sampled regions, thereby generating a normalized quantification for each of the sampled regions. A quantification of sequence reads that is normalized sometimes is a read count (e.g., read count for each genomic portion in a sampled region, sum of read counts in all genomic portions of a sampled region), sometimes is a read density (e.g., read density for each genomic portion in a sampled region, sum of read densities for all genomic portions of a sampled region) and sometimes is a read count or read density fraction for each of the sampled regions (e.g., for genomic portions in each of the sampled regions). Normalizing often includes generating a standard score (e.g., z-score, z-value, normal score, standardized variable) for each of the sampled regions, sometimes includes generating a student's t-statistic, studentized residual, standardized moment, coefficient of variation, or variance to mean ratio for each of the sampled regions, and sometimes includes feature scaling. In certain embodiments, a normalized quantification of sequence reads for each sampled region is a z-score, and sometimes the z-score is determined from read count fractions according to the following relation:

$$\text{segment region } z\text{-score} = (F_{SR} - \text{median } F_{SR}) / MAD_{SR}$$

where $F_{SR}$ is a read count fraction determined for a particular sampled region, median $F_{SR}$ is a median of read count fractions determined for the plurality of sampled regions generated from a selected region containing a candidate region, and $MAD_{SR}$ is a median absolute deviation generated from the read count fractions determined for the plurality of sampled regions.

One or more or all steps for generating sampled regions and processing a quantification of sequence reads mapped to genomic portions in the sampled regions can be performed by an apparatus that includes memory and a processor (e.g., a computer). Genomic portions in each sampled region, sequence read quantifications associated with genomic portions in the sampled regions, shifts, read count fractions, and/or normalized quantifications for the sampled regions sometimes are stored in memory. In some embodiments, instructions for shifting, instructions for sampling, instructions for modifying a sequence read quantification for sampled regions, instructions for generating read count fractions and/or instructions for generating normalized quantifications for sampled regions, are stored in memory and are accessible to a processor. Programming instructions (e.g., module programming instructions) sometimes are in R programming language, and sometimes features of programming instructions for performing methods described herein are selected from the "stats" R package (e.g., R function "sample" can be used for random sampling).

Reference Samples

Processes described herein often include determining a measure of variability (e.g., measure of dispersion, measure of scatter, measure of spread) of sequence read quantifications associated with a candidate region (identified for a test sample) in reference samples not having a significant copy number variation in the candidate region. In some embodiments, a quantification of sequence reads is determined for each reference sample based on a quantification of sequence reads mapped to genomic portions in each reference sample, where the genomic portions for the reference sample are the same genomic portions within the candidate region being assessed for a test sample. The quantification of sequence reads generated for each of the reference samples often is the same type of quantification of sequence reads generated for each of the sampled regions. A quantification of sequence reads generated for each of the reference samples sometimes is a sequence read count mapped to each of the genomic portions in the candidate region, sometimes is a sum of sequence read counts for genomic portions in the candidate region, and sometimes is a sequence read count fraction for the candidate region (e.g., each read count fraction sometimes is the sum of read counts of genomic portions in the candidate region divided by the sum of read counts in the selected region for each of the reference samples). Any suitable measure of variability can be utilized, non-limiting examples of which include sample standard deviation, interquartile range (IQR), range, mean absolute difference (e.g., Gini mean absolute difference), median absolute deviation (MAD), average absolute deviation (or simply called average deviation) and distance standard deviation.

Reference samples sometimes are samples that have been classified for absence of chromosome trisomy. Reference samples sometimes are samples that have been classified for absence of a CNA, or for absence of a fetal CNA, of about 0.5 megabases or greater in the genome or all autosomes (e.g., classified for absence of a CNA greater than about 0.6, 0.7, 0.75, 0.8, 0.9, 1, 1.1, 1.2, 1.25, 1.3, 1.4, 1.5, 1.6, 1.7, 1.75, 1.8, 1.9, 2, 2.5, 3, 4, 5, 6, 7, 8, 9, 10, 11, 12, 13, 14, 15, 16, 17, 18, 19, 20 megabases in the genome (e.g., all chromosomes) or all autosomes (e.g., in the fetal genome (e.g., all fetal chromosomes) or in all fetal autosomes)). Reference samples sometimes are samples that have been classified for absence of a CNA of 0.5 megabases or greater in the candidate region or in the selected region (e.g., classified for absence of a CNA greater than about 0.6, 0.7, 0.75, 0.8, 0.9, 1, 1.1, 1.2, 1.25, 1.3, 1.4, 1.5, 1.6, 1.7, 1.75, 1.8, 1.9, 2, 2.5, 3, 4, 5, 6, 7, 8, 9, 10, 11, 12, 13, 14, 15, 16, 17, 18, 19, 20 megabases in the candidate region or in the selected region (e.g., in the candidate region or the selected region for a fetus)). A set of reference samples often includes about 200 or more samples (e.g., about 300, 400, 500, 600, 700, 800, 900, 1000, 2000, 3000, 4000, 5000 or more samples).

One or more or all steps for generating measure of variability of sequence read quantifications associated with the candidate region for reference samples can be performed by an apparatus that includes memory and a processor (e.g., a computer). Genomic portions in each candidate region, sequence read quantifications associated with genomic portions in each candidate region, and one or more identifiers for each reference sample sometimes are stored in memory. In some embodiments, instructions for generating measure of variability are stored in memory and are accessible to a processor. Programming instructions (e.g., module programming instructions) sometimes are in R programming language, and sometimes features of programming instructions for performing methods described herein are selected from the "stats" R package).

Confidence Determination

Processes herein generally include determining a confidence that a candidate region is a true copy number alteration (CNA) region. Any suitable confidence determination that makes use of a plurality of sampled regions can be utilized. In certain embodiments, a confidence determination is generated by a process that includes comparing a normalized quantification for each sampled region to a measure of variability for a quantification of sequence reads mapped to the candidate region in reference samples. A normalized quantification for each sampled region utilized for a comparison sometimes is a normalized quantification described in the preceding section entitled "Sampled regions," and a measure of variability for reference samples utilized for a comparison sometimes is a measure of variability described in the preceding section entitled "Reference samples." In certain embodiments, each normalized quantification for each sampled region (e.g., an absolute value of each normalized quantification for each sampled region) is compared to a measure of variability threshold for quantifications of sequence reads mapped to the candidate region in reference samples. Each normalized quantification for each sampled region sometimes is a z-score for each sampled region (e.g., an absolute value for each z-score sometimes is compared to the measure of variability threshold). A measure of variability threshold for quantifications of sequence reads mapped to the candidate region in reference samples sometimes is a number of median absolute deviations (MADs) for read count fractions for candidate regions for the reference samples. The number of MADs sometimes is about 3 to about 5, sometimes is about 3.8 to about 4.1 and sometimes is about 3.95.

For embodiments in which a confidence determination is generated, a proportion of sampled regions for which a normalized quantification (e.g., an absolute value of each normalized quantification) is greater than or less than a threshold sometimes is determined. The threshold often is a measure of variability threshold, and the threshold and normalized quantification (e.g., absolute value of each normalized quantification) for each sampled region utilized for determining a proportion sometimes are those described in the paragraph directly preceding this paragraph. A proportion sometimes is a ratio of (i) the number of sampled regions for which the normalized quantification is greater than or less than the threshold to (ii) the total number of sampled regions. In certain embodiments, a shift described herein is applied to the sequence read quantification of each genomic portion in each sampled region prior to determining the normalized quantification for each of the sampled regions, and the ratio is (i) the number of sampled regions for which the normalized quantification is greater than the threshold to (ii) the total number of sampled regions. In some embodiments, a shift described herein is not applied to the sequence read quantification of each genomic portion in each sampled region prior to determining the normalized quantification for each of the sampled regions, and the ratio is (i) the number of sampled regions for which the normalized quantification is less than the threshold to (ii) the total number of sampled regions. When comparing a normalized quantification to a threshold, an absolute value of each normalized quantification often is compared to the threshold.

One or more or all steps for generating a confidence determination can be performed by an apparatus that includes memory and a processor (e.g., a computer). Normalized quantifications for sampled regions utilized for a comparison, and a measure of variability for reference samples utilized for a comparison, sometimes are stored in memory. In some embodiments, instructions for generating a confidence determination (e.g., a ratio) are stored in memory and are accessible to a processor. Programming instructions (e.g., module programming instructions) sometimes are in R programming language, and sometimes features of programming instructions for performing methods described herein are selected from the "stats" R package.

Figure 12:
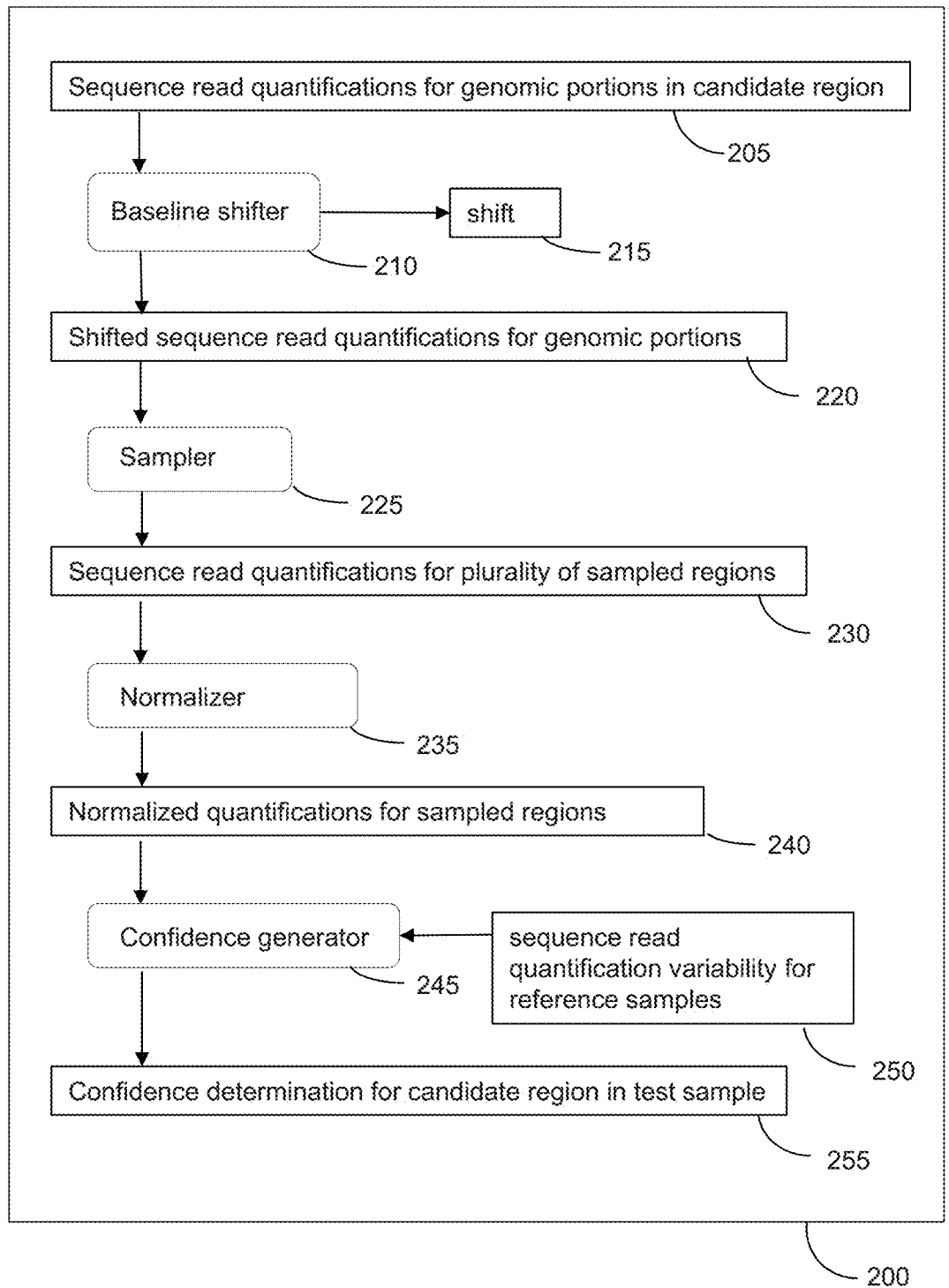
FIG. 12 to FIG. 17 show exemplary flows for classifying presence or absence of a chromosome copy number variation or sub-chromosome copy number variation for a test sample in accordance with some embodiments.

FIG. 12 shows a non-limiting embodiment of a process for generating a confidence determination for a candidate region. In process embodiment 200, sequence read quantifications 205 for genomic portions in a candidate region are shifted by baseline shifter 210 to shifted sequence read quantifications 220 for genomic portions. The shifted sequence read quantifications 220 sometimes are shifted to or near a baseline sequence read quantification level for a region outside the candidate region and in a selected region that includes the candidate region. Baseline shifter 210 often generates a shift 215, which can be stored and utilized. Genomic portions coupled to the shifted sequence read quantifications 220 can be randomly sampled from the selected region (e.g., a chromosome) that contains the candidate region and outside region by sampler 225, which can generate a plurality of sampled regions having genomic portions to which sequence read quantifications 230 are coupled.

Sequence read quantifications 230 coupled to genomic portions in each sampled region can be expressed as a fraction of (i) sequence read counts summed for genomic portions in the sampled region, divided by (ii) sequence read counts summed for genomic portions in the selected region. Shift 215 can be applied to each of the sequence read quantifications 230 coupled to genomic portions in each sampled region prior to determining a fraction.

For each sampled region, sequence read quantifications 230 can be converted to a normalized quantification 240 by normalizer 235. Normalizer 235 can convert a sequence read quantification 230 expressed as a fraction for each of the sampled regions to a z-score for each of the sampled regions, in certain embodiments (i.e., each normalized sequence read quantification for each sampled region is a z-score). Each normalized quantification 240 for each sampled region can be utilized as input for confidence generator 245 that yields confidence determination 255 for the candidate region for a test sample. Confidence generator 245 can utilize as input a sequence read quantification variability 250 (e.g., a MAD) determined from sequence read quantifications associated with genomic portions in the candidate region for a set of reference samples.

Figure 13:
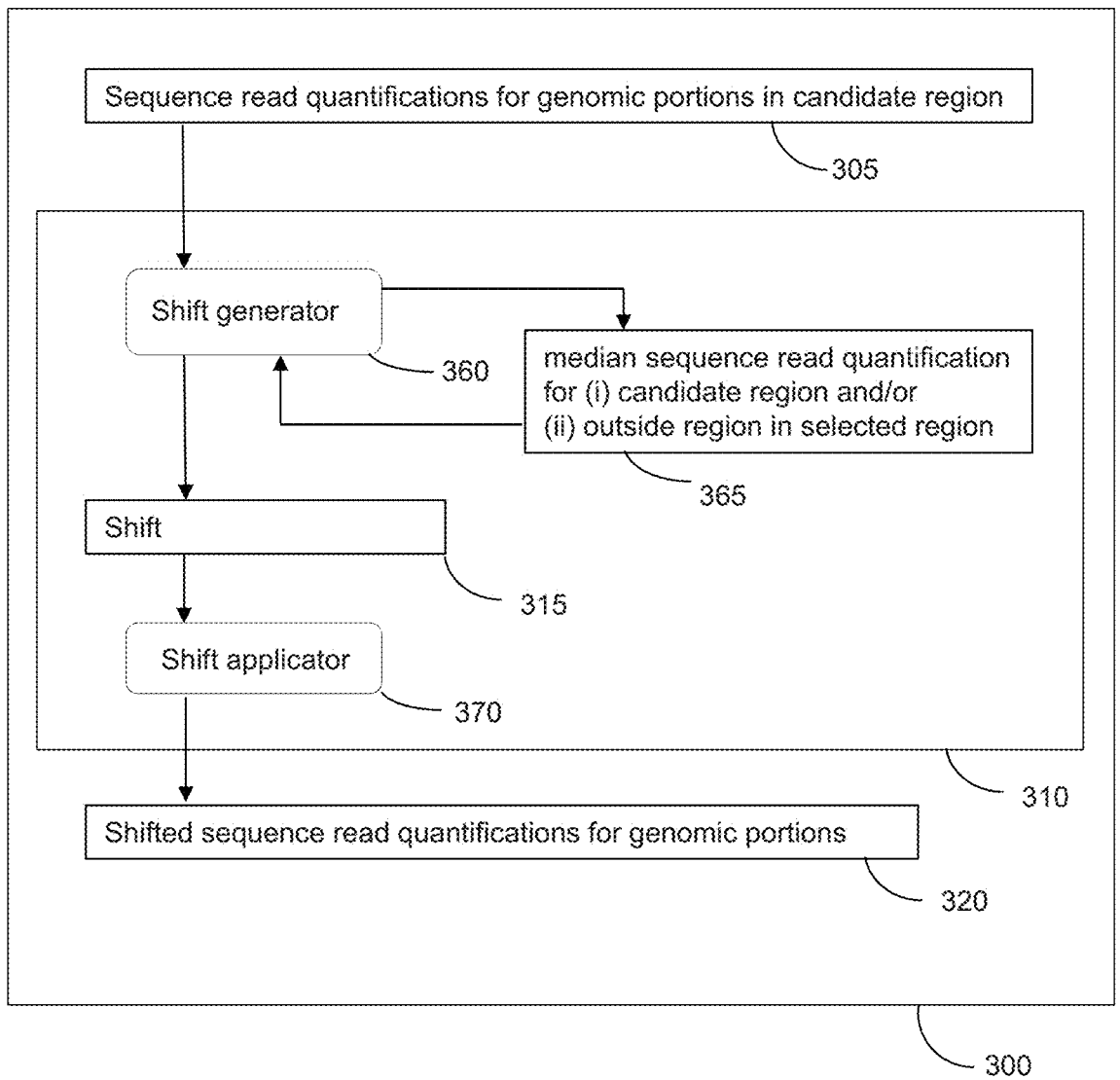

FIG. 13 shows a non-limiting embodiment of a process for shifting a quantification of sequence reads for a candidate region prior to sampling. Process 300 includes shifting quantifications of sequence reads 305 for a candidate region by baseline shifter 310. Baseline shifter 310 includes a shift generator 360 that generates shift 315. Shift generator 360 sometimes determines a median sequence read quantification 365 for (i) the candidate region and/or (ii) the outside region in the selected region. Shift generator 360 sometimes subtracts (ii) from (i) to generate shift 315 (e.g., for a candidate copy number duplication region), and sometimes adds (ii) to (i) to generate shift 315 (e.g., for a candidate copy number deletion region). Baseline shifter 310 sometimes includes shift applicator 370 that applies the shift to each quantification of sequence reads for each genomic portion in a candidate region (e.g., the shift is applied to each portion (e.g., bin) separately). Where a candidate region is a copy number duplication region, shift applicator 370 sometimes subtracts shift 315, or the absolute value of shift 315, from each sequence read quantification 305 (e.g., a sequence read count) for each genomic portion in the candidate region. Where a candidate region is a copy number deletion region, shift applicator 370 sometimes adds shift 315, or adds the absolute value of shift 315, to each sequence read quantification 305 (e.g., sequence read count) for each genomic portion in the candidate region. Upon applying shift 315, shift applicator 370 generates shifted sequence read quantifications 320 for genomic portions in the candidate region. After applying shift 315 by shift applicator 370, genomic portions sometimes are randomly sampled, along with the sequence read quantification coupled to each sampled genomic portion, from the selected region, which includes the candidate region and outside region, to generate sampled regions.

Figure 14:
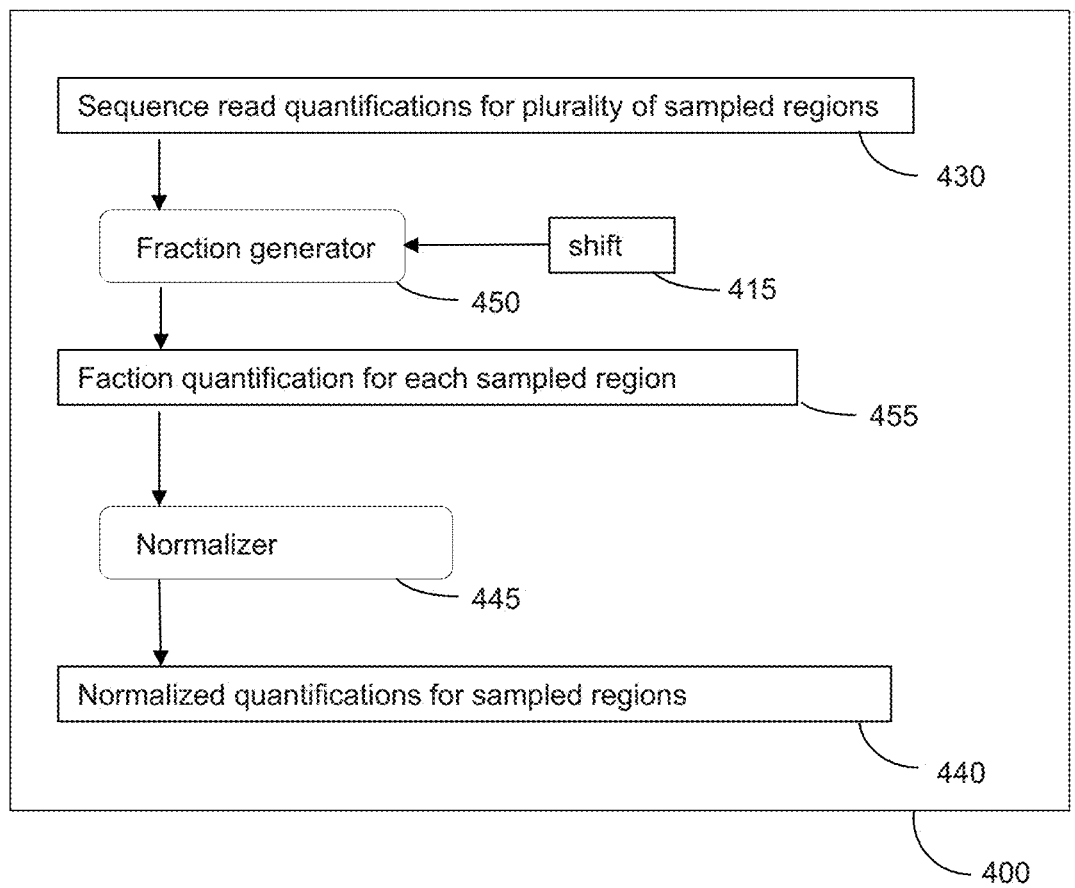

FIG. 14 shows a non-limiting embodiment of a process for generating a normalized quantification of sequence reads for each sampled region. Process 400 includes generating fraction quantification 455 of sequence reads for genomic portions in each sampled region by fraction generator 450. Fraction generator 450 often divides (i) the sum of sequence read counts coupled to genomic portions in each sampled region, by (ii) the sum of sequence read counts coupled to genomic portions in the selected region (e.g., a chromosome from which genomic portions were sampled to generate each of the sampled regions). In certain embodiments, shift 415, which sometimes is shift 215 obtained in process 200 or shift 315 obtained in process 300, is applied by fraction generator 450 to a count of sequence reads in each genomic portion in each sampled region (e.g., the shift is applied to each portion (e.g., bin) separately). Where a candidate region is a copy number duplication region, fraction generator 450 sometimes adds shift 415 (e.g., adds the absolute value of shift 415) to each sequence read quantification 430 (e.g., sequence read count) for each genomic portion in each sampled region prior to determining fraction 455. Where a candidate region is a copy number deletion region, fraction generator sometimes subtracts shift 415 (e.g., subtracts the absolute value of shift 415) from each sequence read quantification 430 (e.g., sequence read count) for each genomic portion in each sampled region prior to determining fraction 455. In process 400, fraction 455 for each sampled region is normalized by normalizer 445 to generate a normalized quantification 440 of sequence reads for each sampled region. Normalizer 445 sometimes generates a standard score (e.g., z-score, z-value, normal score, standardized variable) for each of the sampled regions, and in certain embodiments, generates a student's t-statistic, studentized residual, standardized moment, coefficient of variation, or variance to mean ratio for each of the sampled regions.

Figure 15:
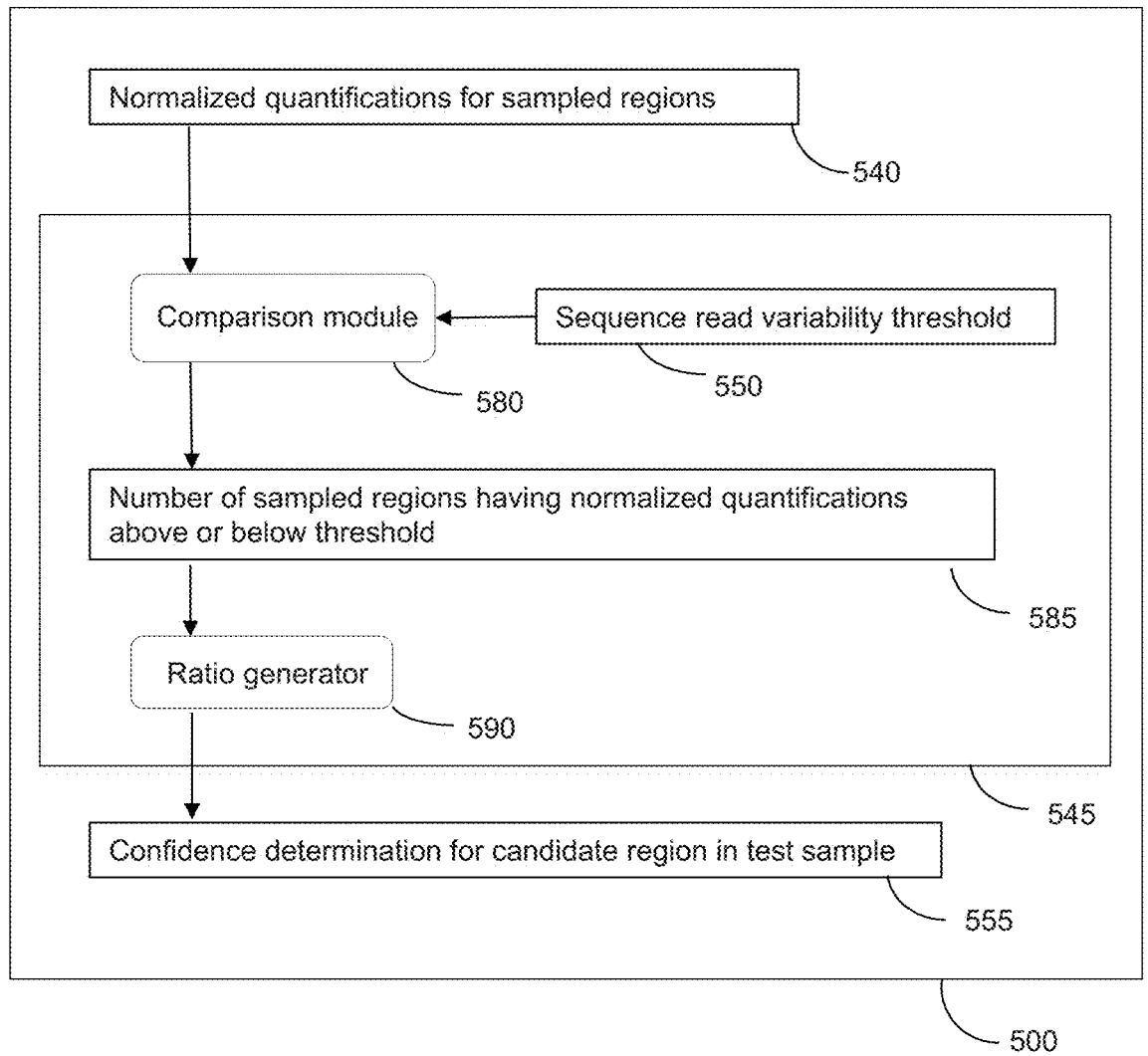

FIG. 15 shows a non-limiting embodiment of a process for generating a confidence determination for a candidate region in a test sample. In process 500 normalized quantifications 540 of sequence reads for sampled regions are input for confidence generator 545. In confidence generator 545, normalized quantifications 540 are compared by comparison module 580 to a sequence read variability threshold 550 determined according to variability of sequence reads mapped to the candidate region in a set of reference samples not having a CNA in the candidate region. The sequence read variability sometimes is a median absolute deviation (MAD) and threshold 550 sometimes is about 2 to about 5 MADs, sometimes is about 3.8 to about 4.1 MADs, sometimes is about 3 to about 3.95 MADs, and sometimes is about 3.95 MADs. Comparison module 580 sometimes determines a number of sampled regions 585 having normalized quantifications above threshold 500 (e.g., in embodiments where a shift (e.g., absolute value of a shift) is applied to each portion in a sampled region prior to determining a fraction quantification for each sampled region). Comparison module 580 sometimes determines a number of sampled regions 585 having normalized quantifications below threshold 500 (e.g., in embodiments where a shift is not applied to each portion in a sampled region prior to determining a fraction quantification for each sampled region). Ratio generator 590 sometimes determines a ratio of (i) the number of sampled regions 585, to (ii) the number of sampled regions 540 for which normalized quantifications 540 are utilized as input to process 500. Ratio generator 590 generates confidence determination 555 for a candidate region for a test sample in process 500 (e.g., the ratio generated by ratio generator 590 is the confidence determination 555 generated by process 500).

Use of Confidence Determination

In certain embodiments, a confidence determination is utilized for providing a classification of presence or absence of a chromosome copy number variation or sub-chromosome copy number variation for a test sample. A confidence determination threshold sometimes is utilized. Where a confidence determination provided for a test sample is below a confidence determination threshold, a classification sometimes is not provided for a candidate region for the test sample, and a test report may indicate that a test result is not reportable for the candidate region. Where a confidence determination provided for a test sample is equal to or above a confidence determination threshold, a classification often is provided for a candidate region for the test sample. A confidence determination threshold sometimes is 0.90 to about 0.999 (e.g., threshold sometimes is 0.95, 0.99, 0.995 or 0.999).

A classification of presence or absence of a chromosome copy number variation or sub-chromosome copy number variation for a test sample sometimes is based in part on a normalized quantification of sequence reads mapped to a candidate region identified by a segmentation process. Any suitable segmentation process can be used to identify a candidate region, non-limiting examples of which are described herein (e.g., a circular binary segmentation (CBS) process). A segmentation process sometimes includes a merging process (described herein).

A segmentation process sometimes generates a normalized CNA quantification for each segment identified, and any suitable normalized CNA quantification can be utilized. Non-limiting examples of normalized CNA quantifications include standard score (e.g., z-score, z-value, normal score, standardized variable) for each of the identified segments, sometimes includes generating a student's t-statistic, studentized residual, standardized moment, coefficient of variation, or variance to mean ratio for each of the identified segments, and sometimes includes feature scaling. In certain embodiments, a segmentation process includes generating a z-score for an identified segment ($Z_{SEG}$), and sometimes the z-score is determined according to:

$$Z_{SEG} = (S_{scr} - S_{mcr})/MAD$$

where $S_{scr}$ is a test sample count representation of a segment (e.g., the total normalized counts in the segment divided by the total normalized autosome counts for the test sample); $S_{mcr}$ is a median count representation for the segment generated for a reference set of samples; and the MAD is a median absolute deviation determined for the count representation of the segment for a reference set of samples.

A classification of presence or absence of a chromosome copy number variation or sub-chromosome copy number variation for a test sample sometimes includes determining a log odds ratio (LOR) for a CNA region for a test sample. A LOR sometimes is determined for a chromosome CNA region ($LOR_{CHR}$) and sometimes is determined for a sub-chromosome CNA region ($LOR_{SUB}$), such as a LOR for a segment ($LOR_{SEG}$). A LOR sometimes is the log of the quotient of (i) a first multiplication product of (1) a conditional probability of having a CNA and (2) a prior probability of having the CNA, and (ii) a second multiplication product of (1) a conditional probability of not having the CNA and (2) a prior probability of not having the CNA. In some embodiments, the conditional probability of having the CNA is determined according to fetal fraction determined for the test sample, a z-score of the count representation for the CNA region determined for the test sample, and a distribution for the fetal fraction of z-scores for the count representation for the CNA region. A count representation for a CNA region sometimes is a ratio of (i) the counts summed for genomic portions included in a CNA region, and (ii) the counts summed for genomic portions included in the genome or a part of the genome larger than the CNA region (e.g., all autosomes, all chromosomes in the genome, a chromosome in which a segment CNA region resides). A conditional probability of having the CNA sometimes is determined by the relationship in the following equation (1):

$$Z \sim \text{Normal}\left(\frac{\mu_X}{\sigma_X} \frac{f}{2}, 1\right) \quad (1)$$

where f is fetal fraction, X is the summed portion count for the segment covering the CNA, $X \sim f(\mu X, \sigma X)$, where $\mu X$ and $\sigma X$ are the mean and standard deviation of X, respectively, and $f(\cdot)$ is a distribution function. A conditional probability of having the CNA sometimes is the intersection between the z-score for the test sample of the count representation for the CNA region and a distribution for the fetal fraction of z-scores for the count representation for the CNA region. A conditional probability of not having the CNA sometimes is the intersection between the z-score of the count representation for the CNA region determined for the test sample and a distribution of z-scores for the count representation for the CNA region in euploids. A prior probability of having the CNA and the prior probability of not having the CNA sometimes are determined from multiple samples that do not include the test subject.

A classification of presence or absence of a chromosome copy number variation or sub-chromosome copy number variation for a test sample sometimes includes generating a normalized CNA quantification for a chromosome for a test sample. Non-limiting examples of normalized CNA quantifications for a chromosome include standard score (e.g., z-score, z-value, normal score, standardized variable) for the chromosome, sometimes includes generating a student's t-statistic, studentized residual, standardized moment, coefficient of variation, or variance to mean ratio for the chromosome, and sometimes includes feature scaling. In certain embodiments, a classification includes generating a z-score for a chromosome ($Z_{CHR}$), and sometimes the z-score is determined according to:

$$Z_{CHR} = (C_{scr} - C_{mcr})/MAD$$

where $C_{scr}$ is a test sample count representation of the chromosome (e.g., the total normalized counts in the chromosome divided by the total normalized autosome counts for the test sample); $S_{mcr}$ is a median count representation for the chromosome generated for a reference set of samples; and the MAD is a median absolute deviation determined for the count representation of the chromosome for the reference set of samples.

In certain embodiments, presence of a chromosome trisomy or monosomy is classified for a test sample when the absolute value of $Z_{CHR}$ is greater than or equal to a predetermined cutoff value, $LOR_{CHR}$ is greater than zero, the absolute value of $Z_{CHR}$ is greater than or equal to the product of a and $Z_{SEG}$, where a is between 0 and about 1 (e.g., about 0.6 to about 0.8), and a confidence determination for the chromosome is greater than a predetermined level. In some embodiments, absence of a chromosome trisomy or monosomy is classified for a test sample when the absolute value of $Z_{CHR}$ is less than a predetermined cutoff value, $LOR_{CHR}$ is less than zero, the absolute value of $Z_{CHR}$ is less than the product of a and $Z_{SEG}$, where a is between 0 and about 1 (e.g., about 0.6 to about 0.8), and/or the confidence determination for the chromosome is less than a predetermined level. The predetermined cutoff value sometimes is between about 2 and about 5, sometimes is between about 3 and 4 and sometimes is about 3.00 or about 3.95. The predetermined level (i.e., confidence threshold) sometimes is 0.99 or greater (e.g., 0.999).

In some embodiments, presence of a sub-chromosome CNA is classified for a test sample when there is absence of a chromosome trisomy or monosomy classified for the test sample, the absolute value of $Z_{SEG}$ is greater than or equal to a predetermined cutoff value, $LOR_{SEG}$ is greater than zero and a confidence determination for the segment is greater than a predetermined level. In certain embodiments, absence of a sub-chromosome CNA is classified for a test sample when the absolute value of $Z_{SEG}$ is less than a predetermined cutoff value, the $LOR_{SEG}$ is less than zero, and/or a confidence determination for the segment is less than a predetermined level. The predetermined cutoff value sometimes is between about 2 and about 5, sometimes is between about 3 and 4 and sometimes is about 3.95. The predetermined level (i.e., confidence threshold) sometimes is 0.99 or greater (e.g., 0.999).

One or more or all steps for using a confidence determination in a classification process can be performed by an apparatus that includes memory and a processor (e.g., a computer). One or more of the following sometimes are stored in memory: confidence determination for each sub-chromosome region (e.g., segment) or chromosome region, confidence determination predetermined level (i.e., confidence determination threshold), normalized quantification for chromosome ($Z_{CHR}$), $LOR_{CHR}$, chromosome MAD, normalized quantification for segment ($Z_{SEG}$), $LOR_{SEG}$, segment MAD, constant a, predetermined cutoff value for $Z_{CHR}$, and predetermined cutoff value for $Z_{SEG}$. In some embodiments, instructions for generating a classification are stored in memory and are accessible to a processor. Programming instructions (e.g., module programming instructions) sometimes are in R programming language, and sometimes features of programming instructions for performing methods described herein are selected from the "stats" R package (e.g., the function "trapz" in R package "caTools" can be used for computing LOR calculations (e.g., computing an integral for LOR calculations)).

Figure 16:
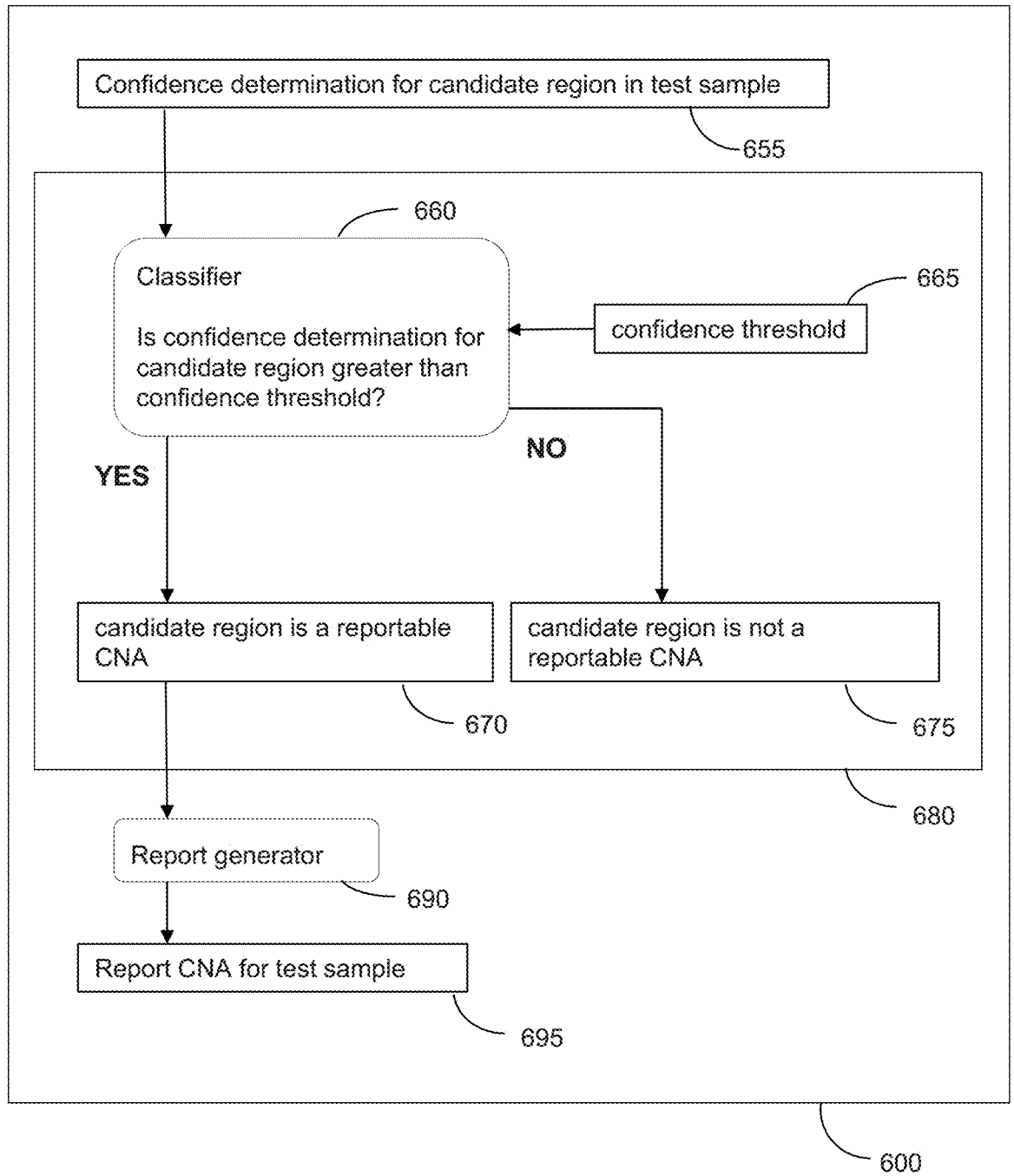

FIG. 16 shows a non-limiting embodiment of a process for utilizing a confidence determination. In process 600, confidence determination 655 for a candidate region for a test sample is utilized as input for classification module 680. In classification module 680, classifier 660 determines whether confidence determination 655 is greater than or less than confidence threshold 655, the latter of which sometimes is within classifier 660 or exists outside the classifier and is utilized by the classifier. Threshold 655 sometimes is 0.99 or greater (e.g., 0.999). Classifier 660 sometimes determines whether confidence determination 655 is greater than or equal to, or less than or equal to, threshold 665. A positive classification by classifier 660 results in an outcome that the candidate region is a reportable CNA region 670, and a negative classification by classifier 660 results in an outcome that the candidate region is not a CNA or is not a reportable CNA region 675. A reportable CNA region outcome 670 sometimes is output from classification module 680 and input for report generator 690, which generates report 695. A CNA region sometimes is a chromosome and sometimes is a sub-chromosome region.

Figure 17:
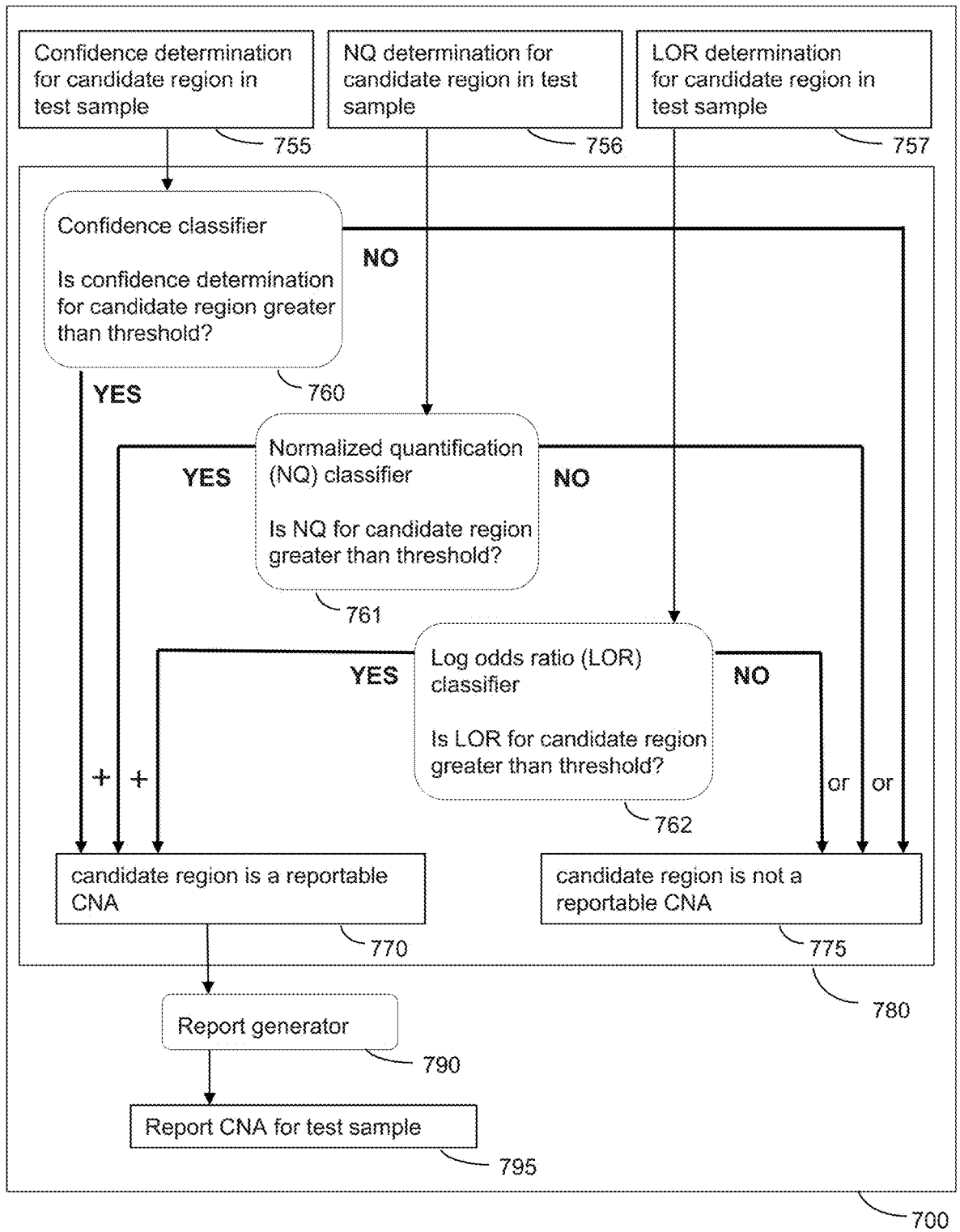

FIG. 17 shows a non-limiting embodiment of a process for utilizing a confidence determination in combination with other determinations for a candidate region of a test sample. In process 700, confidence determination 755, normalized quantification (NQ) 756 and log odds ratio (LOR) 757 for a candidate region for a test sample is utilized as input for classification module 780.

In classification module 780, confidence classifier 760 determines whether confidence determination 755 is greater than or less than a confidence threshold, the latter of which sometimes is within confidence classifier 760 or exists outside the classifier and is utilized by the classifier. Confidence classifier 760 sometimes determines whether confidence determination 755 is greater than or equal to, or less than or equal to, the confidence threshold. The confidence threshold sometimes is 0.99 or greater (e.g., 0.999).

In classification module 780, normalized quantification (NQ) classifier 761 determines whether NQ 756, or absolute value thereof, is greater than or less than a NQ threshold, the latter of which sometimes is within NQ classifier 761 or exists outside the classifier and is utilized by the classifier. NQ classifier 761 sometimes determines whether NQ 756, or absolute value thereof, is greater than or equal to, or less than or equal to, a NQ threshold. In certain embodiments, NQ 756 for a candidate region is a standard score (e.g., z-score, z-value, normal score, standardized variable), and in certain embodiments, NQ 756 for a candidate region is a student's t-statistic, studentized residual, standardized moment, coefficient of variation, or variance to mean ratio. NQ 756 for a candidate region sometimes is determined by a segmentation process. A NQ threshold sometimes is for a z-score NQ 756 and sometimes is about 2 to about 5, sometimes is about 2.9 to about 4.1 and sometimes is about 3 to about 3.95 (e.g., is about 3, is about 3.95).

In classification module 780, log odds ratio (LOR) classifier 762 determines whether LOR 757 for a candidate region of a test sample is greater than or less than a LOR threshold, the latter of which sometimes is within confidence classifier 762 or exists outside the classifier and is utilized by the classifier. LOR classifier 762 sometimes determines whether LOR 757 is greater than or equal to, or less than or equal to, a LOR threshold. A LOR threshold sometimes is zero.

A positive classification by confidence classifier 760 and NQ classifier 761 and LOR classifier 762 generally results in an outcome that the candidate region is a reportable CNA region 770. A negative classification by confidence classifier 760 or NQ classifier 761 or LOR classifier 762 generally results in an outcome that the candidate region is not a CNA or is not a reportable CNA region 775. A reportable CNA region outcome 770 sometimes is output from classification module 780 and input for report generator 790, which generates report 795. A CNA region sometimes is a chromosome and sometimes is a sub-chromosome region.

Samples

Provided herein are systems, methods and products for analyzing nucleic acids. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, fetal vs. maternal origins, cell or tissue origins, cancer vs. non-cancer origin, tumor vs. non-tumor origin, sample origins, subject origins, and the like), or combinations thereof.

Nucleic acid or a nucleic acid mixture utilized in systems, methods and products described herein often is isolated from a sample obtained from a subject (e.g., test subject). A subject can be any living or non-living organism, including but not limited to a human, a non-human animal, a plant, a bacterium, a fungus, a protest or a pathogen. Any human or non-human animal can be selected, and may include, for example, mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman, a pregnant woman). A subject may be any age (e.g., an embryo, a fetus, an infant, a child, an adult). A subject may be a cancer patient, a patient suspected of having cancer, a patient in remission, a patient with a family history of cancer, and/or a subject obtaining a cancer screen. In some embodiments, a test subject is a female. In some embodiments, a test subject is a human female. In some embodiments, a test subject is a male. In some embodiments, a test subject is a human male.

Nucleic acid may be isolated from any type of suitable biological specimen or sample (e.g., a test sample). A sample or test sample can be any specimen that is isolated or obtained from a subject or part thereof (e.g., a human subject, a pregnant female, a cancer patient, a fetus, a tumor). Non-limiting examples of specimens include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo; cancer biopsy), celocentesis sample, cells (blood cells, placental cells, embryo or fetal cells, fetal nucleated cells or fetal cellular remnants, normal cells, abnormal cells (e.g., cancer cells)) or parts thereof (e.g., mitochondrial, nucleus, extracts, or the like), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a biological sample is a cervical swab from a subject. A fluid or tissue sample from which nucleic acid is extracted may be acellular (e.g., cell-free). In some embodiments, a fluid or tissue sample may contain cellular elements or cellular remnants. In some embodiments, fetal cells or cancer cells may be included in the sample.

A sample can be a liquid sample. A liquid sample can comprise extracellular nucleic acid (e.g., circulating cell-free DNA). Non-limiting examples of liquid samples, include, blood or a blood product (e.g., serum, plasma, or the like), urine, biopsy sample (e.g., liquid biopsy for the detection of cancer), a liquid sample described above, the like or combinations thereof. In certain embodiments, a sample is a liquid biopsy, which generally refers to an assessment of a liquid sample from a subject for the presence, absence, progression or remission of a disease (e.g., cancer). A liquid biopsy can be used in conjunction with, or as an alternative to, a sold biopsy (e.g., tumor biopsy). In certain instances, extracellular nucleic acid is analyzed in a liquid biopsy.

In some embodiments, a biological sample may be blood, plasma or serum. The term "blood" encompasses whole blood, blood product or any fraction of blood, such as serum, plasma, buffy coat, or the like as conventionally defined. Blood or fractions thereof often comprise nucleosomes. Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3 to 40 milliliters, between 5 to 50 milliliters) often is collected and can be stored according to standard procedures prior to or after preparation.

An analysis of nucleic acid found in a subjects blood may be performed using, e.g., whole blood, serum, or plasma. An analysis of fetal DNA found in maternal blood, for example, may be performed using, e.g., whole blood, serum, or plasma. An analysis of tumor DNA found in a patient's blood, for example, may be performed using, e.g., whole blood, serum, or plasma. Methods for preparing serum or plasma from blood obtained from a subject (e.g., a maternal subject; cancer patient) are known. For example, a subject's blood (e.g., a pregnant woman's blood; cancer patient's blood) can be placed in a tube containing EDTA or a specialized commercial product such as Vacutainer SST (Becton Dickinson, Franklin Lakes, N.J.) to prevent blood clotting, and plasma can then be obtained from whole blood through centrifugation. Serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for nucleic acid extraction. In addition to the acellular portion of the whole blood, nucleic acid may also be recovered from the cellular fraction, enriched in the buffy coat portion, which can be obtained following centrifugation of a whole blood sample from the subject and removal of the plasma.

A sample may be heterogeneous. For example, a sample may include more than one cell type and/or one or more nucleic acid species. In some instances, a sample may include (i) fetal cells and maternal cells, (ii) cancer cells and non-cancer cells, and/or (iii) pathogenic cells and host cells. In some instances, a sample may include (i) cancer and non-cancer nucleic acid, (ii) pathogen and host nucleic acid, (iii) fetal derived and maternal derived nucleic acid, and/or more generally, (iv) mutated and wild-type nucleic acid. In some instances, a sample may include a minority nucleic acid species and a majority nucleic acid species, as described in further detail below. In some instances, a sample may include cells and/or nucleic acid from a single subject or may include cells and/or nucleic acid from multiple subjects.

Cell Types

As used herein, a "cell type" refers to a type of cell that can be distinguished from another type of cell. Extracellular nucleic acid can include nucleic acid from several different cell types. Non-limiting examples of cell types that can contribute nucleic acid to circulating cell-free nucleic acid include liver cells (e.g., hepatocytes), lung cells, spleen cells, pancreas cells, colon cells, skin cells, bladder cells, eye cells, brain cells, esophagus cells, cells of the head, cells of the neck, cells of the ovary, cells of the testes, prostate cells, placenta cells, epithelial cells, endothelial cells, adipocyte cells, kidney/renal cells, heart cells, muscle cells, blood cells (e.g., white blood cells), central nervous system (CNS) cells, the like and combinations of the foregoing. In some embodiments, cell types that contribute nucleic acid to circulating cell-free nucleic acid analyzed include white blood cells, endothelial cells and hepatocyte liver cells. Different cell types can be screened as part of identifying and selecting nucleic acid loci for which a marker state is the same or substantially the same for a cell type in subjects having a medical condition and for the cell type in subjects not having the medical condition, as described in further detail herein.

A particular cell type sometimes remains the same or substantially the same in subjects having a medical condition and in subjects not having a medical condition. In a non-limiting example, the number of living or viable cells of a particular cell type may be reduced in a cell degenerative condition, and the living, viable cells are not modified, or are not modified significantly, in subjects having the medical condition.

A particular cell type sometimes is modified as part of a medical condition and has one or more different properties than in its original state. In a non-limiting example, a particular cell type may proliferate at a higher than normal rate, may transform into a cell having a different morphology, may transform into a cell that expresses one or more different cell surface markers and/or may become part of a tumor, as part of a cancer condition. In embodiments for which a particular cell type (i.e., a progenitor cell) is modified as part of a medical condition, the marker state for each of the one or more markers assayed often is the same or substantially the same for the particular cell type in subjects having the medical condition and for the particular cell type in subjects not having the medical condition. Thus, the term "cell type" sometimes pertains to a type of cell in subjects not having a medical condition, and to a modified version of the cell in subjects having the medical condition. In some embodiments, a "cell type" is a progenitor cell only and not a modified version arising from the progenitor cell. A "cell type" sometimes pertains to a progenitor cell and a modified cell arising from the progenitor cell. In such embodiments, a marker state for a marker analyzed often is the same or substantially the same for a cell type in subjects having a medical condition and for the cell type in subjects not having the medical condition.

In certain embodiments, a cell type is a cancer cell. Certain cancer cell types include, for example, leukemia cells (e.g., acute myeloid leukemia, acute lymphoblastic leukemia, chronic myeloid leukemia, chronic lymphoblastic leukemia); cancerous kidney/renal cells (e.g., renal cell cancer (clear cell, papillary type 1, papillary type 2, chromophobe, oncocytic, collecting duct), renal adenocarcinoma, hypernephroma, Wilm's tumor, transitional cell carcinoma); brain tumor cells (e.g., acoustic neuroma, astrocytoma (grade I: pilocytic astrocytoma, grade II: low-grade astrocytoma, grade III: anaplastic astrocytoma, grade IV: glioblastoma (GBM)), chordoma, cns lymphoma, craniopharyngioma, glioma (brain stem glioma, ependymoma, mixed glioma, optic nerve glioma, subependymoma), medulloblastoma, meningioma, metastatic brain tumors, oligodendroglioma, pituitary tumors, primitive neuroectodermal (PNET), schwannoma, juvenile pilocytic astrocytoma (JPA), pineal tumor, rhabdoid tumor).

Different cell types can be distinguished by any suitable characteristic, including without limitation, one or more different cell surface markers, one or more different morphological features, one or more different functions, one or more different protein (e.g., histone) modifications and one or more different nucleic acid markers. Non-limiting examples of nucleic acid markers include single-nucleotide polymorphisms (SNPs), methylation state of a nucleic acid locus, short tandem repeats, insertions (e.g., microinsertions), deletions (microdeletions) the like and combinations thereof. Non-limiting examples of protein (e.g., histone) modifications include acetylation, methylation, ubiquitylation, phosphorylation, sumoylation, the like and combinations thereof.

As used herein, the term a "related cell type" refers to a cell type having multiple characteristics in common with another cell type. In related cell types, 75% or more cell surface markers sometimes are common to the cell types (e.g., about 80%, 85%, 90% or 95% or more of cell surface markers are common to the related cell types).

Nucleic Acid

Provided herein are methods for analyzing nucleic acid. The terms "nucleic acid" and "nucleic acid molecule" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by a fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid may be, or may be from, a plasmid, phage, virus, bacterium, autonomously replicating sequence (ARS), mitochondria, centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense," "plus" strand or "minus" strand, "forward" reading frame or "reverse" reading frame) and double-stranded polynucleotides. The term "gene" refers to a section of DNA involved in producing a polypeptide chain; and generally includes regions preceding and following the coding region (leader and trailer) involved in the transcription/translation of the gene product and the regulation of the transcription/translation, as well as intervening sequences (introns) between individual coding regions (exons). A nucleotide or base generally refers to the purine and pyrimidine molecular units of nucleic acid (e.g., adenine (A), thymine (T), guanine (G), and cytosine (C)). For RNA, the base thymine is replaced with uracil. Nucleic acid length or size may be expressed as a number of bases.

Nucleic acid may be single or double stranded. Single stranded DNA, for example, can be generated by denaturing double stranded DNA by heating or by treatment with alkali, for example. In certain embodiments, nucleic acid is in a D-loop structure, formed by strand invasion of a duplex DNA molecule by an oligonucleotide or a DNA-like molecule such as peptide nucleic acid (PNA). D loop formation can be facilitated by addition of *E. Coli* RecA protein and/or by alteration of salt concentration, for example, using methods known in the art.

Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acid may be derived from one or more sources (e.g., biological sample, blood, cells, serum, plasma, buffy coat, urine, lymphatic fluid, skin, soil, and the like) by methods known in the art. Any suitable method can be used for isolating, extracting and/or purifying DNA from a biological sample (e.g., from blood or a blood product), non-limiting examples of which include methods of DNA preparation (e.g., described by Sambrook and Russell, Molecular Cloning: A Laboratory Manual 3d ed., 2001), various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Ws.), and GFX™ Genomic Blood DNA Purification Kit (Amersham, Piscataway, N.J.), the like or combinations thereof.

In some embodiments, nucleic acid is extracted from cells using a cell lysis procedure. Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. In some instances, a high salt and/or an alkaline lysis procedure may be utilized.

Nucleic acids can include extracellular nucleic acid in certain embodiments. The term "extracellular nucleic acid" as used herein can refer to nucleic acid isolated from a source having substantially no cells and also is referred to as "cell-free" nucleic acid, "circulating cell-free nucleic acid" (e.g., CCF fragments, ccf DNA) and/or "cell-free circulating nucleic acid." Extracellular nucleic acid can be present in and obtained from blood (e.g., from the blood of a human subject). Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder"). In some embodiments, sample nucleic acid from a test subject is circulating cell-free nucleic acid. In some embodiments, circulating cell free nucleic acid is from blood plasma or blood serum from a test subject.

Extracellular nucleic acid can include different nucleic acid species, and therefore is referred to herein as "heterogeneous" in certain embodiments. For example, blood serum or plasma from a person having cancer can include nucleic acid from cancer cells (e.g., tumor, neoplasia) and nucleic acid from non-cancer cells. In another example, blood serum or plasma from a pregnant female can include maternal nucleic acid and fetal nucleic acid. In some instances, cancer or fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is cancer or fetal nucleic acid).

At least two different nucleic acid species can exist in different amounts in extracellular nucleic acid and sometimes are referred to as minority species and majority species. In certain instances, a minority species of nucleic acid is from an affected cell type (e.g., cancer cell, wasting cell, cell attacked by immune system). In certain embodiments, a genetic variation (e.g., copy number alteration, single nucleotide variation, chromosome alteration, translocation) is determined for a minority nucleic acid species. In certain embodiments, a genetic variation is determined for a majority nucleic acid species. Generally it is not intended that the terms "minority" or "majority" be rigidly defined in any respect. In one aspect, a nucleic acid that is considered "minority," for example, can have an abundance of at least about 0.1% of the total nucleic acid in a sample to less than 50% of the total nucleic acid in a sample. In some embodiments, a minority nucleic acid can have an abundance of at least about 1% of the total nucleic acid in a sample to about 40% of the total nucleic acid in a sample. In some embodiments, a minority nucleic acid can have an abundance of at least about 2% of the total nucleic acid in a sample to about 30% of the total nucleic acid in a sample. In some embodiments, a minority nucleic acid can have an abundance of at least about 3% of the total nucleic acid in a sample to about 25% of the total nucleic acid in a sample. For example, a minority nucleic acid can have an abundance of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% of the total nucleic acid in a sample. In some instances, a minority species of extracellular nucleic acid sometimes is about 1% to about 40% of the overall nucleic acid (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% of the nucleic acid is minority species nucleic acid). In some embodiments, the minority nucleic acid is extracellular DNA. In some embodiments, the minority nucleic acid is extracellular DNA from apoptotic tissue. In some embodiments, the minority nucleic acid is extracellular DNA from tissue affected by a cell proliferative disorder. In some embodiments, the minority nucleic acid is extracellular DNA from a tumor cell. In some embodiments, the minority nucleic acid is extracellular fetal DNA.

In another aspect, a nucleic acid that is considered "majority," for example, can have an abundance greater than 50% of the total nucleic acid in a sample to about 99.9% of the total nucleic acid in a sample. In some embodiments, a majority nucleic acid can have an abundance of at least about 60% of the total nucleic acid in a sample to about 99% of the total nucleic acid in a sample. In some embodiments, a majority nucleic acid can have an abundance of at least about 70% of the total nucleic acid in a sample to about 98% of the total nucleic acid in a sample. In some embodiments, a majority nucleic acid can have an abundance of at least about 75% of the total nucleic acid in a sample to about 97% of the total nucleic acid in a sample. For example, a majority nucleic acid can have an abundance of at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the total nucleic acid in a sample. In some embodiments, the majority nucleic acid is extracellular DNA. In some embodiments, the majority nucleic acid is extracellular maternal DNA. In some embodiments, the majority nucleic acid is DNA from healthy tissue. In some embodiments, the majority nucleic acid is DNA from non-tumor cells.

In some embodiments, a minority species of extracellular nucleic acid is of a length of about 500 base pairs or less (e.g., about 80, 85, 90, 91, 92, 93, 94, 95, 96, 97, 98, 99 or 100% of minority species nucleic acid is of a length of about 500 base pairs or less). In some embodiments, a minority species of extracellular nucleic acid is of a length of about 300 base pairs or less (e.g., about 80, 85, 90, 91, 92, 93, 94, 95, 96, 97, 98, 99 or 100% of minority species nucleic acid is of a length of about 300 base pairs or less). In some embodiments, a minority species of extracellular nucleic acid is of a length of about 250 base pairs or less (e.g., about 80, 85, 90, 91, 92, 93, 94, 95, 96, 97, 98, 99 or 100% of minority species nucleic acid is of a length of about 250 base pairs or less). In some embodiments, a minority species of extracellular nucleic acid is of a length of about 200 base pairs or less (e.g., about 80, 85, 90, 91, 92, 93, 94, 95, 96, 97, 98, 99 or 100% of minority species nucleic acid is of a length of about 200 base pairs or less). In some embodiments, a minority species of extracellular nucleic acid is of a length of about 150 base pairs or less (e.g., about 80, 85, 90, 91, 92, 93, 94, 95, 96, 97, 98, 99 or 100% of minority species nucleic acid is of a length of about 150 base pairs or less). In some embodiments, a minority species of extracellular nucleic acid is of a length of about 100 base pairs or less (e.g., about 80, 85, 90, 91, 92, 93, 94, 95, 96, 97, 98, 99 or 100% of minority species nucleic acid is of a length of about 100 base pairs or less). In some embodiments, a minority species of extracellular nucleic acid is of a length of about 50 base pairs or less (e.g., about 80, 85, 90, 91, 92, 93, 94, 95, 96, 97, 98, 99 or 100% of minority species nucleic acid is of a length of about 50 base pairs or less).

Nucleic acid may be provided for conducting methods described herein with or without processing of the sample(s) containing the nucleic acid. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, small fragments of fetal nucleic acid (e.g., 30 to 500 bp fragments) can be purified, or partially purified, from a mixture comprising both fetal and maternal nucleic acid fragments. In certain examples, nucleosomes comprising smaller fragments of fetal nucleic acid can be purified from a mixture of larger nucleosome complexes comprising larger fragments of maternal nucleic acid. In certain examples, cancer cell nucleic acid can be purified from a mixture comprising cancer cell and non-cancer cell nucleic acid. In certain examples, nucleosomes comprising small fragments of cancer cell nucleic acid can be purified from a mixture of larger nucleosome complexes comprising larger fragments of non-cancer nucleic acid. In some embodiments, nucleic acid is provided for conducting methods described herein without prior processing of the sample(s) containing the nucleic acid. For example, nucleic acid may be analyzed directly from a sample without prior extraction, purification, partial purification, and/or amplification.

In some embodiments nucleic acids are sheared or cleaved prior to, during or after a method described herein. The term "shearing" or "cleavage" generally refers to a procedure or conditions in which a nucleic acid molecule, such as a nucleic acid template gene molecule or amplified product thereof, may be severed into two (or more) smaller nucleic acid molecules. Such shearing or cleavage can be sequence specific, base specific, or nonspecific, and can be accomplished by any of a variety of methods, reagents or conditions, including, for example, chemical, enzymatic, physical shearing (e.g., physical fragmentation). Sheared or cleaved nucleic acids may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs.

Sheared or cleaved nucleic acids can be generated by a suitable method, non-limiting examples of which include physical methods (e.g., shearing, e.g., sonication, French press, heat, UV irradiation, the like), enzymatic processes (e.g., enzymatic cleavage agents (e.g., a suitable nuclease, a suitable restriction enzyme, a suitable methylation sensitive restriction enzyme)), chemical methods (e.g., alkylation, DMS, piperidine, acid hydrolysis, base hydrolysis, heat, the like, or combinations thereof), processes described in U.S. Patent Application Publication No. 2005/0112590, the like or combinations thereof. The average, mean or nominal length of the resulting nucleic acid fragments can be controlled by selecting an appropriate fragment-generating method.

The term "amplified" as used herein refers to subjecting a target nucleic acid in a sample to a process that linearly or exponentially generates amplicon nucleic acids having the same or substantially the same nucleotide sequence as the target nucleic acid, or part thereof. In certain embodiments the term "amplified" refers to a method that comprises a polymerase chain reaction (PCR). In certain instances, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule).

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any suitable form useful for conducting a sequence analysis.

Enriching Nucleic Acids

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, cancer nucleic acid, patient nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with a method provided herein. Thus, in certain embodiments, methods of the technology comprise an additional step of enriching for a subpopulation of nucleic acid in a sample, such as, for example, cancer or fetal nucleic acid. In certain embodiments, a method for determining fraction of cancer cell nucleic acid or fetal fraction also can be used to enrich for cancer or fetal nucleic acid. In certain embodiments, nucleic acid from normal tissue (e.g., non-cancer cells) is selectively removed (partially, substantially, almost completely or completely) from the sample. In certain embodiments, maternal nucleic acid is selectively removed (partially, substantially, almost completely or completely) from the sample. In certain embodiments, enriching for a particular low copy number species nucleic acid (e.g., cancer or fetal nucleic acid) may improve quantitative sensitivity. Methods for enriching a sample for a particular species of nucleic acid are described, for example, in U.S. Pat. No. 6,927,028, International Patent Application Publication No. WO 2007/140417, International Patent Application Publication No. WO 2007/147063, International Patent Application Publication No. WO 2009/032779, International Patent Application Publication No. WO 2009/032781, International Patent Application Publication No. WO 2010/033639, International Patent Application Publication No. WO 2011/034631, International Patent Application Publication No. WO 2006/056480, and International Patent Application Publication No. WO 2011/143659, the entire content of each is incorporated herein by reference, including all text, tables, equations and drawings.

In some embodiments, nucleic acid is enriched for certain target fragment species and/or reference fragment species. In certain embodiments, nucleic acid is enriched for a specific nucleic acid fragment length or range of fragment lengths using one or more length-based separation methods described below. In certain embodiments, nucleic acid is enriched for fragments from a select genomic region (e.g., chromosome) using one or more sequence-based separation methods described herein and/or known in the art.

Non-limiting examples of methods for enriching for a nucleic acid subpopulation in a sample include methods that exploit epigenetic differences between nucleic acid species (e.g., methylation-based fetal nucleic acid enrichment methods described in U.S. Patent Application Publication No. 2010/0105049, which is incorporated by reference herein); restriction endonuclease enhanced polymorphic sequence approaches (e.g., such as a method described in U.S. Patent Application Publication No. 2009/0317818, which is incorporated by reference herein); selective enzymatic degradation approaches; massively parallel signature sequencing (MPSS) approaches; amplification (e.g., PCR)-based approaches (e.g., loci-specific amplification methods, multiplex SNP allele PCR approaches; universal amplification methods); pull-down approaches (e.g., biotinylated ultramer pull-down methods); extension and ligation-based methods (e.g., molecular inversion probe (MIP) extension and ligation); and combinations thereof.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments often are isolated away from the remaining fragments in the nucleic acid sample. In certain embodiments, the separated target fragments and the separated reference fragments also are isolated away from each other (e.g., isolated in separate assay compartments). In certain embodiments, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from a nucleic acid sample. Commercially available nucleic acid capture systems include, for example, Nimblegen sequence capture system (Roche NimbleGen, Madison, Wis.); Illumina BEADARRAY platform (Illumina, San Diego, Calif.); Affymetrix GENECHIP platform (Affymetrix, Santa Clara, Calif.); Agilent SureSelect Target Enrichment System (Agilent Technologies, Santa Clara, Calif.); and related platforms. Such methods typically involve hybridization of a capture oligonucleotide to a part or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome). In certain embodiments, a hybridization-based method (e.g., using oligonucleotide arrays) can be used to enrich for nucleic acid sequences from certain chromosomes (e.g., a potentially aneuploid chromosome, reference chromosome or other chromosome of interest), genes or regions of interest thereof. Thus, in some embodiments, a nucleic acid sample is optionally enriched by capturing a subset of fragments using capture oligonucleotides complementary to, for example, selected genes in the sample DNA. In certain instances, captured fragments are amplified. For example, captured fragments containing adapters may be amplified using primers complementary to the adapter oligonucleotides to form collections of amplified fragments, indexed according adapter sequence. In some embodiments, nucleic acid is enriched for fragments from a select genomic region (e.g., chromosome, a gene) by amplification of one or more regions of interest using oligonucleotides (e.g., PCR primers) complementary to sequences in fragments containing the region(s) of interest, or part(s) thereof.

In some embodiments, nucleic acid is enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In certain instances, length-based separation approaches can include selective sequence tagging approaches, fragment circularization, chemical treatment (e.g., formaldehyde, polyethylene glycol (PEG) precipitation), mass spectrometry and/or size-specific nucleic acid amplification, for example.

Nucleic Acid Quantification

The amount of nucleic acid (e.g., concentration, relative amount, absolute amount, copy number, and the like) in a sample may be determined. The amount of a minority nucleic acid (e.g., concentration, relative amount, absolute amount, copy number, and the like) in nucleic acid is determined in some embodiments. In certain embodiments, the amount of a minority nucleic acid species in a sample is referred to as "minority species fraction." In some embodiments "minority species fraction" refers to the fraction of a minority nucleic acid species in circulating cell-free nucleic acid in a sample (e.g., a blood sample, a serum sample, a plasma sample, a urine sample) obtained from a subject.

The amount of a minority nucleic acid in extracellular nucleic acid can be quantified and used in conjunction with a method provided herein. Thus, in certain embodiments, methods described herein comprise an additional step of determining the amount of a minority nucleic acid. The amount of a minority nucleic acid can be determined in a sample from a subject before or after processing to prepare sample nucleic acid. In certain embodiments, the amount of a minority nucleic acid is determined in a sample after sample nucleic acid is processed and prepared, which amount is utilized for further assessment. In some embodiments, an outcome comprises factoring the minority species fraction in the sample nucleic acid (e.g., adjusting counts, removing samples, making a call or not making a call).

A determination of minority species fraction can be performed before, during, or at any one point in a method described herein, or after certain methods described herein (e.g., detection of a genetic variation). For example, to conduct a genetic variation determination method with a certain sensitivity or specificity, a minority nucleic acid quantification method may be implemented prior to, during or after genetic variation determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more minority nucleic acid. In some embodiments, samples determined as having a certain threshold amount of minority nucleic acid (e.g., about 15% or more minority nucleic acid; about 4% or more minority nucleic acid) are further analyzed for a genetic variation, or the presence or absence of a genetic variation, for example. In certain embodiments, determinations of, for example, a genetic variation are selected (e.g., selected and communicated to a patient) only for samples having a certain threshold amount of a minority nucleic acid (e.g., about 15% or more minority nucleic acid; about 4% or more minority nucleic acid).

The amount of cancer cell nucleic acid (e.g., concentration, relative amount, absolute amount, copy number, and the like) in nucleic acid is determined in some embodiments. In certain instances, the amount of cancer cell nucleic acid in a sample is referred to as "fraction of cancer cell nucleic acid," and sometimes is referred to as "cancer fraction" or "tumor fraction." In some embodiments "fraction of cancer cell nucleic acid" refers to the fraction of cancer cell nucleic acid in circulating cell-free nucleic acid in a sample (e.g., a blood sample, a serum sample, a plasma sample, a urine sample) obtained from a subject.

The amount of fetal nucleic acid (e.g., concentration, relative amount, absolute amount, copy number, and the like) in nucleic acid is determined in some embodiments. In certain embodiments, the amount of fetal nucleic acid in a sample is referred to as "fetal fraction." In some embodiments "fetal fraction" refers to the fraction of fetal nucleic acid in circulating cell-free nucleic acid in a sample (e.g., a blood sample, a serum sample, a plasma sample, a urine sample) obtained from a pregnant female. Certain methods described herein or known in the art for determining fetal fraction can be used for determining a fraction of cancer cell nucleic acid and/or a minority species fraction.

In certain instances, fetal fraction may be determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation) between mother and fetus, or fetal RNA markers in maternal blood plasma (see, e.g., Lo, 2005, Journal of Histochemistry and Cytochemistry 53 (3): 293-296)). Determination of fetal fraction sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample.

In certain embodiments, a minority species fraction can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method for determining fetal fraction, for example, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome.

A minority species fraction can be determined, in some embodiments, using methods that incorporate information derived from chromosomal aberrations as described, for example, in International Patent Application Publication No. WO 2014/055774, which is incorporated by reference herein. A minority species fraction can be determined, in some embodiments, using methods that incorporate information derived from sex chromosomes as described, for example, in U.S. Patent Application Publication No. 2013/0288244 and U.S. Patent Application Publication No. 2013/0338933, each of which is incorporated by reference herein.

A minority species fraction can be determined in some embodiments using methods that incorporate fragment length information (e.g., fragment length ratio (FLR) analysis, fetal ratio statistic (FRS) analysis as described in International Patent Application Publication No. WO 2013/177086, which is incorporated by reference herein). Cell-free fetal nucleic acid fragments generally are shorter than maternally-derived nucleic acid fragments (see, e.g., Chan et al. (2004) Clin. Chem. 50:88-92; Lo et al. (2010) Sci. Transl. Med. 2:61ra91). Thus, fetal fraction can be determined, in some embodiments, by counting fragments under a particular length threshold and comparing the counts, for example, to counts from fragments over a particular length threshold and/or to the amount of total nucleic acid in the sample. Methods for counting nucleic acid fragments of a particular length are described in further detail in International Patent Application Publication No. WO 2013/177086.

A minority species fraction can be determined, in some embodiments, according to portion-specific fraction estimates (e.g., as described in International Patent Application Publication No. WO 2014/205401, which is incorporated by reference herein). Without being limited to theory, the amount of reads from fetal CCF fragments (e.g., fragments of a particular length, or range of lengths) often map with ranging frequencies to portions (e.g., within the same sample, e.g., within the same sequencing run). Also, without being limited to theory, certain portions, when compared among multiple samples, tend to have a similar representation of reads from fetal CCF fragments (e.g., fragments of a particular length, or range of lengths), and that the representation correlates with portion-specific fetal fractions (e.g., the relative amount, percentage or ratio of CCF fragments originating from a fetus). Portion-specific fetal fraction estimates generally are determined according to portion-specific parameters and their relation to fetal fraction.

In some embodiments, the determination of minority species fraction (e.g., fraction of cancer cell nucleic acid; fetal fraction) is not required or necessary for identifying the presence or absence of a genetic variation. In some embodiments, identifying the presence or absence of a genetic variation does not require a sequence differentiation of a minority nucleic acid versus a majority nucleic acid. In certain embodiments, this is because the summed contribution of both minority and majority sequences in a particular chromosome, chromosome portion or part thereof is analyzed. In some embodiments, identifying the presence or absence of a genetic variation does not rely on a priori sequence information that would distinguish minority nucleic acid from majority nucleic acid.

Nucleic Acid Library

In some embodiments a nucleic acid library is a plurality of polynucleotide molecules (e.g., a sample of nucleic acids) that are prepared, assembled and/or modified for a specific process, non-limiting examples of which include immobilization on a solid phase (e.g., a solid support, a flow cell, a bead), enrichment, amplification, cloning, detection and/or for nucleic acid sequencing. In certain embodiments, a nucleic acid library is prepared prior to or during a sequencing process. A nucleic acid library (e.g., sequencing library) can be prepared by a suitable method as known in the art. A nucleic acid library can be prepared by a targeted or a non-targeted preparation process.

In some embodiments a library of nucleic acids is modified to comprise a chemical moiety (e.g., a functional group) configured for immobilization of nucleic acids to a solid support. In some embodiments a library of nucleic acids is modified to comprise a biomolecule (e.g., a functional group) and/or member of a binding pair configured for immobilization of the library to a solid support, non-limiting examples of which include thyroxin-binding globulin, steroid-binding proteins, antibodies, antigens, haptens, enzymes, lectins, nucleic acids, repressors, protein A, protein G, avidin, streptavidin, biotin, complement component C1q, nucleic acid-binding proteins, receptors, carbohydrates, oligonucleotides, polynucleotides, complementary nucleic acid sequences, the like and combinations thereof. Some examples of specific binding pairs include, without limitation: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; an oligonucleotide or polynucleotide and its corresponding complement; the like or combinations thereof.

In some embodiments, a library of nucleic acids is modified to comprise one or more polynucleotides of known composition, non-limiting examples of which include an identifier (e.g., a tag, an indexing tag), a capture sequence, a label, an adapter, a restriction enzyme site, a promoter, an enhancer, an origin of replication, a stem loop, a complimentary sequence (e.g., a primer binding site, an annealing site), a suitable integration site (e.g., a transposon, a viral integration site), a modified nucleotide, the like or combinations thereof. Polynucleotides of known sequence can be added at a suitable position, for example on the 5' end, 3' end or within a nucleic acid sequence. Polynucleotides of known sequence can be the same or different sequences. In some embodiments a polynucleotide of known sequence is configured to hybridize to one or more oligonucleotides immobilized on a surface (e.g., a surface in flow cell). For example, a nucleic acid molecule comprising a 5' known sequence may hybridize to a first plurality of oligonucleotides while the 3' known sequence may hybridize to a second plurality of oligonucleotides. In some embodiments a library of nucleic acid can comprise chromosome-specific tags, capture sequences, labels and/or adapters. In some embodiments, a library of nucleic acids comprises one or more detectable labels. In some embodiments one or more detectable labels may be incorporated into a nucleic acid library at a 5' end, at a 3' end, and/or at any nucleotide position within a nucleic acid in the library. In some embodiments a library of nucleic acids comprises hybridized oligonucleotides. In certain embodiments hybridized oligonucleotides are labeled probes. In some embodiments a library of nucleic acids comprises hybridized oligonucleotide probes prior to immobilization on a solid phase.

In some embodiments, a polynucleotide of known sequence comprises a universal sequence. A universal sequence is a specific nucleotide sequence that is integrated into two or more nucleic acid molecules or two or more subsets of nucleic acid molecules where the universal sequence is the same for all molecules or subsets of molecules that it is integrated into. A universal sequence is often designed to hybridize to and/or amplify a plurality of different sequences using a single universal primer that is complementary to a universal sequence. In some embodiments two (e.g., a pair) or more universal sequences and/or universal primers are used. A universal primer often comprises a universal sequence. In some embodiments adapters (e.g., universal adapters) comprise universal sequences. In some embodiments one or more universal sequences are used to capture, identify and/or detect multiple species or subsets of nucleic acids.

In certain embodiments of preparing a nucleic acid library, (e.g., in certain sequencing by synthesis procedures), nucleic acids are size selected and/or fragmented into lengths of several hundred base pairs, or less (e.g., in preparation for library generation). In some embodiments, library preparation is performed without fragmentation (e.g., when using cell-free DNA).

In certain embodiments, a ligation-based library preparation method is used (e.g., ILLUMINA TRUSEQ, Illumina, San Diego Calif.). Ligation-based library preparation methods often make use of an adapter (e.g., a methylated adapter) design which can incorporate an index sequence at the initial ligation step and often can be used to prepare samples for single-read sequencing, paired-end sequencing and multiplexed sequencing. For example, nucleic acids (e.g., fragmented nucleic acids or cell-free DNA) may be end repaired by a fill-in reaction, an exonuclease reaction or a combination thereof. In some embodiments the resulting blunt-end repaired nucleic acid can then be extended by a single nucleotide, which is complementary to a single nucleotide overhang on the 3' end of an adapter/primer. Any nucleotide can be used for the extension/overhang nucleotides. In some embodiments nucleic acid library preparation comprises ligating an adapter oligonucleotide. Adapter oligonucleotides are often complementary to flow-cell anchors, and sometimes are utilized to immobilize a nucleic acid library to a solid support, such as the inside surface of a flow cell, for example. In some embodiments, an adapter oligonucleotide comprises an identifier, one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing). In some embodiments, an adapter oligonucleotide comprises one or more of primer annealing polynucleotide (e.g., for annealing to flow cell attached oligonucleotides and/or to free amplification primers), an index polynucleotide (e.g., for tracking nucleic acid from different samples), and a barcode polynucleotide (e.g., for tracking individual molecules of sample nucleic acid that are amplified prior to sequencing).

An identifier can be a suitable detectable label incorporated into or attached to a nucleic acid (e.g., a polynucleotide) that allows detection and/or identification of nucleic acids that comprise the identifier. In some embodiments an identifier is incorporated into or attached to a nucleic acid during a sequencing method (e.g., by a polymerase). Non-limiting examples of identifiers include nucleic acid tags, nucleic acid indexes or barcodes, a radiolabel (e.g., an isotope), metallic label, a fluorescent label, a chemiluminescent label, a phosphorescent label, a fluorophore quencher, a dye, a protein (e.g., an enzyme, an antibody or part thereof, a linker, a member of a binding pair), the like or combinations thereof. In some embodiments an identifier (e.g., a nucleic acid index or barcode) is a unique, known and/or identifiable sequence of nucleotides or nucleotide analogues. In some embodiments identifiers are six or more contiguous nucleotides. A multitude of fluorophores are available with a variety of different excitation and emission spectra. Any suitable type and/or number of fluorophores can be used as an identifier. In some embodiments 1 or more, 2 or more, 3 or more, 4 or more, 5 or more, 6 or more, 7 or more, 8 or more, 9 or more, 10 or more, 20 or more, 30 or more or 50 or more different identifiers are utilized in a method described herein (e.g., a nucleic acid detection and/or sequencing method). In some embodiments, one or two types of identifiers (e.g., fluorescent labels) are linked to each nucleic acid in a library. Detection and/or quantification of an identifier can be performed by a suitable method, apparatus or machine, non-limiting examples of which include flow cytometry, quantitative polymerase chain reaction (qPCR), gel electrophoresis, a luminometer, a fluorometer, a spectrophotometer, a suitable gene-chip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof.

In some embodiments, a transposon-based library preparation method is used (e.g., EPICENTRE NEXTERA, Epicentre, Madison, Wis.). Transposon-based methods typically use in vitro transposition to simultaneously fragment and tag DNA in a single-tube reaction (often allowing incorporation of platform-specific tags and optional barcodes), and prepare sequencer-ready libraries.

In some embodiments a nucleic acid library or parts thereof are amplified (e.g., amplified by a PCR-based method). In some embodiments a sequencing method comprises amplification of a nucleic acid library. A nucleic acid library can be amplified prior to or after immobilization on a solid support (e.g., a solid support in a flow cell). Nucleic acid amplification includes the process of amplifying or increasing the numbers of a nucleic acid template and/or of a complement thereof that are present (e.g., in a nucleic acid library), by producing one or more copies of the template and/or its complement. Amplification can be carried out by a suitable method. A nucleic acid library can be amplified by a thermocycling method or by an isothermal amplification method. In some embodiments a rolling circle amplification method is used. In some embodiments amplification takes place on a solid support (e.g., within a flow cell) where a nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support. In some embodiments, modified nucleic acid (e.g., nucleic acid modified by addition of adapters) is amplified.

In some embodiments solid phase amplification comprises a nucleic acid amplification reaction comprising only one species of oligonucleotide primer immobilized to a surface. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge amplification, emulsion PCR, WildFire amplification (e.g., U.S. Patent Application Publication No. 2013/0012399), the like or combinations thereof.

Nucleic Acid Sequencing and Processing

Methods provided herein generally include nucleic acid sequencing and analysis. In some embodiments, nucleic acid is sequenced and the sequencing product (e.g., a collection of sequence reads) is processed prior to, or in conjunction with, an analysis of the sequenced nucleic acid. For example, sequence reads may be processed according to one or more of the following: aligning, mapping, filtering portions, selecting portions, counting, normalizing, weighting, generating a profile, and the like, and combinations thereof. Certain processing steps may be performed in any order and certain processing steps may be repeated. For example, portions may be filtered followed by sequence read count normalization, and, in certain embodiments, sequence read counts may be normalized followed by portion filtering. In some embodiments, a portion filtering step is followed by sequence read count normalization followed by a further portion filtering step. Certain sequencing methods and processing steps are described in further detail below.

Sequencing

In some embodiments, nucleic acid (e.g., nucleic acid fragments, sample nucleic acid, cell-free nucleic acid) is sequenced. In certain instances, a full or substantially full sequence is obtained and sometimes a partial sequence is obtained. Nucleic acid sequencing generally produces a collection of sequence reads. As used herein, "reads" (e.g., "a read," "a sequence read") are short nucleotide sequences produced by any sequencing process described herein or known in the art. Reads can be generated from one end of nucleic acid fragments ("single-end reads"), and sometimes are generated from both ends of nucleic acid fragments (e.g., paired-end reads, double-end reads).

The length of a sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 bp to about 900 bp long. In certain embodiments sequence reads are of a mean, median, average or absolute length of about 1000 bp or more.

In some embodiments the nominal, average, mean or absolute length of single-end reads sometimes is about 15 contiguous nucleotides to about 50 or more contiguous nucleotides, about 15 contiguous nucleotides to about 40 or more contiguous nucleotides, and sometimes about 15 contiguous nucleotides or about 36 or more contiguous nucleotides. In certain embodiments the nominal, average, mean or absolute length of single-end reads is about 20 to about 30 bases, or about 24 to about 28 bases in length. In certain embodiments the nominal, average, mean or absolute length of single-end reads is about 1, 2, 3, 4, 5, 6, 7, 8, 9, 10, 11, 12, 13, 14, 15, 16, 17, 18, 19, 21, 22, 23, 24, 25, 26, 27, 28 or about 29 bases or more in length. In certain embodiments, the nominal, average, mean or absolute length of paired-end reads sometimes is about 10 contiguous nucleotides to about 25 contiguous nucleotides or more (e.g., about 10, 11, 12, 13, 14, 15, 16, 17, 18, 19, 20, 21, 22, 23, 24 or 25 nucleotides in length or more), about 15 contiguous nucleotides to about 20 contiguous nucleotides or more, and sometimes is about 17 contiguous nucleotides or about 18 contiguous nucleotides.

In some embodiments, nucleotide sequence reads obtained from a sample are partial nucleotide sequence reads. As used herein, "partial nucleotide sequence reads" refers to sequence reads of any length with incomplete sequence information, also referred to as sequence ambiguity. Partial nucleotide sequence reads may lack information regarding nucleobase identity and/or nucleobase position or order. Partial nucleotide sequence reads generally do not include sequence reads in which the only incomplete sequence information (or in which less than all of the bases are sequenced or determined) is from inadvertent or unintentional sequencing errors. Such sequencing errors can be inherent to certain sequencing processes and include, for example, incorrect calls for nucleobase identity, and missing or extra nucleobases. Thus, for partial nucleotide sequence reads herein, certain information about the sequence is often deliberately excluded. That is, one deliberately obtains sequence information with respect to less than all of the nucleobases or which might otherwise be characterized as or be a sequencing error. In some embodiments, a partial nucleotide sequence read can span a portion of a nucleic acid fragment. In some embodiments, a partial nucleotide sequence read can span the entire length of a nucleic acid fragment. Partial nucleotide sequence reads are described, for example, in International Patent Application Publication No. WO2013/052907, the entire content of which is incorporated herein by reference, including all text, tables, equations and drawings.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from a sample from a subject can be reads from a mixture of a minority nucleic acid and a majority nucleic acid. For example, sequence reads obtained from the blood of a cancer patient can be reads from a mixture of cancer nucleic acid and non-cancer nucleic acid. In another example, sequence reads obtained from the blood of a pregnant female can be reads from a mixture of fetal nucleic acid and maternal nucleic acid. A mixture of relatively short reads can be transformed by processes described herein into a representation of genomic nucleic acid present in the subject, and/or a representation of genomic nucleic acid present in a tumor or a fetus. In certain instances, a mixture of relatively short reads can be transformed into a representation of a copy number alteration, a genetic variation or an aneuploidy, for example. In one example, reads of a mixture of cancer and non-cancer nucleic acid can be transformed into a representation of a composite chromosome or a part thereof comprising features of one or both cancer cell and non-cancer cell chromosomes. In another example, reads of a mixture of maternal and fetal nucleic acid can be transformed into a representation of a composite chromosome or a part thereof comprising features of one or both maternal and fetal chromosomes.

In some instances, circulating cell free nucleic acid fragments (CCF fragments) obtained from a cancer patient comprise nucleic acid fragments originating from normal cells (i.e., non-cancer fragments) and nucleic acid fragments originating from cancer cells (i.e., cancer fragments). Sequence reads derived from CCF fragments originating from normal cells (i.e., non-cancerous cells) are referred to herein as "non-cancer reads." Sequence reads derived from CCF fragments originating from cancer cells are referred to herein as "cancer reads." CCF fragments from which non-cancer reads are obtained may be referred to herein as non-cancer templates and CCF fragments from which cancer reads are obtained may be referred herein to as cancer templates.

In some instances, circulating cell free nucleic acid fragments (CCF fragments) obtained from a pregnant female comprise nucleic acid fragments originating from fetal cells (i.e., fetal fragments) and nucleic acid fragments originating from maternal cells (i.e., maternal fragments). Sequence reads derived from CCF fragments originating from a fetus are referred to herein as "fetal reads." Sequence reads derived from CCF fragments originating from the genome of a pregnant female (e.g., a mother) bearing a fetus are referred to herein as "maternal reads." CCF fragments from which fetal reads are obtained are referred to herein as fetal templates and CCF fragments from which maternal reads are obtained are referred herein to as maternal templates.

In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, some or all nucleic acids in a sample are enriched and/or amplified (e.g., non-specifically, e.g., by a PCR based method) prior to or during sequencing. In certain embodiments specific nucleic acid species or subsets in a sample are enriched and/or amplified prior to or during sequencing. In some embodiments, a species or subset of a pre-selected pool of nucleic acids is sequenced randomly. In some embodiments, nucleic acids in a sample are not enriched and/or amplified prior to or during sequencing.

In some embodiments, a representative fraction of a genome is sequenced and is sometimes referred to as "coverage" or "fold coverage." For example, a 1-fold coverage indicates that roughly 100% of the nucleotide sequences of the genome are represented by reads. In some instances, fold coverage is referred to as (and is directly proportional to) "sequencing depth." In some embodiments, "fold coverage" is a relative term referring to a prior sequencing run as a reference. For example, a second sequencing run may have 2-fold less coverage than a first sequencing run. In some embodiments a genome is sequenced with redundancy, where a given region of the genome can be covered by two or more reads or overlapping reads (e.g., a "fold coverage" greater than 1, e.g., a 2-fold coverage). In some embodiments, a genome (e.g., a whole genome) is sequenced with about 0.1-fold to about 100-fold coverage, about 0.2-fold to 20-fold coverage, or about 0.2-fold to about 1-fold coverage (e.g., about 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage). In some embodiments, specific parts of a genome (e.g., genomic parts from targeted and/or probe-based methods) are sequenced and fold coverage values generally refer to the fraction of the specific genomic parts sequenced (i.e., fold coverage values do not refer to the whole genome). In some instances, specific genomic parts are sequenced at 1000-fold coverage or more. For example, specific genomic parts may be sequenced at 2000-fold, 5,000-fold, 10,000-fold, 20,000-fold, 30,000-fold, 40,000-fold or 50,000-fold coverage. In some embodiments, sequencing is at about 1,000-fold to about 100,000-fold coverage. In some embodiments, sequencing is at about 10,000-fold to about 70,000-fold coverage. In some embodiments, sequencing is at about 20,000-fold to about 60,000-fold coverage. In some embodiments, sequencing is at about 30,000-fold to about 50,000-fold coverage.

In some embodiments, one nucleic acid sample from one individual is sequenced. In certain embodiments, nucleic acids from each of two or more samples are sequenced, where samples are from one individual or from different individuals. In certain embodiments, nucleic acid samples from two or more biological samples are pooled, where each biological sample is from one individual or two or more individuals, and the pool is sequenced. In the latter embodiments, a nucleic acid sample from each biological sample often is identified by one or more unique identifiers.

In some embodiments, a sequencing method utilizes identifiers that allow multiplexing of sequence reactions in a sequencing process. The greater the number of unique identifiers, the greater the number of samples and/or chromosomes for detection, for example, that can be multiplexed in a sequencing process. A sequencing process can be performed using any suitable number of unique identifiers (e.g., 4, 8, 12, 24, 48, 96, or more).

A sequencing process sometimes makes use of a solid phase, and sometimes the solid phase comprises a flow cell on which nucleic acid from a library can be attached and reagents can be flowed and contacted with the attached nucleic acid. A flow cell sometimes includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments the number of samples analyzed in a given flow cell lane is dependent on the number of unique identifiers utilized during library preparation and/or probe design. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell. Non-limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively).

Any suitable method of sequencing nucleic acids can be used, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments, sequencing technologies that include the use of nucleic acid imaging technologies (e.g., transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments, MPS sequencing methods utilize a targeted approach, where specific chromosomes, genes or regions of interest are sequenced. In certain embodiments, a non-targeted approach is used where most or all nucleic acids in a sample are sequenced, amplified and/or captured randomly.

In some embodiments a targeted enrichment, amplification and/or sequencing approach is used. A targeted approach often isolates, selects and/or enriches a subset of nucleic acids in a sample for further processing by use of sequence-specific oligonucleotides. In some embodiments a library of sequence-specific oligonucleotides are utilized to target (e.g., hybridize to) one or more sets of nucleic acids in a sample. Sequence-specific oligonucleotides and/or primers are often selective for particular sequences (e.g., unique nucleic acid sequences) present in one or more chromosomes, genes, exons, introns, and/or regulatory regions of interest. Any suitable method or combination of methods can be used for enrichment, amplification and/or sequencing of one or more subsets of targeted nucleic acids. In some embodiments targeted sequences are isolated and/or enriched by capture to a solid phase (e.g., a flow cell, a bead) using one or more sequence-specific anchors. In some embodiments targeted sequences are enriched and/or amplified by a polymerase-based method (e.g., a PCR-based method, by any suitable polymerase based extension) using sequence-specific primers and/or primer sets. Sequence specific anchors often can be used as sequence-specific primers.

MPS sequencing sometimes makes use of sequencing by synthesis and certain imaging processes. A nucleic acid sequencing technology that may be used in a method described herein is sequencing-by-synthesis and reversible terminator-based sequencing (e.g., Illumina's Genome Analyzer; Genome Analyzer II; HISEQ 2000; HISEQ 2500 (Illumina, San Diego Calif.)). With this technology, millions of nucleic acid (e.g., DNA) fragments can be sequenced in parallel. In one example of this type of sequencing technology, a flow cell is used which contains an optically transparent slide with 8 individual lanes on the surfaces of which are bound oligonucleotide anchors (e.g., adapter primers).

Sequencing by synthesis generally is performed by iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEMFET sensor), the like or combinations thereof.

Any suitable MPS method, system or technology platform for conducting methods described herein can be used to obtain nucleic acid sequence reads. Non-limiting examples of MPS platforms include Illumina/Solex/HiSeq (e.g., Illumina's Genome Analyzer; Genome Analyzer 11; HISEQ 2000; HISEQ), SOLiD, Roche/454, PACBIO and/or SMRT, Helicos True Single Molecule Sequencing, Ion Torrent and Ion semiconductor-based sequencing (e.g., as developed by Life Technologies), WildFire, 5500, 5500xl W and/or 5500xl W Genetic Analyzer based technologies (e.g., as developed and sold by Life Technologies, U.S. Patent Application Publication No. 2013/0012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing, the like or combinations thereof. Other sequencing methods that may be used to conduct methods herein include digital PCR, sequencing by hybridization, nanopore sequencing, chromosome-specific sequencing (e.g., using DANSR (digital analysis of selected regions) technology.

In some embodiments, sequence reads are generated, obtained, gathered, assembled, manipulated, transformed, processed, and/or provided by a sequence module. A machine comprising a sequence module can be a suitable machine and/or apparatus that determines the sequence of a nucleic acid utilizing a sequencing technology known in the art. In some embodiments a sequence module can align, assemble, fragment, complement, reverse complement, and/or or error check (e.g., error correct sequence reads).

Mapping Reads

Sequence reads can be mapped and the number of reads mapping to a specified nucleic acid region (e.g., a chromosome or portion thereof) are referred to as counts. Any suitable mapping method (e.g., process, process, program, software, module, the like or combination thereof) can be used. Certain aspects of mapping processes are described hereafter.

Mapping nucleotide sequence reads (i.e., sequence information from a fragment whose physical genomic position is unknown) can be performed in a number of ways, and often comprises alignment of the obtained sequence reads with a matching sequence in a reference genome. In such alignments, sequence reads generally are aligned to a reference sequence and those that align are designated as being "mapped," as "a mapped sequence read" or as "a mapped read." In certain embodiments, a mapped sequence read is referred to as a "hit" or "count." In some embodiments, mapped sequence reads are grouped together according to various parameters and assigned to particular genomic portions, which are discussed in further detail below.

The terms "aligned," "alignment," or "aligning" generally refer to two or more nucleic acid sequences that can be identified as a match (e.g., 100% identity) or partial match. Alignments can be done manually or by a computer (e.g., a software, program, module, or process), non-limiting examples of which include the Efficient Local Alignment of Nucleotide Data (ELAND) computer program distributed as part of the Illumina Genomics Analysis pipeline. Alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand (e.g., sense or antisense strand). In certain embodiments a nucleic acid sequence is aligned with the reverse complement of another nucleic acid sequence.

Various computational methods can be used to map each sequence read to a portion. Non-limiting examples of computer process that can be used to align sequences include, without limitation, BLAST, BLITZ, FASTA, BOWTIE 1, BOWTIE 2, ELAND, MAQ, PROBEMATCH, SOAP, BWA or SEQMAP, or variations thereof or combinations thereof. In some embodiments, sequence reads can be aligned with sequences in a reference genome. In some embodiments, sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search identified sequences against a sequence database. Search hits can then be used to sort the identified sequences into appropriate portions (described hereafter), for example.

In some embodiments, a read may uniquely or non-uniquely map to portions in a reference genome. A read is considered as "uniquely mapped" if it aligns with a single sequence in the reference genome. A read is considered as "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, the term "reference genome" can refer to any particular known, sequenced or characterized genome, whether partial or complete, of any organism or virus which may be used to reference identified sequences from a subject. For example, a reference genome used for human subjects as well as many other organisms can be found at the National Center for Biotechnology Information at World Wide Web URL ncbi.nlm.nih.gov. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes.

In certain embodiments, mappability is assessed for a genomic region (e.g., portion, genomic portion). Mappability is the ability to unambiguously align a nucleotide sequence read to a portion of a reference genome, typically up to a specified number of mismatches, including, for example, 0, 1, 2 or more mismatches. For a given genomic region, the expected mappability can be estimated using a sliding-window approach of a preset read length and averaging the resulting read-level mappability values. Genomic regions comprising stretches of unique nucleotide sequence sometimes have a high mappability value.

Portions

In some embodiments, mapped sequence reads are grouped together according to various parameters and assigned to particular genomic portions (e.g., portions of a reference genome). A "portion" also may be referred to herein as a "genomic section," "bin," "partition," "portion of a reference genome," "portion of a chromosome" or "genomic portion."

A portion often is defined by partitioning of a genome according to one or more features. Non-limiting examples of certain partitioning features include length (e.g., fixed length, non-fixed length) and other structural features. Genomic portions sometimes include one or more of the following features: fixed length, non-fixed length, random length, non-random length, equal length, unequal length (e.g., at least two of the genomic portions are of unequal length), do not overlap (e.g., the 3' ends of the genomic portions sometimes abut the 5' ends of adjacent genomic portions), overlap (e.g., at least two of the genomic portions overlap), contiguous, consecutive, not contiguous, and not consecutive. Genomic portions sometimes are about 1 to about 1,000 kilobases in length (e.g., about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900 kilobases in length), about 5 to about 500 kilobases in length, about 10 to about 100 kilobases in length, or about 40 to about 60 kilobases in length.

Partitioning sometimes is based on, or is based in part on certain informational features, such as, information content and information gain, for example. Non-limiting examples of certain informational features include speed and/or convenience of alignment, sequencing coverage variability, GC content (e.g., stratified GC content, particular GC contents, high or low GC content), uniformity of GC content, other measures of sequence content (e.g., fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, uncertainty value assigned to individual portions of a reference genome, and/or a targeted search for particular features. In some embodiments, information content may be quantified using a p-value profile measuring the significance of particular genomic locations for distinguishing between groups of confirmed normal and abnormal subjects (e.g. euploid and trisomy subjects, respectively).

In some embodiments, partitioning a genome may eliminate similar regions (e.g., identical or homologous regions or sequences) across a genome and only keep unique regions. Regions removed during partitioning may be within a single chromosome, may be one or more chromosomes, or may span multiple chromosomes. In some embodiments, a partitioned genome is reduced and optimized for faster alignment, often focusing on uniquely identifiable sequences.

In some embodiments, genomic portions result from a partitioning based on non-overlapping fixed size, which results in consecutive, non-overlapping portions of fixed length. Such portions often are shorter than a chromosome and often are shorter than a copy number variation region (e.g., a region that is duplicated or is deleted), the latter of which can be referred to as a segment. A "segment" or "genomic segment" often includes two or more fixed-length genomic portions, and often includes two or more consecutive fixed-length portions (e.g., about 2 to about 100 such portions (e.g., 2, 3, 4, 5, 6, 7, 8, 9, 10, 11, 12, 13, 14, 15, 16, 17, 18, 19, 20, 25, 30, 35, 40, 45, 50, 60, 70, 80, 90 such portions)).

Multiple portions sometimes are analyzed in groups, and sometimes reads mapped to portions are quantified according to a particular group of genomic portions. Where portions are partitioned by structural features and correspond to regions in a genome, portions sometimes are grouped into one or more segments and/or one or more regions. Non-limiting examples of regions include sub-chromosome (i.e., shorter than a chromosome), chromosome, autosome, sex chromosome and combinations thereof. One or more sub-chromosome regions sometimes are genes, gene fragments, regulatory sequences, introns, exons, segments (e.g., a segment spanning a copy number alteration region), microduplications, microdeletions and the like. A region sometimes is smaller than a chromosome of interest or is the same size of a chromosome of interest, and sometimes is smaller than a reference chromosome or is the same size as a reference chromosome.

Filtering and/or Selecting Portions

In some embodiments, one or more processing steps can comprise one or more portion filtering steps and/or portion selection steps. The term "filtering" as used herein refers to removing portions or portions of a reference genome from consideration. In certain embodiments one or more portions are filtered (e.g., subjected to a filtering process) thereby providing filtered portions. In some embodiments a filtering process removes certain portions and retains portions (e.g., a subset of portions). Following a filtering process, retained portions are often referred to herein as filtered portions.

Portions of a reference genome can be selected for removal based on any suitable criteria, including but not limited to redundant data (e.g., redundant or overlapping mapped reads), non-informative data (e.g., portions of a reference genome with zero median counts), portions of a reference genome with over represented or under represented sequences, noisy data, the like, or combinations of the foregoing. A filtering process often involves removing one or more portions of a reference genome from consideration and subtracting the counts in the one or more portions of a reference genome selected for removal from the counted or summed counts for the portions of a reference genome, chromosome or chromosomes, or genome under consideration. In some embodiments, portions of a reference genome can be removed successively (e.g., one at a time to allow evaluation of the effect of removal of each individual portion), and in certain embodiments all portions of a reference genome marked for removal can be removed at the same time. In some embodiments, portions of a reference genome characterized by a variance above or below a certain level are removed, which sometimes is referred to herein as filtering "noisy" portions of a reference genome. In certain embodiments, a filtering process comprises obtaining data points from a data set that deviate from the mean profile level of a portion, a chromosome, or part of a chromosome by a predetermined multiple of the profile variance, and in certain embodiments, a filtering process comprises removing data points from a data set that do not deviate from the mean profile level of a portion, a chromosome or part of a chromosome by a predetermined multiple of the profile variance. In some embodiments, a filtering process is utilized to reduce the number of candidate portions of a reference genome analyzed for the presence or absence of a genetic variation and/or copy number alteration (e.g., aneuploidy, microdeletion, microduplication). Reducing the number of candidate portions of a reference genome analyzed for the presence or absence of a genetic variation and/or copy number alteration often reduces the complexity and/or dimensionality of a data set, and sometimes increases the speed of searching for and/or identifying genetic variations and/or copy number alterations by two or more orders of magnitude.

Portions may be processed (e.g., filtered and/or selected) by any suitable method and according to any suitable parameter. Non-limiting examples of features and/or parameters that can be used to filter and/or select portions include redundant data (e.g., redundant or overlapping mapped reads), non-informative data (e.g., portions of a reference genome with zero mapped counts), portions of a reference genome with over represented or under represented sequences, noisy data, counts, count variability, coverage, mappability, variability, a repeatability measure, read density, variability of read density, a level of uncertainty, guanine-cytosine (GC) content, CCF fragment length and/or read length (e.g., a fragment length ratio (FLR), a fetal ratio statistic (FRS)), DNaseI-sensitivity, methylation state, acetylation, histone distribution, chromatin structure, percent repeats, the like or combinations thereof. Portions can be filtered and/or selected according to any suitable feature or parameter that correlates with a feature or parameter listed or described herein. Portions can be filtered and/or selected according to features or parameters that are specific to a portion (e.g., as determined for a single portion according to multiple samples) and/or features or parameters that are specific to a sample (e.g., as determined for multiple portions within a sample). In some embodiments portions are filtered and/or removed according to relatively low mappability, relatively high variability, a high level of uncertainty, relatively long CCF fragment lengths (e.g., low FRS, low FLR), relatively large fraction of repetitive sequences, high GC content, low GC content, low counts, zero counts, high counts, the like, or combinations thereof. In some embodiments portions (e.g., a subset of portions) are selected according to suitable level of mappability, variability, level of uncertainty, fraction of repetitive sequences, count, GC content, the like, or combinations thereof. In some embodiments portions (e.g., a subset of portions) are selected according to relatively short CCF fragment lengths (e.g., high FRS, high FLR). Counts and/or reads mapped to portions are sometimes processed (e.g., normalized) prior to and/or after filtering or selecting portions (e.g., a subset of portions). In some embodiments counts and/or reads mapped to portions are not processed prior to and/or after filtering or selecting portions (e.g., a subset of portions).

In some embodiments, portions may be filtered according to a measure of error (e.g., standard deviation, standard error, calculated variance, p-value, mean absolute error (MAE), average absolute deviation and/or mean absolute deviation (MAD)). In certain instances, a measure of error may refer to count variability. In some embodiments portions are filtered according to count variability. In certain embodiments count variability is a measure of error determined for counts mapped to a portion (i.e., portion) of a reference genome for multiple samples (e.g., multiple sample obtained from multiple subjects, e.g., 50 or more, 100 or more, 500 or more 1000 or more, 5000 or more or 10,000 or more subjects). In some embodiments, portions with a count variability above a pre-determined upper range are filtered (e.g., excluded from consideration). In some embodiments portions with a count variability below a pre-determined lower range are filtered (e.g., excluded from consideration). In some embodiments, portions with a count variability outside a pre-determined range are filtered (e.g., excluded from consideration). In some embodiments portions with a count variability within a pre-determined range are selected (e.g., used for determining the presence or absence of a copy number alteration). In some embodiments, count variability of portions represents a distribution (e.g., a normal distribution). In some embodiments portions are selected within a quantile of the distribution. In some embodiments portions within a 99% quantile of the distribution of count variability are selected.

Sequence reads from any suitable number of samples can be utilized to identify a subset of portions that meet one or more criteria, parameters and/or features described herein. Sequence reads from a group of samples from multiple subjects sometimes are utilized. In some embodiments, the multiple subjects include pregnant females. In some embodiments, the multiple subjects include healthy subjects. In some embodiments, the multiple subjects include cancer patients. One or more samples from each of the multiple subjects can be addressed (e.g., 1 to about 20 samples from each subject (e.g., about 2, 3, 4, 5, 6, 7, 8, 9, 10, 11, 12, 13, 14, 15, 16, 17, 18 or 19 samples)), and a suitable number of subjects may be addressed (e.g., about 2 to about 10,000 subjects (e.g., about 10, 20, 30, 40, 50, 60, 70, 80, 90, 100, 150, 200, 250, 300, 350, 400, 500, 600, 700, 800, 900, 1000, 2000, 3000, 4000, 5000, 6000, 7000, 8000, 9000 subjects)). In some embodiments, sequence reads from the same test sample(s) from the same subject are mapped to portions in the reference genome and are used to generate the subset of portions.

Portions can be selected and/or filtered by any suitable method. In some embodiments portions are selected according to visual inspection of data, graphs, plots and/or charts. In certain embodiments portions are selected and/or filtered (e.g., in part) by a system or a machine comprising one or more microprocessors and memory. In some embodiments portions are selected and/or filtered (e.g., in part) by a non-transitory computer-readable storage medium with an executable program stored thereon, where the program instructs a microprocessor to perform the selecting and/or filtering.

In some embodiments, sequence reads derived from a sample are mapped to all or most portions of a reference genome and a pre-selected subset of portions are thereafter selected. For example, a subset of portions to which reads from fragments under a particular length threshold preferentially map may be selected. Certain methods for pre-selecting a subset of portions are described in U.S. Patent Application Publication No. 2014/0180594, which is incorporated by reference herein. Reads from a selected subset of portions often are utilized in further steps of a determination of the presence or absence of a genetic variation, for example. Often, reads from portions not selected are not utilized in further steps of a determination of the presence or absence of a genetic variation (e.g., reads in the non-selected portions are removed or filtered).

In some embodiments portions associated with read densities (e.g., where a read density is for a portion) are removed by a filtering process and read densities associated with removed portions are not included in a determination of the presence or absence of a copy number alteration (e.g., a chromosome aneuploidy, microduplication, microdeletion). In some embodiments a read density profile comprises and/or consists of read densities of filtered portions. Portions are sometimes filtered according to a distribution of counts and/or a distribution of read densities. In some embodiments portions are filtered according to a distribution of counts and/or read densities where the counts and/or read densities are obtained from one or more reference samples. One or more reference samples may be referred to herein as a training set. In some embodiments portions are filtered according to a distribution of counts and/or read densities where the counts and/or read densities are obtained from one or more test samples. In some embodiments portions are filtered according to a measure of uncertainty for a read density distribution. In certain embodiments, portions that demonstrate a large deviation in read densities are removed by a filtering process. For example, a distribution of read densities (e.g., a distribution of average mean, or median read densities) can be determined, where each read density in the distribution maps to the same portion. A measure of uncertainty (e.g., a MAD) can be determined by comparing a distribution of read densities for multiple samples where each portion of a genome is associated with measure of uncertainty. According to the foregoing example, portions can be filtered according to a measure of uncertainty (e.g., a standard deviation (SD), a MAD) associated with each portion and a predetermined threshold. In certain instances, portions comprising MAD values within the acceptable range are retained and portions comprising MAD values outside of the acceptable range are removed from consideration by a filtering process. In some embodiments, according to the foregoing example, portions comprising read densities values (e.g., median, average or mean read densities) outside a pre-determined measure of uncertainty are often removed from consideration by a filtering process. In some embodiments portions comprising read densities values (e.g., median, average or mean read densities) outside an inter-quartile range of a distribution are removed from consideration by a filtering process. In some embodiments portions comprising read densities values outside more than 2 times, 3 times, 4 times or 5 times an inter-quartile range of a distribution are removed from consideration by a filtering process. In some embodiments portions comprising read densities values outside more than 2 sigma, 3 sigma, 4 sigma, 5 sigma, 6 sigma, 7 sigma or 8 sigma (e.g., where sigma is a range defined by a standard deviation) are removed from consideration by a filtering process.

Sequence Read Quantification

Sequence reads that are mapped or partitioned based on a selected feature or variable can be quantified to determine the amount or number of reads that are mapped to one or more portions (e.g., portion of a reference genome), in some embodiments. In certain embodiments the quantity of sequence reads that are mapped to a portion or segment is referred to as a count or read density.

A count often is associated with a genomic portion. In some embodiments a count is determined from some or all of the sequence reads mapped to (i.e., associated with) a portion. In certain embodiments, a count is determined from some or all of the sequence reads mapped to a group of portions (e.g., portions in a segment or region (described herein)).

A count can be determined by a suitable method, operation or mathematical process. A count sometimes is the direct sum of all sequence reads mapped to a genomic portion or a group of genomic portions corresponding to a segment, a group of portions corresponding to a sub-region of a genome (e.g., copy number variation region, copy number duplication region, copy number deletion region, microduplication region, microdeletion region, chromosome region, autosome region, sex chromosome region) and/or sometimes is a group of portions corresponding to a genome. A read quantification sometimes is a ratio, and sometimes is a ratio of a quantification for portion(s) in region a to a quantification for portion(s) in region b. Region a sometimes is one portion, segment region, copy number variation region, copy number duplication region, copy number deletion region, microduplication region, microdeletion region, chromosome region, autosome region and/or sex chromosome region. Region b independently sometimes is one portion, segment region, copy number variation region, copy number duplication region, copy number deletion region, microduplication region, microdeletion region, chromosome region, autosome region, sex chromosome region, a region including all autosomes, a region including sex chromosomes and/or a region including all chromosomes.

In some embodiments, a count is derived from raw sequence reads and/or filtered sequence reads. In certain embodiments a count is an average, mean or sum of sequence reads mapped to a genomic portion or group of genomic portions (e.g., genomic portions in a region). In some embodiments, a count is associated with an uncertainty value. A count sometimes is adjusted. A count may be adjusted according to sequence reads associated with a genomic portion or group of portions that have been weighted, removed, filtered, normalized, adjusted, averaged, derived as a mean, derived as a median, added, or combination thereof.

A sequence read quantification sometimes is a read density. A read density may be determined and/or generated for one or more segments of a genome. In certain instances, a read density may be determined and/or generated for one or more chromosomes. In some embodiments a read density comprises a quantitative measure of counts of sequence reads mapped to a segment or portion of a reference genome. A read density can be determined by a suitable process. In some embodiments a read density is determined by a suitable distribution and/or a suitable distribution function. Non-limiting examples of a distribution function include a probability function, probability distribution function, probability density function (PDF), a kernel density function (kernel density estimation), a cumulative distribution function, probability mass function, discrete probability distribution, an absolutely continuous univariate distribution, the like, any suitable distribution, or combinations thereof. A read density may be a density estimation derived from a suitable probability density function. A density estimation is the construction of an estimate, based on observed data, of an underlying probability density function. In some embodiments a read density comprises a density estimation (e.g., a probability density estimation, a kernel density estimation). A read density may be generated according to a process comprising generating a density estimation for each of the one or more portions of a genome where each portion comprises counts of sequence reads. A read density may be generated for normalized and/or weighted counts mapped to a portion or segment. In some instances, each read mapped to a portion or segment may contribute to a read density, a value (e.g., a count) equal to its weight obtained from a normalization process described herein. In some embodiments read densities for one or more portions or segments are adjusted. Read densities can be adjusted by a suitable method. For example, read densities for one or more portions can be weighted and/or normalized.

Reads quantified for a given portion or segment can be from one source or different sources. In one example, reads may be obtained from nucleic acid from a subject having cancer or suspected of having cancer. In such circumstances, reads mapped to one or more portions often are reads representative of both healthy cells (i.e., non-cancer cells) and cancer cells (e.g., tumor cells). In certain embodiments, some of the reads mapped to a portion are from cancer cell nucleic acid and some of the reads mapped to the same portion are from non-cancer cell nucleic acid. In another example, reads may be obtained from a nucleic acid sample from a pregnant female bearing a fetus. In such circumstances, reads mapped to one or more portions often are reads representative of both the fetus and the mother of the fetus (e.g., a pregnant female subject). In certain embodiments some of the reads mapped to a portion are from a fetal genome and some of the reads mapped to the same portion are from a maternal genome.

Levels

In some embodiments, a value (e.g., a number, a quantitative value) is ascribed to a level. A level can be determined by a suitable method, operation or mathematical process (e.g., a processed level). A level often is, or is derived from, counts (e.g., normalized counts) for a set of portions. In some embodiments a level of a portion is substantially equal to the total number of counts mapped to a portion (e.g., counts, normalized counts). Often a level is determined from counts that are processed, transformed or manipulated by a suitable method, operation or mathematical process known in the art. In some embodiments a level is derived from counts that are processed and non-limiting examples of processed counts include weighted, removed, filtered, normalized, adjusted, averaged, derived as a mean (e.g., mean level), added, subtracted, transformed counts or combination thereof. In some embodiments a level comprises counts that are normalized (e.g., normalized counts of portions). A level can be for counts normalized by a suitable process, non-limiting examples of which are described herein. A level can comprise normalized counts or relative amounts of counts. In some embodiments a level is for counts or normalized counts of two or more portions that are averaged and the level is referred to as an average level. In some embodiments a level is for a set of portions having a mean count or mean of normalized counts which is referred to as a mean level. In some embodiments a level is derived for portions that comprise raw and/or filtered counts. In some embodiments, a level is based on counts that are raw. In some embodiments a level is associated with an uncertainty value (e.g., a standard deviation, a MAD). In some embodiments a level is represented by a Z-score or p-value.

A level for one or more portions is synonymous with a "genomic section level" herein. The term "level" as used herein is sometimes synonymous with the term "elevation." A determination of the meaning of the term "level" can be determined from the context in which it is used. For example, the term "level," when used in the context of portions, profiles, reads and/or counts often means an elevation. The term "level," when used in the context of a substance or composition (e.g., level of RNA, plexing level) often refers to an amount. The term "level," when used in the context of uncertainty (e.g., level of error, level of confidence, level of deviation, level of uncertainty) often refers to an amount.

Normalized or non-normalized counts for two or more levels (e.g., two or more levels in a profile) can sometimes be mathematically manipulated (e.g., added, multiplied, averaged, normalized, the like or combination thereof) according to levels. For example, normalized or non-normalized counts for two or more levels can be normalized according to one, some or all of the levels in a profile. In some embodiments normalized or non-normalized counts of all levels in a profile are normalized according to one level in the profile. In some embodiments normalized or non-normalized counts of a first level in a profile are normalized according to normalized or non-normalized counts of a second level in the profile.

Non-limiting examples of a level (e.g., a first level, a second level) are a level for a set of portions comprising processed counts, a level for a set of portions comprising a mean, median or average of counts, a level for a set of portions comprising normalized counts, the like or any combination thereof. In some embodiments, a first level and a second level in a profile are derived from counts of portions mapped to the same chromosome. In some embodiments, a first level and a second level in a profile are derived from counts of portions mapped to different chromosomes.

In some embodiments a level is determined from normalized or non-normalized counts mapped to one or more portions. In some embodiments, a level is determined from normalized or non-normalized counts mapped to two or more portions, where the normalized counts for each portion often are about the same. There can be variation in counts (e.g., normalized counts) in a set of portions for a level. In a set of portions for a level there can be one or more portions having counts that are significantly different than in other portions of the set (e.g., peaks and/or dips). Any suitable number of normalized or non-normalized counts associated with any suitable number of portions can define a level.

In some embodiments one or more levels can be determined from normalized or non-normalized counts of all or some of the portions of a genome. Often a level can be determined from all or some of the normalized or non-normalized counts of a chromosome, or part thereof. In some embodiments, two or more counts derived from two or more portions (e.g., a set of portions) determine a level. In some embodiments two or more counts (e.g., counts from two or more portions) determine a level. In some embodiments, counts from 2 to about 100,000 portions determine a level. In some embodiments, counts from 2 to about 50,000, 2 to about 40,000, 2 to about 30,000, 2 to about 20,000, 2 to about 10,000, 2 to about 5000, 2 to about 2500, 2 to about 1250, 2 to about 1000, 2 to about 500, 2 to about 250, 2 to about 100 or 2 to about 60 portions determine a level. In some embodiments counts from about 10 to about 50 portions determine a level. In some embodiments counts from about 20 to about 40 or more portions determine a level. In some embodiments, a level comprises counts from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60 or more portions. In some embodiments, a level corresponds to a set of portions (e.g., a set of portions of a reference genome, a set of portions of a chromosome or a set of portions of a part of a chromosome).

In some embodiments, a level is determined for normalized or non-normalized counts of portions that are contiguous. In some embodiments portions (e.g., a set of portions) that are contiguous represent neighboring regions of a genome or neighboring regions of a chromosome or gene. For example, two or more contiguous portions, when aligned by merging the portions end to end, can represent a sequence assembly of a DNA sequence longer than each portion. For example two or more contiguous portions can represent of an intact genome, chromosome, gene, intron, exon or part thereof. In some embodiments a level is determined from a collection (e.g., a set) of contiguous portions and/or non-contiguous portions.

Data Processing and Normalization

Mapped sequence reads that have been counted are referred to herein as raw data, since the data represents unmanipulated counts (e.g., raw counts). In some embodiments, sequence read data in a data set can be processed further (e.g., mathematically and/or statistically manipulated) and/or displayed to facilitate providing an outcome. In certain embodiments, data sets, including larger data sets, may benefit from pre-processing to facilitate further analysis. Pre-processing of data sets sometimes involves removal of redundant and/or uninformative portions or portions of a reference genome (e.g., portions of a reference genome with uninformative data, redundant mapped reads, portions with zero median counts, over represented or under represented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing." Processing can render data more amenable to further analysis, and can generate an outcome in some embodiments. In some embodiments one or more or all processing methods (e.g., normalization methods, portion filtering, mapping, validation, the like or combinations thereof) are performed by a processor, a micro-processor, a computer, in conjunction with memory and/or by a microprocessor controlled apparatus.

The term "noisy data" as used herein refers to (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being overrepresented when prepared using PCR-based methods. Methods described herein can reduce or eliminate the contribution of noisy data, and therefore reduce the effect of noisy data on the provided outcome.

The terms "uninformative data," "uninformative portions of a reference genome," and "uninformative portions" as used herein refer to portions, or data derived therefrom, having a numerical value that is significantly different from a predetermined threshold value or falls outside a predetermined cutoff range of values. The terms "threshold" and "threshold value" herein refer to any number that is calculated using a qualifying data set and serves as a limit of diagnosis of a genetic variation (e.g., a copy number alteration, an aneuploidy, a microduplication, a microdeletion, a chromosomal aberration, and the like). In certain embodiments, a threshold is exceeded by results obtained by methods described herein and a subject is diagnosed with a copy number alteration. A threshold value or range of values often is calculated by mathematically and/or statistically manipulating sequence read data (e.g., from a reference and/or subject), in some embodiments, and in certain embodiments, sequence read data manipulated to generate a threshold value or range of values is sequence read data (e.g., from a reference and/or subject). In some embodiments, an uncertainty value is determined. An uncertainty value generally is a measure of variance or error and can be any suitable measure of variance or error. In some embodiments an uncertainty value is a standard deviation, standard error, calculated variance, p-value, or mean absolute deviation (MAD). In some embodiments an uncertainty value can be calculated according to a formula described herein.

Any suitable procedure can be utilized for processing data sets described herein. Non-limiting examples of procedures suitable for use for processing data sets include filtering, normalizing, weighting, monitoring peak heights, monitoring peak areas, monitoring peak edges, peak level analysis, peak width analysis, peak edge location analysis, peak lateral tolerances, determining area ratios, mathematical processing of data, statistical processing of data, application of statistical process, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., subject gender, subject age, subject ploidy, percent contribution of cancer cell nucleic acid, fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set.

In some embodiments one or more processing steps can comprise one or more normalization steps. Normalization can be performed by a suitable method described herein or known in the art. In certain embodiments, normalization comprises adjusting values measured on different scales to a notionally common scale. In certain embodiments, normalization comprises a sophisticated mathematical adjustment to bring probability distributions of adjusted values into alignment. In some embodiments normalization comprises aligning distributions to a normal distribution. In certain embodiments normalization comprises mathematical adjustments that allow comparison of corresponding normalized values for different datasets in a way that eliminates the effects of certain gross influences (e.g., error and anomalies). In certain embodiments normalization comprises scaling. Normalization sometimes comprises division of one or more data sets by a predetermined variable or formula. Normalization sometimes comprises subtraction of one or more data sets by a predetermined variable or formula. Non-limiting examples of normalization methods include portion-wise normalization, normalization by GC content, median count (median bin count, median portion count) normalization, linear and nonlinear least squares regression, LOESS, GC LOESS, LOWESS (locally weighted scatterplot smoothing), principal component normalization, repeat masking (RM), GC-normalization and repeat masking (GCRM), cQn and/or combinations thereof. In some embodiments, the determination of a presence or absence of a copy number alteration (e.g., an aneuploidy, a microduplication, a microdeletion) utilizes a normalization method (e.g., portion-wise normalization, normalization by GC content, median count (median bin count, median portion count) normalization, linear and nonlinear least squares regression, LOESS, GC LOESS, LOWESS (locally weighted scatterplot smoothing), principal component normalization, repeat masking (RM), GC-normalization and repeat masking (GCRM), cQn, a normalization method known in the art and/or a combination thereof). Described in greater detail hereafter are certain examples of normalization processes that can be utilized, such as LOESS normalization, principal component normalization, and hybrid normalization methods, for example. Aspects of certain normalization processes also are described, for example, in International Patent Application Publication No. WO 2013/052913 and International Patent Application Publication No. WO 2015/051163, each of which is incorporated by reference herein.

Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference portions to the total number of counts mapped to the chromosome or the entire genome on which the selected portion or sections are mapped; normalizing raw count data for one or more selected portions to a median reference count for one or more portions or the chromosome on which a selected portion is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data. Normalizing portions, or portions of a reference genome, with respect to a normalizing value sometimes is referred to as "portion-wise normalization."

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak levels, determination of peak edge locations, calculation of peak area ratios, analysis of median chromosomal level, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median levels, mean levels, count distribution within a genomic region, relative representation of nucleic acid species, the like or combinations thereof.

In some embodiments, a processing step can comprise the use of one or more statistical process. Any suitable statistical process, alone or in combination, may be used to analyze and/or manipulate a data set described herein. Any suitable number of statistical process can be used. In some embodiments, a data set can be analyzed using 1 or more, 5 or more, 10 or more or 20 or more statistical process. Non-limiting examples of statistical process suitable for use with methods described herein include principal component analysis, decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical process include raw counts, filtered counts, normalized counts, peak heights, peak widths, peak edges, lateral tolerances, P-values, median levels, mean levels, count distribution within a genomic region, relative representation of nucleic acid species, the like or combinations thereof.

In certain embodiments, a data set can be analyzed by utilizing multiple (e.g., 2 or more) statistical process (e.g., least squares regression, principal component analysis, linear discriminant analysis, quadratic discriminant analysis, bagging, neural networks, support vector machine models, random forests, classification tree models, K-nearest neighbors, logistic regression and/or smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation and/or copy number alteration, depending on the status of the reference samples (e.g., positive or negative for a selected copy number alteration). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation and/or copy number alteration and/or medical condition.

After data sets have been counted, optionally filtered, normalized, and optionally weighted the processed data sets can be further manipulated by one or more filtering and/or normalizing and/or weighting procedures, in some embodiments. A data set that has been further manipulated by one or more filtering and/or normalizing and/or weighting procedures can be used to generate a profile, in certain embodiments. The one or more filtering and/or normalizing and/or weighting procedures sometimes can reduce data set complexity and/or dimensionality, in some embodiments. An outcome can be provided based on a data set of reduced complexity and/or dimensionality. In some embodiments, a profile plot of processed data further manipulated by weighting, for example, is generated to facilitate classification and/or providing an outcome. An outcome can be provided based on a profile plot of weighted data, for example.

Filtering or weighting of portions can be performed at one or more suitable points in an analysis. For example, portions may be filtered or weighted before or after sequence reads are mapped to portions of a reference genome. Portions may be filtered or weighted before or after an experimental bias for individual genome portions is determined in some embodiments. In certain embodiments, portions may be filtered or weighted before or after levels are calculated.

After data sets have been counted, optionally filtered, normalized, and optionally weighted, the processed data sets can be manipulated by one or more mathematical and/or statistical (e.g., statistical functions or statistical process) manipulations, in some embodiments. In certain embodiments, processed data sets can be further manipulated by calculating Z-scores for one or more selected portions, chromosomes, or portions of chromosomes. In some embodiments, processed data sets can be further manipulated by calculating P-values. In certain embodiments, mathematical and/or statistical manipulations include one or more assumptions pertaining to ploidy and/or fraction of a minority species (e.g., fraction of cancer cell nucleic acid; fetal fraction). In some embodiments, a profile plot of processed data further manipulated by one or more statistical and/or mathematical manipulations is generated to facilitate classification and/or providing an outcome. An outcome can be provided based on a profile plot of statistically and/or mathematically manipulated data. An outcome provided based on a profile plot of statistically and/or mathematically manipulated data often includes one or more assumptions pertaining to ploidy and/or fraction of a minority species (e.g., fraction of cancer cell nucleic acid; fetal fraction).

In some embodiments, analysis and processing of data can include the use of one or more assumptions. A suitable number or type of assumptions can be utilized to analyze or process a data set. Non-limiting examples of assumptions that can be used for data processing and/or analysis include subject ploidy, cancer cell contribution, maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a nucleic acid quantification assay (e.g., fetal quantifier assay (FQA)), assumptions regarding twins (e.g., if 2 twins and only 1 is affected the effective fetal fraction is only 50% of the total measured fetal fraction (similarly for triplets, quadruplets and the like)), cell free DNA (e.g., cfDNA) uniformly covers the entire genome, the like and combinations thereof.

In those instances where the quality and/or depth of mapped sequence reads does not permit an outcome prediction of the presence or absence of a genetic variation and/or copy number alteration at a desired confidence level (e.g., 95% or higher confidence level), based on the normalized count profiles, one or more additional mathematical manipulation process and/or statistical prediction process, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

Described in greater detail hereafter are non-limiting examples of processing steps and normalization methods that can be utilized, such as normalizing to a window (static or sliding), weighting, determining bias relationship, LOESS normalization, principal component normalization, hybrid normalization, generating a profile and performing a comparison.

Normalizing to a Window (Static or Sliding)

In certain embodiments, a processing step comprises normalizing to a static window, and in some embodiments, a processing step comprises normalizing to a moving or sliding window. The term "window" as used herein refers to one or more portions chosen for analysis, and sometimes is used as a reference for comparison (e.g., used for normalization and/or other mathematical or statistical manipulation). The term "normalizing to a static window" as used herein refers to a normalization process using one or more portions selected for comparison between a test subject and reference subject data set. In some embodiments the selected portions are utilized to generate a profile. A static window generally includes a predetermined set of portions that do not change during manipulations and/or analysis. The terms "normalizing to a moving window" and "normalizing to a sliding window" as used herein refer to normalizations performed to portions localized to the genomic region (e.g., immediate surrounding portions, adjacent portion or sections, and the like) of a selected test portion, where one or more selected test portions are normalized to portions immediately surrounding the selected test portion. In certain embodiments, the selected portions are utilized to generate a profile. A sliding or moving window normalization often includes repeatedly moving or sliding to an adjacent test portion, and normalizing the newly selected test portion to portions immediately surrounding or adjacent to the newly selected test portion, where adjacent windows have one or more portions in common. In certain embodiments, a plurality of selected test portions and/or chromosomes can be analyzed by a sliding window process.

In some embodiments, normalizing to a sliding or moving window can generate one or more values, where each value represents normalization to a different set of reference portions selected from different regions of a genome (e.g., chromosome). In certain embodiments, the one or more values generated are cumulative sums (e.g., a numerical estimate of the integral of the normalized count profile over the selected portion, domain (e.g., part of chromosome), or chromosome). The values generated by the sliding or moving window process can be used to generate a profile and facilitate arriving at an outcome. In some embodiments, cumulative sums of one or more portions can be displayed as a function of genomic position. Moving or sliding window analysis sometimes is used to analyze a genome for the presence or absence of microdeletions and/or microduplications. In certain embodiments, displaying cumulative sums of one or more portions is used to identify the presence or absence of regions of copy number alteration (e.g., microdeletion, microduplication).

Weighting

In some embodiments, a processing step comprises a weighting. The terms "weighted," "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more portions or portions of a reference genome, based on the quality or usefulness of the data in the selected portion or portions of a reference genome). A weighting function can be used to increase the influence of data with a relatively small measurement variance, and/or to decrease the influence of data with a relatively large measurement variance, in some embodiments. For example, portions of a reference genome with under represented or low quality sequence data can be "down weighted" to minimize the influence on a data set, whereas selected portions of a reference genome can be "up weighted" to increase the influence on a data set. A non-limiting example of a weighting function is $[1/(\text{standard deviation})^2]$. Weighting portions sometimes removes portion dependencies. In some embodiments one or more portions are weighted by an eigen function (e.g., an eigenfunction). In some embodiments an eigen function comprises replacing portions with orthogonal eigen-portions. A weighting step sometimes is performed in a manner substantially similar to a normalizing step. In some embodiments, a data set is adjusted (e.g., divided, multiplied, added, subtracted) by a predetermined variable (e.g., weighting variable). In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

Bias Relationships

In some embodiments, a processing step comprises determining a bias relationship. For example, one or more relationships may be generated between local genome bias estimates and bias frequencies. The term "relationship" as use herein refers to a mathematical and/or a graphical relationship between two or more variables or values. A relationship can be generated by a suitable mathematical and/or graphical process. Non-limiting examples of a relationship include a mathematical and/or graphical representation of a function, a correlation, a distribution, a linear or non-linear equation, a line, a regression, a fitted regression, the like or a combination thereof. Sometimes a relationship comprises a fitted relationship. In some embodiments a fitted relationship comprises a fitted regression. Sometimes a relationship comprises two or more variables or values that are weighted. In some embodiments a relationship comprise a fitted regression where one or more variables or values of the relationship a weighted. Sometimes a regression is fitted in a weighted fashion. Sometimes a regression is fitted without weighting. In certain embodiments, generating a relationship comprises plotting or graphing.

In certain embodiments, a relationship is generated between GC densities and GC density frequencies. In some embodiments generating a relationship between (i) GC densities and (ii) GC density frequencies for a sample provides a sample GC density relationship. In some embodiments generating a relationship between (i) GC densities and (ii) GC density frequencies for a reference provides a reference GC density relationship. In some embodiments, where local genome bias estimates are GC densities, a sample bias relationship is a sample GC density relationship and a reference bias relationship is a reference GC density relationship. GC densities of a reference GC density relationship and/or a sample GC density relationship are often representations (e.g., mathematical or quantitative representation) of local GC content.

In some embodiments a relationship between local genome bias estimates and bias frequencies comprises a distribution. In some embodiments a relationship between local genome bias estimates and bias frequencies comprises a fitted relationship (e.g., a fitted regression). In some embodiments a relationship between local genome bias estimates and bias frequencies comprises a fitted linear or non-linear regression (e.g., a polynomial regression). In certain embodiments a relationship between local genome bias estimates and bias frequencies comprises a weighted relationship where local genome bias estimates and/or bias frequencies are weighted by a suitable process. In some embodiments a weighted fitted relationship (e.g., a weighted fitting) can be obtained by a process comprising a quantile regression, parameterized distributions or an empirical distribution with interpolation. In certain embodiments a relationship between local genome bias estimates and bias frequencies for a test sample, a reference or part thereof, comprises a polynomial regression where local genome bias estimates are weighted. In some embodiments a weighed fitted model comprises weighting values of a distribution. Values of a distribution can be weighted by a suitable process. In some embodiments, values located near tails of a distribution are provided less weight than values closer to the median of the distribution. For example, for a distribution between local genome bias estimates (e.g., GC densities) and bias frequencies (e.g., GC density frequencies), a weight is determined according to the bias frequency for a given local genome bias estimate, where local genome bias estimates comprising bias frequencies closer to the mean of a distribution are provided greater weight than local genome bias estimates comprising bias frequencies further from the mean.

In some embodiments, a processing step comprises normalizing sequence read counts by comparing local genome bias estimates of sequence reads of a test sample to local genome bias estimates of a reference (e.g., a reference genome, or part thereof). In some embodiments, counts of sequence reads are normalized by comparing bias frequencies of local genome bias estimates of a test sample to bias frequencies of local genome bias estimates of a reference. In some embodiments counts of sequence reads are normalized by comparing a sample bias relationship and a reference bias relationship, thereby generating a comparison.

Counts of sequence reads may be normalized according to a comparison of two or more relationships. In certain embodiments two or more relationships are compared thereby providing a comparison that is used for reducing local bias in sequence reads (e.g., normalizing counts). Two or more relationships can be compared by a suitable method. In some embodiments a comparison comprises adding, subtracting, multiplying and/or dividing a first relationship from a second relationship. In certain embodiments comparing two or more relationships comprises a use of a suitable linear regression and/or a non-linear regression. In certain embodiments comparing two or more relationships comprises a suitable polynomial regression (e.g., a $3^{rd}$ order polynomial regression). In some embodiments a comparison comprises adding, subtracting, multiplying and/or dividing a first regression from a second regression. In some embodiments two or more relationships are compared by a process comprising an inferential framework of multiple regressions. In some embodiments two or more relationships are compared by a process comprising a suitable multivariate analysis. In some embodiments two or more relationships are compared by a process comprising a basis function (e.g., a blending function, e.g., polynomial bases, Fourier bases, or the like), splines, a radial basis function and/or wavelets.

In certain embodiments a distribution of local genome bias estimates comprising bias frequencies for a test sample and a reference is compared by a process comprising a polynomial regression where local genome bias estimates are weighted. In some embodiments a polynomial regression is generated between (i) ratios, each of which ratios comprises bias frequencies of local genome bias estimates of a reference and bias frequencies of local genome bias estimates of a sample and (ii) local genome bias estimates. In some embodiments a polynomial regression is generated between (i) a ratio of bias frequencies of local genome bias estimates of a reference to bias frequencies of local genome bias estimates of a sample and (ii) local genome bias estimates. In some embodiments a comparison of a distribution of local genome bias estimates for reads of a test sample and a reference comprises determining a log ratio (e.g., a log 2 ratio) of bias frequencies of local genome bias estimates for the reference and the sample. In some embodiments a comparison of a distribution of local genome bias estimates comprises dividing a log ratio (e.g., a log 2 ratio) of bias frequencies of local genome bias estimates for the reference by a log ratio (e.g., a log 2 ratio) of bias frequencies of local genome bias estimates for the sample.

Normalizing counts according to a comparison typically adjusts some counts and not others. Normalizing counts sometimes adjusts all counts and sometimes does not adjust any counts of sequence reads. A count for a sequence read sometimes is normalized by a process that comprises determining a weighting factor and sometimes the process does not include directly generating and utilizing a weighting factor. Normalizing counts according to a comparison sometimes comprises determining a weighting factor for each count of a sequence read. A weighting factor is often specific to a sequence read and is applied to a count of a specific sequence read. A weighting factor is often determined according to a comparison of two or more bias relationships (e.g., a sample bias relationship compared to a reference bias relationship). A normalized count is often determined by adjusting a count value according to a weighting factor. Adjusting a count according to a weighting factor sometimes includes adding, subtracting, multiplying and/or dividing a count for a sequence read by a weighting factor. A weighting factor and/or a normalized count sometimes are determined from a regression (e.g., a regression line). A normalized count is sometimes obtained directly from a regression line (e.g., a fitted regression line) resulting from a comparison between bias frequencies of local genome bias estimates of a reference (e.g., a reference genome) and a test sample. In some embodiments each count of a read of a sample is provided a normalized count value according to a comparison of (i) bias frequencies of a local genome bias estimates of reads compared to (ii) bias frequencies of a local genome bias estimates of a reference. In certain embodiments, counts of sequence reads obtained for a sample are normalized and bias in the sequence reads is reduced.

LOESS Normalization

In some embodiments, a processing step comprises a LOESS normalization. LOESS is a regression modeling method known in the art that combines multiple regression models in a k-nearest-neighbor-based meta-model. LOESS is sometimes referred to as a locally weighted polynomial regression. GC LOESS, in some embodiments, applies an LOESS model to the relationship between fragment count (e.g., sequence reads, counts) and GC composition for portions of a reference genome. Plotting a smooth curve through a set of data points using LOESS is sometimes called an LOESS curve, particularly when each smoothed value is given by a weighted quadratic least squares regression over the span of values of the y-axis scattergram criterion variable. For each point in a data set, the LOESS method fits a low-degree polynomial to a subset of the data, with explanatory variable values near the point whose response is being estimated. The polynomial is fitted using weighted least squares, giving more weight to points near the point whose response is being estimated and less weight to points further away. The value of the regression function for a point is then obtained by evaluating the local polynomial using the explanatory variable values for that data point. The LOESS fit is sometimes considered complete after regression function values have been computed for each of the data points. Many of the details of this method, such as the degree of the polynomial model and the weights, are flexible.

Principal Component Analysis

In some embodiments, a processing step comprises a principal component analysis (PCA). In some embodiments, sequence read counts (e.g., sequence read counts of a test sample) is adjusted according to a principal component analysis (PCA). In some embodiments a read density profile (e.g., a read density profile of a test sample) is adjusted according to a principal component analysis (PCA). A read density profile of one or more reference samples and/or a read density profile of a test subject can be adjusted according to a PCA. Removing bias from a read density profile by a PCA related process is sometimes referred to herein as adjusting a profile. A PCA can be performed by a suitable PCA method, or a variation thereof. Non-limiting examples of a PCA method include a canonical correlation analysis (CCA), a Karhunen-Loève transform (KLT), a Hotelling transform, a proper orthogonal decomposition (POD), a singular value decomposition (SVD) of X, an eigenvalue decomposition (EVD) of XTX, a factor analysis, an Eckart-Young theorem, a Schmidt-Mirsky theorem, empirical orthogonal functions (EOF), an empirical eigenfunction decomposition, an empirical component analysis, quasiharmonic modes, a spectral decomposition, an empirical modal analysis, the like, variations or combinations thereof. A PCA often identifies and/or adjusts for one or more biases in a read density profile. A bias identified and/or adjusted for by a PCA is sometimes referred to herein as a principal component. In some embodiments one or more biases can be removed by adjusting a read density profile according to one or more principal component using a suitable method. A read density profile can be adjusted by adding, subtracting, multiplying and/or dividing one or more principal components from a read density profile. In some embodiments, one or more biases can be removed from a read density profile by subtracting one or more principal components from a read density profile. Although bias in a read density profile is often identified and/or quantitated by a PCA of a profile, principal components are often subtracted from a profile at the level of read densities. A PCA often identifies one or more principal components. In some embodiments a PCA identifies a $1^{st}$, $2^{nd}$, $3^{rd}$, $4^{th}$, $5^{th}$, $6^{th}$, $7^{th}$, $8^{th}$, $9^{th}$, and a $10^{th}$ or more principal components. In certain embodiments, 1, 2, 3, 4, 5, 6, 7, 8, 9, 10 or more principal components are used to adjust a profile. In certain embodiments, 5 principal components are used to adjust a profile. Often, principal components are used to adjust a profile in the order of appearance in a PCA. For example, where three principal components are subtracted from a read density profile, a $1^{st}$, $2^{nd}$ and $3^{rd}$ principal component are used. Sometimes a bias identified by a principal component comprises a feature of a profile that is not used to adjust a profile. For example, a PCA may identify a copy number alteration (e.g., an aneuploidy, microduplication, microdeletion, deletion, translocation, insertion) and/or a gender difference as a principal component. Thus, in some embodiments, one or more principal components are not used to adjust a profile. For example, sometimes a $1^{st}$, $2^{nd}$ and $4^{th}$ principal component are used to adjust a profile where a $3^{rd}$ principal component is not used to adjust a profile.

A principal component can be obtained from a PCA using any suitable sample or reference. In some embodiments principal components are obtained from a test sample (e.g., a test subject). In some embodiments principal components are obtained from one or more references (e.g., reference samples, reference sequences, a reference set). In certain instances, a PCA is performed on a median read density profile obtained from a training set comprising multiple samples resulting in the identification of a $1^{st}$ principal component and a $2^{nd}$ principal component. In some embodiments, principal components are obtained from a set of subjects devoid of a copy number alteration in question. In some embodiments, principal components are obtained from a set of known euploids. Principal component are often identified according to a PCA performed using one or more read density profiles of a reference (e.g., a training set). One or more principal components obtained from a reference are often subtracted from a read density profile of a test subject thereby providing an adjusted profile.

Hybrid Normalization

In some embodiments, a processing step comprises a hybrid normalization method. A hybrid normalization method may reduce bias (e.g., GC bias), in certain instances. A hybrid normalization, in some embodiments, comprises (i) an analysis of a relationship of two variables (e.g., counts and GC content) and (ii) selection and application of a normalization method according to the analysis. A hybrid normalization, in certain embodiments, comprises (i) a regression (e.g., a regression analysis) and (ii) selection and application of a normalization method according to the regression. In some embodiments counts obtained for a first sample (e.g., a first set of samples) are normalized by a different method than counts obtained from another sample (e.g., a second set of samples). In some embodiments counts obtained for a first sample (e.g., a first set of samples) are normalized by a first normalization method and counts obtained from a second sample (e.g., a second set of samples) are normalized by a second normalization method. For example, in certain embodiments a first normalization method comprises use of a linear regression and a second normalization method comprises use of a non-linear regression (e.g., a LOESS, GC-LOESS, LOWESS regression, LOESS smoothing).

In some embodiments a hybrid normalization method is used to normalize sequence reads mapped to portions of a genome or chromosome (e.g., counts, mapped counts, mapped reads). In certain embodiments raw counts are normalized and in some embodiments adjusted, weighted, filtered or previously normalized counts are normalized by a hybrid normalization method. In certain embodiments, levels or Z-scores are normalized. In some embodiments counts mapped to selected portions of a genome or chromosome are normalized by a hybrid normalization approach. Counts can refer to a suitable measure of sequence reads mapped to portions of a genome, non-limiting examples of which include raw counts (e.g., unprocessed counts), normalized counts (e.g., normalized by LOESS, principal component, or a suitable method), portion levels (e.g., average levels, mean levels, median levels, or the like), Z-scores, the like, or combinations thereof. The counts can be raw counts or processed counts from one or more samples (e.g., a test sample, a sample from a pregnant female). In some embodiments counts are obtained from one or more samples obtained from one or more subjects.

In some embodiments a normalization method (e.g., the type of normalization method) is selected according to a regression (e.g., a regression analysis) and/or a correlation coefficient. A regression analysis refers to a statistical technique for estimating a relationship among variables (e.g., counts and GC content). In some embodiments a regression is generated according to counts and a measure of GC content for each portion of multiple portions of a reference genome. A suitable measure of GC content can be used, non-limiting examples of which include a measure of guanine, cytosine, adenine, thymine, purine (GC), or pyrimidine (AT or ATU) content, melting temperature ($T_m$) (e.g., denaturation temperature, annealing temperature, hybridization temperature), a measure of free energy, the like or combinations thereof. A measure of guanine (G), cytosine (C), adenine (A), thymine (T), purine (GC), or pyrimidine (AT or ATU) content can be expressed as a ratio or a percentage. In some embodiments any suitable ratio or percentage is used, non-limiting examples of which include GC/AT, GC/total nucleotide, GC/A, GC/T, AT/total nucleotide, AT/GC, AT/G, AT/C, G/A, C/A, G/T, G/A, G/AT, C/T, the like or combinations thereof. In some embodiments a measure of GC content is a ratio or percentage of GC to total nucleotide content. In some embodiments a measure of GC content is a ratio or percentage of GC to total nucleotide content for sequence reads mapped to a portion of reference genome. In certain embodiments the GC content is determined according to and/or from sequence reads mapped to each portion of a reference genome and the sequence reads are obtained from a sample. In some embodiments a measure of GC content is not determined according to and/or from sequence reads. In certain embodiments, a measure of GC content is determined for one or more samples obtained from one or more subjects.

In some embodiments generating a regression comprises generating a regression analysis or a correlation analysis. A suitable regression can be used, non-limiting examples of which include a regression analysis, (e.g., a linear regression analysis), a goodness of fit analysis, a Pearson's correlation analysis, a rank correlation, a fraction of variance unexplained, Nash-Sutcliffe model efficiency analysis, regression model validation, proportional reduction in loss, root mean square deviation, the like or a combination thereof. In some embodiments a regression line is generated. In certain embodiments generating a regression comprises generating a linear regression. In certain embodiments generating a regression comprises generating a non-linear regression (e.g., an LOESS regression, an LOWESS regression).

In some embodiments a regression determines the presence or absence of a correlation (e.g., a linear correlation), for example between counts and a measure of GC content. In some embodiments a regression (e.g., a linear regression) is generated and a correlation coefficient is determined. In some embodiments a suitable correlation coefficient is determined, non-limiting examples of which include a coefficient of determination, an $R^2$ value, a Pearson's correlation coefficient, or the like.

In some embodiments goodness of fit is determined for a regression (e.g., a regression analysis, a linear regression). Goodness of fit sometimes is determined by visual or mathematical analysis. An assessment sometimes includes determining whether the goodness of fit is greater for a non-linear regression or for a linear regression. In some embodiments a correlation coefficient is a measure of a goodness of fit. In some embodiments an assessment of a goodness of fit for a regression is determined according to a correlation coefficient and/or a correlation coefficient cutoff value. In some embodiments an assessment of a goodness of fit comprises comparing a correlation coefficient to a correlation coefficient cutoff value. In some embodiments an assessment of a goodness of fit for a regression is indicative of a linear regression. For example, in certain embodiments, a goodness of fit is greater for a linear regression than for a non-linear regression and the assessment of the goodness of fit is indicative of a linear regression. In some embodiments an assessment is indicative of a linear regression and a linear regression is used to normalized the counts. In some embodiments an assessment of a goodness of fit for a regression is indicative of a non-linear regression. For example, in certain embodiments, a goodness of fit is greater for a non-linear regression than for a linear regression and the assessment of the goodness of fit is indicative of a non-linear regression. In some embodiments an assessment is indicative of a non-linear regression and a non-linear regression is used to normalized the counts.

In some embodiments an assessment of a goodness of fit is indicative of a linear regression when a correlation coefficient is equal to or greater than a correlation coefficient cutoff. In some embodiments an assessment of a goodness of fit is indicative of a non-linear regression when a correlation coefficient is less than a correlation coefficient cutoff. In some embodiments a correlation coefficient cutoff is predetermined. In some embodiments a correlation coefficient cut-off is about 0.5 or greater, about 0.55 or greater, about 0.6 or greater, about 0.65 or greater, about 0.7 or greater, about 0.75 or greater, about 0.8 or greater or about 0.85 or greater.

In some embodiments a specific type of regression is selected (e.g., a linear or non-linear regression) and, after the regression is generated, counts are normalized by subtracting the regression from the counts. In some embodiments subtracting a regression from the counts provides normalized counts with reduced bias (e.g., GC bias). In some embodiments a linear regression is subtracted from the counts. In some embodiments a non-linear regression (e.g., a LOESS, GC-LOESS, LOWESS regression) is subtracted from the counts.

Any suitable method can be used to subtract a regression line from the counts. For example, if counts x are derived from portion i (e.g., a portion i) comprising a GC content of 0.5 and a regression line determines counts y at a GC content of 0.5, then x-y=normalized counts for portion i. In some embodiments counts are normalized prior to and/or after subtracting a regression. In some embodiments, counts normalized by a hybrid normalization approach are used to generate levels, Z-scores, levels and/or profiles of a genome or a part thereof. In certain embodiments, counts normalized by a hybrid normalization approach are analyzed by methods described herein to determine the presence or absence of a genetic variation (e.g., copy number alteration).

In some embodiments a hybrid normalization method comprises filtering or weighting one or more portions before or after normalization. A suitable method of filtering portions, including methods of filtering portions (e.g., portions of a reference genome) described herein can be used. In some embodiments, portions (e.g., portions of a reference genome) are filtered prior to applying a hybrid normalization method. In some embodiments, only counts of sequencing reads mapped to selected portions (e.g., portions selected according to count variability) are normalized by a hybrid normalization. In some embodiments counts of sequencing reads mapped to filtered portions of a reference genome (e.g., portions filtered according to count variability) are removed prior to utilizing a hybrid normalization method. In some embodiments a hybrid normalization method comprises selecting or filtering portions (e.g., portions of a reference genome) according to a suitable method (e.g., a method described herein). In some embodiments a hybrid normalization method comprises selecting or filtering portions (e.g., portions of a reference genome) according to an uncertainty value for counts mapped to each of the portions for multiple test samples. In some embodiments a hybrid normalization method comprises selecting or filtering portions (e.g., portions of a reference genome) according to count variability. In some embodiments a hybrid normalization method comprises selecting or filtering portions (e.g., portions of a reference genome) according to GC content, repetitive elements, repetitive sequences, introns, exons, the like or a combination thereof.

Profiles

In some embodiments, a processing step comprises generating one or more profiles (e.g., profile plot) from various aspects of a data set or derivation thereof (e.g., product of one or more mathematical and/or statistical data processing steps known in the art and/or described herein).

The term "profile" as used herein refers to a product of a mathematical and/or statistical manipulation of data that can facilitate identification of patterns and/or correlations in large quantities of data. A "profile" often includes values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a part or subset of a data set. That is, a profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a portion. In certain embodiments, a data point in a profile includes results of data manipulation for groups of portions. In some embodiments, groups of portions may be adjacent to one another, and in certain embodiments, groups of portions may be from different parts of a chromosome or genome.

Data points in a profile derived from a data set can be representative of any suitable data categorization. Non-limiting examples of categories into which data can be grouped to generate profile data points include: portions based on size, portions based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile (e.g., a genomic profile, a chromosome profile, a profile of a part of a chromosome) often is a collection of normalized or non-normalized counts for two or more portions. A profile often includes at least one level, and often comprises two or more levels (e.g., a profile often has multiple levels). A level generally is for a set of portions having about the same counts or normalized counts. Levels are described in greater detail herein. In certain embodiments, a profile comprises one or more portions, which portions can be weighted, removed, filtered, normalized, adjusted, averaged, derived as a mean, added, subtracted, processed or transformed by any combination thereof. A profile often comprises normalized counts mapped to portions defining two or more levels, where the counts are further normalized according to one of the levels by a suitable method. Often counts of a profile (e.g., a profile level) are associated with an uncertainty value.

A profile comprising one or more levels is sometimes padded (e.g., hole padding). Padding (e.g., hole padding) refers to a process of identifying and adjusting levels in a profile that are due to copy number alterations (e.g., microduplications or microdeletions in a patient's genome, maternal microduplications or microdeletions). In some embodiments, levels are padded that are due to microduplications or microdeletions in a tumor or a fetus. Microduplications or microdeletions in a profile can, in some embodiments, artificially raise or lower the overall level of a profile (e.g., a profile of a chromosome) leading to false positive or false negative determinations of a chromosome aneuploidy (e.g., a trisomy). In some embodiments, levels in a profile that are due to microduplications and/or deletions are identified and adjusted (e.g., padded and/or removed) by a process sometimes referred to as padding or hole padding.

A profile comprising one or more levels can include a first level and a second level. In some embodiments a first level is different (e.g., significantly different) than a second level. In some embodiments a first level comprises a first set of portions, a second level comprises a second set of portions and the first set of portions is not a subset of the second set of portions. In certain embodiments, a first set of portions is different than a second set of portions from which a first and second level are determined. In some embodiments a profile can have multiple first levels that are different (e.g., significantly different, e.g., have a significantly different value) than a second level within the profile. In some embodiments a profile comprises one or more first levels that are significantly different than a second level within the profile and one or more of the first levels are adjusted. In some embodiments a first level within a profile is removed from the profile or adjusted (e.g., padded). A profile can comprise multiple levels that include one or more first levels significantly different than one or more second levels and often the majority of levels in a profile are second levels, which second levels are about equal to one another. In some embodiments greater than 50%, greater than 60%, greater than 70%, greater than 80%, greater than 90% or greater than 95% of the levels in a profile are second levels.

A profile sometimes is displayed as a plot. For example, one or more levels representing counts (e.g., normalized counts) of portions can be plotted and visualized. Non-limiting examples of profile plots that can be generated include raw count (e.g., raw count profile or raw profile), normalized count, portion-weighted, z-score, p-value, area ratio versus fitted ploidy, median level versus ratio between fitted and measured minority species fraction, principal components, the like, or combinations thereof. Profile plots allow visualization of the manipulated data, in some embodiments. In certain embodiments, a profile plot can be utilized to provide an outcome (e.g., area ratio versus fitted ploidy, median level versus ratio between fitted and measured minority species fraction, principal components). The terms "raw count profile plot" or "raw profile plot" as used herein refer to a plot of counts in each portion in a region normalized to total counts in a region (e.g., genome, portion, chromosome, chromosome portions of a reference genome or a part of a chromosome). In some embodiments, a profile can be generated using a static window process, and in certain embodiments, a profile can be generated using a sliding window process.

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions, e.g., assumptions described herein. In certain embodiments, a test profile often centers around a predetermined value representative of the absence of a copy number alteration, and often deviates from a predetermined value in areas corresponding to the genomic location in which the copy number alteration is located in the test subject, if the test subject possessed the copy number alteration. In test subjects at risk for, or suffering from a medical condition associated with a copy number alteration, the numerical value for a selected portion is expected to vary significantly from the predetermined value for non-affected genomic locations. Depending on starting assumptions (e.g., fixed ploidy or optimized ploidy, fixed fraction of cancer cell nucleic acid or optimized fraction of cancer cell nucleic acid, fixed fetal fraction or optimized fetal fraction, or combinations thereof) the predetermined threshold or cutoff value or threshold range of values indicative of the presence or absence of a copy number alteration can vary while still providing an outcome useful for determining the presence or absence of a copy number alteration. In some embodiments, a profile is indicative of and/or representative of a phenotype.

In some embodiments, the use of one or more reference samples that are substantially free of a copy number alteration in question can be used to generate a reference count profile (e.g., a reference median count profile), which may result in a predetermined value representative of the absence of the copy number alteration, and often deviates from a predetermined value in areas corresponding to the genomic location in which the copy number alteration is located in the test subject, if the test subject possessed the copy number alteration. In test subjects at risk for, or suffering from a medical condition associated with a copy number alteration, the numerical value for the selected portion or sections is expected to vary significantly from the predetermined value for non-affected genomic locations. In certain embodiments, the use of one or more reference samples known to carry the copy number alteration in question can be used to generate a reference count profile (a reference median count profile), which may result in a predetermined value representative of the presence of the copy number alteration, and often deviates from a predetermined value in areas corresponding to the genomic location in which a test subject does not carry the copy number alteration. In test subjects not at risk for, or suffering from a medical condition associated with a copy number alteration, the numerical value for the selected portion or sections is expected to vary significantly from the predetermined value for affected genomic locations.

By way of a non-limiting example, normalized sample and/or reference count profiles can be obtained from raw sequence read data by (a) calculating reference median counts for selected chromosomes, portions or parts thereof from a set of references known not to carry a copy number alteration, (b) removal of uninformative portions from the reference sample raw counts (e.g., filtering); (c) normalizing the reference counts for all remaining portions of a reference genome to the total residual number of counts (e.g., sum of remaining counts after removal of uninformative portions of a reference genome) for the reference sample selected chromosome or selected genomic location, thereby generating a normalized reference subject profile; (d) removing the corresponding portions from the test subject sample; and (e) normalizing the remaining test subject counts for one or more selected genomic locations to the sum of the residual reference median counts for the chromosome or chromosomes containing the selected genomic locations, thereby generating a normalized test subject profile. In certain embodiments, an additional normalizing step with respect to the entire genome, reduced by the filtered portions in (b), can be included between (c) and (d).

In some embodiments a read density profile is determined. In some embodiments a read density profile comprises at least one read density, and often comprises two or more read densities (e.g., a read density profile often comprises multiple read densities). In some embodiments, a read density profile comprises a suitable quantitative value (e.g., a mean, a median, a Z-score, or the like). A read density profile often comprises values resulting from one or more read densities. A read density profile sometimes comprises values resulting from one or more manipulations of read densities based on one or more adjustments (e.g., normalizations). In some embodiments a read density profile comprises unmanipulated read densities. In some embodiments, one or more read density profiles are generated from various aspects of a data set comprising read densities, or a derivation thereof (e.g., product of one or more mathematical and/or statistical data processing steps known in the art and/or described herein). In certain embodiments, a read density profile comprises normalized read densities. In some embodiments a read density profile comprises adjusted read densities. In certain embodiments a read density profile comprises raw read densities (e.g., unmanipulated, not adjusted or normalized), normalized read densities, weighted read densities, read densities of filtered portions, z-scores of read densities, p-values of read densities, integral values of read densities (e.g., area under the curve), average, mean or median read densities, principal components, the like, or combinations thereof. Often read densities of a read density profile and/or a read density profile is associated with a measure of uncertainty (e.g., a MAD). In certain embodiments, a read density profile comprises a distribution of median read densities. In some embodiments a read density profile comprises a relationship (e.g., a fitted relationship, a regression, or the like) of a plurality of read densities. For example, sometimes a read density profile comprises a relationship between read densities (e.g., read densities value) and genomic locations (e.g., portions, portion locations). In some embodiments, a read density profile is generated using a static window process, and in certain embodiments, a read density profile is generated using a sliding window process. In some embodiments a read density profile is sometimes printed and/or displayed (e.g., displayed as a visual representation, e.g., a plot or a graph).

In some embodiments, a read density profile corresponds to a set of portions (e.g., a set of portions of a reference genome, a set of portions of a chromosome or a subset of portions of a part of a chromosome). In some embodiments a read density profile comprises read densities and/or counts associated with a collection (e.g., a set, a subset) of portions. In some embodiments, a read density profile is determined for read densities of portions that are contiguous. In some embodiments, contiguous portions comprise gaps comprising regions of a reference sequence and/or sequence reads that are not included in a density profile (e.g., portions removed by a filtering). Sometimes portions (e.g., a set of portions) that are contiguous represent neighboring regions of a genome or neighboring regions of a chromosome or gene. For example, two or more contiguous portions, when aligned by merging the portions end to end, can represent a sequence assembly of a DNA sequence longer than each portion. For example two or more contiguous portions can represent an intact genome, chromosome, gene, intron, exon or part thereof. Sometimes a read density profile is determined from a collection (e.g., a set, a subset) of contiguous portions and/or non-contiguous portions. In some cases, a read density profile comprises one or more portions, which portions can be weighted, removed, filtered, normalized, adjusted, averaged, derived as a mean, added, subtracted, processed or transformed by any combination thereof.

A read density profile is often determined for a sample and/or a reference (e.g., a reference sample). A read density profile is sometimes generated for an entire genome, one or more chromosomes, or for a part of a genome or a chromosome. In some embodiments, one or more read density profiles are determined for a genome or part thereof. In some embodiments, a read density profile is representative of the entirety of a set of read densities of a sample, and in certain embodiments, a read density profile is representative of a part or subset of read densities of a sample. That is, sometimes a read density profile comprises or is generated from read densities representative of data that has not been filtered to remove any data, and sometimes a read density profile includes or is generated from data points representative of data that has been filtered to remove unwanted data.

In some embodiments a read density profile is determined for a reference (e.g., a reference sample, a training set). A read density profile for a reference is sometimes referred to herein as a reference profile. In some embodiments a reference profile comprises a read densities obtained from one or more references (e.g., reference sequences, reference samples). In some embodiments a reference profile comprises read densities determined for one or more (e.g., a set of) known euploid samples. In some embodiments a reference profile comprises read densities of filtered portions. In some embodiments a reference profile comprises read densities adjusted according to the one or more principal components.

Performing a Comparison

In some embodiments, a processing step comprises preforming a comparison (e.g., comparing a test profile to a reference profile). Two or more data sets, two or more relationships and/or two or more profiles can be compared by a suitable method. Non-limiting examples of statistical methods suitable for comparing data sets, relationships and/or profiles include Behrens-Fisher approach, bootstrapping, Fisher's method for combining independent tests of significance, Neyman-Pearson testing, confirmatory data analysis, exploratory data analysis, exact test, F-test, Z-test, T-test, calculating and/or comparing a measure of uncertainty, a null hypothesis, counternulls and the like, a chi-square test, omnibus test, calculating and/or comparing level of significance (e.g., statistical significance), a meta analysis, a multivariate analysis, a regression, simple linear regression, robust linear regression, the like or combinations of the foregoing. In certain embodiments comparing two or more data sets, relationships and/or profiles comprises determining and/or comparing a measure of uncertainty. A "measure of uncertainty" as used herein refers to a measure of significance (e.g., statistical significance), a measure of error, a measure of variance, a measure of confidence, the like or a combination thereof. A measure of uncertainty can be a value (e.g., a threshold) or a range of values (e.g., an interval, a confidence interval, a Bayesian confidence interval, a threshold range). Non-limiting examples of a measure of uncertainty include p-values, a suitable measure of deviation (e.g., standard deviation, sigma, absolute deviation, mean absolute deviation, the like), a suitable measure of error (e.g., standard error, mean squared error, root mean squared error, the like), a suitable measure of variance, a suitable standard score (e.g., standard deviations, cumulative percentages, percentile equivalents, Z-scores, T-scores, R-scores, standard nine (stanine), percent in stanine, the like), the like or combinations thereof. In some embodiments determining the level of significance comprises determining a measure of uncertainty (e.g., a p-value). In certain embodiments, two or more data sets, relationships and/or profiles can be analyzed and/or compared by utilizing multiple (e.g., 2 or more) statistical methods (e.g., least squares regression, principal component analysis, linear discriminant analysis, quadratic discriminant analysis, bagging, neural networks, support vector machine models, random forests, classification tree models, K-nearest neighbors, logistic regression and/or loss smoothing) and/or any suitable mathematical and/or statistical manipulations (e.g., referred to herein as manipulations).

In some embodiments, a processing step comprises a comparison of two or more profiles (e.g., two or more read density profiles). Comparing profiles may comprise comparing profiles generated for a selected region of a genome. For example, a test profile may be compared to a reference profile where the test and reference profiles were determined for a region of a genome (e.g., a reference genome) that is substantially the same region. Comparing profiles sometimes comprises comparing two or more subsets of portions of a profile (e.g., a read density profile). A subset of portions of a profile may represent a region of a genome (e.g., a chromosome, or region thereof). A profile (e.g., a read density profile) can comprise any amount of subsets of portions. Sometimes a profile (e.g., a read density profile) comprises two or more, three or more, four or more, or five or more subsets. In certain embodiments, a profile (e.g., a read density profile) comprises two subsets of portions where each portion represents regions of a reference genome that are adjacent. In some embodiments, a test profile can be compared to a reference profile where the test profile and reference profile both comprise a first subset of portions and a second subset of portions where the first and second subsets represent different regions of a genome. Some subsets of portions of a profile may comprise copy number alterations and other subsets of portions are sometimes substantially free of copy number alterations. Sometimes all subsets of portions of a profile (e.g., a test profile) are substantially free of a copy number alteration. Sometimes all subsets of portions of a profile (e.g., a test profile) comprise a copy number alteration. In some embodiments a test profile can comprise a first subset of portions that comprise a copy number alteration and a second subset of portions that are substantially free of a copy number alteration.

In certain embodiments, comparing two or more profiles comprises determining and/or comparing a measure of uncertainty for two or more profiles. Profiles (e.g., read density profiles) and/or associated measures of uncertainty are sometimes compared to facilitate interpretation of mathematical and/or statistical manipulations of a data set and/or to provide an outcome. A profile (e.g., a read density profile) generated for a test subject sometimes is compared to a profile (e.g., a read density profile) generated for one or more references (e.g., reference samples, reference subjects, and the like). In some embodiments, an outcome is provided by comparing a profile (e.g., a read density profile) from a test subject to a profile (e.g., a read density profile) from a reference for a chromosome, portions or parts thereof, where a reference profile is obtained from a set of reference subjects known not to possess a copy number alteration (e.g., a reference). In some embodiments an outcome is provided by comparing a profile (e.g., a read density profile) from a test subject to a profile (e.g., a read density profile) from a reference for a chromosome, portions or parts thereof, where a reference profile is obtained from a set of reference subjects known to possess a specific copy number alteration (e.g., a chromosome aneuploidy, a microduplication, a microdeletion).

In certain embodiments, a profile (e.g., a read density profile) of a test subject is compared to a predetermined value representative of the absence of a copy number alteration, and sometimes deviates from a predetermined value at one or more genomic locations (e.g., portions) corresponding to a genomic location in which a copy number alteration is located. For example, in test subjects (e.g., subjects at risk for, or suffering from a medical condition associated with a copy number alteration), profiles are expected to differ significantly from profiles of a reference (e.g., a reference sequence, reference subject, reference set) for selected portions when a test subject comprises a copy number alteration in question. Profiles (e.g., read density profiles) of a test subject are often substantially the same as profiles (e.g., read density profiles) of a reference (e.g., a reference sequence, reference subject, reference set) for selected portions when a test subject does not comprise a copy number alteration in question. Profiles (e.g., read density profiles) may be compared to a predetermined threshold and/or threshold range. The term "threshold" as used herein refers to any number that is calculated using a qualifying data set and serves as a limit of diagnosis of a copy number alteration (e.g., an aneuploidy, a microduplication, a microdeletion, and the like). In certain embodiments a threshold is exceeded by results obtained by methods described herein and a subject is diagnosed with a copy number alteration. In some embodiments, a threshold value or range of values may be calculated by mathematically and/or statistically manipulating sequence read data (e.g., from a reference and/or subject). A predetermined threshold or threshold range of values indicative of the presence or absence of a copy number alteration can vary while still providing an outcome useful for determining the presence or absence of a copy number alteration. In certain embodiments, a profile (e.g., a read density profile) comprising normalized read densities and/or normalized counts is generated to facilitate classification and/or providing an outcome. An outcome can be provided based on a plot of a profile (e.g., a read density profile) comprising normalized counts (e.g., using a plot of such a read density profile).

Decision Analysis

In some embodiments, a determination of an outcome (e.g., making a call) or a determination of the presence or absence of a copy number alteration (e.g., chromosome aneuploidy, microduplication, microdeletion) is made according to a decision analysis. Certain decision analysis features are described in International Patent Application Publication No. WO 2014/190286, which is incorporated by reference herein. For example, a decision analysis sometimes comprises applying one or more methods that produce one or more results, an evaluation of the results, and a series of decisions based on the results, evaluations and/or the possible consequences of the decisions and terminating at some juncture of the process where a final decision is made. In some embodiments a decision analysis is a decision tree. A decision analysis, in some embodiments, comprises coordinated use of one or more processes (e.g., process steps, e.g., process). A decision analysis can be performed by a person, a system, an apparatus, software (e.g., a module), a computer, a processor (e.g., a microprocessor), the like or a combination thereof. In some embodiments a decision analysis comprises a method of determining the presence or absence of a copy number alteration (e.g., chromosome aneuploidy, microduplication or microdeletion) with reduced false negative and reduced false positive determinations, compared to an instance in which no decision analysis is utilized (e.g., a determination is made directly from normalized counts). In some embodiments a decision analysis comprises determining the presence or absence of a condition associated with one or more copy number alterations.

In some embodiments a decision analysis comprises generating a profile for a genome or a region of a genome (e.g., a chromosome or part thereof). A profile can be generated by any suitable method, known or described herein. In some embodiments, a decision analysis comprises a segmenting process. Segmenting can modify and/or transform a profile thereby providing one or more decomposition renderings of a profile. A profile subjected to a segmenting process often is a profile of normalized counts mapped to portions in a reference genome or part thereof. As addressed herein, raw counts mapped to the portions can be normalized by one or more suitable normalization processes (e.g., LOESS, GC-LOESS, principal component normalization, or combination thereof) to generate a profile that is segmented as part of a decision analysis. A decomposition rendering of a profile is often a transformation of a profile. A decomposition rendering of a profile is sometimes a transformation of a profile into a representation of a genome, chromosome or part thereof.

In certain embodiments, a segmenting process utilized for the segmenting locates and identifies one or more levels within a profile that are different (e.g., substantially or significantly different) than one or more other levels within a profile. A level identified in a profile according to a segmenting process that is different than another level in the profile, and has edges that are different than another level in the profile, is referred to herein as a level for a discrete segment. A segmenting process can generate, from a profile of normalized counts or levels, a decomposition rendering in which one or more discrete segments can be identified. A discrete segment generally covers fewer portions than what is segmented (e.g., chromosome, chromosomes, autosomes).

In some embodiments, segmenting locates and identifies edges of discrete segments within a profile. In certain embodiments, one or both edges of one or more discrete segments are identified. For example, a segmentation process can identify the location (e.g., genomic coordinates, e.g., portion location) of the right and/or the left edges of a discrete segment in a profile. A discrete segment often comprises two edges. For example, a discrete segment can include a left edge and a right edge. In some embodiments, depending upon the representation or view, a left edge can be a 5'-edge and a right edge can be a 3'-edge of a nucleic acid segment in a profile. In some embodiments, a left edge can be a 3'-edge and a right edge can be a 5'-edge of a nucleic acid segment in a profile. Often the edges of a profile are known prior to segmentation and therefore, in some embodiments, the edges of a profile determine which edge of a level is a 5'-edge and which edge is 3'-edge. In some embodiments one or both edges of a profile and/or discrete segment is an edge of a chromosome.

In some embodiments, the edges of a discrete segment are determined according to a decomposition rendering generated for a reference sample (e.g., a reference profile). In some embodiments a null edge height distribution is determined according to a decomposition rendering of a reference profile (e.g., a profile of a chromosome or part thereof). In certain embodiments, the edges of a discrete segment in a profile are identified when the level of the discrete segment is outside a null edge height distribution. In some embodiments, the edges of a discrete segment in a profile are identified according a Z-score calculated according to a decomposition rendering for a reference profile.

In some instances, segmenting generates two or more discrete segments (e.g., two or more fragmented levels, two or more fragmented segments) in a profile. In some embodiments, a decomposition rendering derived from a segmenting process is over-segmented or fragmented and comprises multiple discrete segments. Sometimes discrete segments generated by segmenting are substantially different and sometimes discrete segments generated by segmenting are substantially similar. Substantially similar discrete segments (e.g., substantially similar levels) often refers to two or more adjacent discrete segments in a segmented profile each having a level that differs by less than a predetermined level of uncertainty. In some embodiments, substantially similar discrete segments are adjacent to each other and are not separated by an intervening segment. In some embodiments, substantially similar discrete segments are separated by one or more smaller segments. In some embodiments substantially similar discrete segments are separated by about 1 to about 20, about 1 to about 15, about 1 to about 10 or about 1 to about 5 portions where one or more of the intervening portions have a level significantly different than the level of each of the substantially similar discrete segments. In some embodiments, the level of substantially similar discrete segments differs by less than about 3 times, less than about 2 times, less than about 1 time or less than about 0.5 times a level of uncertainty. Substantially similar discrete segments, in some embodiments, comprise a median level that differs by less than 3 MAD (e.g., less than 3 sigma), less than 2 MAD, less than 1 MAD or less than about 0.5 MAD, where a MAD is calculated from a median level of each of the segments. Substantially different discrete segments, in some embodiments, are not adjacent or are separated by 10 or more, 15 or more or 20 or more portions. Substantially different discrete segments generally have substantially different levels. In certain embodiments, substantially different discrete segments comprises levels that differ by more than about 2.5 times, more than about 3 times, more than about 4 times, more than about 5 times, more than about 6 times a level of uncertainty. Substantially different discrete segments, in some embodiments, comprise a median level that differs by more than 2.5 MAD (e.g., more than 2.5 sigma), more than 3 MAD, more than 4 MAD, more than about 5 MAD or more than about 6 MAD, where a MAD is calculated from a median level of each of the discrete segments.

In some embodiments, a segmentation process comprises determining (e.g., calculating) a level (e.g., a quantitative value, e.g., a mean or median level), a level of uncertainty (e.g., an uncertainty value), Z-score, Z-value, p-value, the like or combinations thereof for one or more discrete segments in a profile or part thereof. In some embodiments a level (e.g., a quantitative value, e.g., a mean or median level), a level of uncertainty (e.g., an uncertainty value), Z-score, Z-value, p-value, the like or combinations thereof are determined (e.g., calculated) for a discrete segment.

Segmenting can be performed, in full or in part, by one or more decomposition generating processes. A decomposition generating process may provide, for example, a decomposition rendering of a profile. Any decomposition generating process described herein or known in the art may be used. Non-limiting examples of a decomposition generating process include circular binary segmentation (CBS) (see, e.g., Olshen et al. (2004) Biostatistics 5(4):557-72; Venkatraman, E S, Olshen, A B (2007) Bioinformatics 23(6):657-63); Haar wavelet segmentation (see, e.g., Haar, Alfred (1910) Mathematische Annalen 69(3):331-371); maximal overlap discrete wavelet transform (MODWT) (see, e.g., Hsu et al. (2005) Biostatistics 6 (2):211-226); stationary wavelet (SWT) (see, e.g., Y. Wang and S. Wang (2007) International Journal of Bioinformatics Research and Applications 3(2): 206-222); dual-tree complex wavelet transform (DTCWT) (see, e.g., Nguyen et al. (2007) Proceedings of the 7th IEEE International Conference, Boston Mass., on Oct. 14-17, 2007, pages 137-144); maximum entropy segmentation, convolution with edge detection kernel, Jensen Shannon Divergence, Kullback-Leibler divergence, Binary Recursive Segmentation, a Fourier transform, the like or combinations thereof.

In some embodiments, segmenting is accomplished by a process that comprises one process or multiple sub-processes, non-limiting examples of which include a decomposition generating process, thresholding, leveling, smoothing, polishing, the like or combination thereof. Thresholding, leveling, smoothing, polishing and the like can be performed in conjunction with a decomposition generating process, for example.

In some embodiments, a decision analysis comprises identifying a candidate segment in a decomposition rendering. A candidate segment is determined as being the most significant discrete segment in a decomposition rendering. A candidate segment may be the most significant in terms of the number of portions covered by the segment and/or in terms of the absolute value of the level of normalized counts for the segment. A candidate segment sometimes is larger and sometimes substantially larger than other discrete segments in a decomposition rendering. A candidate segment can be identified by a suitable method. In some embodiments, a candidate segment is identified by an area under the curve (AUC) analysis. In certain embodiments, where a first discrete segment has a level and/or covers a number of portions substantially larger than for another discrete segment in a decomposition rendering, the first segment comprises a larger AUC. Where a level is analyzed for AUC, an absolute value of a level often is utilized (e.g., a level corresponding to normalized counts can have a negative value for a deletion and a positive value for a duplication). In certain embodiments, an AUC is determined as an absolute value of a calculated AUC (e.g., a resulting positive value). In certain embodiments, a candidate segment, once identified (e.g., by an AUC analysis or by a suitable method) and optionally after it is validated, is selected for a z-score calculation, or the like, to determine if the candidate segment represents a genetic variation (e.g., an aneuploidy, microdeletion or microduplication).

In some embodiments, a decision analysis comprises a comparison. In some embodiments, a comparison comprises comparing at least two decomposition renderings. In some embodiments, a comparison comprises comparing at least two candidate segments. In certain embodiments, each of the at least two candidate segments is from a different decomposition rendering. For example, a first candidate segment can be from a first decomposition rendering and a second candidate segment can be from a second decomposition rendering. In some embodiments, a comparison comprises determining if two decomposition renderings are substantially the same or different. In some embodiments, a comparison comprises determining if two candidate segments are substantially the same or different. Two candidate segments can be determined as substantially the same or different by a suitable comparison method, non-limiting examples of which include by visual inspection, by comparing levels or Z-scores of the two candidate segments, by comparing the edges of the two candidate segments, by overlaying either the two candidate segments or their corresponding decomposition renderings, the like or combinations thereof.

Classifications and Uses Thereof

Methods described herein can provide an outcome indicative of a genotype and/or presence or absence of a genetic variation in a genomic region for a test sample (e.g., providing an outcome determinative of the presence or absence of a genetic variation). Methods described herein sometimes provide an outcome indicative of a phenotype and/or presence or absence of a medical condition for a test sample (e.g., providing an outcome determinative of the presence or absence of a medical condition and/or phenotype). An outcome often is part of a classification process, and a classification (e.g., classification of presence or absence of a genotype, phenotype, genetic variation and/or medical condition for a test sample) sometimes is based on and/or includes an outcome. An outcome and/or classification sometimes is based on and/or includes a result of data processing for a test sample that facilitates determining presence or absence of a genotype, phenotype, genetic variation and/or medical condition in a classification process (e.g., a statistic value (e.g., standard score (e.g., z-score)). An outcome and/or classification sometimes includes or is based on a score determinative of, or a call of, presence or absence of a genotype, phenotype, genetic variation and/or medical condition. In certain embodiments, an outcome and/or classification includes a conclusion that predicts and/or determines presence or absence of a genotype, phenotype, genetic variation and/or medical condition in a classification process.

A genotype and/or genetic variation often includes a gain, a loss and/or alteration of a region comprising one or more nucleotides (e.g., duplication, deletion, fusion, insertion, short tandem repeat (STR), mutation, single nucleotide alteration, reorganization, substitution or aberrant methylation) that results in a detectable change in the genome or genetic information for a test sample. A genotype and/or genetic variation often is in a particular genomic region (e.g., chromosome, portion of a chromosome (i.e., sub-chromosome region), STR, polymorphic region, translocated region, altered nucleotide sequence, the like or combinations of the foregoing). A genetic variation sometimes is a copy number alteration for a particular region, such as a trisomy or monosomy for chromosome region, or a microduplication or microdeletion event for a particular region (e.g., gain or loss of a region of about 10 megabases or less (e.g., about 9 megabases or less, 8 megabases or less, 7 megabases or less, 6 megabases or less, 5 megabases or less, 4 megabases or less, 3 megabases or less, 2 megabases or less or 1 megabase or less)), for example. A copy number alteration sometimes is expressed as having no copy or one, two, three or four or more copies of a particular region (e.g., chromosome, sub-chromosome, STR, microduplication or microdeletion region).

Presence or absence of a genotype, phenotype, genetic variation and/or medical condition can be determined by transforming, analyzing and/or manipulating sequence reads that have been mapped to genomic portions (e.g., counts, counts of genomic portions of a reference genome). In certain embodiments, an outcome and/or classification is determined according to normalized counts, read densities, read density profiles, and the like, and can be determined by a method described herein. An outcome and/or classification sometimes includes one or more scores and/or calls that refer to the probability that a particular genotype, phenotype, genetic variation, or medical condition is present or absent for a test sample. The value of a score may be used to determine, for example, a variation, difference, or ratio of mapped sequence reads that may correspond to a genotype, phenotype, genetic variation, or medical condition. For example, calculating a positive score for a selected genotype, phenotype, genetic variation, or medical condition from a data set, with respect to a reference genome, can lead to a classification of the genotype, phenotype, genetic variation, or medical condition, for a test sample.

Any suitable expression of an outcome and/or classification can be provided. An outcome and/or classification sometimes is based on and/or includes one or more numerical values generated using a processing method described herein in the context of one or more considerations of probability. Non-limiting examples of values that can be utilized include a sensitivity, specificity, standard deviation, median absolute deviation (MAD), measure of certainty, measure of confidence, measure of certainty or confidence that a value obtained for a test sample is inside or outside a particular range of values, measure of uncertainty, measure of uncertainty that a value obtained for a test sample is inside or outside a particular range of values, coefficient of variation (CV), confidence level, confidence interval (e.g., about 95% confidence interval), standard score (e.g., z-score), chi value, phi value, result of a t-test, p-value, ploidy value, fitted minority species fraction, area ratio, median level, the like or combination thereof. In some embodiments, an outcome and/or classification comprises a read density, a read density profile and/or a plot (e.g., a profile plot). In certain embodiments, multiple values are analyzed together, sometimes in a profile for such values (e.g., z-score profile, p-value profile, chi value profile, phi value profile, result of a t-test, value profile, the like, or combination thereof). A consideration of probability can facilitate determining whether a subject is at risk of having, or has, a genotype, phenotype, genetic variation and/or medical condition, and an outcome and/or classification determinative of the foregoing sometimes includes such a consideration.

In certain embodiments, an outcome and/or classification is based on and/or includes a conclusion that predicts and/or determines a risk or probability of the presence or absence of a genotype, phenotype, genetic variation and/or medical condition for a test sample. A conclusion sometimes is based on a value determined from a data analysis method described herein (e.g., a statistics value indicative of probability, certainty and/or uncertainty (e.g., standard deviation, median absolute deviation (MAD), measure of certainty, measure of confidence, measure of certainty or confidence that a value obtained for a test sample is inside or outside a particular range of values, measure of uncertainty, measure of uncertainty that a value obtained for a test sample is inside or outside a particular range of values, coefficient of variation (CV), confidence level, confidence interval (e.g., about 95% confidence interval), standard score (e.g., z-score), chi value, phi value, result of a t-test, p-value, sensitivity, specificity, the like or combination thereof). An outcome and/or classification sometimes is expressed in a laboratory test report (described in greater detail hereafter) for particular test sample as a probability (e.g., odds ratio, p-value), likelihood, or risk factor, associated with the presence or absence of a genotype, phenotype, genetic variation and/or medical condition. An outcome and/or classification for a test sample sometimes is provided as "positive" or "negative" with respect a particular genotype, phenotype, genetic variation and/or medical condition. For example, an outcome and/or classification sometimes is designated as "positive" in a laboratory test report for a particular test sample where presence of a genotype, phenotype, genetic variation and/or medical condition is determined, and sometimes an outcome and/or classification is designated as "negative" in a laboratory test report for a particular test sample where absence of a genotype, phenotype, genetic variation and/or medical condition is determined. An outcome and/or classification sometimes is determined and sometimes includes an assumption used in data processing.

An outcome and/or classification sometimes is based on or is expressed as a value in or out of a cluster, value over or under a threshold value, value within a range (e.g., a threshold range), and/or a value with a measure of variance or confidence. In some embodiments, an outcome and/or classification is based on or is expressed as a value above or below a predetermined threshold or cutoff value and/or a measure of uncertainty, confidence level or confidence interval associated with the value. In certain embodiments, a predetermined threshold or cutoff value is an expected level or an expected level range. In some embodiments, a value obtained for a test sample is a standard score (e.g., z-score), where presence of a genotype, phenotype, genetic variation and/or medical condition is determined when the absolute value of the score is greater than a particular score threshold (e.g., threshold between about 2 and about 5; between about 3 and about 4), and where the absence of a genotype, phenotype, genetic variation and/or medical condition is determined when the absolute value of the score is less than the particular score threshold. In certain embodiments, an outcome and/or classification is based on or is expressed as a value that falls within or outside a predetermined range of values (e.g., a threshold range) and the associated uncertainty or confidence level for that value being inside or outside the range. In some embodiments, an outcome and/or classification comprises a value that is equal to a predetermined value (e.g., equal to 1, equal to zero), or is equal to a value within a predetermined value range, and its associated uncertainty or confidence level for that value being equal or within or outside the range. An outcome and/or classification sometimes is graphically represented as a plot (e.g., profile plot). An outcome and/or classification sometimes comprises use of a reference value or reference profile, and sometimes a reference value or reference profile is obtained from one or more reference samples (e.g., reference sample(s) euploid for a selected part of a genome (e.g., region)).

In some embodiments, an outcome and/or classification is based on or includes use of a measure of uncertainty between a test value or profile and a reference value or profile for a selected region. In some embodiments, a determination of the presence or absence of a genotype, phenotype, genetic variation and/or medical condition is according to the number of deviations (e.g., sigma) between a test value or profile and a reference value or profile for a selected region (e.g., a chromosome, or part thereof). A measure of deviation often is an absolute value or absolute measure of deviation (e.g., mean absolute deviation or median absolute deviation (MAD)). In some embodiments, the presence of a genotype, phenotype, genetic variation and/or medical condition is determined when the number of deviations between a test value or profile and a reference value or profile is about 1 or greater (e.g., about 1.5, 2, 2.5, 2.6, 2.7, 2.8, 2.9, 3, 3.1, 3.2, 3.3, 3.4, 3.5, 3.6, 3.7, 3.8, 3.9, 4, 5 or 6 deviations or greater). In certain embodiments, presence of a genotype, phenotype, genetic variation and/or medical condition is determined when a test value or profile and a reference value or profile differ by about 2 to about 5 measures of deviation (e.g., sigma, MAD), or more than 3 measures of deviation (e.g., 3 sigma, 3 MAD). A deviation of greater than three between a test value or profile and a reference value or profile often is indicative of a non-euploid test subject (e.g., presence of a genetic variation (e.g., presence of trisomy, monosomy, microduplication, microdeletion) for a selected region. Test values or profiles significantly above a reference profile, which reference profile is indicative of euploidy, sometimes are determinative of a trisomy, sub-chromosome duplication or microduplication. Test values or profiles significantly below a reference profile, which reference profile is indicative of euploidy, sometimes are determinative of a monosomy, sub-chromosome deletion or microdeletion. In some embodiments, absence of a genotype, phenotype, genetic variation and/or medical condition is determined when the number of deviations between a test value or profile and reference value or profile for a selected region of a genome is about 3.5 or less (e.g., about less than about 3.4, 3.3, 3.2, 3.1, 3, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1 or less). In certain embodiments, absence of a genotype, phenotype, genetic variation and/or medical condition is determined when a test value or profile differs from a reference value or profile by less than three measures of deviation (e.g., 3 sigma, 3 MAD). In some embodiments, a measure of deviation of less than three between a test value or profile and reference value or profile (e.g., 3-sigma for standard deviation) often is indicative of a region that is euploid (e.g., absence of a genetic variation). A measure of deviation between a test value or profile for a test sample and a reference value or profile for one or more reference subjects can be plotted and visualized (e.g., z-score plot).

In some embodiments, an outcome and/or classification is determined according to a call zone. In certain embodiments, a call is made (e.g., a call determining presence or absence of a genotype, phenotype, genetic variation and/or medical condition) when a value (e.g., a profile, a read density profile and/or a measure of uncertainty) or collection of values falls within a pre-defined range (e.g., a zone, a call zone). In some embodiments, a call zone is defined according to a collection of values (e.g., profiles, read density profiles, measures or determination of probability and/or measures of uncertainty) obtained from a particular group of samples. In certain embodiments, a call zone is defined according to a collection of values that are derived from the same chromosome or part thereof. In some embodiments, a call zone for determining presence or absence of a genotype, phenotype, genetic variation and/or medical condition is defined according a measure of uncertainty (e.g., high level of confidence or low measure of uncertainty) and/or a quantification of a minority nucleic acid species (e.g., about 1% minority species or greater (e.g., about 2, 3, 4, 5, 6, 7, 8, 9, 10% or more minority nucleic acid species)) determined for a test sample. A minority nucleic acid species quantification sometimes is a fraction or percent of cancer cell nucleic acid or fetal nucleic acid (i.e., fetal fraction) ascertained for a test sample. In some embodiments, a call zone is defined by a confidence level or confidence interval (e.g., a confidence interval for 95% level of confidence). A call zone sometimes is defined by a confidence level, or confidence interval based on a particular confidence level, of about 90% or greater (e.g., about 91, 92, 93, 94, 95, 96, 97, 98, 99, 99.1, 99.2, 99.3, 99.4, 99.5, 99.6, 99.7, 99.8, 99.9% or greater). In some embodiments, a call is made using a call zone and additional data or information. In some embodiments, a call is made without using a call zone. In some embodiments, a call is made based on a comparison without the use of a call zone. In some embodiments, a call is made based on visual inspection of a profile (e.g., visual inspection of read densities).

In some embodiments, a classification or call is not provided for a test sample when a test value or profile is in a no-call zone. In some embodiments, a no-call zone is defined by a value (e.g., collection of values) or profile that indicates low accuracy, high risk, high error, low level of confidence, high measure of uncertainty, the like or combination thereof. In some embodiments, a no-call zone is defined, in part, by a minority nucleic acid species quantification (e.g., a minority nucleic acid species of about 10% or less (e.g., about 9, 8, 7, 6, 5, 4, 3, 2% or less minority nucleic acid species)). An outcome and/or classification generated for determining the presence or absence of a genotype, phenotype, genetic variation and/or medical condition sometimes includes a null result. A null result sometimes is a data point between two clusters, a numerical value with a standard deviation that encompasses values for both the presence and absence of a genotype, phenotype, genetic variation and/or medical condition, a data set with a profile plot that is not similar to profile plots for subjects having or free from the genetic variation being investigated). In some embodiments, an outcome and/or classification indicative of a null result is considered a determinative result, and the determination can include a conclusion of the need for additional information and/or a repeat of data generation and/or analysis for determining the presence or absence of a genotype, phenotype, genetic variation and/or medical condition.

There typically are four types of classifications generated in a classification process: true positive, false positive, true negative and false negative. The term "true positive" as used herein refers to presence of a genotype, phenotype, genetic variation, or medical condition correctly determined for a test sample. The term "false positive" as used herein refers to presence of a genotype, phenotype, genetic variation, or medical condition incorrectly determined for a test sample. The term "true negative" as used herein refers to absence of a genotype, phenotype, genetic variation, or medical condition correctly determined for a test sample. The term "false negative" as used herein refers to absence of a genotype, phenotype, genetic variation, or medical condition incorrectly determined for a test sample. Two measures of performance for a classification process can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative.

In certain embodiments, a laboratory test report generated for a classification process includes a measure of test performance (e.g., sensitivity and/or specificity) and/or a measure of confidence (e.g., a confidence level, confidence interval). A measure of test performance and/or confidence sometimes is obtained from a clinical validation study performed prior to performing a laboratory test for a test sample. In certain embodiments, one or more of sensitivity, specificity and/or confidence are expressed as a percentage. In some embodiments, a percentage expressed independently for each of sensitivity, specificity or confidence level, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). A confidence interval expressed for a particular confidence level (e.g., a confidence level of about 90% to about 99.9% (e.g., about 95%)) can be expressed as a range of values, and sometimes is expressed as a range or sensitivities and/or specificities for a particular confidence level. Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome and/or classification is not due to chance) in certain embodiments is expressed as a standard score (e.g., z-score), a p-value, or result of a t-test. In some embodiments, a measured variance, confidence level, confidence interval, sensitivity, specificity and the like (e.g., referred to collectively as confidence parameters) for an outcome and/or classification can be generated using one or more data processing manipulations described herein. Specific examples of generating an outcome and/or classification and associated confidence levels are described, for example, in International Patent Application Publication Nos. WO 2013/052913, WO 2014/190286 and WO 2015/051163, the entire content of which is incorporated herein by reference, including all text, tables, equations and drawings.

An outcome and/or classification for a test sample often is ordered by, and often is provided to, a health care professional or other qualified individual (e.g., physician or assistant) who transmits an outcome and/or classification to a subject from whom the test sample is obtained. In certain embodiments, an outcome and/or classification is provided using a suitable visual medium (e.g., a peripheral or component of a machine, e.g., a printer or display). A classification and/or outcome often is provided to a healthcare professional or qualified individual in the form of a report. A report typically comprises a display of an outcome and/or classification (e.g., a value, or an assessment or probability of presence or absence of a genotype, phenotype, genetic variation and/or medical condition), sometimes includes an associated confidence parameter, and sometimes includes a measure of performance for a test used to generate the outcome and/or classification. A report sometimes includes a recommendation for a follow-up procedure (e.g., a procedure that confirms the outcome or classification). A report sometimes includes a visual representation of a chromosome or portion thereof (e.g., a chromosome ideogram or karyogram), and sometimes shows a visualization of a duplication and/or deletion region for a chromosome (e.g., a visualization of a whole chromosome for a chromosome deletion or duplication; a visualization of a whole chromosome with a deleted region or duplicated region shown; a visualization of a portion of chromosome duplicated or deleted; a visualization of a portion of a chromosome remaining in the event of a deletion of a portion of a chromosome) identified for a test sample.

A report can be displayed in a suitable format that facilitates determination of presence or absence of a genotype, phenotype, genetic variation and/or medical condition by a health professional or other qualified individual. Non-limiting examples of formats suitable for use for generating a report include digital data, a graph, a 2D graph, a 3D graph, and 4D graph, a picture (e.g., a jpg, bitmap (e.g., bmp), pdf, tiff, gif, raw, png, the like or suitable format), a pictograph, a chart, a table, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, or combination of the foregoing.

A report may be generated by a computer and/or by human data entry, and can be transmitted and communicated using a suitable electronic medium (e.g., via the internet, via computer, via facsimile, from one network location to another location at the same or different physical sites), or by another method of sending or receiving data (e.g., mail service, courier service and the like). Non-limiting examples of communication media for transmitting a report include auditory file, computer readable file (e.g., pdf file), paper file, laboratory file, medical record file, or any other medium described in the previous paragraph. A laboratory file or medical record file may be in tangible form or electronic form (e.g., computer readable form), in certain embodiments. After a report is generated and transmitted, a report can be received by obtaining, via a suitable communication medium, a written and/or graphical representation comprising an outcome and/or classification, which upon review allows a healthcare professional or other qualified individual to make a determination as to presence or absence of a genotype, phenotype, genetic variation and/or or medical condition for a test sample.

An outcome and/or classification may be provided by and obtained from a laboratory (e.g., obtained from a laboratory file). A laboratory file can be generated by a laboratory that carries out one or more tests for determining presence or absence of a genotype, phenotype, genetic variation and/or medical condition for a test sample. Laboratory personnel (e.g., a laboratory manager) can analyze information associated with test samples (e.g., test profiles, reference profiles, test values, reference values, level of deviation, patient information) underlying an outcome and/or classification. For calls pertaining to presence or absence of a genotype, phenotype, genetic variation and/or medical condition that are close or questionable, laboratory personnel can re-run the same procedure using the same (e.g., aliquot of the same sample) or different test sample from a test subject. A laboratory may be in the same location or different location (e.g., in another country) as personnel assessing the presence or absence of a genotype, phenotype, genetic variation and/or a medical condition from the laboratory file. For example, a laboratory file can be generated in one location and transmitted to another location in which the information for a test sample therein is assessed by a healthcare professional or other qualified individual, and optionally, transmitted to the subject from which the test sample was obtained. A laboratory sometimes generates and/or transmits a laboratory report containing a classification of presence or absence of genomic instability, a genotype, phenotype, a genetic variation and/or a medical condition for a test sample. A laboratory generating a laboratory test report sometimes is a certified laboratory, and sometimes is a laboratory certified under the Clinical Laboratory Improvement Amendments (CLIA).

An outcome and/or classification sometimes is a component of a diagnosis for a subject, and sometimes an outcome and/or classification is utilized and/or assessed as part of providing a diagnosis for a test sample. For example, a healthcare professional or other qualified individual may analyze an outcome and/or classification and provide a diagnosis based on, or based in part on, the outcome and/or classification. In some embodiments, determination, detection or diagnosis of a medical condition, disease, syndrome or abnormality comprises use of an outcome and/or classification determinative of presence or absence of a genotype, phenotype, genetic variation and/or medical condition. In some embodiments, an outcome and/or classification based on counted mapped sequence reads, normalized counts and/or transformations thereof is determinative of presence or absence of a genotype and/or genetic variation. In certain embodiments, a diagnosis comprises determining presence or absence of a condition, syndrome or abnormality. In certain instances, a diagnosis comprises a determination of a genotype or genetic variation as the nature and/or cause of a medical condition, disease, syndrome or abnormality. Thus, provided herein are methods for diagnosing presence or absence of a genotype, phenotype, a genetic variation and/or a medical condition for a test sample according to an outcome or classification generated by methods described herein, and optionally according to generating and transmitting a laboratory report that includes a classification for presence or absence of the genotype, phenotype, a genetic variation and/or a medical condition for the test sample.

An outcome and/or classification sometimes is a component of health care and/or treatment of a subject. An outcome and/or classification sometimes is utilized and/or assessed as part of providing a treatment for a subject from whom a test sample was obtained. For example, an outcome and/or classification indicative of presence or absence of a genotype, phenotype, genetic variation, and/or medical condition is a component of health care and/or treatment of a subject from whom a test sample was obtained. Medical care, treatment and or diagnosis can be in any suitable area of health, such as medical treatment of subjects for prenatal care, cell proliferative conditions, cancer and the like, for example. An outcome and/or classification determinative of presence or absence of a genotype, phenotype, genetic variation and/or medical condition, disease, syndrome or abnormality by methods described herein sometimes is independently verified by further testing. Any suitable type of further test to verify an outcome and/or classification can be utilized, non-limiting examples of which include blood level test (e.g., serum test), biopsy, scan (e.g., CT scan, MRI scan), invasive sampling (e.g., amniocentesis or chorionic villus sampling), karyotyping, microarray assay, ultrasound, sonogram, and the like, for example.

A healthcare professional or qualified individual can provide a suitable healthcare recommendation based on the outcome and/or classification provided in a laboratory report. In some embodiments, a recommendation is dependent on the outcome and/or classification provided (e.g., cancer, stage and/or type of cancer, Down's syndrome, Turner syndrome, medical conditions associated with genetic variations in T13, medical conditions associated with genetic variations in T18). Non-limiting examples of recommendations that can be provided based on an outcome or classification in a laboratory report includes, without limitation, surgery, radiation therapy, chemotherapy, genetic counseling, after-birth treatment solutions (e.g., life planning, long term assisted care, medicaments, symptomatic treatments), pregnancy termination, organ transplant, blood transfusion, further testing described in the previous paragraph, the like or combinations of the foregoing. Thus, methods for treating a subject and methods for providing health care to a subject sometimes include generating a classification for presence or absence of a genotype, phenotype, a genetic variation and/or a medical condition for a test sample by a method described herein, and optionally generating and transmitting a laboratory report that includes a classification of presence or absence of a genotype, phenotype, genetic variation and/or medical condition for the test sample.

Generating an outcome and/or classification can be viewed as a transformation of nucleic acid sequence reads from a test sample into a representation of a subject's cellular nucleic acid. For example, transmuting sequence reads of nucleic acid from a subject by a method described herein, and generating an outcome and/or classification can be viewed as a transformation of relatively small sequence read fragments to a representation of relatively large and complex structure of nucleic acid in the subject. In some embodiments, an outcome and/or classification results from a transformation of sequence reads from a subject into a representation of an existing nucleic acid structure present in the subject (e.g., a genome, a chromosome, chromosome segment, mixture of circulating cell-free nucleic acid fragments in the subject).

Machines, Software and Interfaces

Certain processes and methods described herein (e.g., mapping, counting, normalizing, range setting, adjusting, categorizing and/or determining sequence reads, counts, levels and/or profiles) often cannot be performed without a computer, microprocessor, software, module or other machine. Methods described herein typically are computer-implemented methods, and one or more portions of a method sometimes are performed by one or more processors (e.g., microprocessors), computers, systems, apparatuses, or machines (e.g., microprocessor-controlled machine).

Computers, systems, apparatuses, machines and computer program products suitable for use often include, or are utilized in conjunction with, computer readable storage media. Non-limiting examples of computer readable storage media include memory, hard disk, CD-ROM, flash memory device and the like. Computer readable storage media generally are computer hardware, and often are non-transitory computer-readable storage media. Computer readable storage media are not computer readable transmission media, the latter of which are transmission signals per se.

Provided herein are computer readable storage media with an executable program stored thereon, where the program instructs a microprocessor to perform a method described herein. Provided also are computer readable storage media with an executable program module stored thereon, where the program module instructs a microprocessor to perform part of a method described herein. Also provided herein are systems, machines, apparatuses and computer program products that include computer readable storage media with an executable program stored thereon, where the program instructs a microprocessor to perform a method described herein. Provided also are systems, machines and apparatuses that include computer readable storage media with an executable program module stored thereon, where the program module instructs a microprocessor to perform part of a method described herein.

Also provided are computer program products. A computer program product often includes a computer usable medium that includes a computer readable program code embodied therein, the computer readable program code adapted for being executed to implement a method or part of a method described herein. Computer usable media and readable program code are not transmission media (i.e., transmission signals per se). Computer readable program code often is adapted for being executed by a processor, computer, system, apparatus, or machine.

In some embodiments, methods described herein (e.g., quantifying, counting, filtering, normalizing, transforming, clustering and/or determining sequence reads, counts, levels, profiles and/or outcomes) are performed by automated methods. In some embodiments, one or more steps of a method described herein are carried out by a microprocessor and/or computer, and/or carried out in conjunction with memory. In some embodiments, an automated method is embodied in software, modules, microprocessors, peripherals and/or a machine comprising the like, that perform methods described herein. As used herein, software refers to computer readable program instructions that, when executed by a microprocessor, perform computer operations, as described herein.

Sequence reads, counts, levels and/or profiles sometimes are referred to as "data" or "data sets." In some embodiments, data or data sets can be characterized by one or more features or variables (e.g., sequence based (e.g., GC content, specific nucleotide sequence, the like), function specific (e.g., expressed genes, cancer genes, the like), location based (genome specific, chromosome specific, portion or portion-specific), the like and combinations thereof). In certain embodiments, data or data sets can be organized into a matrix having two or more dimensions based on one or more features or variables. Data organized into matrices can be organized using any suitable features or variables. In certain embodiments, data sets characterized by one or more features or variables sometimes are processed after counting.

Machines, software and interfaces may be used to conduct methods described herein. Using machines, software and interfaces, a user may enter, request, query or determine options for using particular information, programs or processes (e.g., mapping sequence reads, processing mapped data and/or providing an outcome), which can involve implementing statistical analysis process, statistical significance process, statistical process, iterative steps, validation process, and graphical representations, for example. In some embodiments, a data set may be entered by a user as input information, a user may download one or more data sets by suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A system typically comprises one or more machines. Each machine comprises one or more of memory, one or more microprocessors, and instructions. Where a system includes two or more machines, some or all of the machines may be located at the same location, some or all of the machines may be located at different locations, all of the machines may be located at one location and/or all of the machines may be located at different locations. Where a system includes two or more machines, some or all of the machines may be located at the same location as a user, some or all of the machines may be located at a location different than a user, all of the machines may be located at the same location as the user, and/or all of the machine may be located at one or more locations different than the user.

A system sometimes comprises a computing machine and a sequencing apparatus or machine, where the sequencing apparatus or machine is configured to receive physical nucleic acid and generate sequence reads, and the computing apparatus is configured to process the reads from the sequencing apparatus or machine. The computing machine sometimes is configured to determine a classification outcome from the sequence reads.

A user may, for example, place a query to software which then may acquire a data set via internet access, and in certain embodiments, a programmable microprocessor may be prompted to acquire a suitable data set based on given parameters. A programmable microprocessor also may prompt a user to select one or more data set options selected by the microprocessor based on given parameters. A programmable microprocessor may prompt a user to select one or more data set options selected by the microprocessor based on information found via the internet, other internal or external information, or the like. Options may be chosen for selecting one or more data feature selections, one or more statistical process, one or more statistical analysis process, one or more statistical significance process, iterative steps, one or more validation process, and one or more graphical representations of methods, machines, apparatuses, computer programs or a non-transitory computer-readable storage medium with an executable program stored thereon.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output components may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus or machine may serve as data that can be input via an input device. In certain embodiments, mapped sequence reads may serve as data that can be input via an input device. In certain embodiments, nucleic acid fragment size (e.g., length) may serve as data that can be input via an input device. In certain embodiments, output from a nucleic acid capture process (e.g., genomic region origin data) may serve as data that can be input via an input device. In certain embodiments, a combination of nucleic acid fragment size (e.g., length) and output from a nucleic acid capture process (e.g., genomic region origin data) may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process or part of a process described herein, and software can include one or more modules for performing such processes (e.g., sequencing module, logic processing module, data display organization module). The term "software" refers to computer readable program instructions that, when executed by a computer, perform computer operations. Instructions executable by the one or more microprocessors sometimes are provided as executable code, that when executed, can cause one or more microprocessors to implement a method described herein. A module described herein can exist as software, and instructions (e.g., processes, routines, subroutines) embodied in the software can be implemented or performed by a microprocessor. For example, a module (e.g., a software module) can be a part of a program that performs a particular process or task. The term "module" refers to a self-contained functional unit that can be used in a larger machine or software system. A module can comprise a set of instructions for carrying out a function of the module. A module can transform data and/or information. Data and/or information can be in a suitable form. For example, data and/or information can be digital or analogue. In certain embodiments, data and/or information sometimes can be packets, bytes, characters, or bits. In some embodiments, data and/or information can be any gathered, assembled or usable data or information. Non-limiting examples of data and/or information include a suitable media, pictures, video, sound (e.g. frequencies, audible or non-audible), numbers, constants, a value, objects, time, functions, instructions, maps, references, sequences, reads, mapped reads, levels, ranges, thresholds, signals, displays, representations, or transformations thereof. A module can accept or receive data and/or information, transform the data and/or information into a second form, and provide or transfer the second form to an machine, peripheral, component or another module. A module can perform one or more of the following non-limiting functions: mapping sequence reads, providing counts, assembling portions, providing or determining a level, providing a count profile, normalizing (e.g., normalizing reads, normalizing counts, and the like), providing a normalized count profile or levels of normalized counts, comparing two or more levels, providing uncertainty values, providing or determining expected levels and expected ranges (e.g., expected level ranges, threshold ranges and threshold levels), providing adjustments to levels (e.g., adjusting a first level, adjusting a second level, adjusting a profile of a chromosome or a part thereof, and/or padding), providing identification (e.g., identifying a copy number alteration, genetic variation or aneuploidy), categorizing, plotting, and/or determining an outcome, for example. A microprocessor can, in certain embodiments, carry out the instructions in a module. In some embodiments, one or more microprocessors are required to carry out instructions in a module or group of modules. A module can provide data and/or information to another module, machine or source and can receive data and/or information from another module, machine or source.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and microprocessor capable of implementing instructions from a module can be located in a machine or in a different machine. A module and/or microprocessor capable of implementing an instruction for a module can be located in the same location as a user (e.g., local network) or in a different location from a user (e.g., remote network, cloud system). In embodiments in which a method is carried out in conjunction with two or more modules, the modules can be located in the same machine, one or more modules can be located in different machine in the same physical location, and one or more modules may be located in different machines in different physical locations.

A machine, in some embodiments, comprises at least one microprocessor for carrying out the instructions in a module. Sequence read quantifications (e.g., counts) sometimes are accessed by a microprocessor that executes instructions configured to carry out a method described herein. Sequence read quantifications that are accessed by a microprocessor can be within memory of a system, and the counts can be accessed and placed into the memory of the system after they are obtained. In some embodiments, a machine includes a microprocessor (e.g., one or more microprocessors) which microprocessor can perform and/or implement one or more instructions (e.g., processes, routines and/or subroutines) from a module. In some embodiments, a machine includes multiple microprocessors, such as microprocessors coordinated and working in parallel. In some embodiments, a machine operates with one or more external microprocessors (e.g., an internal or external network, server, storage device and/or storage network (e.g., a cloud)). In some embodiments, a machine comprises a module (e.g., one or more modules). A machine comprising a module often is capable of receiving and transferring one or more of data and/or information to and from other modules.

In certain embodiments, a machine comprises peripherals and/or components. In certain embodiments, a machine can comprise one or more peripherals or components that can transfer data and/or information to and from other modules, peripherals and/or components. In certain embodiments, a machine interacts with a peripheral and/or component that provides data and/or information. In certain embodiments, peripherals and components assist a machine in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., iPads, tablets), touch screens, smart phones, mobile phones, USB I/O devices, USB mass storage devices, keyboards, a computer mouse, digital pens, modems, hard drives, jump drives, flash drives, a microprocessor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like), the world wide web (www), the internet, a computer and/or another module.

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash memory devices (e.g., flash drives), RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

Software can include one or more process in certain embodiments. An process may be used for processing data and/or providing an outcome or report according to a finite sequence of instructions. An process often is a list of defined instructions for completing a task. Starting from an initial state, the instructions may describe a computation that proceeds through a defined series of successive states, eventually terminating in a final ending state. The transition from one state to the next is not necessarily deterministic (e.g., some process incorporate randomness). By way of example, and without limitation, an process can be a search process, sorting process, merge process, numerical process, graph process, string process, modeling process, computational genometric process, combinatorial process, machine learning process, cryptography process, data compression process, parsing process and the like. An process can include one process or two or more process working in combination. An process can be of any suitable complexity class and/or parameterized complexity. An process can be used for calculation and/or data processing, and in some embodiments, can be used in a deterministic or probabilistic/predictive approach. An process can be implemented in a computing environment by use of a suitable programming language, non-limiting examples of which are C, C++, Java, Perl, Python, Fortran, and the like. In some embodiments, an process can be configured or modified to include margin of errors, statistical analysis, statistical significance, and/or comparison to other information or data sets (e.g., applicable when using a neural net or clustering process).

In certain embodiments, several process may be implemented for use in software. These process can be trained with raw data in some embodiments. For each new raw data sample, the trained process may produce a representative processed data set or outcome. A processed data set sometimes is of reduced complexity compared to the parent data set that was processed. Based on a processed set, the performance of a trained process may be assessed based on sensitivity and specificity, in some embodiments. An process with the highest sensitivity and/or specificity may be identified and utilized, in certain embodiments.

In certain embodiments, simulated (or simulation) data can aid data processing, for example, by training an process or testing an process. In some embodiments, simulated data includes hypothetical various samplings of different groupings of sequence reads.

Simulated data may be based on what might be expected from a real population or may be skewed to test an process and/or to assign a correct classification. Simulated data also is referred to herein as "virtual" data. Simulations can be performed by a computer program in certain embodiments. One possible step in using a simulated data set is to evaluate the confidence of identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more microprocessors in certain embodiments. A microprocessor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A microprocessor may implement software in a system. In some embodiments, a microprocessor may be programmed to automatically perform a task described herein that a user could perform. Accordingly, a microprocessor, or process conducted by such a microprocessor, can require little to no supervision or input from a user (e.g., software may be programmed to implement a function automatically). In some embodiments, the complexity of a process is so large that a single person or group of persons could not perform the process in a timeframe short enough for determining the presence or absence of a genetic variation.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

Figure 11:
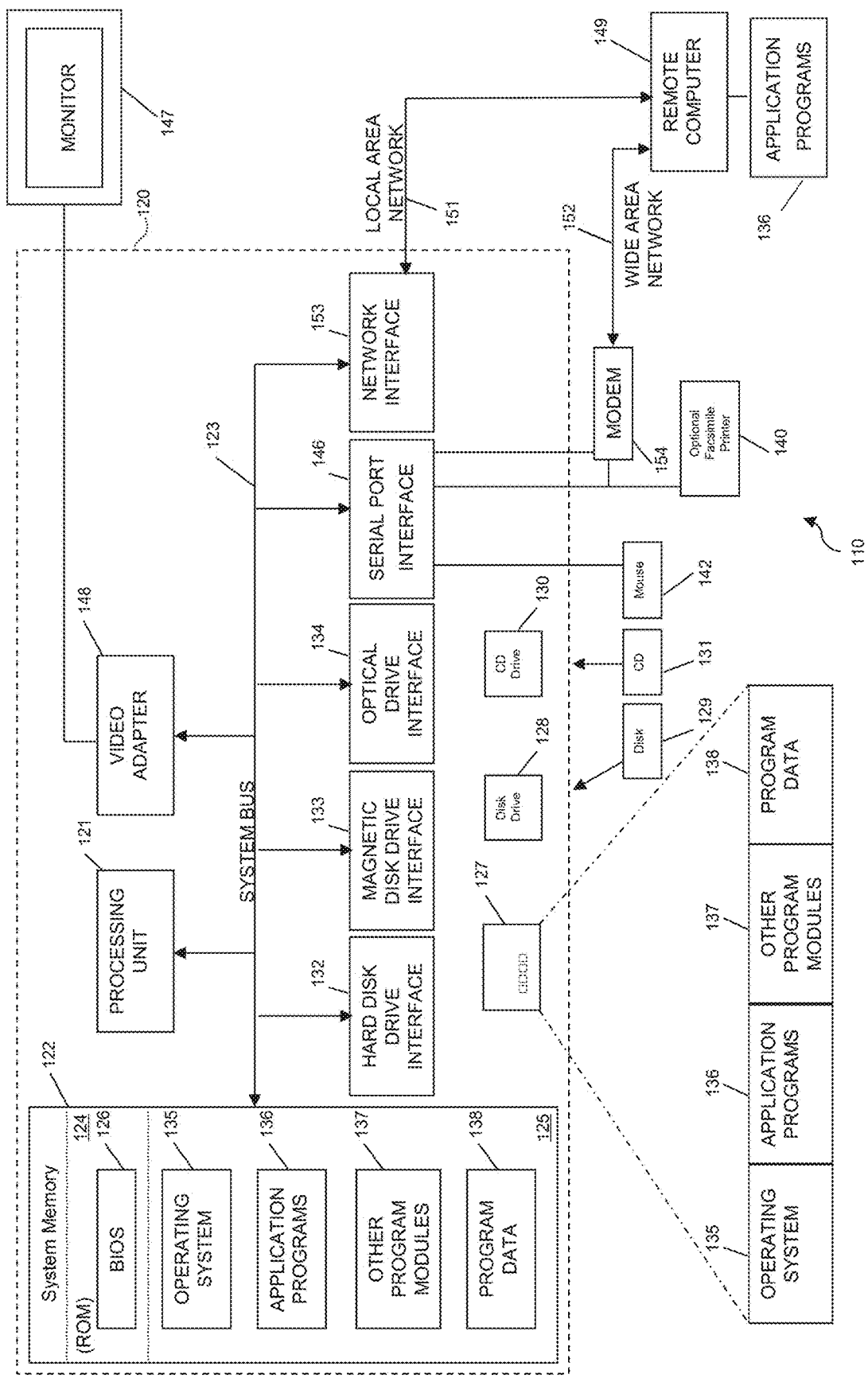
FIG. 11 shows an illustrative embodiment of a system in which certain embodiments of the technology may be implemented.

FIG. 11 illustrates a non-limiting example of a computing environment 110 in which various systems, methods, process, and data structures described herein may be implemented. The computing environment 110 is only one example of a suitable computing environment and is not intended to suggest any limitation as to the scope of use or functionality of the systems, methods, and data structures described herein. Neither should computing environment 110 be interpreted as having any dependency or requirement relating to any one or combination of components illustrated in computing environment 110. A subset of systems, methods, and data structures shown in FIG. 11 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 110 of FIG. 11 includes a general purpose computing device in the form of a computer 120, including a processing unit 121, a system memory 122, and a system bus 123 that operatively couples various system components including the system memory 122 to the processing unit 121. There may be only one or there may be more than one processing unit 121, such that the processor of computer 120 includes a single central-processing unit (CPU), or a plurality of processing units, commonly referred to as a parallel processing environment. The computer 120 may be a conventional computer, a distributed computer, or any other type of computer.

The system bus 123 may be any of several types of bus structures including a memory bus or memory controller, a peripheral bus, and a local bus using any of a variety of bus architectures. The system memory may also be referred to as simply the memory, and includes read only memory (ROM) 124 and random access memory (RAM). A basic input/output system (BIOS) 126, containing the basic routines that help to transfer information between elements within the computer 120, such as during start-up, is stored in ROM 124. The computer 120 may further include a hard disk drive interface 127 for reading from and writing to a hard disk, not shown, a magnetic disk drive 128 for reading from or writing to a removable magnetic disk 129, and an optical disk drive 130 for reading from or writing to a removable optical disk 131 such as a CD ROM or other optical media.

The hard disk drive 127, magnetic disk drive 128, and optical disk drive 130 are connected to the system bus 123 by a hard disk drive interface 132, a magnetic disk drive interface 133, and an optical disk drive interface 134, respectively. The drives and their associated computer-readable media provide nonvolatile storage of computer-readable instructions, data structures, program modules and other data for the computer 120. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 129, optical disk 131, ROM 124, or RAM, including an operating system 135, one or more application programs 136, other program modules 137, and program data 138. A user may enter commands and information into the personal computer 120 through input devices such as a keyboard 140 and pointing device 142. Other input devices (not shown) may include a microphone, joystick, game pad, satellite dish, scanner, or the like. These and other input devices are often connected to the processing unit 121 through a serial port interface 146 that is coupled to the system bus, but may be connected by other interfaces, such as a parallel port, game port, or a universal serial bus (USB). A monitor 147 or other type of display device is also connected to the system bus 123 via an interface, such as a video adapter 148. In addition to the monitor, computers typically include other peripheral output devices (not shown), such as speakers and printers.

The computer 120 may operate in a networked environment using logical connections to one or more remote computers, such as remote computer 149. These logical connections may be achieved by a communication device coupled to or a part of the computer 120, or in other manners. The remote computer 149 may be another computer, a server, a router, a network PC, a client, a peer device or other common network node, and typically includes many or all of the elements described above relative to the computer 120, although only a memory storage device 150 has been illustrated in FIG. 11. The logical connections depicted in FIG. 11 include a local-area network (LAN) 151 and a wide-area network (WAN) 152. Such networking environments are commonplace in office networks, enterprise-wide computer networks, intranets and the Internet, which all are types of networks.

When used in a LAN-networking environment, the computer 120 is connected to the local network 151 through a network interface or adapter 153, which is one type of communications device. When used in a WAN-networking environment, the computer 120 often includes a modem 154, a type of communications device, or any other type of communications device for establishing communications over the wide area network 152. The modem 154, which may be internal or external, is connected to the system bus 123 via the serial port interface 146. In a networked environment, program modules depicted relative to the personal computer 120, or portions thereof, may be stored in the remote memory storage device. It is appreciated that the network connections shown are non-limiting examples and other communications devices for establishing a communications link between computers may be used.

Transformations

As noted above, data sometimes is transformed from one form into another form. The terms "transformed," "transformation," and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion, duplication or deletion; represent the presence or absence of a variation in the physical amount of a sequence associated with medical conditions). A virtual representation sometimes is further transformed into one or more numerical values or graphical representations of the digital representation of the starting material. These methods can transform physical starting material into a numerical value or graphical representation, or a representation of the physical appearance of a test subject's nucleic acid.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fetal gender prediction, fragment size (e.g., length of CCF fragments, reads or a suitable representation thereof (e.g., FRS)), fragment sequence, identification of a copy number alteration, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principal component analysis of derived quantities; and the like or combinations thereof.

Genetic Variations/Genetic Alterations and Medical Conditions

The presence or absence of a genetic variation can be determined using a method or apparatus described herein. A genetic variation also may be referred to as a genetic alteration, and the terms are often used interchangeably herein and in the art. In certain instances, "genetic alteration" may be used to describe a somatic alteration whereby the genome in a subset of cells in a subject contains the alteration (such as, for example, in tumor or cancer cells). In certain instances, "genetic variation" may be used to describe a variation inherited from one or both parents (such as, for example, a genetic variation in a fetus).

In certain embodiments, the presence or absence of one or more genetic variations or genetic alterations is determined according to an outcome provided by methods and apparatuses described herein. A genetic variation generally is a particular genetic phenotype present in certain individuals, and often a genetic variation is present in a statistically significant sub-population of individuals. In some embodiments, a genetic variation or genetic alteration is a chromosome abnormality or copy number alteration (e.g., aneuploidy, duplication of one or more chromosomes, loss of one or more chromosomes, partial chromosome abnormality or mosaicism (e.g., loss or gain of one or more regions of a chromosome), translocation, inversion, each of which is described in greater detail herein). Non-limiting examples of genetic variations/genetic alterations include one or more copy number alterations/variations, deletions (e.g., microdeletions), duplications (e.g., microduplications), insertions, mutations (e.g., single nucleotide variations, single nucleotide alterations), polymorphisms (e.g., single-nucleotide polymorphisms), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 50,000 kilobases (kb) in length (e.g., about 10 bp, 50 bp, 100 bp, 500 bp, 1 kb, 5 kb, 10 kb, 50 kb, 100 kb, 500 kb, 1000 kb, 5000 kb or 10,000 kb in length).

A genetic variation or genetic alteration is sometime a deletion. In certain instances, a deletion is a mutation (e.g., a genetic aberration) in which a part of a chromosome or a sequence of DNA is missing. A deletion is often the loss of genetic material. Any number of nucleotides can be deleted. A deletion can comprise the deletion of one or more entire chromosomes, a region of a chromosome, an allele, a gene, an intron, an exon, any non-coding region, any coding region, a part thereof or combination thereof. A deletion can comprise a microdeletion. A deletion can comprise the deletion of a single base.

A genetic variation or genetic alteration is sometimes a duplication. In certain instances, a duplication is a mutation (e.g., a genetic aberration) in which a part of a chromosome or a sequence of DNA is copied and inserted back into the genome. In certain embodiments, a genetic duplication (e.g., duplication) is any duplication of a region of DNA. In some embodiments, a duplication is a nucleic acid sequence that is repeated, often in tandem, within a genome or chromosome. In some embodiments, a duplication can comprise a copy of one or more entire chromosomes, a region of a chromosome, an allele, a gene, an intron, an exon, any non-coding region, any coding region, part thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation or genetic alteration is sometimes an insertion. An insertion is sometimes the addition of one or more nucleotide base pairs into a nucleic acid sequence. An insertion is sometimes a microinsertion. In certain embodiments, an insertion comprises the addition of a region of a chromosome into a genome, chromosome, or part thereof. In certain embodiments, an insertion comprises the addition of an allele, a gene, an intron, an exon, any non-coding region, any coding region, part thereof or combination thereof into a genome or part thereof. In certain embodiments, an insertion comprises the addition (e.g., insertion) of nucleic acid of unknown origin into a genome, chromosome, or part thereof. In certain embodiments, an insertion comprises the addition (e.g., insertion) of a single base.

As used herein a "copy number alteration" generally is a class or type of genetic variation, genetic alteration or chromosomal aberration. A copy number alteration also may be referred to as a copy number variation, and the terms are often used interchangeably herein and in the art. In certain instances, "copy number alteration" may be used to describe a somatic alteration whereby the genome in a subset of cells in a subject contains the alteration (such as, for example, in tumor or cancer cells). In certain instances, "copy number variation" may be used to describe a variation inherited from one or both parents (such as, for example, a copy number variation in a fetus). A copy number alteration can be a deletion (e.g., microdeletion), duplication (e.g., a microduplication) or insertion (e.g., a microinsertion). Often, the prefix "micro" as used herein sometimes is a region of nucleic acid less than 5 Mb in length. A copy number alteration can include one or more deletions (e.g., microdeletion), duplications and/or insertions (e.g., a microduplication, microinsertion) of a part of a chromosome. In certain embodiments, a duplication comprises an insertion. In certain embodiments, an insertion is a duplication. In certain embodiments, an insertion is not a duplication.

In some embodiments, a copy number alteration is a copy number alteration from a tumor or cancer cell. In some embodiments, a copy number alteration is a copy number alteration from a non-cancer cell. In certain embodiments, a copy number alteration is a copy number alteration within the genome of a subject (e.g., a cancer patient) and/or within the genome of a cancer cell or tumor in a subject. A copy number alteration can be a heterozygous copy number alteration where the variation (e.g., a duplication or deletion) is present on one allele of a genome. A copy number alteration can be a homozygous copy number alteration where the alteration is present on both alleles of a genome. In some embodiments, a copy number alteration is a heterozygous or homozygous copy number alteration. In some embodiments, a copy number alteration is a heterozygous or homozygous copy number alteration from a cancer cell or non-cancer cell. A copy number alteration sometimes is present in a cancer cell genome and a non-cancer cell genome, a cancer cell genome and not a non-cancer cell genome, or a non-cancer cell genome and not a cancer cell genome.

In some embodiments, a copy number alteration is a fetal copy number alteration. Often, a fetal copy number alteration is a copy number alteration in the genome of a fetus. In some embodiments, a copy number alteration is a maternal and/or fetal copy number alteration. In certain embodiments, a maternal and/or fetal copy number alteration is a copy number alteration within the genome of a pregnant female (e.g., a female subject bearing a fetus), a female subject that gave birth or a female capable of bearing a fetus. A copy number alteration can be a heterozygous copy number alteration where the alteration (e.g., a duplication or deletion) is present on one allele of a genome. A copy number alteration can be a homozygous copy number alteration where the alteration is present on both alleles of a genome. In some embodiments, a copy number alteration is a heterozygous or homozygous fetal copy number alteration. In some embodiments, a copy number alteration is a heterozygous or homozygous maternal and/or fetal copy number alteration. A copy number alteration sometimes is present in a maternal genome and a fetal genome, a maternal genome and not a fetal genome, or a fetal genome and not a maternal genome.

"Ploidy" is a reference to the number of chromosomes present in a subject. In certain embodiments, "ploidy" is the same as "chromosome ploidy." In humans, for example, autosomal chromosomes are often present in pairs. For example, in the absence of a genetic variation or genetic alteration, most humans have two of each autosomal chromosome (e.g., chromosomes 1-22). The presence of the normal complement of 2 autosomal chromosomes in a human is often referred to as euploid or diploid. "Microploidy" is similar in meaning to ploidy. "Microploidy" often refers to the ploidy of a part of a chromosome. The term "microploidy" sometimes is a reference to the presence or absence of a copy number alteration (e.g., a deletion, duplication and/or an insertion) within a chromosome (e.g., a homozygous or heterozygous deletion, duplication, or insertion, the like or absence thereof).

A genetic variation or genetic alteration for which the presence or absence is identified for a subject is associated with a medical condition in certain embodiments. Thus, technology described herein can be used to identify the presence or absence of one or more genetic variations or genetic alterations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations/genetic alterations, medical conditions and states are described hereafter.

Chromosome Abnormalities

In some embodiments, the presence or absence of a chromosome abnormality can be determined by using a method and/or apparatus described herein. Chromosome abnormalities include, without limitation, copy number alterations, and a gain or loss of an entire chromosome or a region of a chromosome comprising one or more genes. Chromosome abnormalities include monosomies, trisomies, polysomies, loss of heterozygosity, translocations, deletions and/or duplications of one or more nucleotide sequences (e.g., one or more genes), including deletions and duplications caused by unbalanced translocations. The term "chromosomal abnormality" or "aneuploidy" as used herein refer to a deviation between the structure of the subject chromosome and a normal homologous chromosome. The term "normal" refers to the predominate karyotype or banding pattern found in healthy individuals of a particular species, for example, a euploid genome (e.g., diploid in humans, e.g., 46,XX or 46,XY). As different organisms have widely varying chromosome complements, the term "aneuploidy" does not refer to a particular number of chromosomes, but rather to the situation in which the chromosome content within a given cell or cells of an organism is abnormal. In some embodiments, the term "aneuploidy" herein refers to an imbalance of genetic material caused by a loss or gain of a whole chromosome, or part of a chromosome. An "aneuploidy" can refer to one or more deletions and/or insertions of a region of a chromosome. The term "euploid," in some embodiments, refers a normal complement of chromosomes.

The term "monosomy" as used herein refers to lack of one chromosome of the normal complement. Partial monosomy can occur in unbalanced translocations or deletions, in which only a part of the chromosome is present in a single copy. Monosomy of sex chromosomes (45, X) causes Turner syndrome, for example. The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47,XYY in Jacobs Syndrome). In some embodiments, a trisomy is a duplication of most or all of an autosome. In certain embodiments, a trisomy is a whole chromosome aneuploidy resulting in three instances (e.g., three copies) of a particular type of chromosome (e.g., instead of two instances (e.g., a pair) of a particular type of chromosome for a euploid).

The terms "tetrasomy" and "pentasomy" as used herein refer to the presence of four or five copies of a chromosome, respectively. Although rarely seen with autosomes, sex chromosome tetrasomy and pentasomy have been reported in humans, including)(XXX, XXXY, XXYY, XYYY, XXXXX, XXXXY, XXXYY, XXYYY and XYYYY.

Medical Disorders and Medical Conditions

Methods described herein can be applicable to any suitable medical disorder or medical condition. Non-limiting examples of medical disorders and medical conditions include cell proliferative disorders and conditions, wasting disorders and conditions, degenerative disorders and conditions, autoimmune disorders and conditions, pre-eclampsia, chemical or environmental toxicity, liver damage or disease, kidney damage or disease, vascular disease, high blood pressure, and myocardial infarction.

In some embodiments, a cell proliferative disorder or condition sometimes is a cancer, tumor, neoplasm, metastatic disease, the like or combination thereof. A cell proliferative disorder or condition sometimes is a disorder or condition of the liver, lung, spleen, pancreas, colon, skin, bladder, eye, brain, esophagus, head, neck, ovary, testes, prostate, the like or combination thereof. Non-limiting examples of cancers include hematopoietic neoplastic disorders, which are diseases involving hyperplastic/neoplastic cells of hematopoietic origin (e.g., arising from myeloid, lymphoid or erythroid lineages, or precursor cells thereof), and can arise from poorly differentiated acute leukemias (e.g., erythroblastic leukemia and acute megakaryoblastic leukemia). Certain myeloid disorders include, but are not limited to, acute promyeloid leukemia (APML), acute myelogenous leukemia (AML) and chronic myelogenous leukemia (CML). Certain lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Certain forms of malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. A cell proliferative disorder sometimes is a non-endocrine tumor or endocrine tumor. Illustrative examples of non-endocrine tumors include, but are not limited to, adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor sometimes is an islet cell tumor.

In some embodiments, a wasting disorder or condition, or degenerative disorder or condition, is cirrhosis, amyotrophic lateral sclerosis (ALS), Alzheimer's disease, Parkinson's disease, multiple system atrophy, atherosclerosis, progressive supranuclear palsy, Tay-Sachs disease, diabetes, heart disease, keratoconus, inflammatory bowel disease (IBD), prostatitis, osteoarthritis, osteoporosis, rheumatoid arthritis, Huntington's disease, chronic traumatic encephalopathy, chronic obstructive pulmonary disease (COPD), tuberculosis, chronic diarrhea, acquired immune deficiency syndrome (AIDS), superior mesenteric artery syndrome, the like or combination thereof.

In some embodiments, an autoimmune disorder or condition is acute disseminated encephalomyelitis (ADEM), Addison's disease, alopecia areata, ankylosing spondylitis, antiphospholipid antibody syndrome (APS), autoimmune hemolytic anemia, autoimmune hepatitis, autoimmune inner ear disease, bullous pemphigoid, celiac disease, Chagas disease, chronic obstructive pulmonary disease, Crohns Disease (a type of idiopathic inflammatory bowel disease "IBD"), dermatomyositis, diabetes mellitus type 1, endometriosis, Goodpasture's syndrome, Graves' disease, Guillain-Barré syndrome (GBS), Hashimoto's disease, hidradenitis suppurativa, idiopathic thrombocytopenic purpura, interstitial cystitis, Lupus erythematosus, mixed connective tissue disease, morphea, multiple sclerosis (MS), myasthenia gravis, narcolepsy, euromyotonia, pemphigus vulgaris, pernicious anaemia, polymyositis, primary biliary cirrhosis, rheumatoid arthritis, schizophrenia, scleroderma, Sjögren's syndrome, temporal arteritis (also known as "giant cell arteritis"), ulcerative colitis (a type of idiopathic inflammatory bowel disease "IBD"), vasculitis, vitiligo, Wegener's granulomatosis, the like or combination thereof.

Preeclampsia

In some embodiments, the presence or absence of preeclampsia is determined by using a method or apparatus described herein. Preeclampsia is a condition in which hypertension arises in pregnancy (e.g., pregnancy-induced hypertension) and is associated with significant amounts of protein in the urine. In certain instances, preeclampsia may be associated with elevated levels of extracellular nucleic acid and/or alterations in methylation patterns. For example, a positive correlation between extracellular fetal-derived hypermethylated RASSF1A levels and the severity of preeclampsia has been observed. In certain instances, increased DNA methylation is observed for the H19 gene in preeclamptic placentas compared to normal controls.

Pathogens

In some embodiments, the presence or absence of a pathogenic condition is determined by a method or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods, machines and apparatus provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g., strain).

Use of Cell Free Nucleic Acid

In certain instances, nucleic acid from abnormal or diseased cells associated with a particular condition or disorder is released from the cells as circulating cell-free nucleic acid (CCF-NA). For example, cancer cell nucleic acid is present in CCF-NA, and analysis of CCF-NA using methods provided herein can be used to determining whether a subject has, or is at risk of having, cancer. Analysis of the presence or absence of cancer cell nucleic acid in CCF-NA can be used for cancer screening, for example. In certain instances, levels of CCF-NA in serum can be elevated in patients with various types of cancer compared with healthy patients. Patients with metastatic diseases, for example, can sometimes have serum DNA levels approximately twice as high as non-metastatic patients. Accordingly, methods described herein can provide an outcome by processing sequencing read counts obtained from CCF-NA extracted from a sample from a subject (e.g., a subject having, suspected of having, predisposed to, or suspected as being predisposed to, a particular condition or disease).

Markers

In certain instances, a polynucleotide in abnormal or diseased cells is modified with respect to nucleic acid in normal or non-diseased cells (e.g., single nucleotide variation, copy number variation). In some instances, a polynucleotide is present in abnormal or diseased cells and not present in normal or non-diseased cells, and sometimes a polynucleotide is not present in abnormal or diseased cells and is present in normal or non-diseased cells. Thus, a marker sometimes is a single nucleotide variation and/or a copy number variation (e.g., a differentially expressed DNA or RNA (e.g., mRNA)). For example, patients with metastatic diseases may be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Accordingly, methods described herein sometimes provide an outcome based on determining the presence or absence of a particular marker, and sometimes an outcome is presence or absence of a particular type of condition (e.g., a particular type of cancer).

Certain methods described herein may be performed in conjunction with methods described, for example in International Patent Application Publication No. WO 2013/052913, International Patent Application Publication No. WO 2013/052907, International Patent Application Publication No. WO 2013/055817, International Patent Application Publication No. WO 2013/109981, International Patent Application Publication No. WO 2013/177086, International Patent Application Publication No. WO 2013/192562, International Patent Application Publication No. WO 2014/116598, International Patent Application Publication No. WO 2014/055774, International Patent Application Publication No. WO 2014/190286, International Patent Application Publication No. WO 2014/205401, International Patent Application Publication No. WO 2015/051163, International Patent Application Publication No. WO 2015/138774, International Patent Application Publication No. WO 2015/054080, International Patent Application Publication No. WO 2015/183872, International Patent Application Publication No. WO 2016/019042, and International Patent Application Publication No. WO 2016/057901, the entire content of each is incorporated herein by reference, including all text, tables, equations and drawings.

EXAMPLES

The examples set forth below illustrate certain embodiments and do not limit the technology.

Example 1: Enhancement of Classification Using Confidence Determination

Current cell-free DNA assessment of fetal chromosomes does not analyze and report on all chromosomes. Hence, a significant proportion of fetal chromosomal abnormalities are not detectable by current noninvasive methods. Here it is reported that the clinical validation of a novel noninvasive prenatal test (NIPT) designed to detect genomewide gains and losses of chromosomal material greater than or equal to 7 Mb and losses associated with specific deletions less than 7 Mb. Also reported here is a clinical validation of the sensitivity and specificity of a novel NIPT for detection of genomewide abnormalities. This retrospective, blinded study included maternal plasma collected from 1222 study subjects with pregnancies at increased risk for fetal chromosomal abnormalities that were assessed for trisomy 21 (T21), trisomy 18 (T18), trisomy 13 (T13), sex chromosome aneuploidies (SCAs), fetal sex, genomewide copy number variants (CNVs) greater than or equal to 7 Mb, and select deletions less than 7 Mb. Performance was assessed by comparing test results with findings from G-band karyotyping, microarray data, or high coverage sequencing. Clinical sensitivity within this study was determined to be 100% for T21 (95% confidence interval [CI], 94.6-100%), T18 (95% CI, 84.4-100%), T13 (95% CI, 74.7-100%), and SCAs (95% CI, 84-100%), and 97.7% for genomewide CNVs (95% CI, 86.2-99.9%). Clinical specificity within this study was determined to be 100% for T21 (95% CI, 99.6-100%), T18 (95% CI, 99.6-100%), and T13 (95% CI, 99.6-100%), and 99.9% for SCAs and CNVs (95% CI, 99.4-100% for both). Fetal sex classification had an accuracy of 99.6% (95% CI, 98.9-99.8%). This study has demonstrated that genomewide NIPT for fetal chromosomal abnormalities can provide high resolution, sensitive, and specific detection of a wide range of subchromosomal and whole chromosomal abnormalities that were previously only detectable by invasive karyotype analysis. In some instances, this NIPT also provided additional clarification about the origin of genetic material that had not been identified by invasive karyotype analysis. The study in Example 1 was reported in Lefkowitz et al., Clinical validation of genomewide cell-free DNA testing, Am J Obstet Gynecol 2016.

Materials and Methods
Study Design

This blinded, retrospective clinical study included samples from women considered at increased risk for fetal aneuploidy based on advanced maternal age greater than or equal to 35 years, a positive serum screen, an abnormal ultrasound finding, and/or a history of aneuploidy. Archived samples were selected for inclusion in the study by an unblinded internal third party according to the requirements documented in the study plan. Samples were then blind-coded to all operators and the analysts who processed the samples. After sequencing, an automated bioinformatics analysis was performed to detect whole chromosome aneuploidies and subchromosomal CNVs. Results were compiled electronically and were reviewed by a subject matter expert who assigned the final classification. This manual review mimics the process in the clinical laboratory, where cases are reviewed by a laboratory director before a result is signed out. Completed classification results were provided to the internal third party for determination of concordance. Analyzed samples had confirmation of positive or negative events by either G-band karyotype or microarray findings from samples collected through either chorionic villus sampling (CVS) or amniocentesis. Circulating cell-free "fetal" DNA is believed to originate largely from placental trophoblasts. Genetic differences between the fetus and the placenta can occur (e.g., confined placental mosaicism), leading to discordance between NIPT results and cytogenetic studies on amniocytes or postnatally obtained samples (see, e.g., Grati et al. Genet Med 2014; 16: 620-4). Results from CVS by chromosomal microarray were thus considered the most accurate ground truth. Therefore, discordant results originating from amniocytes (karyotype or microarray) were resolved by sequencing at high coverage (an average of 226 million reads per sample). Sequencing depth has been shown as a limiting factor in NIPT methods, with increased depth allowing improved detection of events in samples with lower fetal fractions or improved detection of smaller events (see, e.g., Fan et al. PLoS One 2010; 5:e10439). High coverage sequencing has been used in multiple studies to unambiguously identify subchromosomal events (see, e.g., Zhao et al. Clin Chem 2015; 61:608-16; Jensen et al. Clin Chem 2014; 60:1298-305; Srinivasan et al. Am J Hum Genet 2013; 92:167-76; Peters et al. N Engl J Med 2011; 365: 1847-8) and was used here as a reference for performance evaluation in discrepant amniocentesis samples.

Details of the sample demographics are described in Table 1. Indications for invasive testing are described in Table 2.

TABLE 1

Demographic and pregnancy-related data

| Demographic | Median | Range |
| --- | --- | --- |
| Maternal age, y (Ntotal = 1177) | 36.0 | 17.8-47 |
| Gestational age, wk (Ntotal = 1183) | 17 | 8-38 |
| Maternal weight, lb (Ntotal = 1168) | 150 | 93-366 |

| | Percent | (Naffected/Ntotal) |
| --- | --- | --- |
| Procedure | | |
| CVS | 14.5 | (175/1203) |
| Amniocentesis | 85.2 | (1025/1203) |
| Both | 0.2 | (3/1203) |
| Confirmation | | |
| Karyotype | 90.4 | (1089/1205) |
| Microarray | 5.8 | (70/1205) |
| Both | 3.8 | (46/1205) |

Choice of invasive procedure, choice of diagnostic test, and demographic data were not available for all 1208 samples included in study.
Naffected refers to the number of samples with the indicated procedure or confirmation; Ntotal refers to number of samples where that data were available.
CVS, chorionic villus sampling.

TABLE 2

Indications for testing

| Indication | Euploid, n = 1009 | T21, n = 87 | T18, n = 29 | T13, n = 15 | SCA, n = 26 | CNV, n = 44 | Total, n = 1210 |
|---|---|---|---|---|---|---|---|
| Positive serum screening | 404 (40%) | 36 (41.4%) | 13 (44.8%) | 4 (26.7%) | 3 (11.5%) | 16 (36.4%) | 476 (39.3%) |
| Maternal age >35 y | 418 (41.4%) | 28 (32.2%) | 10 (34.5%) | 4 (26.7%) | 2 (7.7%) | 10 (22.7%) | 472 (39%) |
| Ultrasound abnormality | 152 (15.1%) | 34 (39.1%) | 6 (20.7%) | 10 (66.7%) | 16 (61.5%) | 22 (50%) | 239 (19.8%) |
| Family history | 33 (3.3%) | 4 (4.6%) | 1 (3.4%) | 0 (0%) | 1 (3.8%) | 1 (2.3%) | 40 (3.3%) |
| Not specified | 85 (8.4%) | 11 (12.6%) | 5 (17.2%) | 2 (13.3%) | 4 (15.4%) | 2 (4.5%) | 109 (9%) |

Each cell lists count (%) of indication within chromosome category.
Samples may have multiple indications for testing and therefore do not sum to 100%.
As 2 T18 samples also had SCA, total number of abnormalities and euploid samples sum to 1210.
CNV, copy number variant; SCA, sex chromosome aneuploidy; T13, trisomy 13; T18, trisomy 18; T21, trisomy 21.

Sample Collection

In total, 1222 maternal plasma samples were previously collected using 4 investigational review board (IRB)-approved protocols with a small subset (9 samples) comprising remnant plasma samples collected from previously consented patients in accordance with the Food and Drug Administration guidance on informed consent for in vitro diagnostic devices using leftover human specimens that are not individually identifiable (see, e.g., USFDA, Guidance for Sponsors, Institutional Review Boards, Clinical Investigators and FDA Staff. OMB Control 0910-0582 (2006)). Samples from 2 of the protocols (Compass IRB no. 00508 and Western IRB no. 20120148) were collected from high-risk pregnant subjects prior to undergoing a confirmatory invasive procedure (1189 samples). Samples from the other 2 protocols (Compass IRB no. 00351 and Columbia University IRB no. AAAN9002) came from subjects who were enrolled in the studies after receiving the fetal karyotype and/or microarray results of a confirmatory invasive procedure (24 samples). All subjects provided written informed consent prior to undergoing any study-related procedures. A total of 5321 high-risk subjects were recruited into the 4 clinical studies indicated above at the time of sample selection. To be eligible for inclusion into this study, subjects had to have met all protocol inclusion and no exclusion criteria, have fetal outcome determined by karyotype and/or microarray, and have at least 1 plasma aliquot of greater than or equal to 3.5 mL obtained from whole blood collected in a BCT tube (Streck, Omaha, Nebr.). There was no sample selection preference based on high-risk indication. All subjects meeting these selection criteria with an abnormal fetal outcome as needed for the study were identified and pulled from inventory. These were then supplemented with randomly selected subjects with samples meeting the same selection criteria but with a normal karyotype to reach the total of 1222 samples for testing.

Library Preparation, Sequencing, and Analytical Methods

Libraries were prepared and quantified as described previously (see, e.g., Tynan et al. Prenat Diagn 2016; 36:56-62). To reduce noise and increase signal, sequencing depth for this analysis was increased to target 32 million reads per sample. Sequencing reads were aligned to hg19 using Bowtie 2 (see, e.g., Langmead et al. Nat Methods 2012; 9:357-9). The genome was then partitioned into 50-kbp nonoverlapping segments and the total number of reads per segment was determined, by counting the number of reads with 5′ ends overlapping with a segment. Segments with high read count variability or low mapability were excluded. The 50 kbp read counts were then normalized to remove coverage and guanine/cytosine biases and other higher-order artifacts using the methods previously described previously (see, e.g., Zhao et al. Clin Chem 2015; 61:608-16). The presence of fetal DNA was quantified using the regional counts of whole genome single-end sequencing data as described previously (see, e.g., Kim et al. Prenat Diagn 2015; 35:810-5).

Genomewide Detection of Abnormalities

Circular binary segmentation (CBS) was used to identify CNVs throughout the entire genome by segmenting each chromosome into contiguous regions of equal copy number (see, e.g., Olshen et al. Biostatistics 2004; 5:557-72). A segment-merging process was then used to compensate for oversegmentation by CBS when the signal-to-noise ratio was low (see, e.g., Willenbrock et al. Bioinformatics 2005; 21:4084-91). Z-scores were calculated for both CBS-identified CNVs and whole chromosome variants by comparing the signal amplitude with a reference set of samples in the same region. The measured Z-scores form part of an enhanced version of Chromosomal Aberration Decision Tree previously described previously (see, e.g., Zhao et al. Clin Chem 2015; 61:608-16).

To further improve specificity of CNV detection, bootstrap analysis was performed as an additional measure for the confidence of the candidate CNVs. The within sample read count variability was compared to a normal population (represented by 371 euploid samples) and quantified by bootstrap confidence level. To assess within sample variability, the bootstrap resampling described below was applied to every candidate CNV.

For each identified segment within the CNV, the median shift of segment fraction from the normal level across the chromosome was calculated. This median shift was then corrected to create a read count baseline for bootstrapping. Next, a bootstrapped segment of the same segment length as the candidate CNV was randomly sampled with replacement from the baseline read counts. The median shift was then applied to this bootstrapped fragment. The segment fraction of the bootstrapped fragment was calculated as follows:

segment fraction=sum of read counts within segment/sum of read counts across the autosome.

This process was repeated 1000 times to generate a bootstrap distribution of segment fractions for an affected population. A normal reference distribution was created based on the segment fraction of the same location as the candidate CNV in 371 euploid samples. A threshold was then calculated as the segment fraction that was at least 3.95 median absolute deviations away from the median segment fraction of the reference distribution. Lastly, the bootstrap confidence level was calculated as the proportion of bootstrap segments whose fractions had absolute z-statistics above the significance threshold.

A whole chromosome or subchromosomal abnormality is detected as described previously (see, e.g., Zhao et al. Clin Chem 2015; 61:608-16).

Results

The study comprised a total of 1222 maternal plasma samples. After unblinding, 11 samples were excluded because they had no or insufficient karyotype or microarray information (FIGS. 1) and 3 samples were excluded because of confirmed mosaicism. As shown in FIG. 1, one trisomy 18 (T18) sample was a XXY sample and another T18 sample was also a X sample. For samples with discordant results for sequencing vs karyotype or microarray derived from testing of amniocytes, uniplex sequencing was used for confirmation. CNV, copy number variant; QC, quality control; T13, trisomy 13; T21, trisomy 21.

Of the remaining 1208 samples, 42 were flagged as nonreportable using quality criteria that had been established prior to analysis, leaving 1166 reportable samples for analyses comprising 13% (n=153) of samples with common whole chromosome 21, 18, 13, X, or Y aneuploidies and crepancy was adjudicated through high coverage uniplex sequencing (typically with greater than 180 million reads) according to the study plan (FIG. 4D). The sample showed 16.3% fetal fraction, but the gain of genetic material from chromosome 21 was concordant with 6.5% fetal fraction. This is suggestive of confined placental mosaicism, a relatively common cause of discordant results between amniocyte results and CVS or placentally derived cell-free DNA (cfDNA) analysis (see, e.g., Grati et al. Genet Med 2014; 16: 620-4). Table 3 summarizes the performance for T21, T18, and T13. For T21, the sensitivity was 100% (95% confidence interval [CI], 94.6-100%) and the specificity was 100% (95% CI, 99.6-100%). For T18, the sensitivity was 100% (95% CI, 84.4-100%) and the specificity was 100% (95% CI, 99.6-100%). For T13, the sensitivity was 100% (95% CI, 74.7-100%) and the specificity was 100% (95% CI, 99.6-100%).

TABLE 3

Clinical performance for indicated abnormalities and fetal sex

| Abnormality | Concordant positive | Discordant positive | Concordant negative | Discordant negative | Sensitivity (95% CI) | Specificity (95% CI) |
|---|---|---|---|---|---|---|
| T21 | 85 | 0 | 1081 | 0 | 100% (94.6 = 100%) | 100% (99.6 = 100%) |
| T18 | 27 | 0 | 1139 | 0 | 100% (84.4 = 100%) | 100% (99.6e100%) |
| T13 | 15 | 0 | 1151 | 0 | 100% (74.7 = 100%) | 100% (99.6e100%) |
| SCA | 26 | 1 | 1117 | 0 | 100% (84.0 = 100%) | 99.9% (99.4 = 100%) |
| CNVs | 42 | 1 | 1122 | 1 | 97.7% (86.2 = 99.9%) | 99.9% (99.4 = 100%) |

| Analyte | Concordant Male | Discordant Male | Concordant Female | Discordant Female | Accuracy (95% CI) |
|---|---|---|---|---|---|
| Fetal sex | 583 | 4 | 578 | 1 | 99.6% (98.9 = 99.8%) |

CI, confidence interval; CNVs, copy number variants; SCA, sex chromosome aneuploidy; T13, trisomy 13; T18, trisomy 18; T21, trisomy 21.
a Includes 8 samples with detected whole chromosome trisomies, and 35 samples with subchromosomal CNVs.

3.6% (n=43) of samples with subchromosomal CNVs or rarer whole chromosome aneuploidies. Technical failure criteria included but were not limited to: low library concentration, low raw autosomal counts, high GC bias, poor normalization, and high bin variability (FIG. 1). Biological failure criteria included low fetal fraction (less than 4%) and large maternal CNV events. The most common reason for failure was low fetal fraction (n=11). During review of the data, 1 sample was signed out as T18 (and was included in the analyzed cohort), even though it did not meet the autosomal count minimum. This sample had sufficient counts for the determination of standard aneuploidies, but not sufficient counts for the detection of subchromosomal CNVs. The 42 nonreportable samples showed no evidence of enrichment for whole chromosome/subchromosomal positive samples (5 positive of 42 nonreportable samples vs 204 positive of 1166 reportable samples). Details of nonreportable and excluded samples are provided in Table 4. Concordant with previous studies, the overall reportable rate on first aliquots of maternal plasma was 96.5%. The overall no-call rate per patient is expected to be approximately 1% when a second aliquot is available, based on published clinical laboratory experience (see, e.g., McCullough et al. PLoS One 2014; 9:e109173).

T21, T18, and T13 Detection

Among the 1166 reportable samples, there were 85 T21 samples, 27 T18 samples, and 15 T13 samples (FIG. 1). All euploid, T21, T18, and T13 samples (determined by invasive diagnostic procedures) were classified correctly by NIPT. One sample was classified by NIPT as T21 but had a normal (46, XX) karyotype by amniocentesis (Table 5). This dis- SCA Detection In the 1166 samples reportable for all chromosomal abnormalities, there were 21 samples flagged as nonreportable specifically for SCA classification based on thresholds for the chromosome X Z-score and chromosome Y Z-score as described previously (see, e.g., Mazloom et al. Prenat Diagn 2013; 33:591-7). There was also 1 additional sample with an apparent maternal XXX that was flagged as nonreportable for SCA because the maternal event distorted the sex chromosomal representation to a degree that fetal events could not be classified. Among the remaining 1144 samples reportable for SCAs, there were 7 discordant positives that were classified as normal (46, XX) by karyotype and as XO by sequencing at 6-plex (Table 5). In all discordant cases, the karyotype had been obtained from amniocyte samples. This phenomenon is well described and may be attributed to varying levels of placental or maternal mosaicism (see, e.g., Wang et al. Clin Chem 2014; 60:251-9). Uniplex sequencing confirmed 6 of the 7 XO samples. The seventh sample had a nonreportable result at uniplex coverage, hence the existing amniocentesis result was used as truth resulting in 1 false-positive assignment. Overall, the sensitivity for SCA was 100% (95% CI, 84.0-100%) with a specificity of 99.9% (95% CI, 99.4-100%) (Table 3).

Genomewide Detection of CNVs

Figure 2A:
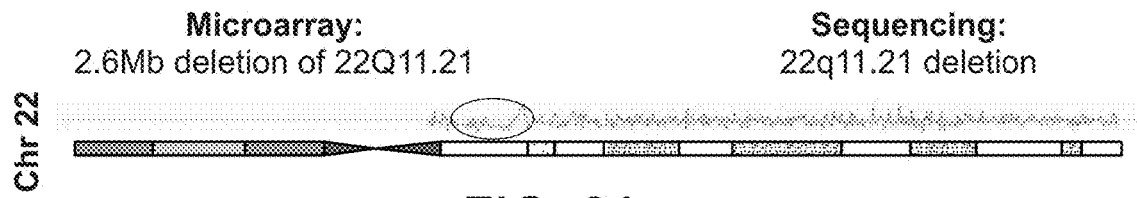
FIGS. 2A-2C show examples of copy number variants detected by sequencing in accordance with some embodiments.
Figure 2B:
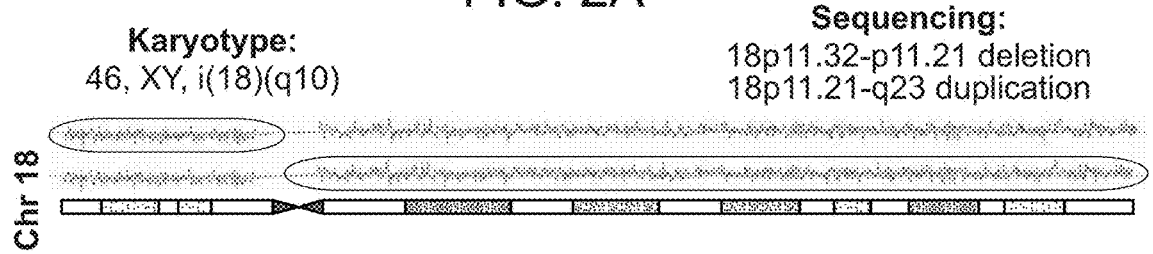
Figure 2C:
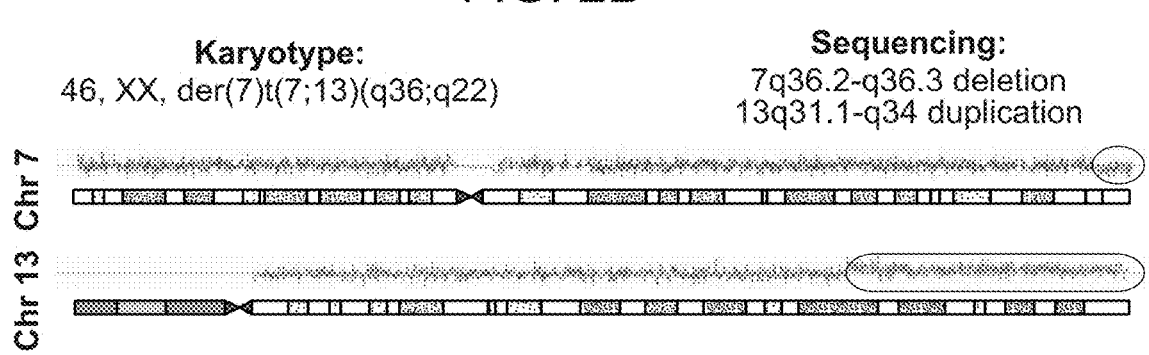

The test was also designed to detect CNVs greater than or equal to 7 Mb (including whole chromosome abnormalities other than T13, T18, T21, and SCAs) as well as select microdeletions less than 7 Mb.5 Among the 1166 samples reportable for sub-chromosomal abnormalities, there were 43 samples that had positive results for a variety of CNV aberrations: Wolf-Hirschhorn syndrome deletions, DiGeorge syndrome deletions, Prader-Willi/Angelman syndrome deletions, cri du chat syndrome deletions, and a variety of greater than or equal to 7-Mb CNVs including both subchromosomal CNVs and whole chromosome trisomies. Several examples of NIPT-detected CNVs confirmed by microarray or karyotype are shown in FIG. 2A-2C. FIG. 2A shows a chromosome (Chr) 22 ideogram illustrating sequencing-based detection of 22q11.21 deletion (DiGeorge syndrome) that was confirmed by karyotype and microarray. FIG. 2B shows a Chr 18 ideogram for a sample with karyotype 46, XY, i(18)(q10). FIG. 2C shows Chr 7 and 13 ideograms for sample with karyotype 46, XX, der(7) t(7; 13)(q36;q22). Circled regions correspond to identified duplication and deletion regions (e.g., a shift in signal above or below the baseline, respectively).

Overall, the sensitivity for detection of whole chromosome and subchromosomal abnormalities other than T13, T18, T21, and SCAs was 97.7% (95% CI, 86.2-99.9%) and the specificity was 99.9% (95% CI, 99.4-100%) (Table 3). One case was clearly mosaic for T22 by both standard coverage and uniplex sequencing (see Table 5 and FIG. 4E), but was classified as normal by microarray analysis. Because the invasive diagnosis came from microarray analysis of cells derived from CVS, the study design considered this as the gold standard, and this outcome was considered a discordant positive. Another case showed no gain or loss of genetic material with both standard and uniplex sequencing for a sample that had a 46, XX, der(12)t(12;19)(p13.1; q13.1) karyotype (FIG. 2B). This outcome was considered as a discordant negative given that the invasive procedure was CVS. A set of 7 samples were classified as full chromosomal trisomies, and because the karyotype or microarray results were derived from amniocytes in these cases, uniplex sequencing was performed for adjudication per the study design. The trisomy finding was confirmed in each case by uniplex sequencing, and these findings were considered as concordant positives (FIG. 4A-4E).

Figure 3:
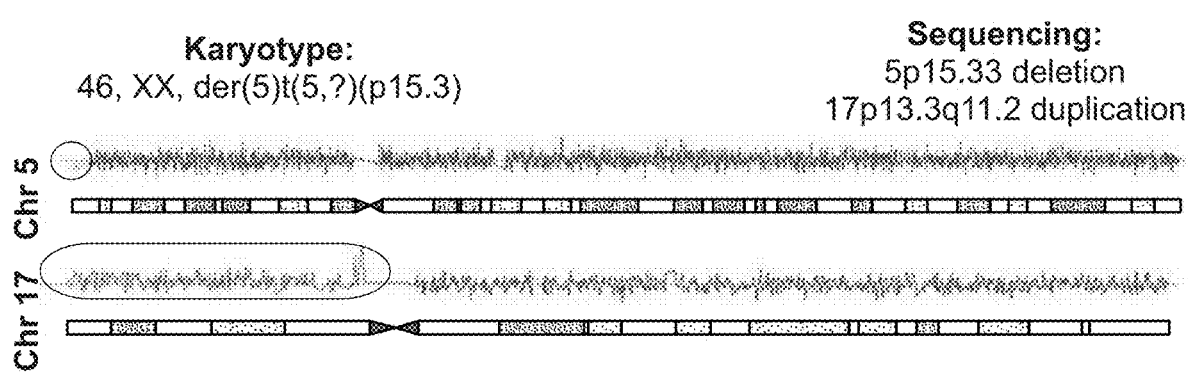
FIG. 3 shows clarification of karyotype findings by sequencing of maternal plasma in accordance with some embodiments.
Figure 6A:
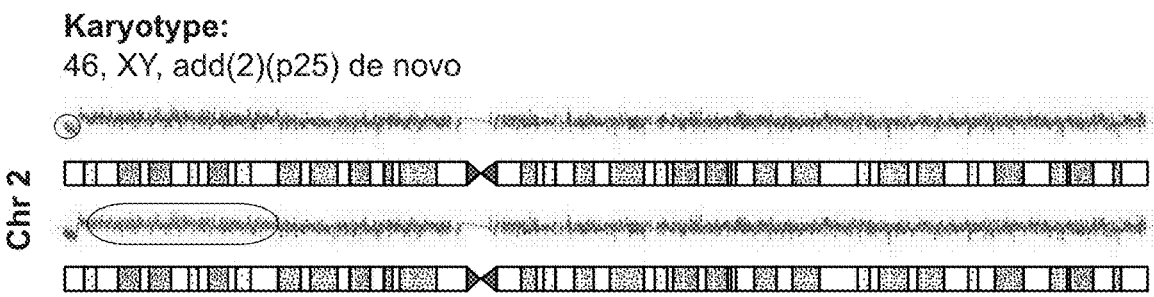
FIGS. 6A-6C show an analysis of karyotypes in accordance with some embodiments.
Figure 6B:
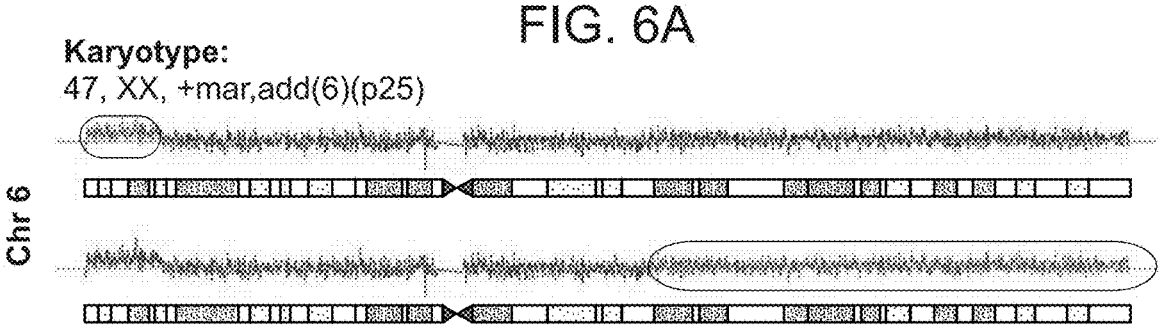
Figure 6C:

In addition to the high accuracy demonstrated in the results, in some cases NIPT could also provide clarification about the origin of extra genetic material when the G-banding pattern was not sufficiently clear. In 1 case, the amniocyte karyotype finding, 46, XX, der(5)t(5;?)(p15.3;?), indicated a deletion on chromosome 5 and a duplication of unknown origin (FIG. 3). Specifically, FIG. 3 shows normal regions, a duplication detected with high bootstrap confidence level (greater than 0.99; circled region in chromosome 17), and a deletion detected with a low bootstrap confidence level (i.e., circled region for chromosome 5). Chromosome (Chr) 5 and 17 ideograms are also shown for a sample with karyotype of 46, XX, der(5)t(5;?)(p15.3;?), and an unidentified duplication on the karyotype is from Chr 17. NIPT identified an 18.6-Mb duplication representing the entire short arm of chromosome 17, indicating this fetal tissue possessed a trisomy of chromosome 17p that was not clarified by standard karyotype. Trisomy 17p is associated with developmental delay, growth retardation, hypotonia, digital abnormalities, congenital heart defects, and distinctive facial features (see, e.g., Jinno et al. Ann Genet 1982; 25:123-5). Additional cases are shown in FIG. 6A-6C.

In summary, this clinical study provides validation for an approach that extends the clinical validity of cfDNA testing, now providing detection of T21, T18, T13, SCAs, fetal sex, and genomewide detection of subchromosomal and whole chromosomal abnormalities. Overall, subchromosomal abnormalities and aneuploidies other than T13, T18, T21, and SCAs were detected with a combined clinical sensitivity and specificity of 97.7% (95% CI, 86.2-99.9%) and 99.9% (95% CI, 99.4-100%), respectively. This enables comprehensive noninvasive chromosomal assessment that was previously available only by karyotype, and in some cases, may clarify cryptic findings otherwise identifiable only by microarray.

TABLE 4

Uniplex sequencing results for discordant samples

| | Invasive test results | | | Noninvasive test results | |
| --- | --- | --- | --- | --- | --- |
| Category | Test type | Sample type | Finding | 6-plex | 1-plex |
| T21 | Karyotype | Amniocentesis | Normal | T21 | T21 |
| SCA | Karyotype | Amniocentesis | Normal | X | X |
| | Karyotype | Amniocentesis | Normal | X | X |
| | Karyotype and microarray | Amniocentesis | Normal | X | NR for SCA |
| | Karyotype | Amniocentesis | Normal | X | X |
| | Karyotype | Amniocentesis | Normal | X | X |
| | Karyotype | Amniocentesis | Normal | X | X |
| | Karyotype | Amniocentesis | Normal | X | X |
| CNVs | Karyotype | CVS | 46, XX, der(12)t(12; 19)(p13.1; q13.1) mat | Normal | Normal |
| | Karyotype | Amniocentesis | 46, XX, der(18) (qter->q11.2::p11.3-> qter) | Normal | Normal |
| | Karyotype | Amniocentesis | 46, XY, add(20)(q11.2) | Normal | Normal |
| | Karyotype | Amniocentesis | 46, XY, add(18)(p11.3) | Normal | Normal |
| | Karyotype | Amniocentesis | Normal | 9p24.3p13.1 duplication | 9p24.3p13.1 duplication |
| | Karyotype | Amniocentesis | Normal | chr1p36.33p36.22 deletion, chr17q25.1q25.3 duplication | chr1p36.33p36.22 deletion, chr17q25.1q25.3 duplication |
| | Karyotype | Amniocentesis | Normal | T16 | T16 |
| | Microarray | Amniocentesis | Normal | T14 | T14 |
| | Karyotype | Amniocentesis | Normal | T8 | T8 |
| | Karyotype | Amniocentesis | Normal | T22 | T22 |
| | Karyotype | Amniocentesis | Normal | T16 | T16 |

TABLE 4-continued

Uniplex sequencing results for discordant samples

| Category | Invasive test results | | | Noninvasive test results | |
|---|---|---|---|---|---|
| | Test type | Sample type | Finding | 6-plex | 1-plex |
| | Microarray | CVS | Normal | T22 | T22 |
| | Karyotype | Amniocentesis | Normal | T16 | T16 |
| | Microarray | Amniocentesis | Normal | T8 | T8 |

Samples with results at 6-plex that were discordant with microarray or karyotype findings were resequenced at higher coverage for confirmation.
CNVs, copy number variants; CVS, chorionic villus sampling; SCA, sex chromosome aneuploidy; T, trisomy.

TABLE 5

Breakdown of excluded and nonreported samples

| Reason | SampleID | Fetal fraction | Karyotype/microarray outcome |
|---|---|---|---|
| | | Exclusions | |
| Missing invasive confirmation | 53063 | 0.130 | Normal |
| | 77320 | 0.079 | Normal |
| | 53863 | 0.068 | Normal |
| | RAS0027851 | 0.065 | Other: T16 by NIPT. SCA46-XY |
| Mosaicism | 54172 | 0.093 | Normal karyotype; low level mosaic T21 by FISH |
| | 77168 | 0.247 | Other: 46, XX, dup(1)(q21q32) - mosaic |
| | 70600 | 0.094 | Other: 47, XX, +i(12)(p10)[13]/46, XX[2].nuc ish (ETV6x4, AML 1/20[25/25] - tetrasomy 12p mosaicism |
| Vague karyotype result | 72938 | 0.093 | Other: 46, XY, var(18)(q11.2) |
| | 71894 | 0.114 | Other: 46XX, 22qvar |
| | 54681 | 0.081 | Other: 47, XX,þmar |
| | 72288 | 0.148 | Other: 47, XX,þmar |
| | 54039 | 0.098 | Other: 47, XX,þmar.ish idic(15; 15)(q13; q13)(D15Z1þþ, SNRPNþþ) |
| | 89063 | 0.096 | Other: 47, XX, þ ESAC considered normal female |
| | 73189 | 0.089 | Other: 47, XY,þ ESAC |
| | | Biological exclusions | |
| Fetal fraction | 55348 | 0.040 | Normal |
| | 53720 | 0.036 | Normal |
| | 54528 | 0.039 | Normal |
| | 89588 | 0.036 | Normal |
| | 89473 | 0.032 | Normal |
| | 77411 | 0.019 | Normal |
| | 77188 | 0.028 | Normal |
| | 53415 | 0.027 | Normal |
| | 53801 | 0.036 | Normal |
| | 53103 | 0.037 | Normal |
| Maternal event | 55197 | 0.065 | Normal |
| | 45424 | 0.149 | T21 |
| | | Technical exclusions | |
| Low aligned counts | 77478 | 0.079 | Normal |
| High variability | 77065 | 0.087 | T18 |
| | 77066 | 0.092 | T21 |
| | 77068 | 0.083 | Normal |
| | 77042 | 0.109 | Normal |
| CADET | 77340 | 0.131 | Normal |
| | 55462 | 0.078 | Normal |
| | 89583 | 0.082 | Normal |
| | 77040 | 0.058 | Normal |
| GC warning | 93693 | 0.112 | Normal |
| | 77392 | 0.091 | Normal |
| | 89526 | 0.105 | Normal |
| | 93679 | 0.074 | Normal |
| | 89152 | 0.076 | Normal |
| | 53815 | 0.077 | Normal |
| | 73161 | 0.161 | Normal |
| | 73017 | 0.158 | Normal |
| | 71006 | 0.072 | Other: 46xx, add(18)(q21.3) |

TABLE 5-continued

Breakdown of excluded and nonreported samples

| Reason | SampleID | Fetal fraction | Karyotype/microarray outcome |
|---|---|---|---|
| Laboratory director review | 77075 | 0.104 | Normal |
| | 54320 | 0.048 | Normal |
| | 54212 | 0.147 | Normal |
| | 77067 | 0.072 | Normal |
| | 53061 | 0.043 | Normal |
| | 89359 | 0.064 | Normal |
| | 89149 | 0.094 | Normal |
| | 53420 | 0.075 | Normal |
| | 55112 | 0.092 | Other: 48, XXX,þ 18 |
| Library failure | 77347 | 0.148 | Normal |
| | 54227 | 0.112 | Normal |
| Nonreportable for sex | 89529 | 0.106 | Normal chromosome aneuploidy |
| | 77445 | 0.232 | Normal |
| | 55123 | 0.084 | Normal |
| | 89185 | 0.068 | Normal |
| | 89607 | 0.076 | Normal |
| | 53057 | 0.057 | Normal |
| | 55444 | 0.041 | Normal |
| | 54458 | 0.215 | Normal |
| | 55220 | 0.068 | Normal |
| | 93678 | 0.145 | Normal |
| | 70268 | 0.094 | Normal |
| | 53109 | 0.087 | Normal |
| | 55454 | 0.047 | Normal |
| | 55064 | 0.099 | Normal |
| | 77285 | 0.120 | Normal |
| | 55260 | 0.154 | Normal |
| | 77157 | 0.042 | Other: 46, XX, der(18)(qter-q11.3-qter). Additional material added to 18p |
| | 73164 | 0.085 | Other: abnormal female karyotype with chromosome 13q deletion |
| | 45364 | 0.102 | T18 |
| | 89582 | 0.099 | T18 |
| | 77476 | 0.108 | T21 |
| | 89220 | 0.130 | T21 |

CADET, Chromosomal Aberration Decision Tree; NIPT, noninvasive prenatal test; SCA, sex chromosome aneuploidy; T18, trisomy 18; T21, trisomy 21.

Example 2: Classification System Decision Tree

The development of sequencing-based noninvasive prenatal testing (NIPT) has been largely focused on whole-chromosome aneuploidies (chromosomes 13, 18, 21, X, and Y). Collectively, they account for only 30% of all live births with a chromosome abnormality. Various structural chromosome changes, such as microdeletion/microduplication (MD) syndromes are more common but more challenging to detect. Recently, several publications have shown results on noninvasive detection of MDs by deep sequencing. These approaches demonstrated the proof of concept but are not economically feasible for large-scale clinical applications. A novel approach that uses low-coverage whole genome sequencing (approximately 0.2_) to detect MDs genome wide without requiring prior knowledge of the event's location is presented here. A normalization method to reduce sequencing noise was developed. Then, a statistical method to search for consistently increased or decreased regions was applied. A decision tree was used to differentiate whole-chromosome events from MDs. A simulation study was demonstrated via the sensitivity difference between this method and the theoretical limit was_5% for MDs_9 Mb. The performance was tested in a blinded study in which the MDs ranged from 3 to 40 Mb. In this study, the process correctly identified 17 of 18 cases with MDs and 156 of 157 unaffected cases. The scripts and data files used in the study are available at world wide web: sourceforge.net/projects/mddetection. The study reported in Example 2 was published in Zhao et al. Clin Chem 2015; 61:608-16.

Methods

Data Normalization

Figure 7A:
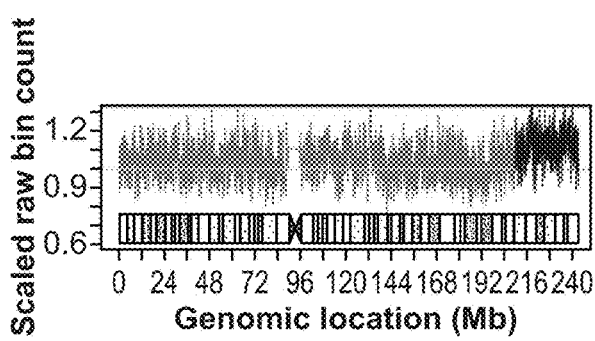
FIGS. 7A-7B show bin count profiles (50 kb) for a sample with microduplication before and after normalization in accordance with some embodiments.
Figure 7B:
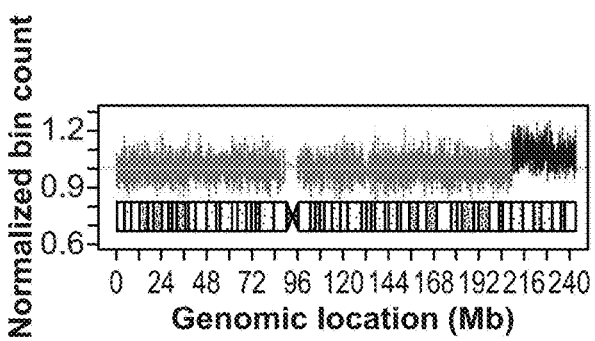

To remove sequencing bias, a 2-step normalization approach was developed. Briefly, reads were aligned to hg19, allowing for only perfect matches within the seed sequence using Bowtie 2 (see, e.g., *Langmead Nat Methods* 2012; 9:357-9). The genome was then partitioned into 50-kbp nonoverlapping bins and the raw count for each bin was determined. After binning, regions with high variability or low mappability were excluded according to a previously established method (see, e.g., *Jensen PLoS One* 2013; 8:e57381). To normalize the 50-kbp raw bin count, GC bias was removed by employing a LOESS-based correction for a sample-wise correction, similar to one described previously (see, e.g., *Alkan Nat Genet* 2009; 41:1061-7). FIGS. 7A-7B show bin count profiles (50 kb) for a sample with microduplication before and after normalization. The diploid region is to the left of each trace and the microduplication region is to the right of each trace. The karyogram is also shown for each trace, where the scheme follows the UCSC genome browser convention. Due to bin filtering, very few bins locate at the centromere regions (triangles). The x-axis is the coordinate of each bin in Mb. FIG. 7A shows a scaled raw bin count and FIG. 7B shows a normalized bin count. After normalization, the expected bin count for the diploid region is 1. Thereafter, principal component analysis (PCA)

was used to remove higher-order artifacts for a population-based correction (see, e.g., *Price Nat Genet* 2006; 38:904-9; *Leek PLoS Genet* 2007; 3:1724-35). To train the PCA normalization step, a data matrix was used comprising LOESS normalized bin counts from 1000 female pregnancies and transformed the data matrix into the principal component space. Then for a new sample, a linear regression model was built between its LOESS normalized bin count and the top principal components from the training set. The residuals of this model serve as final normalized values for this given sample. Intuitively, the top principal components represent noise commonly seen in euploid samples, and therefore removing them can effectively improve normalization. The combination of the last 2 steps replaces the older, region-based normalization previously published (see, e.g., *Jensen PLoS One* 2013; 8:e57381).

Circular Binary Segmentation

A process was developed for detection of MDs regardless of their genomic coordinates. As such, the proposed process needs to search for such events in a nontargeted fashion. To do so, the circular binary segmentation (CBS) method which has been extensively used by the array comparative genomic hybridization (CGH) community for CNV detection (see, e.g., *Olshen Biostatistics* 2004; 5:557-72; *Venkatraman Bioinformatics* 2007; 23:657-63) was applied. CBS works by iteratively partitioning a chromosome into equal copy number regions using the likelihood ratio statistic, and it can pinpoint the change point precisely. Many studies have demonstrated its superior performance over other methods (see, e.g., *Lai Bioinformatics* 2005; 21:3763-70; *Willenbrock Bioinformatics* 2005; 21:4084-91). Although powerful, CBS tends to overly partition the genome when the signal-to-noise ratio is low. To compensate for oversegmentation we further applied a segment-merging process similar to the one described by Willenbrock and Fridlyand (see, e.g., *Willenbrock Bioinformatics* 2005; 21:4084-91).

Quantifying the Statistical Significance of Detected Events

After CBS, each chromosome was partitioned into regions of equal copy number. To quantify the statistical significance of the detected event, two approaches were developed. First, for each chromosome, the segment with the largest area was treated as a potential MD, and its z-score, zCBS, was calculated by comparing the summed bin count with respect to a reference set of samples in the same region (see, e.g., *Jensen PLoS One* 2013; 8:e57381). The whole-chromosome z score, zCHR, was also calculated in the same way. Second, the log odds ratio (LOR) was calculated to quantify the likelihood of the event being true at the measured fetal fraction, f (see, e.g., the LOR Section 1 in the *Detection of Fetal Subchromosomal Abnormalities by Sequencing Circulating Cell-Free DNA from Maternal Plasma*, Chen Zhao et al., Clinical Chemistry April 2015, 61 (4) 608-616; DOI: 10.1373/clinchem.2014.233312 ("hereafter "Zhao Publication")).

Decision Tree for Genome-Wide Aneuploidy or MD Detection

For each chromosome, 4 statistics can be inferred: 1. The z score and LOR for the largest segment partitioned by the CBS process: zCBS and LORCBS. 2. The whole-chromosome z score and LOR: zCHR and LORCHR. Note that the largest segment is defined to be the segment with the largest area (height_length) out of all the segments on a given chromosome. For example, in FIG. 7B, there are 2 segments, and the second segment has the largest area. The latter represents the most significant finding on the chromosome of interest. On the basis of these 4 statistics, the following decision tree method for aneuploidy or MD detection is proposed:

1. A chromosome is classified to be trisomy or monosomy if: _zCHR_ _C, LORCHR_0, and_zCHR_ _a_zCBS_;
2. A chromosome is classified to have microdeletion/microduplication if: It is not a trisomy or monosomy, and_zCBS_ _C, LORCBS_0, where C is a predefined z-score cutoff that controls the tradeoff between sensitivity and specificity. In this report, C was set to be 3 for chromosome 21 and 3.95 for all the other chromosomes. The threshold was selected on the basis of the previous study on trisomy detection, in which more than 99.9% sensitivity and specificity were achieved for all 3 major aneuploidies (see, e.g., *Jensen PLoS One* 2013; 8:e57381). The comparison_zCHR_ _a_zCBS_ allows one to distinguish a whole chromosome event from a subchromosomal event; in practice, it was found that a between 0.6 and 0.8 works well. The value was determined by assessing its impact on the detection of in silico-created MDs at different sizes and fetal fractions (see, e.g., detailed descriptions of the selection of a in the Zhao Publication). Because there might be multiple MD events on the same chromosome, the decision tree process moves to the next-largest segment on the chromosome until there are no further significant segments.

Genomic and Plasma DNA Sample Preparation

A blinded clinical evaluation study was conducted to test the performance of the proposed MD detection process. The study comprised 2 parts: an analytical validation using genomic DNA (gDNA) mixtures and a clinical validation using plasma samples. Forty-five gDNA samples (130_L of 30 ng/_L) were processed for library preparation, and sequencing libraries were created as previously described previously (see, e.g., *Jensen PLoS One* 2013; 8:e57381). gDNA mixture models were created by normalizing gDNA and nonpregnant female plasma (NPP) DNA libraries to 1.6 nmol/L. A starting mix of 20% gDNA library was created in a background of NPP library and subsequently used to create 17.5%, 15%, 12.5%, 10, 7.5%, and 5% mixtures by serial dilution. These were then multiplexed, clustered, and sequenced on the HiSeq2000 for 36_ 7 cycles in a 12-plex format (see, e.g., a detailed description of the protocols in the Zhao Publication). A total of 183 clinical plasma samples were collected using Investigational Review Board—approved clinical protocols. Samples with abnormal G-band karyotype results collected through these clinical protocols were selected for sequencing to determine detection rates for MDs. Euploid samples were chosen on the basis of normal karyotype reports using either fluorescence in situ hybridization (FISH) or G-banding methods. Library preparation and sequencing were conducted similarly to that of gDNA samples. Because the karyotype outcome was based on FISH or G-banding, it was anticipated that some of the "euploid" samples contained MD events. In case of putative FP results at 12-plex sequencing, the library was further sequenced at uniplex to confirm its validity. If the results were confirmed by uniplex sequencing, the results were counted as true positives (TPs) instead of FPs. Previous results have described the limitations of traditional karyotyping and also compared it with sequencing-based results (see, e.g., Srinivasan Am J Hum Genet 2013; 92:167-76).

Results

Normalization

Sequencing bias can cause nonuniform coverage in data, which complicates downstream CNV analysis (see, e.g., *Dohm Nucleic Acids Res* 2008; 36:e105, see, e.g., *Benjamini Nucleic Acids Res* 2012; 40:e72). FIGS. 7A and 7B demonstrate the normalization result on a 12-plex sequencing sample. Without normalization, many regions would aberrantly appear as depletions or duplications (FIG. 7A). After normalization, the microduplication event became more evident (FIG. 7B).

MD Limit of Detection

For subchromosomal abnormality detection, understand the limit of detection (LoD) for MDs is helpful. Four factors affect the LoD: fetal fraction (f), size of the event, coverage, and the biological and technical variability of the event region. The first 3 factors are readily understood: it is easier to detect an event with higher fetal fraction, larger size, and higher sequencing coverage. The fourth factor is related to the fact that certain regions are more variable than others due to various factors (such as GC bias, repetitive elements, and mapping ability) and are harder to detect. FIG. 8 illustrates the impact of the 4 factors. Through a simulation study, we observed that at 0.2_coverage, the sensitivity difference between the proposed decision tree method and the theoretical limit was_5% for MDs_9 Mb (supplemental data at world wide web address: clinchem.org/content/vol61/issue4 can be accessed).

Analytical Validation Using Genomic DNA Mixtures

A blinded gDNA study was conducted to test the performance of the proposed decision tree method on several selected syndromes with high clinical relevance. Due to the rarity of these syndromes, a gDNA mixture model system was created for analytical validation. Forty-five gDNA samples from individuals with DiGeorge, Cridu-chat, Prader-Willi, Angelman, or 1p36 deletion syndromes were obtained from Coriell Cell Repositories or from CombiMatrix Diagnostics. The source, disease, and karyotype results of the gDNAs are provided in Table 6. In total, 17 were positive for Prader-Willi or Angelman syndrome, 14 were positive for Cri-du-chat, 13 were positive for DiGeorge, and 1 was positive for 1p36. All 45 gDNA samples were sequenced once from a 20%-7.5% mixture, and they were sequenced twice at a 5% mixture. A total of 360 gDNA mixtures were sequenced. Fetal fraction plays a crucial role in the detectability of any given MD. The observed fetal fraction by chromosome Y on male samples was measured to confirm the planned titration levels.

Figure 8A:
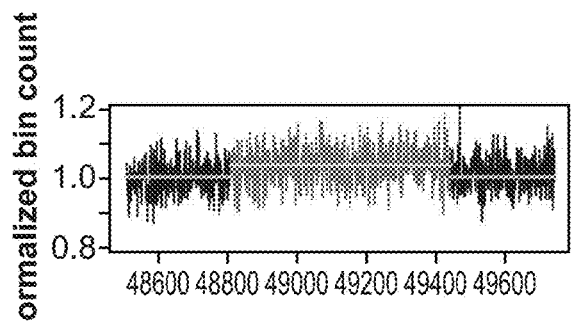
FIGS. 8A-8D show four factors affect the detectability of microdeletions in accordance with some embodiments.
Figure 8A:
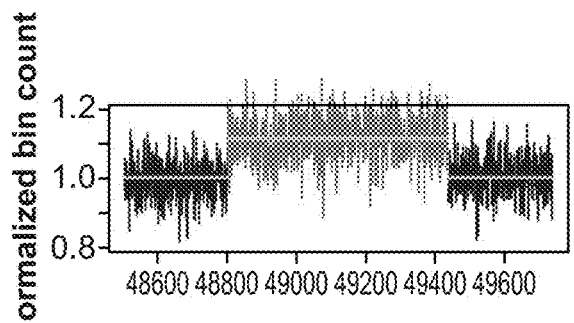
Figure 8B:
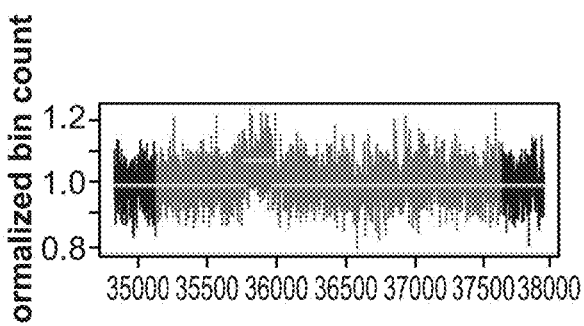
Figure 8B:
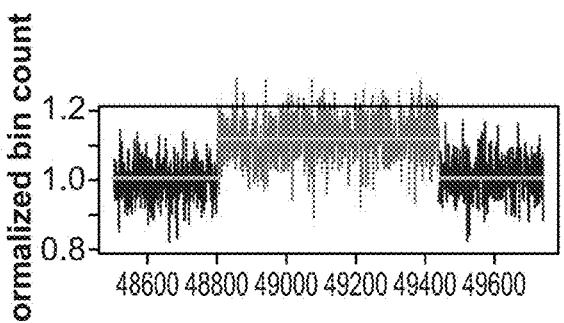
Figure 8C:
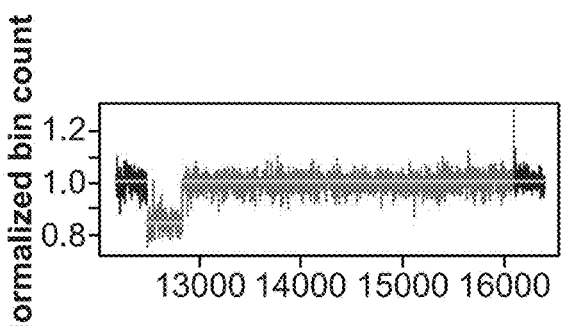
Figure 8C:
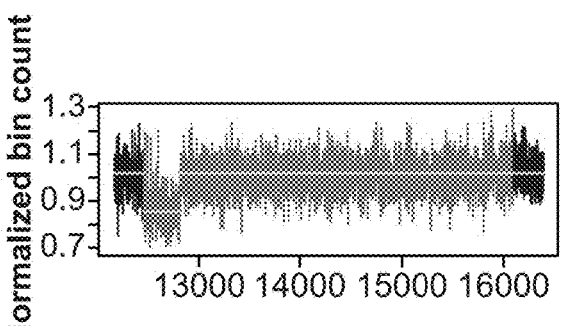
Figure 8D:
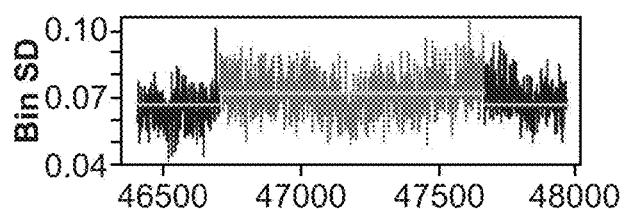

FIGS. 8A-8D show that the measured values agreed well with the planned titrations, with slight overdilution. The plots follow the same convention as FIG. 7A and FIG. 7B. The horizontal line represents the median value of the respective regions. FIG. 8A shows low fetal fraction (6.5%) versus high fetal fraction (21%); FIG. 8B shows small-size microdeletion (MD) (7.5 Mb) versus large-size MD (31.75 Mb); FIG. 8C shows low coverage (15 Mreads) versus high coverage (180 M reads); and FIG. 8D shows bin count SD differs from region to region. The median measured titration concentrations were 18.3%, 16.0%, 14.0%, 11.6%, 9.3%, 7.1%, and 4.7% respectively. Before the gDNA unblinding, the sensitivity was predicted to detect each of the syndromes using the LoD framework. Briefly, the genomic location and size definition of each syndrome is acquired from the DECIPHER database (see, e.g., Firth Am J Hum Genet 2009; 84:524-33). A syndrome-specific microdeletion or microduplication is created by sampling the observed titration values shown in FIGS. 8A-8D. After unblinding, the observed sensitivity for detection of each of these 3 syndromes fell within the 95% CI, with the exception of the 4.7% gDNA fractions (FIG. 9). Such high concordance suggests that the LoD framework is predictive of the actual performance. Note that the discrepancy at 4.7% can be mainly attributed to the size difference between the database size and the tested cases, and that such differences are most obvious at low fetal fractions. For example, the Cri-du-chat syndrome has a size of 12.52 Mb according to the DECIPHER database (see, e.g., Firth Am J Hum Genet 2009; 84:524-33), and the testing cases ranged from 8 to 20 Mb, which made the detection easier at low fetal fractions.

Figure 9A:
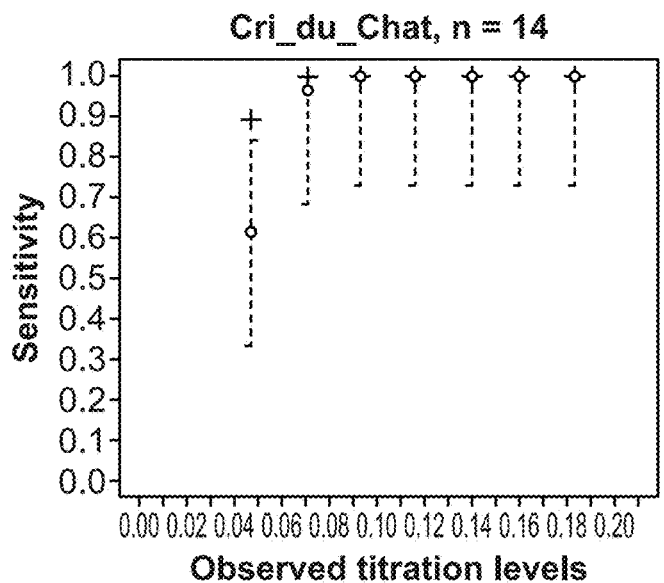
FIGS. 9A-9C show predicted sensitivity (circles), 95% Confidence Interval (bars), and observed sensitivity (crosses) for Cri-du-chat, Prader-Willi/Angelman, and DiGeorge at the observed titration levels in accordance with some embodiments.
Figure 9B:
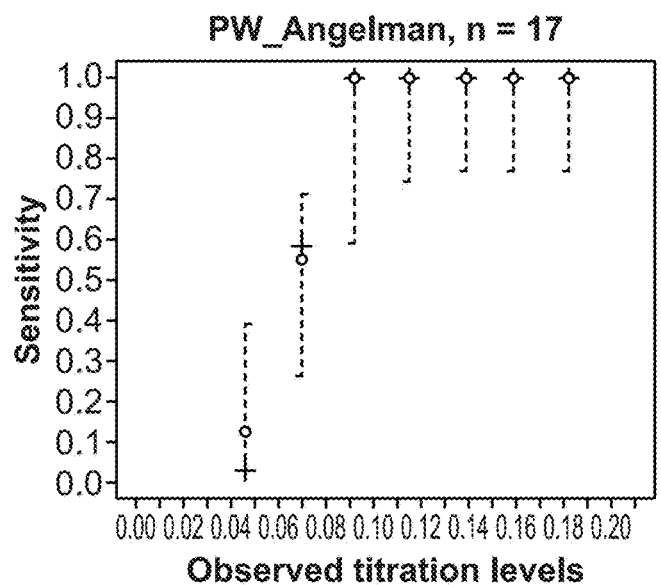
Figure 9C:
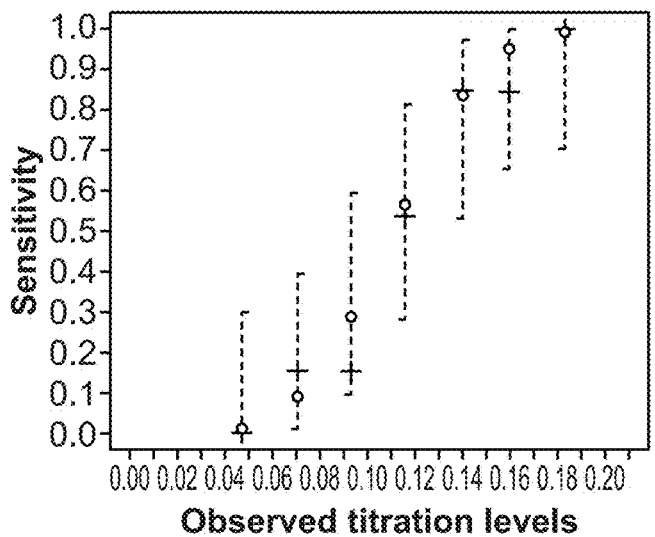

For the 1p36 sample, there was detection at 9.3% titration and above. FIGS. 9A-9C show examples of predicted sensitivity (circles), 95% Confidence Interval (bars), and observed sensitivity (crosses) for Cri-du-chat, Prader-Willi/ Angelman, and DiGeorge at the observed titration levels. The plot is not shown for 1p36 due to limited sample size (n=1), which is detectable until 9.3% titration. Note that this 1p36 sample has a size of only approximately 3 Mb, which is much smaller than its database definition of 12.83 Mb (see, e.g., Firth Am J Hum Genet 2009; 84:524-33). In real life applications, the overall sensitivity is expected to be higher. Within this set of gDNA mixtures each gDNA had a combination of karyotype and microarray results confirming the presence of an MD event for 1 of the 5 syndromes queried in this study. This information is used to determine specificity for the nonaffected syndrome regions in each of the gDNA samples. There was no false-positive result by the decision tree system for any of the 360 gDNA mixtures. An overall specificity of 100% (95% CI, 98.7%-100%) was achieved in the gDNA study. The high specificity value is paramount for good positive predictive values, given the low prevalence of these conditions. The entirety of all supplemental figures and information referenced herein are incorporated herein by reference for all purposes.

Clinical Validation Using Plasma Samples

To further test the performance of the proposed decision tree method in a genome-wide fashion, a blinded study was conducted using maternal plasma DNAs with matched karyotype. For this study, 183 samples were analyzed using 12-plex sequencing. Fetal fractions were measured by the same method used in the current clinical practice (see, e.g., Geis Presented at: 2014 ACMG Annual Clinical Genetics Meeting; 2014 Mar. 25-29; Nashville, Tenn.; Kinnings Clinical Genetics Meeting, Vol. Nashville, Tenn. 2014). On the completion of sequencing, 1 (see, e.g., Lo Lancet 1997; 350:485-7) affected sample and 4 (see, e.g., Ehrich AmJ Obstet Gynecol 2011; 204:205 e1-11) euploid samples failed QC and were subsequently excluded from analysis. Hence, there was a total of 178 plasma samples with a median fetal fraction of 9.2% (range, 2.8%-24.9%). No QC cutoff for fetal fraction was imposed. According to the karyotype table, the expected MD sizes ranged from 3 to 40 Mb (Table 5).

Figure 10A:
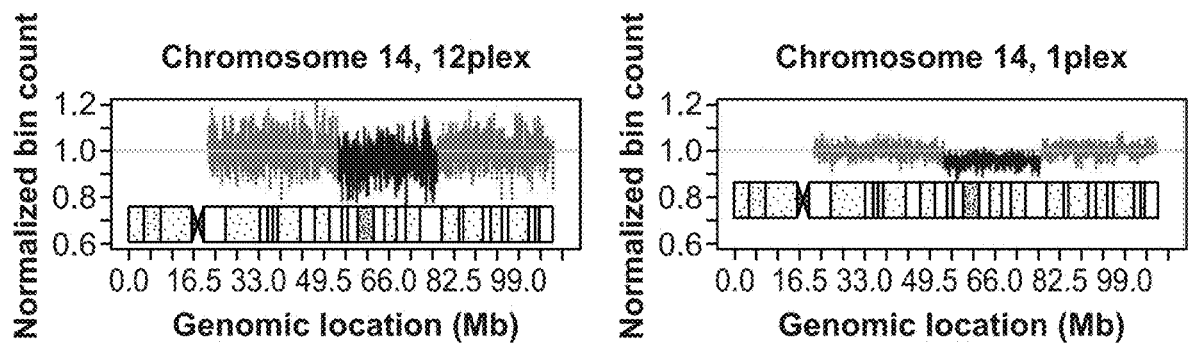
FIGS. 10A-10C show a comparison between 12-plex (left panel) and uniplex (right panel) results in accordance with some embodiments.
Figure 10B:
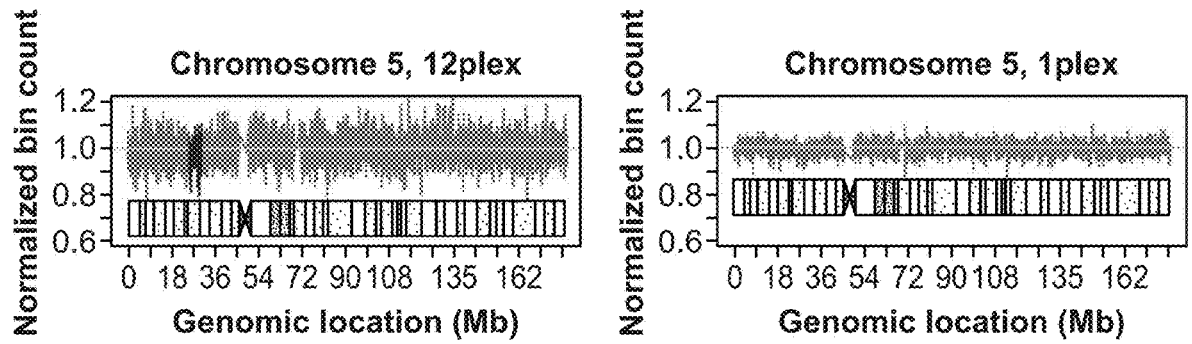
Figure 10C:
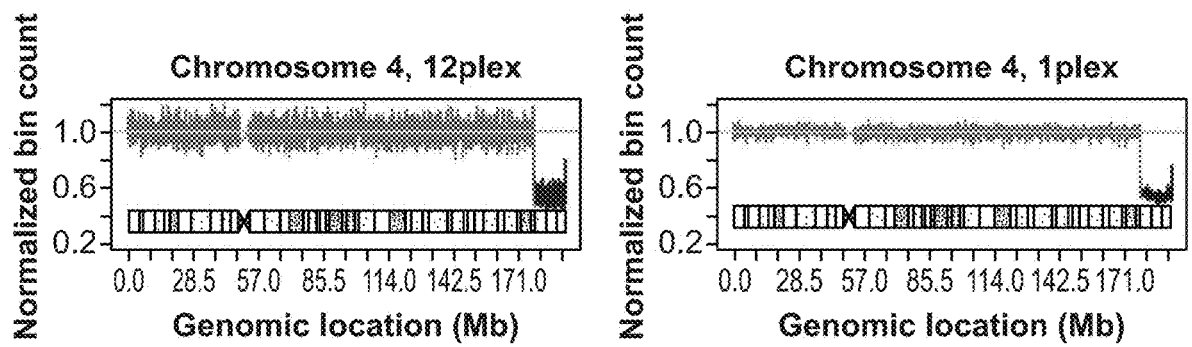

The system detected 13 of the 16 affected samples. Of the 3 supposed FNs, one was expected to show trisomy 8, one was expected to show a deletion of chromosome 4q34, and the third one was expected to show unbalanced translocation between chromosome 12 and chromosome 19. Subsequent detailed review of the first karyotype reports indicated the trisomy 8 sample was a low-level mosaic sample (approximately 8% cells affected). Because this low level of mosaicism would not have met the sample inclusion criteria, this sample was excluded from the remaining analysis. Review of the second karyotype report indicated that the mother also carried the same chromosome 4q34 deletion as the fetus. The process did successfully detect the event and correctly called it as a maternal event. Because the focus was only on de novo fetal events, this sample was also excluded from the analysis. Review of the third sample did not reveal any complex karyotype information, and the negative process outcome was probably a result of a low fetal fraction of 4.8%. Note that this FN sample was still nondetectable at uniplex sequencing. For the remaining 162 presumed euploid samples, 5 MD events were detected. Additionally, in 2 of the 16 affected samples, 2 events were detected, whereas the karyotype report indicated only 1 event. Because the study collection protocol provided only the karyotyping result of amniocytes for these samples, no pure fetal tissue was available for sequencing or array confirmation. Therefore, to confirm the validity of the findings, they were resequenced at higher coverage (uniplex) all the putative FP samples. Of these, 1 sample led to a different outcome based on the higher coverage sequencing and was deemed an FP result. The remaining 4 samples produced the same outcome when sequenced in uniplex. The MD events detected in these 4 samples included MDs of 2.85, 3.25, 22.15, 23.55, 25, 32.45, and 42.3 Mb. FIGS. 10A-10C illustrate comparisons between 12-plex and uniplex results for (A) a confirmed TP sample by uniplex, (B) a confirmed FP by uniplex, and (C) the maternal deletion detected by both 12-plex and uniplex. The plots follow the same convention as FIG. 7A and FIG. 7B. The uniplex results show significantly improved signal to noise ratio compared to the 12-plex results. Specifically, FIG. 10A shows a TP event detected at 12-plex and confirmed by uniplex sequencing; FIG. 10B shows a FP event detected at 12-plex but not by uniplex sequencing; and FIG. 10C shows a maternal deletion detected by both the 12-plex and uniplex sequencing.

Table 6 summarizes the performance of the process on 176 plasma samples (excluding the mosaic trisomy 8 and maternal chr4q34 deletion). The process attained a 94.4% sensitivity (95% CI, 70.6%-99.7%), and a 99.4% specificity (95% CI, 95.96%-99.97%) for the plasma samples. The CI was calculated on the basis of the proportion test with continuity correction (see, e.g., *Newcombe Clinical Chemistry* 61:4 (2015) 615). It is clarified that 4 out of 5 putative FP samples were confirmed by uniplex sequencing and subsequently counted as TP samples. Because pure tissue samples were not available for further invasive arrayCGH confirmation, the interpretation of specificity was limited to the signal detection perspective. Note that other researchers have also observed discrepancies between sequencing and the traditional karyotyping methods (see, e.g., Srinivasan Am J Hum Genet 2013; 92:167-76).

TABLE 6

Contingency table for the plasma study

|  | Known genome abnormality | No known genome abnormality |
|---|---|---|
| TP | 17 | 1 |
| TN | 1 | 156 |
| Not reported | 0 | 1 |

The decision tree process correctly detected 17/18 positives and 156/157 negatives.
Note 4 out of 5 putative FP samples at 12-plex were subsequently confirmed at uniplex and were counted as TP samples here.

Non-Limiting Listing of Embodiments

Provided hereafter is a listing of non-limiting examples of embodiments of the technology.

A1. A method for classifying presence or absence of a chromosome copy number variation or sub-chromosome copy number variation for a test sample, comprising:

(a) providing a set of genomic portions each coupled to a sequence read quantification for a test sample, wherein:
the genomic portions comprise portions of a reference genome to which sequence reads obtained for sample nucleic acid from the test subject have been mapped,
the genomic portions comprise (i) genomic portions within a candidate region identified as a candidate copy number variation region, and/or (ii) genomic portions outside the candidate region and within a selected region larger than the candidate region that includes the candidate region, and the candidate region is a chromosome or sub-chromosome region;

(b) shifting the quantification of the sequence reads mapped to the genomic portions for the candidate region at or near a quantification of sequence reads mapped to genomic portions outside the candidate region and within the selected region;

(c) sampling genomic portions from the selected region, wherein the number of sampled genomic portions is about equal to the number of genomic portions in the candidate region, thereby generating a sampled region, and repeating the sampling to generate a plurality of sampled regions;

(d) normalizing a sequence read quantification for each of the sampled regions, thereby generating a normalized quantification for each of the sampled regions;

(e) generating a confidence determination for the candidate region by a process comprising comparing each normalized quantification to a measure of variability of sequence read quantifications for the candidate region for reference samples not having a significant copy number variation in the candidate region; and (f) providing a classification for presence or absence of the copy number variation for the candidate region for the test sample according to the confidence determination.

A1.1. A method for classifying presence or absence of a chromosome copy number variation or sub-chromosome copy number variation for a test sample, comprising:

shifting a quantification of sequence reads mapped to genomic portions of a reference genome for a candidate region at or near a quantification of sequence reads mapped to genomic portions outside the candidate region and within a selected region, wherein:
the genomic portions each are coupled to a sequence read quantification for a test sample, the genomic portions comprise portions of a reference genome to which sequence reads obtained for sample nucleic acid from the test subject have been mapped,
the genomic portions comprise (i) genomic portions within a candidate region identified as a candidate copy number variation region, and (ii) genomic portions outside the candidate region and/or within a selected region larger than the candidate region that includes the candidate region, and the candidate region is a chromosome or sub-chromosome region;

sampling genomic portions from the selected region, wherein the number of sampled genomic portions is about equal to the number of genomic portions in the candidate region, thereby generating a sampled region, and repeating the sampling to generate a plurality of sampled regions;

normalizing a sequence read quantification for each of the sampled regions, thereby generating a normalized quantification for each of the sampled regions;

generating a confidence determination for the candidate region by a process comprising comparing each normalized quantification to a measure of variability of sequence read quantifications for the candidate region for reference samples not having a significant copy number variation in the candidate region; and providing a classification for presence or absence of the copy number variation for the candidate region for the test sample according to the confidence determination.

A2. The method of embodiment A1 or A1.1, wherein the length of a sub-chromosome copy number variation and the candidate region is greater than or equal to about 7 megabases.

A3. The method of embodiment A1 or A1.1, wherein the length of sub-chromosome copy number variation and the candidate region is less than about 7 megabases.

A4. The method of any one of embodiments A1 to A3, wherein the selected region is a chromosome in which the candidate region is located.

A4.1. The method of any one of embodiments A1 to A3, wherein the selected region is all autosomes.

A5. The method of any one of embodiments A1 to A4.1, wherein the plurality of sampled regions is about 100 or more sampled regions.

A6. The method of embodiment A5, wherein the plurality of sampled regions is about 1,000 or more sampled regions.

A7. The method of embodiment A6, wherein the plurality of sampled regions is about 10,000 or more sampled regions.

A8. The method of any one of embodiments A1 to A7, wherein the quantification of sequence reads in (b) is sequence read count.

A9. The method of embodiment A8, wherein (b) comprises:
  determining a median read count of genomic portions in the candidate region, thereby providing a candidate region median count;
  determining a median read count of genomic portions outside the candidate region and in the selected region, thereby providing an outside median count;
  subtracting the outside median count from the candidate region median count, thereby determining a shift.

A10. The method of embodiment A9, wherein (b) comprises subtracting the shift from sequence read counts for each genomic portion in the candidate region.

A11. The method of any one of embodiments A8 to A10, wherein the shift is added to the sequence read count of each genomic portion in each sampled region.

A12. The method of any one of embodiments A8 to A10, wherein the shift is not added to the sequence read count of each genomic portion in each sampled region.

A13. The method of embodiment A11 or A12, comprising determining a read count fraction for each of the sampled regions, wherein the quantification of sequence reads for each of the sampled regions in (d) is the read count fraction.

A14. The method of embodiment A13, wherein each read count fraction is the sum of read counts of genomic portions in each of the sampled regions, optionally after the shift is added to each of the read counts of the genomic portions, divided by the sum of read counts in the selected region.

A15. The method of any one of embodiments A1 to A14, wherein the normalized quantification in (d) is a standard score for each of the sampled regions.

A15. The method of embodiment A15, wherein the standard score is a z-score.

A16. The method of any one of embodiments A13 to A15, wherein the normalized quantification in (d) is determined from the read count fraction for each of the sampled regions.

A17. The method of any one of embodiments A1 to A16, wherein the measure of variability in (e) is a median absolute deviation (MAD).

A18. The method of any one of embodiments A1 to A17, wherein each of the sequence read count quantifications for the candidate region for each of the reference samples in (e) is a read count fraction for each candidate region in each of the reference samples.

A19. The method of embodiment A18, wherein each read count fraction is the sum of read counts of genomic portions in the candidate region divided by the sum of read counts in the selected region for each of the reference samples.

A20. The method of any one of embodiments A1 to A19, wherein the quantification of sequence reads for genomic portions in the candidate region, outside region and/or selected region is a normalized quantification generated by a normalization process that normalizes GC bias or other bias.

A21. The method of embodiment A20, wherein the normalization process comprises LOESS normalization and/or principal component normalization.

A22. The method of any one of embodiments A1 to A21, wherein comparing in (e) comprises comparing each normalized quantification for each sampled region, or absolute value of each normalized quantification for each sampled region, to a measure of variability threshold for the reference samples.

A23. The method of embodiment A22, wherein the threshold is a number of median absolute deviations (MADs) for read count fractions for candidate regions for the reference samples.

A24. The method of embodiment A22 or A23, wherein each normalized quantification is a z-score for each of the sampled regions.

A25. The method of any one of embodiments A22 to A24, wherein the number of MADs is about 3 to about 5.

A26. The method of embodiment A25, wherein the number of MADs is about 3.95.

A27. The method of any one of embodiments A22 to A26, wherein generating the confidence determination in (e) comprises determining a proportion of the sampled regions for which the normalized quantification (e.g., for which the absolute value of the normalized quantification) is greater than or less than the threshold.

A28. The method of embodiment A27, wherein the proportion is a ratio of (i) the number of sampled regions for which the normalized quantification (e.g., for which the absolute value of the normalized quantification) is greater than or less than the threshold to (ii) the total number of sampled regions.

A29. The method of embodiment A28, wherein the shift is applied to the sequence read count of each genomic portion in each sampled region and the ratio is (i) the number of sampled regions for which the normalized quantification (e.g., for which the absolute value of the normalized quantification) is greater than the threshold, to (ii) the total number of sampled regions.

A30. The method of embodiment A28, wherein the shift is not applied to the sequence read count of each genomic portion in each sampled region and the ratio is (i) the number of sampled regions for which the normalized quantification (e.g., for which the absolute value of the normalized quantification) is less than the threshold, to (ii) the total number of sampled regions.

A31. The method of any one of embodiments A1 to A30, wherein the sampling in (c) is random sampling.

A32. The method of embodiment A31, wherein the random sampling is bootstrap sampling with replacement.

A33. The method of any one of embodiments A1 to A32, wherein the reference samples consist of samples that have been classified for absence of chromosome trisomy.

A34. The method of any one of embodiments A1 to A33, wherein the reference samples consist of samples that have been classified for absence of a copy number variation of greater than 7 megabases in the candidate region.

A35. The method of any one of embodiments A1 to A33, wherein the reference samples consist of samples that have been classified for absence of a copy number variation of greater than 5 megabases in the candidate region.

A36. The method of any one of embodiments A1 to A33, wherein the reference samples consist of samples that have been classified for absence of a copy number variation of greater than 4 megabases in the candidate region.

A37. The method of any one of embodiments A1 to A33, wherein the reference samples consist of samples that have been classified for absence of a copy number variation of greater than 3 megabases in the candidate region.

A38. The method of any one of embodiments A1 to A33, wherein the reference samples consist of samples that have been classified for absence of a copy number variation of greater than 2 megabases in the candidate region.

A39. The method of any one of embodiments A1 to A33, wherein the reference samples consist of samples that have been classified for absence of a copy number variation of greater than 1 megabase in the candidate region.

A40. The method of any one of embodiments A1 to A33, wherein the reference samples consist of samples that have been classified for absence of a copy number variation of about 1.25 megabases or greater in all autosomes.

B1. The method of any one of embodiments A1 to A40, wherein the sample nucleic acid from the test subject is circulating cell free nucleic acid.

B2. The method of embodiment B1, wherein the circulating cell free nucleic acid is from blood plasma or blood serum from the test subject.

B3. The method of any one of embodiments A1 to B2, wherein the test subject is a female.

B4. The method of embodiment B3, wherein the female is a human female.

B5. The method of embodiment B3 or B4, wherein the female is a pregnant female.

B6. The method of any one of embodiments A1 to B2, wherein the test subject is a male.

B6.1. The method of embodiment B6, wherein the test subject is a human male.

B7. The method of any one of embodiments A1 to B6.1, wherein the genomic portions are of fixed length.

B8. The method of embodiment B7, wherein the genomic portions are of equal length.

B9. The method of embodiment B8, wherein the genomic portions are about 50 kilobases in length.

B10. The method of any one of embodiments A1 to B9, wherein at least two of the genomic portions are of unequal length.

B11. The method of any one of embodiments A1 to B10, wherein the genomic portions do not overlap.

B12. The method of embodiment B11, wherein the 3' ends of the genomic portions abut the 5' ends of adjacent genomic portions.

B13. The method of any one of embodiments A1 to B10, wherein at least two of the genomic portions overlap.

B14. The method of any one of embodiments A1 to B13, comprising generating the sequence reads from the nucleic acid sample by a sequencing process.

B15. The method of embodiment B14, wherein the sequence process is a whole-genome sequencing process.

B16. The method of embodiment B14 or B15, wherein the sequencing process comprises sequencing by synthesis.

B17. The method of any one of embodiments A1 to B16, comprising obtaining the sequence reads and mapping the sequence reads to the genomic portions, thereby providing sequence reads mapped to the genomic portions.

B18. The method of any one of embodiments A1 to B17, comprising obtaining sequence reads mapped to the genomic portions and quantifying the sequence reads mapped to each of the genomic portions, thereby generating a quantification of the sequence reads mapped to the genomic portions.

B19. The method of embodiment B19, wherein the quantification of the sequence reads mapped to each of the genomic portions is a count or read density.

B20. The method of any one of embodiments A1 to B19, comprising normalizing the quantification of sequence reads mapped to the genomic portions, thereby generating a normalized quantification of sequence reads mapped to the genomic portions.

B21. The method of embodiment B20, wherein the normalizing comprises a guanine-cytosine GC normalization process.

B22. The method of embodiment B21, wherein the normalization process comprises LOESS, GCRM or combination thereof.

B23. The method of any one of embodiments B20 to B22, wherein the normalizing comprises adjusting the quantification of sequence reads, or the normalized quantification of sequence reads, mapped to the genomic portions by principal component portion weights derived from a training set of samples, thereby generating an adjusted quantification of sequence reads mapped to the genomic portions.

B24. The method of any one of embodiments B20 to B23, wherein certain genomic portions are filtered prior to, or after, the normalizing or the adjusting.

B25. The method of embodiment B24, wherein the filtering is based on mappability, repeat masking or combination thereof.

B26. The method of embodiment B25, wherein filtering is based on variation of the quantification of sequence reads mapped to genomic portions across multiple reference samples, consistently no reads mapped to genomic portions across multiple reference samples, or combination thereof.

B27. The method of any one of embodiments A1 to B26, wherein the candidate region is identified by a process comprising a segmentation process.

B28. The method of embodiment B27, wherein the segmentation process comprises a circular binary segmentation (CBS) process.

B29. The method of embodiment B27 or B28, wherein the process generates a copy number variation quantification for each segment.

B30. The method of embodiment B27 or B28, wherein the copy number variation quantification is z-score.

B31. The method of embodiment B30, wherein the z-score ($Z_{SEG}$) is determined according to:

$$z\text{-score} = (S_{scr} - S_{mcr})/MAD$$

wherein:
the $S_{scr}$ is a test sample count representation of a segment, wherein the $S_{scr}$ is the total normalized counts in the segment divided by the total normalized autosome counts for the test sample;
the $S_{mcr}$ is a median count representation for the segment generated for a reference set of samples; and
the MAD is a median absolute deviation determined for the count representation of the segment for the reference set of samples.

B32. The method of any one of embodiments A1 to A31, comprising determining a log odds ratio (LOR) for the copy number variation for the test sample.

B33. The method of embodiment B32, wherein the LOR is the log of the quotient of (i) a first multiplication product of (1) a conditional probability of having a copy number variation and (2) a prior probability of having the copy number variation, and (ii) a second multiplication product of (1) a conditional probability of not having the copy number variation and (2) a prior probability of not having the copy number variation.

B34. The method of embodiment B33, wherein the conditional probability of having the copy number variation is determined according to fetal fraction determined for the test sample, a z-score of the count representation for the segment determined for the test sample, and a distribution for the fetal fraction of z-scores for the count representation for the segment.

B35. The method of embodiment B34, wherein the conditional probability of having the copy number variation is determined by the relationship in equation (1):

$$Z \sim \text{Normal}\left(\frac{\mu_X}{\sigma_X}\frac{f}{2}, 1\right) \quad (1)$$

wherein f is fetal fraction, X is the summed portion count for the segment covering the copy number variation, X~f($\mu_X$, $\sigma_X$), where $\mu_X$ and $\sigma_X$ are the mean and standard deviation of X, respectively, and f(·) is a distribution function.

B36. The method of any one of embodiments B33 to B35, wherein the conditional probability of having the copy number variation is the intersection between the z-score for the test sample of the count representation for the segment and a distribution for the fetal fraction of z-scores for the count representation for the segment.

B37. The method of any one of embodiments B33 to B36, wherein the conditional probability of not having the copy number variation is the intersection between the z-score of the count representation for the segment determined for the test sample and a distribution of z-scores for the count representation for the segment in euploids.

B38. The method of any one of embodiments B33 to B37, wherein the prior probability of having the copy number variation and the prior probability of not having the copy number variation are determined from multiple samples that do not include the test subject.

B39. The method of any one of embodiments B32 to B38, wherein the LOR is determined for a chromosome copy number variation ($LOR_{CHR}$).

B40. The method of any one of embodiments B32 to B39, wherein the LOR is determined for a sub-chromosome copy number variation ($LOR_{SUB}$).

B41. The method of any one of embodiments A1 to B38, comprising generating a copy number variation quantification for a chromosome for the test sample.

B42. The method of embodiment B41, wherein the quantification is a z-score.

B43. The method of embodiment B42, wherein the z-score ($Z_{CHR}$) is determined according to:

z-score=$(C_{scr}-C_{mcr})/MAD$ wherein:
the $C_{scr}$ is a test sample count representation of the chromosome, wherein the $C_{scr}$ is the total normalized counts in the chromosome divided by the total normalized autosome counts for the test sample;
the $S_{mcr}$ is a median count representation for the chromosome generated for a reference set of samples; and
the MAD is a median absolute deviation determined for the count representation of the chromosome for the reference set of samples.

B44. The method of any one of embodiments B31 to B43, wherein presence of a chromosome trisomy or monosomy is classified for the test sample when the absolute value of $Z_{CHR}$ is greater than or equal to a predetermined cutoff value, $LOR_{CHR}$ is greater than zero, the absolute value of $Z_{CHR}$ is greater than or equal to the product of a and $Z_{SEG}$, wherein a is between 0 and about 1, and the confidence determination for the chromosome is greater than a predetermined level.

B45. The method of embodiment B43, wherein a is between about 0.6 and about 0.8.

B46. The method of embodiment B43 to B43, wherein the predetermined cutoff value is between about 2 and about 5.

B47. The method of embodiment B46, wherein the predetermined cutoff value is between about 3 and 4.

B48. The method of any one of embodiments B44 to B47, wherein the predetermined level is 0.99 or greater.

B49. The method of any one of embodiments B31 to B43, wherein absence of a chromosome trisomy or monosomy is classified for the test sample when the absolute value of $Z_{CHR}$ is less than a predetermined cutoff value, $LOR_{CHR}$ is less than zero, the absolute value of $Z_{CHR}$ is less than the product of a and $Z_{SEG}$, wherein a is between 0 and about 1, and/or the confidence determination for the chromosome is less than a predetermined level.

B50. The method of embodiment B49, wherein a is between about 0.6 and about 0.8.

B51. The method of embodiment B49 or B50, wherein the predetermined cutoff value is between about 2 and about 5.

B52. The method of embodiment B51, wherein the predetermined cutoff value is between about 3 and 4.

B53. The method of any one of embodiments B49 to B52, wherein the predetermined level is 0.99 or greater.

B54. The method of any one of embodiments B31 to B53, wherein presence of a sub-chromosome copy number variation is classified for the test sample when there is absence of a chromosome trisomy or monosomy classified for the test sample, where the absolute value of $Z_{SEG}$ is greater than or equal to a predetermined cutoff value, the $LOR_{SEG}$ is greater than zero and the confidence determination for the segment is greater than a predetermined level.

B55. The method of embodiment B54, wherein the predetermined cutoff value is between about 2 and about 5.

B56. The method of embodiment B55, wherein the predetermined cutoff value is between about 3 and 4.

B57. The method of any one of embodiments B54 to B56, wherein the predetermined level is 0.99 or greater.

B58. The method of any one of embodiments B31 to B53, wherein absence of a sub-chromosome copy number variation is classified for the test sample when the absolute value of $Z_{SEG}$ is less than a predetermined cutoff value, the $LOR_{SEG}$ is less than zero, and/or the confidence determination for the segment is less than a predetermined level.

B59. The method of embodiment B58, wherein the predetermined cutoff value is between about 2 and about 5.

B60. The method of embodiment B59, wherein the predetermined cutoff value is between about 3 and 4.

B61. The method of any one of embodiments B58 to B60, wherein the predetermined level is 0.99 or greater.

B62. The method of any one of embodiments A1 to B61, wherein (b), (c) and/or (d) are performed by a computer.

B63. The method of embodiment B62, wherein (b), (c) and/or (d) are performed by one or more processors in the computer.

B64. The method of embodiment B62 or B63, wherein (b), (c) and/or (d) are performed according to instructions stored in memory and implemented by the computer.

B65. The method of embodiment B64, wherein one or more of the following are stored in memory: genomic portions each coupled to a sequence read quantification for the candidate region, genomic portions each coupled to a sequence read quantification for the selected region, genomic portions each coupled to a sequence read quantification for the outside region, genomic portions each coupled to a sequence read quantification for each of the sampled regions, read count fraction for each of the sampled regions, read count fraction for each of the candidate region for each of the reference samples, deviation measure, threshold, ratio, confidence determination, $Z_{SEG}$, $LOR_{SEG}$, $Z_{CHR}$, and $LOR_{CHR}$.

C1. A system, comprising one or more processors and memory, which memory comprises instructions executable by the one or more processors, and which instructions executable by the one or more processors are configured to perform a method of any one of embodiments A1 to B65.

C2. A machine, comprising one or more processors and memory, which memory comprises instructions executable by the one or more processors, and which instructions executable by the one or more processors are configured to perform a method of any one of embodiments A1 to B65.

C3. A computer program product in a computer readable storage medium, the product comprising programed instructions for the computer to perform a method of any one of embodiments A1 to B65.

D1. A method for classifying presence or absence of a chromosome copy number variation or .sub-chromosome copy number variation for a test sample, comprising:
  shifting, by a computing device, a quantification of sequence reads mapped to genomic portions of a reference genome for a candidate region at or near a quantification of sequence reads mapped to genomic portions outside the candidate region and within a selected region, wherein: (i) the genomic portions each are coupled to a sequence read quantification for a test sample, and/or (ii) the genomic portions comprise portions of a reference genome to which sequence reads obtained for a sample nucleic acid from the test subject have been mapped, and (iii) the genomic portions comprise (A) genomic portions within a candidate region identified as a candidate copy number variation region, and (B) genomic portions outside the candidate region and within a selected region larger than the candidate region that includes the candidate region, and (iv) the candidate region is a chromosome or sub-chromosome region;
  sampling, by the computing device, genomic portions from the selected region, wherein the number of sampled genomic portions is about equal to the number of genomic portions in the candidate region, thereby generating a sampled region, and repeating the sampling to generate a plurality of sampled regions;
  normalizing, by the computing device, a sequence read quantification for each of the sampled regions, thereby generating a normalized quantification for each of the sampled regions;
  generating, by the computing device, a confidence determination for the candidate region by a process comprising comparing each normalized quantification to a measure of variability of sequence read quantifications for the candidate region for reference samples not having a significant copy number variation in the candidate region; and
  providing, by the computing device, a classification for presence or absence of the copy number variation for the candidate region for the test sample according to the confidence determination.

D2. The method of any one of embodiment D1, wherein the selected region is a chromosome in which the candidate region is located.

D3. The method of any one of embodiments D1 to D2, wherein the plurality of sampled regions is about 100 or more sampled regions.

D4. The method of any one of embodiments D1 to D3, wherein the quantification of sequence reads is a sequence read count.

D5. The method of embodiment D4, wherein the shifting further comprises:
  determining a median read count of genomic portions in the candidate region, thereby providing a candidate region median count;
  determining a median read count of genomic portions outside the candidate region and in the selected region, thereby providing an outside median count;
  subtracting the outside median count from the candidate region median count, thereby determining a shift.

D6. The method of any one of embodiments D1 to D5, wherein the normalized quantification is a standard score for each of the sampled regions.

D7. The method of embodiment D6, wherein the standard score is a z-score.

D8. The method of any one of embodiments D1 to D7, wherein each of the sequence read count quantifications for the candidate region for each of the reference samples is a read count fraction for each candidate region in each of the reference samples.

D9. The method of any one of embodiments D1 to D8, wherein the quantification of sequence reads for genomic portions in the candidate region, outside region and/or selected region is a normalized quantification generated by a normalization process that normalizes GC bias or other bias.

D10. The method of any one of embodiments D1 to D9, wherein the generating the confidence determination further comprises comparing each normalized quantification for each sampled region, or absolute value of each normalized quantification for each sampled region, to a measure of variability threshold for the reference samples.

D11. The method of any one of embodiments D1 to D10, wherein the generating the confidence determination further comprises determining a proportion of the sampled regions for which the normalized quantification is greater than or less than the threshold.

D12. The method of embodiment D11, wherein the proportion is a ratio of (i) the number of sampled regions for which the normalized quantification is greater than or less than the threshold to (ii) the total number of sampled regions.

D13. The method of any one of embodiments D1 to D12, wherein the sampling) is a random sampling.

D14. The method of any one of embodiments D1 to D13, wherein the sample nucleic acid from the test subject is circulating cell free nucleic acid.

D15. The method of any one of embodiments D1 to D14, wherein the test subject is a female.

D16. The method of any one of embodiments D1 to D15, wherein the genomic portions are of fixed length.

D17. The method of any one of embodiments D1 to D16, wherein the genomic portions do not overlap.

D18. The method of any one of embodiments D1 to D17, further comprising generating, by the computing device, the sequence reads from the nucleic acid sample by a sequencing process.

D19. The method of any one of embodiments D1 to D18, further comprising obtaining, by the computing device, sequence reads mapped to the genomic portions and quantifying the sequence reads mapped to each of the genomic portions, thereby generating a quantification of the sequence reads mapped to the genomic portions.

D20. The method of any one of embodiments D1 to D19, further comprising normalizing, by the computing device, the quantification of sequence reads mapped to the genomic portions, thereby generating a normalized quantification of sequence reads mapped to the genomic portions.

D21. The method of embodiment D20, wherein certain genomic portions are filtered prior to, or after, the normalizing or the adjusting.

D22. The method of any one of embodiments D1 to D21, wherein the candidate region is identified by a process comprising a segmentation process.

D23. The method of embodiment D22, wherein the copy number variation quantification is z-score.

D24. The method of embodiment D23, wherein the z-score ($Z_{SEG}$) is determined according to:

$$z\text{-score} = (S_{scr} - S_{mcr})/MAD$$

wherein:
the $S_{scr}$ is a test sample count representation of a segment, and the $S_{scr}$ is the total normalized counts in the segment divided by the total normalized autosome counts for the test sample;
the $S_{mcr}$ is a median count representation for the segment generated for a reference set of samples; and
the MAD is a median absolute deviation determined for the count representation of the segment for the reference set of samples.

D25. The method of any one of embodiments D1 to D24, comprising determining a log odds ratio (LOR) for the copy number variation for the test sample.

D26. The method of embodiment D25, wherein the LOR is the log of the quotient of (i) a first multiplication product of (1) a conditional probability of having a copy number variation and (2) a prior probability of having the copy number variation, and (ii) a second multiplication product of (1) a conditional probability of not having the copy number variation and (2) a prior probability of not having the copy number variation.

D27. The method of any one of embodiments D1 to D26, further comprising generating, by the computing device, a copy number variation quantification for a chromosome for the test sample.

D28. The method of embodiment D27, wherein the quantification is a z-score.

D29. The method of embodiment D28, wherein absence of a chromosome, trisomy or monosomy is classified for the test sample when the absolute value of $Z_{CHR}$ is less than a predetermined cutoff value, $LOR_{CHR}$ is less than zero, the absolute value of $Z_{CHR}$ is less than the product of a and $Z_{SEG}$, wherein a is between 0 and about 1, and/or the confidence determination for the chromosome is less than a predetermined level.

D30. The method of any one of embodiments D28 to D29, wherein presence of a sub-chromosome copy number variation is classified for the test sample when there is absence of a chromosome trisomy or monosomy classified for the test sample, where the absolute value of $Z_{SEG}$ is greater than or equal to a predetermined cutoff value, the $LOR_{SEG}$ is greater than zero and the confidence determination for the segment is greater than a predetermined level.

D31. The method of any one of embodiments D28 to D30, wherein absence of a sub-chromosome copy number variation is classified for the test sample when the absolute value of $Z_{SEG}$ is less than a predetermined cutoff value, the $LOR_{SEG}$ is less than zero, and/or the confidence determination for the segment is less than a predetermined level.

E1. A system comprising:
one or more processors and non-transitory machine readable storage medium,
program instructions for selecting a set of genomic portions each coupled to a sequence read quantification for a test sample, wherein:
the genomic portions comprise portions of a reference genome to which sequence reads obtained for sample nucleic acid from the test subject have been mapped,
the genomic portions comprise (i) genomic portions within a candidate region identified as a candidate copy number variation region, and/or (ii) genomic portions outside the candidate region and within a selected region larger than the candidate region that includes the candidate region, and
the candidate region is a chromosome or sub-chromosome region;
program instructions for shifting the quantification of the sequence reads mapped to the genomic portions for the candidate region at or near a quantification of sequence reads mapped to genomic portions outside the candidate region and within the selected region;
program instructions for sampling genomic portions from the selected region, wherein the number of sampled genomic portions is about equal to the number of genomic portions in the candidate region, thereby generating a sampled region, and repeating the sampling to generate a plurality of sampled regions;
program instructions for normalizing a sequence read quantification for each of the sampled regions, thereby generating a normalized quantification for each of the sampled regions;
program instructions for generating a confidence determination for the candidate region by a process comprising comparing each normalized quantification to a measure of variability of sequence read quantifications for the candidate region for reference samples not having a significant copy number variation in the candidate region; and
program instructions for providing a classification for presence or absence of the copy number variation for the candidate region for the test sample according to the confidence determination,
wherein the program instructions are stored on the non-transitory machine readable storage medium for execution by the one or more processors.

F1. A non-transitory machine readable storage medium comprising program instructions that when executed by one or more processors cause the one or more processors to perform a method comprising:

selecting a set of genomic portions each coupled to a sequence read quantification for a test sample, wherein:
the genomic portions comprise portions of a reference genome to which sequence reads obtained for sample nucleic acid from the test subject have been mapped,
the genomic portions comprise (i) genomic portions within a candidate region identified as a candidate copy number variation region, and/or (ii) genomic portions outside the candidate region and within a selected region larger than the candidate region that includes the candidate region, and
the candidate region is a chromosome or sub-chromosome region;
shifting the quantification of the sequence reads mapped to the genomic portions for the candidate region at or near a quantification of sequence reads mapped to genomic portions outside the candidate region and within the selected region;
sampling genomic portions from the selected region, wherein the number of sampled genomic portions is about equal to the number of genomic portions in the candidate region, thereby generating a sampled region, and repeating the sampling to generate a plurality of sampled regions;
normalizing a sequence read quantification for each of the sampled regions, thereby generating a normalized quantification for each of the sampled regions;
generating a confidence determination for the candidate region by a process comprising comparing each normalized quantification to a measure of variability of sequence read quantifications for the candidate region for reference samples not having a significant copy number variation in the candidate region; and
providing a classification for presence or absence of the copy number variation for the candidate region for the test sample according to the confidence determination.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The terms "method" and "process" are used interchangeably herein. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A computer-implemented method for classifying a presence or absence of a chromosome copy number variation or sub-chromosome copy number variation for a test sample, comprising:
sequencing test sample nucleic acid by a massively parallel sequencer that generates thousands to millions of sequence reads, wherein the test sample nucleic acid comprises circulating cell-free nucleic acid from the test sample of a pregnant female bearing a fetus;
mapping, by a computing device, the thousands to millions of sequence reads to genomic portions of a reference genome;
counting, by the computing device, the thousands to millions of sequence reads mapped to the genomic portions, wherein the counting generates a quantification of the thousands to millions of sequence reads mapped to the genomic portions of the reference genome;
shifting, by the computing device, the quantification of the thousands to millions of sequence reads mapped to the genomic portions of the reference genome for a candidate region to or near a baseline sequence read quantification level derived from the quantification of the thousands to millions of sequence reads mapped to the genomic portions outside the candidate region and within a selected region, wherein:
(i) the genomic portions each are coupled to the shifted quantification of the thousands to millions of sequence reads mapped to the genomic portions,
(ii) the genomic portions comprise portions of the reference genome to which the thousands to millions of sequence reads obtained for the test sample nucleic acid from the test sample have been mapped,
(iii) the genomic portions comprise (A) genomic portions within the candidate region identified as a candidate copy number variation region, and/or (B) genomic portions outside the candidate region and within the selected region larger than the candidate region that includes the candidate region, and
(iv) the candidate region is a chromosome or sub-chromosome region;
sampling, by the computing device, the genomic portions from the selected region, wherein a number of the sampled genomic portions is about equal to a number of genomic portions in the candidate region, thereby generating a sampled region, and repeating the sampling to generate a plurality of sampled regions having the genomic portions to which the shifted quantification of the thousands to millions of sequence reads are coupled;

normalizing, by the computing device, the shifted quantification of the thousands to millions of sequence reads coupled to the genomic portions for each of the plurality of sampled regions, thereby generating a normalized quantification of the thousands to millions of sequence reads for each of the plurality of sampled regions;

generating, by the computing device, a confidence determination for the candidate region by a process comprising comparing each normalized quantification of the thousands to millions of sequence reads to a measure of variability of quantifications of sequence reads for the candidate region for reference samples not having a significant copy number variation in the candidate region; and outputting, by the computing device, a classification for the presence or absence of the copy number variation for the candidate region for the test sample according to the confidence determination.

2. The method of claim 1, wherein the selected region is a chromosome in which the candidate region is located.

3. The method of claim 2, wherein the shifting further comprises:
determining a median read count of the genomic portions in the candidate region, thereby providing a candidate region median count;
determining a median read count of the genomic portions outside the candidate region and in the selected region, thereby providing an outside median count; and
subtracting the outside median count from the candidate region median count, thereby determining a shift, which is applied for shifting the quantification of the sequence reads for the candidate region to or near the baseline sequence read quantification level.

4. The method of claim 1, wherein each of the quantifications of the sequence reads for the candidate region for each of the reference samples is a read count fraction for each candidate region in each of the reference samples.

5. The method of claim 1, wherein the quantification of the sequence reads for the genomic portions in the candidate region, outside the candidate region and/or the selected region is a normalized quantification generated by a normalization process that normalizes GC bias or other bias.

6. The method of claim 1, wherein the generating the confidence determination further comprises comparing each normalized quantification of the sequence reads for each of the plurality of sampled regions, or an absolute value of each normalized quantification of the sequence reads for each of the plurality of sampled regions, to a measure of variability threshold for the reference samples.

7. The method of claim 6, wherein the generating the confidence determination further comprises determining a proportion of the plurality of sampled regions for which the normalized quantification of the sequence reads is greater than or less than the measure of variability threshold.

8. The method of claim 7, wherein the proportion is a ratio of (i) a number of the plurality of sampled regions for which the normalized quantification of the sequence reads is greater than or less than the measure of variability threshold to (ii) a total number of the plurality of sampled regions.

9. The method of claim 1, further comprising normalizing, by the computing device, the quantification of the sequence reads mapped to the genomic portions of the reference genome, thereby generating a normalized quantification of the sequence reads mapped to the genomic portions.

10. The method of claim 9, wherein the classification for the presence or absence of the copy number variation for the candidate region is based in part on the normalized quantification of the sequence reads mapped to the candidate region identified by a segmentation process, wherein the segmentation process generates a normalized copy number variation quantification for each segment identified, and wherein the copy number variation quantification is a z-score.

11. The method of claim 10, wherein the z-score (ZSEG) is determined according to:

$$z\text{-score} = (Sscr - Smcr)/MAD$$

wherein:
the Sscr is a test sample count representation of a segment, and the Sscr is the total normalized counts in the segment divided by the total normalized autosome counts for the test sample;
the Smcr is a median count representation for the segment generated for a reference set of samples; and
the MAD is a median absolute deviation determined for the count representation of the segment for the reference set of samples.

12. The method of claim 1, further comprising determining a log odds ratio (LOR) for the copy number variation for the test sample, wherein the LOR is the log of the quotient of (i) a first multiplication product of (1) a conditional probability of having a copy number variation and (2) a prior probability of having the copy number variation, and (ii) a second multiplication product of (1) a conditional probability of not having the copy number variation and (2) a prior probability of not having the copy number variation.

13. The method of claim 12, further comprising generating, by the computing device, a copy number variation quantification for a chromosome for the test sample.

14. The method of claim 13, wherein the copy number variation quantification is a z-score (ZCHR).

15. The method of claim 14, wherein absence of a chromosome, trisomy or monosomy is classified for the test sample when the absolute value of ZCHR is less than a predetermined cutoff value, LORCHR is less than zero, the absolute value of ZCHR is less than the product of a and ZSEG, wherein a is between 0 and about 1, and/or the confidence determination for the chromosome is less than a predetermined level.

16. The method of claim 15, wherein presence of a sub-chromosome copy number variation is classified for the test sample when there is absence of a chromosome trisomy or monosomy classified for the test sample, where the absolute value of ZSEG is greater than or equal to a predetermined cutoff value, the LORSEG is greater than zero and the confidence determination for the segment is greater than a predetermined level.

17. The method of claim 15, wherein absence of a sub-chromosome copy number variation is classified for the test sample when the absolute value of ZSEG is less than a predetermined cutoff value, the LORSEG is less than zero, and/or the confidence determination for the segment is less than a predetermined level.

18. A computer-program product tangibly embodied in a non-transitory machine-readable storage medium, including instructions configured to cause one or more data processors to perform actions including:

sequencing test sample nucleic acid by a massively parallel sequencer that generates thousands to millions of sequence reads, wherein the test sample nucleic acid comprises circulating cell-free nucleic acid from the test sample of a pregnant female bearing a fetus;

mapping the thousands to millions of sequence reads to genomic portions of a reference genome;

counting the thousands to millions of sequence reads mapped to the genomic portions, wherein the counting generates a quantification of the thousands to millions of sequence reads mapped to the genomic portions of the reference genome;

shifting the quantification of the thousands to millions of sequence reads mapped to the genomic portions of the reference genome for a candidate region to or near a baseline sequence read quantification level derived from the quantification of the thousands to millions of sequence reads mapped to the genomic portions outside the candidate region and within a selected region, wherein:
  (i) the genomic portions each are coupled to the shifted quantification of the thousands to millions of sequence reads mapped to the genomic portions,
  (ii) the genomic portions comprise portions of the reference genome to which the thousands to millions of sequence reads obtained for & the test sample nucleic acid from the test sample have been mapped,
  (iii) the genomic portions comprise (A) genomic portions within the candidate region identified as a candidate copy number variation region, and/or (B) genomic portions outside the candidate region and within the selected region larger than the candidate region that includes the candidate region, and
  (iv) the candidate region is a chromosome or sub-chromosome region;

sampling, by the computing device, the genomic portions from the selected region, wherein a number of the sampled genomic portions is about equal to a number of genomic portions in the candidate region, thereby generating a sampled region, and repeating the sampling to generate a plurality of sampled regions having the genomic portions to which the shifted quantification of the thousands to millions of sequence reads are coupled;

normalizing the shifted quantification of the thousands to millions of sequence reads coupled to the genomic portions for each of the plurality of sampled regions, thereby generating a normalized quantification of the thousands to millions of sequence reads for each of the plurality of sampled regions;

generating a confidence determination for the candidate region by a process comprising comparing each normalized quantification of the thousands to millions of sequence reads to a measure of variability of quantification of sequence reads for the candidate region for reference samples not having a significant copy number variation in the candidate region; and outputting a classification for the presence or absence of the copy number variation for the candidate region for the test sample according to the confidence determination.

19. A system comprising:
one or more data processors; and
a non-transitory computer readable storage medium containing instructions which, when executed on the one or more data processors, cause the one or more data processors to perform actions including:

sequencing test sample nucleic acid by a massively parallel sequencer that generates thousands to millions of sequence reads, wherein the test sample nucleic acid comprises circulating cell-free nucleic acid from the test sample of a pregnant female bearing a fetus;

mapping the thousands to millions of sequence reads to genomic portions of a reference genome;

counting the thousands to millions of sequence reads mapped to the genomic portions, wherein the counting generates a quantification of the thousands to millions of sequence reads mapped to the genomic portions of the reference genome;

shifting the quantification of the thousands to millions of sequence reads mapped to the genomic portions of the reference genome for a candidate region to or near a baseline sequence read quantification level derived from the quantification of the thousands to millions of sequence reads mapped to the genomic portions outside the candidate region and within a selected region, wherein:
  (i) the genomic portions each are coupled to the shifted quantification of the thousands to millions of sequence reads mapped to the genomic portions,
  (ii) the genomic portions comprise portions of the reference genome to which the thousands to millions of sequence reads obtained for & the test sample nucleic acid from the test sample have been mapped,
  (iii) the genomic portions comprise (A) genomic portions within the candidate region identified as a candidate copy number variation region, and/or (B) genomic portions outside the candidate region and within the selected region larger than the candidate region that includes the candidate region, and
  (iv) the candidate region is a chromosome or sub-chromosome region;

sampling, by the computing device, the genomic portions from the selected region, wherein a number of the sampled genomic portions is about equal to a number of genomic portions in the candidate region, thereby generating a sampled region, and repeating the sampling to generate a plurality of sampled regions having the genomic portions to which the shifted quantification of the thousands to millions of sequence reads are coupled;

normalizing the shifted quantification of the thousands to millions of sequence reads coupled to the genomic portions for each of the plurality of sampled regions, thereby generating a normalized quantification of the thousands to millions of sequence reads for each of the plurality of sampled regions;

generating a confidence determination for the candidate region by a process comprising comparing each normalized quantification of the sequence reads to a measure of variability of quantification of thousands to millions of sequence reads for the candidate region for reference samples not having a significant copy number variation in the candidate region; and outputting a classification for the presence or absence of the copy number variation for the candidate region for the test sample according to the confidence determination.

* * * * *